(12) United States Patent
Russell et al.

(10) Patent No.: US 10,030,268 B2
(45) Date of Patent: Jul. 24, 2018

(54) HYBRIDIZATION PROBES AND METHODS

(71) Applicant: ABBOTT MOLECULAR INC., Des Plaines, IL (US)

(72) Inventors: John Russell, Des Plaines, IL (US); Ekaterina Pestova, Des Plaines, IL (US); Neeraj Adya, Des Plaines, IL (US)

(73) Assignee: ABBOTT MOLECULAR INC., Des Plaines, IL (US)

( * ) Notice: Subject to any disclaimer, the term of this patent is extended or adjusted under 35 U.S.C. 154(b) by 43 days.

(21) Appl. No.: 14/938,240

(22) Filed: Nov. 11, 2015

(65) Prior Publication Data
US 2016/0215334 A1  Jul. 28, 2016

Related U.S. Application Data

(60) Provisional application No. 62/078,252, filed on Nov. 11, 2014.

(51) Int. Cl.
*C12Q 1/6876* (2018.01)
*C12Q 1/6816* (2018.01)

(52) U.S. Cl.
CPC ......... *C12Q 1/6876* (2013.01); *C12Q 1/6816* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,965,188 A | 10/1990 | Mullis et al. | |
| 5,063,081 A | 11/1991 | Cozzette et al. | |
| 5,130,238 A | 7/1992 | Malek et al. | |
| 5,143,854 A | 9/1992 | Pirrung et al. | |
| 5,270,184 A | 12/1993 | Walker et al. | |
| 5,399,491 A | 3/1995 | Kacian et al. | |
| 5,447,841 A | 9/1995 | Gray et al. | |
| 5,455,166 A | 10/1995 | Walker | |
| 5,480,784 A | 1/1996 | Kacian et al. | |
| 5,491,224 A | 2/1996 | Bittner et al. | |
| 5,641,658 A | 6/1997 | Adams et al. | |
| 5,756,696 A | 5/1998 | Gray et al. | |
| 5,776,688 A | 7/1998 | Bittner et al. | |
| 5,824,518 A | 10/1998 | Kacian et al. | |
| 5,867,402 A | 2/1999 | Schneider et al. | |
| 6,406,850 B2 | 6/2002 | Volkers et al. | |
| 6,569,621 B1 | 5/2003 | Cremer et al. | |
| 6,596,479 B1 | 7/2003 | Gray et al. | |
| 6,828,097 B1 | 12/2004 | Knoll et al. | |
| 7,014,997 B2 | 3/2006 | Knoll et al. | |
| 7,734,424 B1 | 6/2010 | Rogan | |
| 7,790,418 B2 | 9/2010 | Mayer | |
| 7,972,820 B2 | 7/2011 | Mayer | |
| 8,058,055 B2 | 11/2011 | Barrett et al. | |
| 8,209,129 B2 | 6/2012 | Rogan | |
| 8,407,013 B2 | 3/2013 | Rogan | |
| 8,420,798 B2 | 4/2013 | Farrell | |
| 2003/0170881 A1 | 9/2003 | Davis et al. | |
| 2003/0224356 A1 | 12/2003 | Knoll et al. | |
| 2004/0018577 A1 | 1/2004 | Emerson et al. | |
| 2005/0054078 A1 | 3/2005 | Miller et al. | |
| 2006/0046265 A1 | 3/2006 | Becker et al. | |
| 2006/0160164 A1 | 7/2006 | Miller et al. | |
| 2006/0223075 A1 | 10/2006 | Davis et al. | |
| 2007/0059703 A1 | 3/2007 | Fu et al. | |
| 2008/0057513 A1* | 3/2008 | Farrell ................. | C12Q 1/6876 435/6.14 |
| 2013/0183670 A1 | 7/2013 | Farrell et al. | |
| 2013/0237437 A1 | 9/2013 | Russell et al. | |

FOREIGN PATENT DOCUMENTS

| | | |
|---|---|---|
| EP | 0684315 B1 | 6/2002 |
| WO | WO-9318186 A1 | 9/1993 |
| WO | WO-9617958 A1 | 6/1996 |
| WO | WO-0018957 A1 | 4/2000 |
| WO | WO-2014036525 A1 | 3/2014 |

OTHER PUBLICATIONS

Adessi C., et al., "Solid Phase DNA Amplification: Characterisation of Primer Attachment and Amplification Mechanisms," Nucleic Acids Research, 2000, vol. 28 (20), pp. E87.

Boyle S., et al., "Fluorescence in Situ Hybridization with High-Complexity Repeat-Free Oligonucleotide Probes Generated by Massively Parallel Synthesis," Chromosome Research : an International Journal on the Molecular, Supramolecular and Evolutionary Aspects of Chromosome Biology, 2011, vol. 19 (7), pp. 901-909.

Brison O., et al., "General Method for Cloning Amplified DNA by Differential Screening with Genomic Probes," Molecular and Cellular Biology, 1982, vol. 2 (5), pp. 578-587.

Craig J.M., et al., "Removal of Repetitive Sequences from Fish Probes Using Pcr-Assisted Affinity Chromatography," Human Genetics, 1997, vol. 100 (3-4), pp. 472-476.

Dorman S.N.., et al., "Expanding Probe Repertoire and Improving Reproducibility in Human Genomic Hybridization," Nucleic Acids Research, 2013, vol. 41 (7), p. e81.

Dressman D., et al., "Transforming Single Dna Molecules into Fluorescent Magnetic Particles for Detection and Enumeration of Genetic Variations," Proceedings of the National Academy of Sciences of the United States of America, 2003, vol. 100 (15), pp. 8817-8822.

Fodor S.P.A., et al., "Light-Directed, Spatially Addressable Parallel Chemical Synthesis," Science, 1991, vol. 251 (4995), pp. 767-773.

Guatelli J.C., et al., "Isothermal, in Vitro Amplification of Nucleic Acids by a Multienzyme Reaction Modeled after Retroviral Replication," Proceedings of the National Academy of Sciences, 1990, vol. 87 (5), pp. 1874-1878.

Hood L., et al., Molecular Biology of Eucaryotic Cells, W. A. Benjamin, Menlo Park, CA, 1975, pp. 47-51.

(Continued)

*Primary Examiner* — Joseph G. Dauner
(74) *Attorney, Agent, or Firm* — Casimir Jones, S.C.; David A. Casimir

(57) ABSTRACT

The present invention relates to compositions and methods for detection, analysis, and treatment of nucleic acids. In particular, the present invention relates to compositions and methods for generating and using hybridization probes.

14 Claims, 14 Drawing Sheets

(56) References Cited

OTHER PUBLICATIONS

Kwoh D.Y., et al., "Transcription-Based Amplification System and Detection of Amplified Human Immunodeficiency Viru: Type 1 with A Bead-Based Sandwixh Hybridization Format," Proceeding of the National Academy of Sciences of the USA, 1989, vol. 86 (4), pp. 1173-1177.

Leamon J.H., et al., "A Massively Parallel Picotiterplate Based Platform for Discrete Picoliter-scale Polymerase Chain Reactions," Electrophoresis, 2003, vol. 24 (21), pp. 3769-3777.

Lizardi P.M., et al., "Exponential Amplification of Recombinant-RNA Hybridization Probes," Bio/Technology, 1988, vol. 6, pp. 1197-1202.

Lizardi P.M., et al., "Mutation Detection and Single-molecule Counting using Isothermal Rolling-circle Amplification," Nature Genetics, 1998, vol. 19 (3), pp. 225-232.

Mitra R.D., et al., "In Situ Localized Amplification and Contact Replication of Many Individual DNA Molecules," Nucleic Acids Research, 1999, vol. 27 (24), pp. e34.

Morrison, L.E. et al., "Labeling Fluorescence in Situ Hybridization Probes for Genomic Targets," Methods in Molecular Biology, 2002, vol. 204, pp. 21-40.

Mullis K.B., et al., "Specific Synthesis of Dna In Vitro Via a Polymerase-catalyzed Chain Reaction," Methods in Enzymology, 1987, vol. 155, pp. 335-350.

Murakawa G.J., et al., "Direct Detection of HIV-1 RNA from AIDS and ARC Patient Samples," DNA: A Journal of Molecular Biology, 1988, vol. 7 (4), pp. 287-295.

Newkirk H.L., et al., "Distortion of Quantitative Genomic and Expression Hybridization by Cot-1 DNA: Mitigation of This Effect," Nucleic Acids Research, 2005, vol. 33 (22), p. e191.

Perler F.B., et al., "Thermostable Dna Polymerases," Advances in Protein Chemistry, 1996, vol. 48, pp. 377-435.

Persing D.H., "In Vitro Nucleic Acid Amplification Techniques," in: Diagnostic Medical Microbiology : Principles and Applications, American Society for Microbiology, Washington, DC, 1993, pp. 51-87.

Rogan P.K., et al., "Sequence-Based Design of Single-Copy Genomic DNA Probes for Fluorescence in Situ Hybridization," Genome Research, 2001, vol. 11 (6), pp. 1086-1094.

Sealey P.G., et al., "Removal of Repeated Sequences from Hybridisation Probes," Nucleic Acids Research, 1985, vol. 13 (6), pp. 1905-1922.

Smoczynski M., et al., "Routine Brush Cytology and Fluorescence in Situ Hybridization for Assessment of Pancreatobiliary Strictures," Gastrointestinal Endoscopy, 2012, vol. 75 (1), pp. 65-73.

Thum O., et al., "Functionalized DNA: A New Replicable Biopolymer We Thank Dr. andreas Marx, University of Bonn, for Helpful Advice and Discussions. This Work was Supported by the Fonds Der Chemischen Industrie, the Karl-Ziegler Stiftung, and the Deutsche Forschungsgemeinschaft," Angewandte Chemie, 2001, vol. 40 (21), pp. 3990-3993.

Walker G.T., et al., "Isothermal in Vitro Amplification of DNA by a Restriction Enzyme/DNA Polymerase System," Proceedings of the National Academy of Sciences, 1992, vol. 89 (1) pp. 392-396.

Weiss R., "Hot Prospect for New Gene Amplifier," Science, 1991, vol. 254 (5036), pp. 1292-1293.

International Search Report and Written Opinion for Application No. PCT/US2015/060097, dated Feb. 23, 2016, 15 pages.

Rogan, P., discussion re Cytognomix patent portfolio, Mar. 17, 2011.

Swennenhuis et al., "Construction of repeat-free fluorescence in situ hybridization probes." Nucleic Acids Res. Feb. 2012;40(3):e20.

Search Report of related EP 15859151.1, dated Mar. 29, 2018, 9 pages.

* cited by examiner

FIG. 8A

| | | |
|---|---|---|
| 1 | 12 | CTGGAATGCAAAGCGAATACCCCATGATAAGAAAAGTCTAGGGTACAGGTCACTGAGTTTTCCCACCAGAGGCTGTCACG; |
| 2 | 197 | GGCCCCACCCAAGCCTGTGTGGGTTTGGGTCATTTCTTCCAGACTCCTCTTCCAATCCCAATTCCTTCTCTTCATTCACT; |
| 3 | 685 | AGTGGAGGAGGAGAGACATCGCTTGCAAAGAAAGGAGACTTAGTGCCTTTTATGCCTCTCTCTTCCCAGCAGAAGAGCAG; |
| 4 | 1217 | TCCCACCCCTCTATAAGAACAAAGAGTCAGGGTGAGTGTGAGGGCAATGTGTGCGCCTATGCACTTGGGTATCCGAATGT; |
| 5 | 1394 | GATGGAGTGGGAAAGGGGCCAGTTATGCAGACTTGCGTGCGTTCACAGGAATTGGAGATTTCTATCCGAGTGTGTCCTGA; |
| 6 | 2213 | ACCGCGTCTACGAAGATCCTCTACACGGACCCTCACACTTCACGACAGAAACTCCTCCTGGCAACTTTGGAGGAATTCTT; |
| 7 | 2411 | GAGTAGGGATTGAGATTAGGGAGGTGGAGAAGACCGGGTTGGCCCTGGCTGAGAGACACCCAAATTTTCTAATCACTGCT; |
| 8 | 2660 | CAGGAGCGATTGGCAGGTTCGAGCAGCACAGTCATTCCGCACACAGATGTCCCTGCGTTCACTCTTCTGATATGAATTCT; |
| 9 | 3172 | TTCAAAATTCCAGAACTCCCATGAATTGCAAATCGTCCTGAGTGCCCAGTTCTTATATTGCCCTCTTCGTGGGTGCCCGG; |
| 10 | 3318 | AGAACCTTGGCCACCAGCCAAAAGTGCAGCCTGCCCTTTGATTTAGGAACACAGAAAGGTCAAGTCTCCCTGGCTACTGT; |
| 11 | 4000 | GGGTTGGCCAGGAGGGAGCTTTTCCGTGGTGGTACCAGGGAGAAGTGTCTGCGGGATTTTTCTGTCTTTTTCTACAAGAT; |
| 12 | 4427 | AGAGATGAAGGGAAGAGAGAAAGCCCCAGTGCCCTCACTCCCATTCTCGGGCTGTTCCCAAGGGAGAAGGAAAAAACTAT; |
| 13 | 5303 | CAGAGCAGAACAGCCCTCCCAAGGCAGCTGCGCCCTTTCTTACCACTTCTCACCCAGGGAAACTTTGTCGAGAATTTTTA; |
| 14 | 5384 | AGCTGCAGGACAGAAAGGCAGAAGCTGCTTCAGGATTCAGAACCGGGGCAGGGTTTAAGGTTTCTCACAGTTCAGGTGT; |
| 15 | 5688 | GTAGGTCAGGCTAAAGCTGCTCAGTCCTGGCGTCTGCCTTCTCTTTCTCCTCAGCTGCCTTAAGGACTAAACTGCAGAAT; |
| 16 | 5804 | CAATGGCTCTCCTCAGAGCAGATGAATTCCTGTCAATGATTCTGGGGAAGAGGAGGAAGCAAAGGTTGCCAAGAGAGAAC; |
| 17 | 5889 | CTCTGACCTCTGCCCAGAAATTCTTGTATCCACCAGCTTGTGGACTTTCCCATGAAAGGGAAAAAGAGAAGCAGGCACAG; |
| 18 | 6111 | GAGTCATGGCTGGAACGCAGCTCAACAATGAAGGGACAGGAATGGAGCTCAACAGTGAAGGGACAGGGAGTAACTGCTTT; |
| 19 | 6192 | CTTCCCTTTCCCGCCAGATGGGCAAATGGCCTGGACTCGGAGATACCTCTTTTTCTCTGTCATCTTCCAAATGCTGGACT; |
| 20 | 6865 | AAACAGAATTGAGCCACGTAGGGTAGCTGAAGAACAATGCATAGAAAGAAGTCTGTGGTCTGGCCAGGAGAGCCACATGG; |
| 21 | 6988 | AGCTCTGGACTTCTGAGCGGGTTCTAGGAAACTGACTGAGTAGCGGAGAAGCCCAATTAACCTTGTTCTCACGGCAGGAT; |
| 22 | 7085 | ATAAGTGCCAAGTTCCTTTTCTCTGCAATTGCCCCTGCCAGGCCTTGCTCCACGCCATGAGTGCAGATCAGACTTTTGCA; |
| 23 | 7310 | AGGCCCTAGTCTGTGATCTCACTCTAGAGAGGCGATGCCGGGAGAATTCCAGAGAAGGCAGTGAAATTTTGAAAGAATGC; |
| 24 | 7393 | TAAATGTTCTGAAAACTGCTGGAGAATTCCAGTGCAGCATTGGAAAGGGCCTCCTGCTCCATGTTCCCCTGGGTCAGGCA; |
| 25 | 7770 | GCCTTTGCATGCCTGACCTTAATCCTCAACCCCAACACTACAAACCCCACTTCAGCCCTAAAATGAGTCACAGTGTTTGG; |
| 26 | 7996 | AGTAGGAGGGACTCTATCAGGGAAGTCAGTTAAGAGCTGCCCCTGCCTCTCAGGTTCAGAGAAAAAGAATTGTGAGGCC; |
| 27 | 8092 | AGATGCTCACCCAGTGCCCTTCCTCCCTTCTAAGCCCTTAGGGTTCCCTCTGTTCAGAACTGTACCAGACAGGAAGAAAT; |
| 28 | 8595 | TTTCAAGGGAGGTGCCTGTGCATGTTCAGGAATGAAGAAGTGTAAGCATATCAGTGCTTTAGTGCTCGGAAGGTGCCAGC; |
| 29 | 8728 | TGGTTAGGGAGAGAATACTACCCAAGAATGTCCAGGGTCCCTCTGTTTGGCCTCTGCACAGTCACTTGACACTCTGCCTT; |
| 30 | 8923 | ACTGAACAGAAACACGCAATGCACTTCGGGTGTCCGACGGGAGTTTCATCTTCGCTACAAGAGGAAGGTAAAATTGCGTG; |
| 31 | 9954 | CAAATTGTCTTGGCCTCTCTCTTTCCTCTCAATCCACTTCCCCTCCCGCCAAAATTAAAATCGCAAAACGCGGAGACTGG; |
| 32 | 10517 | GCGGGCAAAGCCAAAAGAAAAGAAGGGAGCCGGCGCGAAGTCTCAGTTATGAAAAAACGCATTGAGCTCCTCGTACATG; |
| 33 | 10720 | GAGTAGTGCATAGAGTAGTGGTAGCTTTTCTCGTGGTCGGGCGAGGAGTCCTGCTTGAGTGAGAAGTTGCCATTGAGACA; |
| 34 | 12494 | ATCCAAATTTGTTTGTTTGCTTCCCTTTTTTCGGTGGTGGGGAAAGGTGGCAGGCTTTTCGGACAACCATCGACGGGTC; |
| 35 | 13648 | TGTGGCTAAACGAAATTCAAACCAAGGGAAAGACAGAGAAAGGGAAAGATGTGCCTGGATGTCTGTGCCTCTGCATGGGC; |
| 36 | 14039 | GACTCAAGCATTCTCCTCCCCTTCTGAAAAATCTGAAAATACTGAAGCCAACCCCAGTAATCCCAAGAGTGGCCAAGGGG; |
| 37 | 14347 | GATAACATACCCCTACTCAGATAGACACATGTATGTGAGCAGGTAATCACAGCCTGGTGTAGACAGACCCTTGCCCACAC; |
| 38 | 14616 | TCTCCCTCTAGGAGGCTCCCCAGGGACCTTGGGCTGGTAAGACACTGATCTGATGTTGGGTAGGTTGGATTAAGTTCTAA; |
| 39 | 14937 | TCAGTGGTCTCTAAAAATAAGCCTACCATGCTTCCCTTCATTCACGAATCCTGGGTCTGCAAGGCGAATCCATCTCTGG; |
| 40 | 16547 | AGATACAATAAAAACCAGGGGAAAATTGGAACAGAGGGAGGTGTGGGATGGGCCTGCTTCAGACATGGGCTTGAAAGAGG; |
| 41 | 18189 | TCCGAATTGTTTCCTTGCTCTAAAGGTGGCGTGACCTTTGCTCCCGTAACCTTTGACTTCTGGCCTCTGAACCCTGTTTT; |

SEQ ID NO: 829
(part 1)

FIG. 8B

| | | |
|---|---|---|
| 42 | 18279 | GCTCTTTCCCTGATGGGCACTGGTCTCTGAGTTTCCCTTTGGTCAAATGCATTCTCATTCCTCACTAAGATGCTTCCTGG; |
| 43 | 18400 | GGAGCTTACCACCCTTTGTTAGAAGGACCCATTTACCCATCTGTCTCCTTGCCTGGACCCTGGTGACGACTTGTTCTGTA; |
| 44 | 19503 | CTTGCTCCTCTGGCTTACCTCACGGGACCAAGGCTACCCACCCTGCACATCCTATCCAAAATGCAAATACCATGCAAACA; |
| 45 | 19707 | CTGGATTTACAAGCCTCATGCCTAGTAATCTTTGTTCAGGCTGTTCTGTCTTCCTGAGGTGTCCAGTCCAGCTTCCTCAC; |
| 46 | 19824 | TCTGGGCAGCACATTTCACGAAGGCAGGAACTGGACCCAGAGCCTGGCACACAGAATATCCTCAATATATAGCTGTGGCA; |
| 47 | 19959 | AAAATGGAAGGCTGCAAGCCAGCACAGGACCTCTACCCACAGGAAGTCCCTCCTCAAAATCTTCCCTCTTTTCTCTTCAG; |
| 48 | 21162 | CCAAAAGGTCACTGGGGCAGAATGTATGGTGTGTGCAGGACACTGTGGTCAGGGCAGGAGGTCACAATTTAACCAGAGAT; |
| 49 | 22392 | CTGGATCTATCAAGTTCTGCTCATGGGTGGGTAGGTGGGTGGAGGCTGCTTCTAAACACAGAGAGGGAGCAGTCACATTA; |
| 50 | 23631 | TTGGATGGGAGCGAGGAAGCTGGAGACCTGGCCCATTTTCATTCTGCATAAAATTTTAATGGTCTCTCTGGCTGATCCGG; |
| 51 | 25113 | GATCTCTGCCTCCTGGAAGAGCAAGAGGGCGTTGTGGTAGCCCCTGATGACTAGAGAAATGGAAGGGCTTTCAGTTAGAT; |
| 52 | 26853 | CGGGTGCCTGGGCAGGAGGACGGGGCAGAGCAGCTGCTGGCGATTTATTAAGCAGTCACGGAAAAATTGGTTTATAAATT; |
| 53 | 26934 | ACAGCTGTTTTAACTTTAGGGCCTCTTCTTCAGGCAATGCAAGCAGCCGACTGGACCGGGATTGGAGTGTGTGTAAGGCT; |
| 54 | 27611 | GTATTCATCTATTCATTCACTTCTCAAACCATCCTCTCGGCGTCATGCAGTGCCTGCTGTATTCTGGGTACTGTGGCAGG; |
| 55 | 29115 | CCGCGGCAGGCATCCAGCAATGGCGTGAAGATACATGATGGGAAAGAAACGCCTCAAAATAGTGTGCTCAGACCTATGGT; |
| 56 | 29230 | CAGTCCAAGCAGAGAGACCCACAGTTCAATCAGAGTTACGTCAAATGAGGTCTTGAATTTGTTCCTTGGACCCAACCGCC; |
| 57 | 29591 | ACCACCTGGCCGCCCACCTGAAAAACTTTTCCCCAAGTTCTTGAGAAGTCGCGTAGGATCCAGGAGAGAAAATCAAAGT; |
| 58 | 30861 | AGAGAGGACGCCAACACAAACAGAGCCCCAGGAAAACATGCATGTACACGTCTACACACACCCTCTCAGTGCTAGACAGA; |
| 59 | 31228 | ATTAGATCCGGAGAGGAAAGACAGGAGCCACGTGAATCTACAGTACATCATGGCAGGGCACATTCCCCTTCTCCCTCACA; |
| 60 | 33435 | TTGGCTGGGGAGGTGGCAGTTTCAGCTTAACTCACCTGGTTCTCTTTGTGCATTTCCCTGGAGCTCAACAGGGACCTAAT; |
| 61 | 34403 | CTGCCAAAGTCCCATGAACAGGAGTCAAAGCTGGAGACTGGGGAGTGGATAAGGTCTGGGAACCCAACTCTATTGGCTTT; |
| 62 | 35536 | CCTCCCCTCCCATTTGCATCCCATTTGCACAGATCTGCACACTGGTCTCCTCTTTCCTGCTTCCCTTTCTCCATGGAAAA; |
| 63 | 36394 | AAGCTTGGATTTGAAGGATCATAGGAATTTAACAGGCAGGCAAGGGCATCCCAGGTCCAAGAAGAGGGAAGAAGGTGTGC; |
| 64 | 36716 | TTTCTAGTCAGGGAGCTGGGGAGATATACCTGAAGGACATAGGAGGGCCTCTTCCTGACTAAGCCCTGTTGCCTACCAAn; |
| 65 | 37717 | CTGGAGCTCTCACACTTGGCTCAAGATGAAGCTCTGCCGCGTCCCCAAGGTCAGGGTAGGGTGATTATTGTGCTTTTAT; |
| 66 | 38043 | TCAGCATCTTGTCTGTGGCCTGTGAACTTTGTGTCGCATATGTTCTAAGATCCTGCCAGCTCCTGCAGCCTCTCCTCAGT; |
| 67 | 38167 | CCTTTCTCTAACCCCTTGCTCCTTTCCATCTTTTGGAAACTTGTCTCCAGCTGCCCACACTGTTCCCTTCCCAGCCCTAT; |
| 68 | 38385 | AGACTATTATGTCCTCAGCCTCGGAATTGTTCTGTCCCTTGGAGCCCGGGGCAGGAGTATGTGGATTGGCATCTATGACT; |
| 69 | 38752 | CTAGCATCTTAGGACAGCTTAAGAGCCAAACATGATCAAATCTACCCCTGGCTGCCTCTGCCCTGGTCTGACACCCATCA; |
| 70 | 38964 | TTGCTTTCCTCGGTCCCTCTGTGCCAGCTGTGCAGCGCATTGCTGAGTCTCACCTGCAGTCTATCAGCAATTTGAATCA; |
| 71 | 39209 | CCTGTGACATGTGGATTAGCTGTGGGTCCTCCTTGAGTATACGAGGACGTCCCCTTCTAGTTCAGTGTCTCATACACGCA; |
| 72 | 39341 | CCGAACTCAGCCCTACCTGAGACATGGGTTTCCTCCATCCTTGGCTCAGTCCCTCTCCCAATCAGGTTTTCCCTAATAAT; |
| 73 | 39424 | TCTCTTCCCTGAGAATTAAGGCCAAGGCCGTTTGGGGTTTGAGGCTAGAGCCAAAAGAGGACTTCCCACCTATGGCAGTA; |
| 74 | 39510 | CGTGAGGACATTCAGGGATGGAGGACCAGGAGAGTCCAACACCCCTGTCACCTGCATTTCACCTACATTTTTGAACCTAG; |
| 75 | 40361 | ATGCAGAAGGGCACCGGGTCAAATGATAGTCCTATGATGGAGCAATATAAACCACCACGACTCCTAGTGGCTCCTGGGTG; |
| 76 | 40615 | TGCAAAGCTTAACCTCAGCCATCAGACACTTAGCTCACACTCCAGGACAGCCGGATGGATACGCAGAGCCTGTGTTCTTA; |
| 77 | 41408 | TATGGAGGATTCCAAGTCACCACTTCTCTCACCGGCTTCTACCAGGGTCCAGGACTAAGGCGTTTTCTCCATAGCCTCA; |
| 78 | 41655 | AGCTGCTCTGCCCCTTTCCCCTTCTTCCCTGACTCCAGGCCTGAACCCTCCCGTGCTGTAATAAATCTTTGTAAATAAC; |
| 79 | 41956 | GGGAAGTCCTTCTCGAATAACTGGATTCCTCCAAAGATTTCCCCATCCCCACAGGACTCCCCTCGGGAAATTCCCCTTTT; |
| 80 | 42793 | GGGCCCTTTGAAGTCTTGAGTTCTTAGAGGTGCATAGTACCATTGACACTCATTTCTAATGACACGTTCCCTCACCCCGC; |
| 81 | 42875 | TTTTGGGTTAGTCAATGTCTCCTGGTTTTCTTCGTACCGCTCTGACAGTCGGTCAAAGTCCCGCTTCACGTTTTCCTCTG; |
| 82 | 43523 | CTGTGTGCACCCTAAGGTCCAATAATACGGCACTGCAGCATGCGCCATGCCTACCCTTGCTGTTCGTATCTTCATGACTT; |
| 83 | 44498 | TCTAGAGAAATGTATAGATCTGGGAACTAGAGGGAGAAAAAGACCAGGGGCGGCTTCTGAGGAGCTGACAGTTAATGGGG; |
| 84 | 44580 | TATAAAGCGATGGAGGATTTTATCAGAGGGAGGCAGAGGCTGGAGTGGGCTCAGAGATCAGAAGCTGGGTCCTCTGAA; |

SEQ ID NO: 829
(part 2)

FIG. 8C

| | | |
|---|---|---|
| 85 | 45655 | CCTTTTCTTGAGAGGGCTGAGATCTCTCCTGGAAGATGACTAGCCCGTTTCCAGACTAACCTTGGGAACTTGACCTCACTG; |
| 86 | 45938 | GTGTGTGGTGGTGAGTCTTGTTTCTATTTGGCTTAACTCTTCCCCTTCCGCTTCCTCAGAAGGAAAGGAGAAACAGAGCC; |
| 87 | 46020 | GCTTTGGCTTTGGGTCTTATTTGTCACTGTAGCTGTGTCCTCCTCTCCCTACACTCCCACTTCTCCAGGGGATTTCCCAA; |
| 88 | 46231 | ACCTACTCCCAAGTTTTTGACTCCAGGATTGATGTCCAACCCCAAACCCACACCCTTTCTCCTGTTCCAGGGTGGACATT; |
| 89 | 46319 | ACACACTAGCTAACTTACTAGACATGTACCGTGCCCAGGCACTGTGGCTGTGACTTGGACCTCAAGCGCTTAGGACACAT; |
| 90 | 46956 | GACATTATGGATCCACAGGCTAACTTACTAGACATGTATCATGGCCAGGCACTGTGACTGTGACTTGGACCTCAAGGGCT; |
| 91 | 50072 | TTCTGGCCTGGGGTATGACGAAGGGCTAGCAAGGAACCCTGTCTGTGGCTCTGCAGCCTGAGATTTGTGGAAATTGAAAA; |
| 92 | 50852 | CCACTGCTCCTAGCCCCATCTTACCCGAAAAGTCTTGCCAGCTACTTAATCTATCTCAACCACCACTGACCAAGCGGTTA; |
| 93 | 52692 | CAGTTCCACGCCACGGTGGGTTTTCATCACTTAGACTGGCAGGTGGTCTGATGGAGCTCAAAGGCCTTTCAAAGTCATCT; |
| 94 | 52782 | CATTTTCAAACCCTAGCCAACGAGGCCTCACTCAGGGTGATGCTGGAGTTTGAGGAAAGGCTGACAGGTGGGATTCAGTA; |
| 95 | 55965 | GTGAAACAGATACAAAAGATGAGGAGAGATGGAGAGAGTGAGGAAGGGAGACAGGTCTGGCTGCAAACAAAAGGGCTGTC; |
| 96 | 59851 | CTCCCCATCAGACTTCCGGATGGCAAGGGCCCTTCCTCCAGGTCTCATGCTTATGTGACAAGAAAACAATGTCTTGTTAA; |
| 97 | 59966 | GGCAAAGAGATTAAGTTTGATTCTGGGCATGTTGAGCTGGAGGGAGAGACAGGGCTCTGAGGGTGACTGTCGATTGTGCA; |
| 98 | 60832 | TGGGAGCATATATTTTTAGTTCGCTGACAGACTGTGTCTGTGTTGCCCAGTGGTTACAAGGACTCAGTAGGGTCGTGCTG; |
| 99 | 61562 | GACAGGGGCAAGGACACATCCACTCCGTCTCCACTTCACCCTCTCAAGCAGCGTGATGGATTTTGCCCATTAAGCATAAA; |
| 100 | 62228 | AGGCAGAGAGGGAGCAGGGAAATGACTTCTGCTGGGTTCTCTTTTGGCAGCATATATCCAGTCTGATCAGAGACTCGCCT; |
| 101 | 62683 | CCAGGTGGGAGAGGGAAGATAAGACCCCTGTGCAAGGTTACATCCAAATTGTCCCAGAGACATGCTGACTCAGTCGTTGT; |
| 102 | 63250 | AGAGGGAATCCTGTCCTTTGGTATCTATAAGGAATCATCCTTCACCCGCTTCCCTGACTTAGCCCCTTGCAGCTCTAGGA; |
| 103 | 63333 | AGAACGTTCTTTCTCCAGCCTAACCCCAGTTTATCCTGCTGCAGACTTGAGAGGGTTCCCAAGCAGCTGCTACCAGGAAT; |
| 104 | 63985 | GGTAGGCTGGGTCTGTTCTTTCTATTCCTTCTATCAGGCTCCCTGGGGAAAGCCAGCAACCCTCTCCCACACACTTTTAT; |
| 105 | 64108 | TCCCCACACTCTCTCCCCACCCCTTGCCATTGTCATCTGTGCCTGTTTTCTGCAGGGTCTGACAATGAATCAGATGAAGA; |
| 106 | 64589 | AGGGGAAGGAGGCCACGGCAGTGGTGGACCAGATCTTGGCCCAGGAAGAGAACTGGAAGTTTGAGAAGAATAATGTAAGA; |
| 107 | 64670 | GCCCTCTCCCACCTGACCTTCCCATGCGTGTTACGAGTTTCTGTTCTCTTTTCTGAGGCCTGAGGAAGAAACCCAAACAT; |
| 108 | 64971 | CATTATCTACAAAGATCGTAGAGAGCTTGGAAAACAGAGAGCAACATGCCCCAGTCCCTCTCTCTGGCCAGTTCTTGTGG; |
| 109 | 65116 | ACTCGACATCAAAAGCCTCTCTCCTGCCAGTGCCATAGGTTTGTTAGAGCTACTGTTTTGTAACAGCTGCTCAGGTGTCC; |
| 110 | 67539 | TCTCTGCCATGCCTGGGCCTCCCCTTTGTCAGCCACCTTTCTTACTTGAAAATTTGGGTCAGGGTCCAGATGGTCTCTTA; |
| 111 | 71992 | CTTGGCTTTGCCTCGGGGTGTGAACGGGGTCAGTGACCTCTAAAACTAACCTGCCTCTCAGTTCTGAATCCAGACAGAAT; |
| 112 | 73911 | GAGATAGCTGAGAGGTGCAAACAGAAGAGAAAAAGAGCAACATCCCTTAGGAGAGGGGCAGAGGAGAGAGAGGTGGAGA; |
| 113 | 74068 | AAATGGAGGCAGATGTGGGACAGGGGTGAGAAACTGCCAGGATTTCCTCGCTGAGCCTGGCTGGTAGGTATAGTTGTTTT; |
| 114 | 75527 | ACCCACCTGGATTCCCTGTTCTTTGAAGTGGCACCTAATAAACAAATAATACCCTGCCGCTGCGGTCAGTCCTGTGTCTG; |
| 115 | 75630 | CCCAGAGATCTGAGTGTCCGGGTAGGGGAGACATTCACCCTAGGCTTTTTTTCCAGAAGCTTCCTTGAGGCTAGCATTCT; |
| 116 | 75977 | TGTTATGATTGAAGCACAATGGCCGAGGGAAGTGAAAGGGAAGAACTGGCTCCAGCTCCCTCTCACAACTGGACTTGAG; |
| 117 | 76249 | TATTAAGCACATCCCTTGCCACCGTCCCACCTTAAAAGTTTTCAGTATCAAAAGAAGCTAGCGCAGGCCACCCGAGTCCC; |
| 118 | 76363 | AAAGAGGGACAAGGGGTCAGGGGCAGAGCAAAATCCAGTCTGCTTCAACCACGGACACTGCCTTTGGCATGGAAGTTT; |
| 119 | 76935 | CAGAGCTGGCGCTCCACAAGTGATTATTGATGGTGACAGGATTCCCTCATCCTGCTCCAACCTCTCAACTGTGGACACAT; |
| 120 | 77782 | CTGGGCCCACATCCTTCATGTCCAAGTTCAAGAAGTTGAAAAGAGAAAATCATCTCAAGGGTTGAGGGGAGAAGGGAGGC; |
| 121 | 77893 | CAGACTCGCTCCAAGGTCTTCAGTCCAGCTTGAACTTGTCCTCTGATTCCTTCAGCAGGTACAGGCTGTCATCTTCCAGA; |
| 122 | 78473 | CAGCCTCCTCTCTCTCCCACCTCAAATTCTTCTCCATTCCTCTACCCCAAGAGTCTCTCTAGAACCTCCTTCTCCAGGAA; |
| 123 | 80417 | GCCAGGGCCCAGGGGAATGTTTGAGGCCTTCTTCCTGGAAATTAGCTGCGTGGAGAGCACAAAAGTTATCTAGCGAAT; |
| 124 | 81947 | TGAAACATGAGTGTTCTCTCCACTTGCCTGACCAGCACAGAACCCCGTCAGCTTCCCATAGAACTGAGGCCTAAGAGGAT; |
| 125 | 82517 | ACCTCAGCTATAGGAAGAGCCCCTCCTCCTTCCTCTGGACCCATGTTCCCATCAATGTGAACCGAACACATCCATTTCTC; |
| 126 | 82598 | TCACTCAGAGTTTGTCATCAAGAGCAAGCAAAGGGGAAAGATGGGCTCTGGAAGGAAGGAGAGTTCCAAGATGCCAAGGC; |
| 127 | 82886 | GAAAATCGAGACAAAAATATCACAGCCGTGAAACTGGTTGGATGCCAAGTGAGCCAGATCTGTCAGGAATTCGACCCGGC; |

SEQ ID NO: 829
(part 3)

FIG. 8D

| | | |
|---|---|---|
| 128 | 84439 | GCTGAGTTGCAGATACCATTGAGGTGAAAAATCCAAGAATCAGGGATGACAAGACCAGATCTGTGAAGTGACCCCTGGCC; |
| 129 | 84520 | CTGGCACATGTTATAAAGACAAGGGGTGGGACCCTCCGATCTAAGAAGGCTCTAAGCTTCTTCAGAGTTCAGGCAGGGCT; |
| 130 | 84671 | TGGAAGAACCCCAAAGGAAAGCAGACAGGTGTAACGTCCTCAGCTTCCCTGCCCTTCCTGCTTTCTTAGCCAGGACTAAA; |
| 131 | 84868 | ACTCAGGGGCCTCTCTGCTCCATCTACTCTTCTACTCCTATTCACACAGCTACAATGGGGCCAAGGTTTCCTGGAATGCT; |
| 132 | 84954 | CAATCCCCTGTCCCCACACATGTATGTGTCTAAGCCTTGCCCCACACATGTATGTGTCTAAGTCCCAGATTAAACCTCTC; |
| 133 | 85525 | GTTGTTGAATAGGAAGTATTAAGGAGGGTCCATATTTCCCAGAGGTTTAACAGCCTCCTTCCCTGACCTCCTTCCCACGC; |
| 134 | 88671 | GCTTCTGTGAGAGCAGGAAGGTGAGTGAATGGAAATTTTTTCCTTAAGGCTTACAGGGGCAGCTCCGACCTAGAGACATC; |
| 135 | 88752 | GTTGCAACCTTTCATTCTCACACCCTTCCCAAGGCCGTCACGGTCCATATCTGCACCCCAGTCTGTGCTTATCACACAAT; |
| 136 | 88835 | AGGCCCTGAATACAGCTCTTTAGACCAGCCGTACTGTGAAGCTGACAGCCCTTTCTGCACCTGCAGATGTAACCATACCT; |
| 137 | 89428 | GGGTCTTTTAGTGGCTTCCTTCTTCAGGACAAGAAAAATGCCCTTCTTTCCTCTCTCCTTCCCAAACAGCCTGACCTAGG; |
| 138 | 89562 | CTTTACCACCCTGCAGCTGCAACTTTAGCCCTGGGAAACAGAGGGGAAGCTGCTAAGTAGAAGCCCTGTTGGCTGTTAAT; |
| 139 | 89827 | TCTTGAAAGAACAGGAACCGGGAGAAGGGCCACTCAAAAAGGAGCAGATGAAGGAGGTTTGAAGGGCAGGCAACCCTCAA; |
| 140 | 90635 | GAAAGGTACCAGCAAACTGTGCCTCGCTAGACAAGCTGAAGCATATTACTGTGAATCCAGACCCCTACTGGAGAAGCAAC; |
| 141 | 90799 | TCTGGGGAGACTCCAAAGCCTTCCAGATATTGCTACTCCAAATCCAGAGGCAGGACACATGGGTCCTATCCAATTCTATG; |
| 142 | 90977 | TATATTACTCCTACCACGCTACTACCATATGCCTACCCTGACCCTCCAACTCACCTTGCCATGGAACTGAGGCACTTTGT; |
| 143 | 91079 | AACGGTGACCCACATACACTCATACTTACAGTCGTCCCGACAGGTCCAGCCTGAAACAGACAAATGTGGCCTGGTGAACT; |
| 144 | 91170 | AGAGGAAAGAGAGAGCATGAATGGGGTCCAAGCGCAAATGTAGGCCAAGAGGGCCTGTAAGTTGGAGAGAACCAGGAGAA; |
| 145 | 92080 | CTTCAACCTGACTTTTCAGGCTCCAAATTGCCTTTCCAACCGTATTGGTCACTACTCCTGTTCATGTACCCTGCTCCCTG; |
| 146 | 92576 | ATGCTTCCTAATCAAAGAGTCTTTCAGGGGCTCAAATCATTCTCTGCCTTGCACTTGAAAAGGCTCATGTCCCCGTGGGG; |
| 147 | 93292 | TGCTGTGTCCATATATCGAGGCGATAGGGTTAAGGGAAGGCGGACGCCTGATGGGTTAATGAGCAAACTGAAGTGTTTTC; |
| 148 | 93734 | AGGGCTATGTCCCTCAAGCTTCCTGACTGCCTGGCCTGGTCTGAATCACTCACTCTTCTTTTTTCTTCTAGTCGCAATTG; |
| 149 | 94035 | GTAATATTTCTAGGAAAATTAGGAACCCTGGGAACAGGACGCTTGCTTTAGTATCCTCTCCCTGCTCACCTCCCTGCAC; |
| 150 | 94432 | GAATAGTGTCCCCTGGAGTTGACCACCCAACTGATACTGACTGAGAAGCTGAAATGAACAAAACAACCCCTTAGCCCTCC; |
| 151 | 95617 | CCTAGGTTAATGGTGGAAGTGGGAGTAGAGACTTCTGTTCTGTTGACTTCTTGGAAGATGGGGTACTGTCTCTCTGGGAC; |
| 152 | 95698 | GCTCTTGAGAATTTCCCTGCCAGCACAGCCCCAGATAACAATCTCTAGATGGCGATTACCTGGCCTCTCTTCCCAACTTT; |
| 153 | 95779 | TAGCCTGGAGCCCCTAGTTCTCCCCTGAGCCTCCTTAGCTTGTCCTTCTTCCTAACTTGTATTTGGCTTCAGATGTGATC; |
| 154 | 99772 | GTTGTATGCTTCTCAAAGGTTCCTCGTCTCCTCTTCCTTGGACCAAAAGTCAGAGGCAAGAATGCCCTCATTCATACCCC; |
| 155 | 99879 | GAGTGAGCAAGTGATGTCCTGAAAGGCCCAGTGGATCAGTGGAATGAAGCGGGCAGGAAGACTTAGTGCTCCTGAAACAA; |
| 156 | 100479 | GAGTGGCCTCCCCATGGTTAGGATACAAGTGCTCATCAAGGGCCACCCCTAGGAAGGACCAATTTTCCTATCAGAAGCTT; |
| 157 | 100724 | ACGACTCCTCCCGATTTCTGTTTGTTTTCAGTCCTCTGACCCCAAGCTCGCTGGTGAAGTAGGTAGAGGGAGGAGACTTT; |
| 158 | 101288 | CTTCCTCTCCTCTTGTCAGACACCAGACGAGGTTTTTCCTCTGGCTTCCCAGCTCTGAATGGCTCATTCTTTTTCAGA; |
| 159 | 101578 | GAAGCAGGATCTTTGTAGAGGGAGGGACCTACAGTTACCTGGACTTCTTTCCTCTGTCTCCCCTCTTGGTACCCTTGACT; |
| 160 | 102127 | GCAGGTTGACCAGGTCCTGGGCTGGATGATGGGGTGAGAGTAAGGGGTCAGTTTTGATACATGCCCAACTTTTCTCTCTA; |
| 161 | 102208 | CCCTAAGACATCCTGGGCAAATTGCTTACCTCAGTTCCCCTGATCCTCACCCTAACCCTAACACCAGCTCAAGAGAAAAT; |
| 162 | 103725 | CCCTAGGATGGCATAGCAACCTGTCCCACAAGAGGTGCCTGCTTTAAGTGTGCTCAGCACATGGAAGCAAGTTTAGAAAT; |
| 163 | 103843 | GGAGGGAAGAGAGAAAGAGATGCTGGTGTCCTTCATTCTCCAGTCCCTGATAGGTGCCTTTGATCCCTTCTTGACCAGTA; |
| 164 | 104078 | AAAAAAGTCTTCCTTCCATCCCCACCCCTACCACTAGGCCTAAGGAATAGGGTCAGGGGCTCCAAATAGAATGTGGTTG; |
| 165 | 106699 | CCTCTGTGAGTGAGTGCATGCCCGTGTTATCTCTGCAGGTCTACGCCAGGGTGTTCCTCAGTTGTGTGGTCTTTGTATTT; |
| 166 | 108009 | GAGGAGGCATTAAGAGGTGGTTAGAGTCTTATTCCAGCCAACAATAATGGGTTGAACAAAGCCTTAGGGGCAGGCAGGTG; |
| 167 | 108411 | TTGGGTGATGGAATGATCTGGAAAGAGATTCCTTCCCTGCCCTCCACCTGTGAGAAGCCCCTCTAGAGTGACATCTCCAT; |
| 168 | 108524 | GAGAGCCGAGGTGGGGTAAGGGATGTGTACTCTTTCAAGGAGTGGGAGAATTATTCTAGCGAATGTTTGTGTTGTCCCAG; |
| 169 | 109794 | TGTTAGCCAGCAAGCCTCCAGTTCCCTGGGAACCGTTCTCAGGGTACCAATTTTACCACCTGTCTGCAAACACTTTAAGA; |
| 170 | 109983 | CTCCGTAGAGCCTGTGGTGTTTATCGGTGGCATTGGGAGAATTAGTGTGTATTTATGTTGGCGTGGGGTGTGGGGTGGAT; |

SEQ ID NO: 829
(part 4)

FIG. 8E

| | | |
|---|---|---|
| 171 | 110625 | CTCCCTCAGGGACATGGACCCTTGAGTTCTATTTCTGTTCCTCCCTCCTGTTCCTCCCTCTTTGTCCTTATCTGCCTAGA; |
| 172 | 111027 | ACCCTTCCGATCTCCTGGGCAAGACACGCCAGGTGATTCATCTCACCAGAGCAGAAAAACAAGTTCAACTGGGCACTTTA; |
| 173 | 111867 | AGGGTGGGCCTAGTCAGAAGAAGCCTTTCCCCTGAAATCCCTCTACTTCCCAAGCACGCAAGCTTTCTCCTGCTGTTAAA; |
| 174 | 112303 | CTCTGTTTACAGGTGGGTGGCAGAAGAAGGTGCCCTGCCCTTCTGTTTCCTCTCTTGTTGTGGTTTCTCAACCAGGAAGT; |
| 175 | 112407 | CATTTTACTGCAGAATCAGTTGACTCTCTCTATAACGTGGCTGGCCGAGGTCATGTCTGGATGGGATGCGTCTGTGTTTC; |
| 176 | 114316 | GCTTTGTTCTTGTTGCGGGTGTGGTGGTGGTGGGACTCAAAGACGGTAAAGATAGCTTTCTCTCCTCCCTGGGAATCTn; |
| 177 | 114452 | GAAGCAGAAGGTGACAGAAGGGGAAAGGGTCCTCTGATCATTGCTCACCCCACAGAGATCTTGAAAGGAGGGGTCTTGAT; |
| 178 | 114833 | TCTGCTGCTGTTTGTGCCTCTCTCTGTTACTAACCCGTCCTCTCGCTGTTAGACATCTCTCTCACTGCCTGTCTCTGGTT; |
| 179 | 115654 | GAGCATATGGGGAGCACTGTCTGCATCTTGCTTTGAGAGCTGGTCATGACAGTTCCTGCCGAGCTGCCTTGTTCTTTCAA; |
| 180 | 116614 | ATTTAACAGATCACCTATTTACTGATGGGCGTTTATGGACTGGGCTCAGACCTGGGGAACCTCTTTCCTCCTCTCACAGG; |
| 181 | 116969 | ACGGTAATGCTGCTCATGGTGGTGCACGAAGGGCCAGGGTATGTGGCTACATGTTCCTGATCTCCTTAGACAACTACCTT; |
| 182 | 117474 | CAGTTACCAGTGCCAATATCCAGGAGTTTGCTGGCTGCAAGAAGATCTTTGGGGAGCCTGGCATTTCTGCCGGAGAGCTTT; |
| 183 | 119250 | GTGTGTGTTCACCTAGACCGTTTATGCATCTGTAGACACACACACAGTGAAGTGTGGTTTTCGTCGTTTTGGTGGGGAGG; |
| 184 | 120711 | TTTGGGCCTGAGGGAGTACTCCTGTAGCAGTAACCTTTCCATGAAAGTCTGCAGAGTGTGCTGGGGATGGAGGAAGATGA; |
| 185 | 121796 | CAGTAGGGTGTGCTATCTGGTAAAATATCCCTGGAGAGGGCTCAGCGCTCAGACCTGAACAGCAACAGAGTGGCAGAAAA; |
| 186 | 122119 | AGCACGGGAAAGGCTTTCTACAGAGCAGTGACTGTTGTTACTCGCTGTTACACCTTAGGTAATGCGTTTTCCTCTCTGGG; |
| 187 | 122567 | TTGCCCCATCAACTGCACCCACTCGTGAGTCCAACGGTCTTTTCTGCAGAAAGGAGGACTTTCCTTTCAGGGGTCTTTCT; |
| 188 | 123422 | AAAGTATAAATGTTACAAAGCCAACGTGCCCTTTCACTCAACTCCCTGTCCACCCAGTCTCTCCTGTCTGCTGGGAGAAC; |
| 189 | 125033 | TGACATATGTCCCTTCCCACCCACTCTTCCACTGTGGAACCTCCTGTCATTTTCCACTTCACCAAGTGACAGAGGACCTG; |
| 190 | 125134 | ACTGCAAGGAAAGATGGCTAGGAAACCCAGTCCCTCCACACCCTAGAGTAACTTGATGCCTTGTGAGGGACACAGGCAAA; |
| 191 | 128146 | TTACACCATGAATTGTTGAAGCCCTAAGCCAGAGCCAAGGGCAAGAGTATAGAGAATCTGGAGATGCGGAGAGGGTTCTG; |
| 192 | 128479 | AGGTTTTAGAGTAGGAGAGGGTCCAAGCCTGTGGGTCACCCTTCCGACTTCCCTTTCCGAATGCCAAACACCTTCATGTn; |
| 193 | 131024 | CCACAAGGGGCATGAAAGGGGACCAGGATGTATGTAGACCCAGGAGCCCTAGTATGTTAGGAGCCTCAAAACCTTCTTGT; |
| 194 | 131479 | TTAAAAGGGAAACTAGAAGAGATGCCAAAGGTTCTGGCTGAAGACCCCAGAGTCTGGTGCTACTTCTCTACCACCTGAGG; |
| 195 | 132160 | AACCCCGGTGGACTAGGGTCCCTTTCTCTGATGTTCCCTCAACTGTCACCTCTCAAGGAAACCCCATTATCCCTACAAAA; |
| 196 | 132241 | ATTCTTACTGCCTTCCAACCCCTGTGACCCCATTCTCTCCACGGTGACTGTGTCATACCCCAAAGGTGACCTCTGTTTTT; |
| 197 | 133560 | TGAGAGGGGAAGCGGCCCTAAGGGAGTGTCTAAGAACAAAAGCGACCCATTCAGAGACTGTCCCTGAAACCTAGTACTGn; |
| 198 | 133795 | TGGCTCTGTGCCATCCCTTCCTGCTCACCTTACACTCAATTCCTCTTTTCCTGGAGGGAGTGGCTGGGAATCTTCAGAAA; |
| 199 | 133980 | TTAGAACGAACTAATTCCTAAGGCCACTCACCAGAATGGGGTTATTTCCTCCTTGTGAGTGAGGAGAGTGGTGGGTAGGG; |
| 200 | 134077 | AGGGTCTACTGTGGGACTCATTTTCCTTGCCTTGGCTATGCCAGAGGAGCTCACTGACCTAAGGAGTAGCTGTCCAGAAA; |
| 201 | 134298 | GCTGACATTGCCCTGGGTTAGCGGAGAATAAATAAAATCTGTGCCATCACACAGCTATTACCGAGCCGAAGAGTGGACTG; |
| 202 | 134720 | AGGAGTGGAATGACAGGATGATGCACTGTTGGGGTAGGGTGACCAAGAGGTCCTCCCAACGCTGTAAATACTCACATCTT; |
| 203 | 135045 | TCGCCTGTGTGCCCCTCGCAACACTCAATAAAGGACTCCCTCCCCTCCAACCCTACACGATTGCAGTCTAATAGGTTTTT; |
| 204 | 135844 | CCCACTCCCCACTCCCGGTGTCGCTGGACTTCATGGCTTCATTTACTCTAATGGACTATCTTAGACTGCAAAGCGCTTT; |
| 205 | 141054 | AAATGTGCCCTCTCCTCTGTGCTTCTACTTAAGTCTAAATACAACTTGCAGGGTCTGGTCTTTGACCGCTACTCCTGCCC; |
| 206 | 141837 | ACTTCTTTGCTGGGCCCACTCATACCGGTTTTCCTAGGAAAACTCTGGAGAAAATTGAGGCAGGAGCCACTCATTCGTGC; |
| 207 | 142008 | CACCTCCTAACCCCTCTCCCAAGTACCCTGTGTTTGCCCAGCACTCAATGAGACAGCTAAAGTGATCCCTGACAGAACTA; |
| 208 | 144510 | AGTCCTGGGTCCTCCCTTATACTAGGAGTCATCCAGGGGTTTCTCACCTTCTCACCTGGGCCCTGCACCCTAAAAAATTA; |
| 209 | 145836 | AAGGGTGGAGGCAGGGCTGTTTTGTTTCTCCTAAGCCAGGAAGTTGTGTGGATGAGTCAAGGTTGAATGGAGAGCCCTA; |
| 210 | 146148 | CACCTCCACCTCTAGTGCTCGTCTTTGCCTGCTGTCCTGTCTTTACTTGTCTTGAGTGTCTGTGCAGCCCCTATAAGTGA; |
| 211 | 147603 | TGGATAATACACAGAGGCTTGCAGGCCACTGCTCCCTTCCCCACACCTCTCTCCCTTTTTCTTCTTGCCACAGGAAACTT; |
| 212 | 148478 | ATCCCTGACACTTGTCTACCCACAGCACTCCCTGTTCCCAGAAAAAATGGTCTCCAGCTGTCTCGATGCACACACTGGTA; |
| 213 | 149236 | TTCAGGACCGAAGCTTTGGAAACGCTTTTTCTGCTTCTTGCGCCGATCTCGGCCTCTATTACTCCACCAAGGGCACCTCTA; |

SEQ ID NO: 829
(part 5)

FIG. 8F

| | | |
|---|---|---|
| 214 | 152296 | CAGCCCAGGCGGTTTCACGCCCCACACTTTGTACAGACCGAGAGGCCAGTTGATCTGCTCTGTTTTATACTAGTGACAAT; |
| 215 | 152947 | CATCCCAGAGAGATTTTCTGACAGTCTAAGTCTAGAGAGGTAATTAACAGGGCCCTGGGAGTTGGAGATGAGTCCGACACC; |
| 216 | 154037 | TAAATATGTCAGATCGACTGCATCTGAACTTGCTGCTTAACTCAGGAGACAGACCCTCCTGCAGACCTGTGAACCCCAAC; |
| 217 | 155852 | CCAGAGTTCCAGGCTGGAGTGAGAGTAAAGGGGTCAAGATGAGTCACCTCTTCAGCATGTCCAGGGGTTCAGACTGTAAA; |
| 218 | 156260 | ATCTGGCCACCTGAGACCAGCAGCAGCCCATTCTTGGTGAGTGTCTGAGATTTCTGGCTTTTTGGAGACGTAGCTGCTAA; |
| 219 | 156673 | AAAAAACTTGAGGGCAAAGGGGAAATTCCTCATCATCTTTCCATGCAGAGGAGGACCCAGTACTGAGAGAGGGTGACAGG; |
| 220 | 157156 | CCTGATGAGGGATGAAGAGAGGAAGGACAGGACACAGACAGGGGAGCCCAAAGCCACTTGGAAGGATTCTTTCTTCCAAA; |
| 221 | 157364 | ATTCAGGAAAAAGGCTTGAACCAGTGAAGTACTGATCTGGTCCAACAGATAGAAAGAGGGCCCAGAGAGGTCAGGGCTTG; |
| 222 | 161181 | TTGCGGAGAAGGGAGGCAGCTGCCTACTTCACAGGTCAAGACAGAGTTAAAAACAAAACCACAGCAAATTCAACACCCCG; |
| 223 | 161861 | GGAGGGATTTGGGGATGGGAAGGCCATATAATCTTCTCTCCAGGGCTGAAAACCAGCTACTGAGGGGCCGTTTTTGAAT; |
| 224 | 162060 | ATGGGACGGAGATGATGCTGATCATGGAGCCAGAGGACGCTGGTGCCAGCCTAGCCCCACATTTGTTAGTCTTAAAACTT; |
| 225 | 162141 | AGACAATCTTTCTCATGCCTCTTCCACAGAAGACGGAAAATGGAGGGTGCTTTAGATGAGGCTGAGCAGAACGCCAGACT; |
| 226 | 162457 | TAAGAAGAATCTCTGTTGAGGGAGGAAGGCAGAGCAGTGACTTGGAATAGGGGTGCACCATGCTGAATGTGCTCATCATG; |
| 227 | 162620 | GGGGCCAGCAGCAGGATCACAGTGGTAGGCTCAGCAAGGCGTCAGGTGAGAACCTTTATTTCAGTGATAATTCATTTTTC; |
| 228 | 162966 | AAACCATCTTTACAGAGGAGTAAACTTCACAGTTCCACACATGGCTGGGCTCCAGGTAGAACTCCATAGGAGTGACGAGG; |
| 229 | 163176 | TGAGCCCCAAACCACATTCTGTTCCTTCCTCGTCATTCTGCAGACAATGGTCATCCACAGACCACACGTGTGGTGGCTTT; |
| 230 | 163288 | TTCCAGTAGCCAAAATGATCCTGCACCAAAGCTCATAGACTGAGAACCTGAGCATGCAAAACCACAGTCTGGGTGAAGGG; |
| 231 | 163549 | GTGTTCTCAGTCTTTCAAGAGAGGAAGAAGCAAAGCGGCACTTACAGAGTGTGAGATAGACACAGATCTGTGCGAGGG; |
| 232 | 163636 | AAGGTGGGTGGCATCTTGGGACTCTCTCCAGGCTTTCTGGAGTGGGGTCAGTGGAGAGATGAACAGTGAGAAACATTTGA; |
| 233 | 164574 | TCAAACTGCAAAACCCTGTGTATCTTCATAACAATGGTGGGGCAAAGACTATCTACAGCTGGGGCAAGGGAGAGGCACAG; |
| 234 | 164770 | CATTCAGTCGTGCTGCCTTGGAGAACAGAGTCCTTTCCTGAGGTGGCCCAGGTCCAGCTGCTGCTTTCAGATCAAAATT; |
| 235 | 165024 | GGACAAAGTTTCACCACTCCCTTTCTCTTCTTGAGCTCACAAGTCCCGATGCTGACTCTTTGAGTCCTCAGATAGCCAC; |
| 236 | 167307 | AAGTCCTGACTCTGCCCTTCTGCTAAGATTCTCCTTCACCCTCACCTCCCCAGCCCTGGCAAGGGGTTTGTTAATTAGTA; |
| 237 | 170222 | AGACAACTGGTTAGCCCAAAGCAGCTCAGCTTTTCACTGGAGATGGGAAGGTAAAGGACAGAAGCAGAAGTGCCATCAG; |
| 238 | 170859 | ACGATGCTGAATACATAGGAGCAATCCCTGAGACCAGATATTCACTTCAGCAGGGCTCTGTGTTCTCCTCTGGCTATGTG; |
| 239 | 170944 | AGAACTCATACCGATCATGGCTTCGATATCCACACATGTTACACTCGAAAGGGTCACGGAAGCCGTGGCAGCCCATGTGA; |
| 240 | 171033 | ATCACATAGTCCAGGAAGAGGACGCGGCAGTGGTCACACCGATACACATCCATCACCTCCCCTTCCTTGTTGATCACTTT; |
| 241 | 171167 | AACCTCCTTCAGAAGTGGCATCCCATTGCGGGCCCGAGACAGGACCATGTGATTTTGCTGATAGATGTGATTCTGGCGTT; |
| 242 | 171572 | ATAGTTGACATCAAAGCAGTGGCGCTTCTCACCTGGAACAAGTGACAGAAAGGGTTACAAAGGGAACACTGCCAAGGCAG; |
| 243 | 171668 | TTCTAGAGACCTCAAAAAGGGAGGAGAGTTAAGTTGCCTGCTGCTCAAGAAGACCAAGCCTGGCAGAATGGTTTCCCATG; |
| 244 | 171762 | GACACTGGTCGGCAGCAACGTGTTTGGATGGTTAAAATAAAGCCAGCAGGCAGAAGAGAGGGGCAGAGATGTGGTTCAGT; |
| 245 | 171846 | GCCACATGGTAAGGTATGCCCACTGTGCATGTTAGAGGAGAGCCCTCAAGAAAGGAGGGAAAGAAGCAGGACACTAGGAT; |
| 246 | 171944 | GAGCCACCAGCCCACAGGAGCCTGGGACTTCTGCTATAGTTCATGATCTCTTAAGACACAGTCGGCTCCCAACTCTTATT; |
| 247 | 172158 | CAGACTCCAACTGGCTACTCCCCAAACTCACCCGTCCTGGCTGACTGAGACTGAAGTGAAAGAGCTTCAAATGTAGAAAG; |
| 248 | 172426 | TGAAAACAGAGTTTAGCCACCTTCAGAGTGTGTGGGTGTTGTGTGTTAGAAAACAGAGGCTCTCTGGTCACAGGGAAGGC; |
| 249 | 175085 | CACAGACCATTGTTCATTGTTAAGGAGATGGGGCAGCCTCAGATGTTCACGTGCATGCAACTTGCAATCATCAGATCCCC; |
| 250 | 175321 | AGTCAAACCACAAAAGTGTAACTGCTTCCAAACCTGCACGGAGCATCTGGTCCAGCTTCTAGTCAAAATCACACCACGCC; |
| 251 | 175449 | CCAACAAAAATACACACGGCAACAGCAAGTCCTAAGTTTAGAAACTAAGGCTGCCTGGTTGGGCCATTCCCTACCTGTGG; |
| 252 | 176711 | CAGAGGTGGTGGTAGTGACGGTGGTGGAGACAGTCATATCTATAATAAGAAGCAGACTAGTAAACTCGCCTGGAGTGCAG; |
| 253 | 177612 | CCAACCATCATCATGGCTCTGATCTCAACCTAAGTGAAACTAACACTTCTTGCAGGAGGTGGAAAACAGAGCGGAGCCAG; |
| 254 | 177750 | GGAAAGCTGAGCTGGAGACCACATTTGGTTGCTGCAGAAGTCTTTGTCCTCTGTGAGACACTGGGAAGTGCTGTGTGGAT; |
| 255 | 178362 | TCACCTGCCAGCTGTGTCACTCCACCTCTCTGATCCTCCTTCCTTCCATGGTAAAAGAGCCTCACTGGTGGTTCCTAATA; |
| 256 | 179168 | CTTGATCCAATCTGTCCCTCTTCCCCAGTTCATCTCTAATGGATGCAAAATGCTCCCTACTGGTAATTATCGCCAGCCCG; |

SEQ ID NO: 829
(part 6)

FIG. 8G

| | | |
|---|---|---|
| 257 | 179249 | CTGAGATAGCAGCGGGCTGACCTGATGGTCTATTTTCACCTTTACCCTCACAGTTCAAGAGGTCAGGGAAGTCAAGGCTG; |
| 258 | 179333 | GAGTGCTGTGCAACTGTCAGCAAGGATTAAAGGGAATGACTCACTCTTCCTTCACACCTTACCCATTGCCATTACCCTGG; |
| 259 | 180343 | CTGGGCCCTGAAGCCCTGAAGTTGCTACCTCAATCAAGAGCTAACTCTACTAGGTTTCTGATTCCAGCACAGAGAGAATG; |
| 260 | 182793 | TTTGCCACATTGCTTGCTAATCTGTCCAGTACGAGAGCTCTTTCACTTCCCATCTCTGCTTTGATGTGTCTTGCCTCCGC; |
| 261 | 182970 | TGGATGCACACTCTATTGTTGTTACCTGTTATAACTGCTCAGATTCTTGCCTGGGGTACCTGCTGTGGTCAGTGAAGCCG; |
| 262 | 183051 | CACCAGGGCACATTCAAATCTTGCAGTCTTATGCCGAGATGGGAAAGCTCGACCCATCCCCAACCAGTACCTTCATTAGC; |
| 263 | 186129 | CCTGAGTGGCTTTTGGGCTAGTGCAAAAGTACTCGACTGACTCTGGCTGACCAGCAGTTGTAAATAACGGGCACTTCAGC; |
| 264 | 186310 | CACACAAAACCACCACCAGATGTGGCACTACCCAAAGCCCCAAGAGCAGAGAGATGAAAGACAAAGCTTGGAATTTGCAG; |
| 265 | 186626 | AGTCTATTGTGGTCCCTCCTCTCACTGCCAAATCATTACCCAGGAATTACCCCAAGCACGGTGCTACCCATCTAGTTTTC; |
| 266 | 190017 | TTCTAGAAAGTCCTGCTTCCCCTTGCAGGCAGGTTTGTCCACAGGCTTGGCTCTCACACTACGCTGCACTTCAACTTACA; |
| 267 | 191547 | GCTTTGCCTATTGTCTGAAATACAGAACTGCAAGTAGAGATGCCTACATTCCGTCCTTGAGCGAGTACTGCCTGACTGCC; |
| 268 | 192279 | AAAAATGTCAGACAACCCAAGCTGCAGAACCAGGCTGACAGCCAACTCAATGGGACAAAGGACAGCTGAAGAGATGTGAC; |
| 269 | 193380 | GGTCAGTGCTCTGAAGAAATGTACGGCAGCGCTCCTTGTGCTCCTCAAGGGAACTTCTCTGCTTGTAACTCCTTCCACAA; |
| 270 | 196469 | CACTGGGCTCTGAGGAATGCACTTCCTAGACAAGGAATGCTCATTTCTCTCACTTACCAGAATGTGTCCTAAGATGCCCC; |
| 271 | 196606 | TCCCCTGTGTGCAGTTTAATGTGGCGGAGGAGGTTACCTTTCTGAGTAAAAGATGCCCCACACTGATTACACTGGAATGG; |
| 272 | 198774 | AGGTCCCAAGTTAGGGAGAACTAAACTCAAGGACTCAAGGATTGTGTAATAGGACTGGATAGGAGAGGAGGGACTGGCTC; |
| 273 | 199478 | CTACATCCCTTCCAAAAAACATCAGTAAGTGTTGCTCCTCTTGCTGCATAGGAGGAAGTACAACTGCAGCTGTGCCTGGC; |
| 274 | 199611 | TCTATATTAACTGTGTTTGCTTAATAGAGCAAGACAGGGCCTAACCACCATCAGAGGAGCCAGGGCTGCCACACAGTTCC; |
| 275 | 200215 | GAGGACATAAGAGACCTGCTCCTTTCCCTCAGGATTTTGGCTTTAGTTGGCCTGACCTGGAATTCAATACGACACCATCC; |
| 276 | 200315 | GCTTTAGTCCTTTAGGAGTCAGCTATAGAGCAAGGAAGACAGTATTTGAGACCCAGGGACATAAGGACACAGGGACAGGG; |
| 277 | 203939 | CAAACTAATATGCTGTCTCCTGGCTACTATGCCTTCTCTGATCAACCCAGCTGGAAAATAGCCTGCTCCTTCTTCCTGGG; |
| 278 | 205747 | AGATGACACACACGAACACACACACACACCCCAGAGAGAATTTTGTAGGCTGAAGAGAACAAAGGTTTGGCTCACTGGGG; |
| 279 | 205906 | CACCTGAGACACTGCAAAAACAATGGGTCCTGGAAAGGATCCAACATCTAAATCCTTCAGGGGCAATAGCAGTCTCAGCC; |
| 280 | 209727 | TGCATCAGAATAAGGTCCATGGCCCACAGTGATAGCCAGTCATCTAGTTGACTTCTTTGCCCATTGTGGTCTGGCTTCTG; |
| 281 | 210850 | ACTGCTTAACAGCTGCCCAGTAACATACTTCAAGGCTGCAAGCAAAGATGCATCCTAGCTCTACTGGAAACTGCAGAGGG; |
| 282 | 217691 | ACTCCTCATTTATCCCTCAGCAGGGTACCTTCCTCTAGCTATCAAATGGCACCAAGGTACACAATGGCTCGGGTCACCGT; |
| 283 | 218275 | CTCTCCAGAGGATCCACTAAGGACAGTGGGCAGCCCCATTTTTCTGTTAACCATTGCAACTGTCTGTGGCTCTTTGGCAG; |
| 284 | 218966 | TAAAAAACGGCACTTCCTTTTGAAGCATATATTTGCGTGTACTAAGCAGTACCGCGGGAGCCTCAGCGAGTGCCTAAGCG; |
| 285 | 219054 | GCGGTCTCTCCCAGCTCGCTCCAGCCACCCTTCTTCACACATCTAAATGTGGCGGTAATTAGCATCCATAAACCACACAT; |
| 286 | 220022 | TGTGCAACTCAGGCAGGGTAAACAGCTAGTGTTGATGGGTATCGAGGTATCGTGTGTACTTTTTACCCCTACAGCAGCTC; |
| 287 | 224481 | ACAAGCCACAGGCACAGCTATCATTTGCCTCATTCTGAGTGAGACTCCATGGATGTCACCTTCAAGAAGTTGCACGAAGC; |
| 288 | 225427 | AAAGTGATTAGATTTATCAACATAAATATCACTATAAAATGTGAGCAATATTAATGTGAATATAATGCTCAAAACTCACn; |

SEQ ID NO: 829
(part 7)

SEQUENCE LISTING

```
<160> NUMBER OF SEQ ID NOS: 829

<210> SEQ ID NO 1
<211> LENGTH: 19
<212> TYPE: DNA
<213> ORGANISM: Artificial Sequence
<220> FEATURE:
<223> OTHER INFORMATION: Synthetic

<400> SEQUENCE: 1 aaagggcca gttatgcag                                             19

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
ggtccgtgga attggattat t                                         21

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
ctggcgaagg ggatctattt                                           20

<210> SEQ ID NO 4
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 4
catctgtgtg cggaatgact                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
ttgtctggaa gacgcagaac                                              20

<210> SEQ ID NO 6
<211> LENGTH: 19
<212> TYPE: DNA
<213> ORGANISM: Artificial Sequence
<220> FEATURE:
<223> OTHER INFORMATION: Synthetic

<400> SEQUENCE: 6
gtgccagtct gtgccactc                                               19

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
ggagtgagct ggttggtcac                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
atctgttctc gccagagtcg                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
ggttttgctt tggctctttg                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
```

-continued gacgtgagaa gaaggccaag                                          20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
gacctgacct agcagccttg                                          20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
tctcttggca acctttgctt                                          20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
tcacccaggg aaactttgtc                                          20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
cccagagatg ctccaagaac                                          20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
aaaagagaag caggcacagc                                          20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
acttatcccg aggcctgatt                                          20

<210> SEQ ID NO 17
<211> LENGTH: 20
<212> TYPE: DNA

```
<213> ORGANISM: Artificial Sequence
<220> FEATURE:
<223> OTHER INFORMATION: Synthetic

<400> SEQUENCE: 17
ctgctcatca caccatctcg                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
ctccctgaca agcaggaaag                                               20

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
ggggtatgtg ccttgctcta                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
tgacatgttt agggtgtgg                                                20

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
ggccaactcc tttcttccat                                               20

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
ttgtatttcg gtggactcag g                                             21

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
tttctctccc tgccttctcc                                               20
```

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
gacacctggg tttgatccac                                                  20

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
ggttcccatg gagacatagc                                                  20

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
gacctcggtc tctcagcatc                                                  20

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
ccgctccacc aaaatacata                                                  20

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
gcatttgacc aaagggaaac                                                  20

<210> SEQ ID NO 29
<211> LENGTH: 18
<212> TYPE: DNA
<213> ORGANISM: Artificial Sequence
<220> FEATURE:
<223> OTHER INFORMATION: Synthetic

<400> SEQUENCE: 29
gagtcctgcc ccatgctc                                                    18

<210> SEQ ID NO 30
<211> LENGTH: 19
<212> TYPE: DNA
<213> ORGANISM: Artificial Sequence
<220> FEATURE:

<223> OTHER INFORMATION: Synthetic

<400> SEQUENCE: 30
aataccggct caggacagg                                                    19

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31 cccccctcaca tctgacaatc                                                  20

<210> SEQ ID NO 32
<211> LENGTH: 22
<212> TYPE: DNA
<213> ORGANISM: Artificial Sequence
<220> FEATURE:
<223> OTHER INFORMATION: Synthetic

<400> SEQUENCE: 32
tgctgaacag ttctccagct aa                                                22

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
acacgctgag ccagattgac                                                   20

<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
ggcacaaacg agtacagcag                                                   20

<210> SEQ ID NO 35
<211> LENGTH: 19
<212> TYPE: DNA
<213> ORGANISM: Artificial Sequence
<220> FEATURE:
<223> OTHER INFORMATION: Synthetic

<400> SEQUENCE: 35 ccctcoccat gtgaatttt                                                    19

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
tgggctcctc tctttctctg                                                   20

```
<210> SEQ ID NO 37
<211> LENGTH: 19
<212> TYPE: DNA
<213> ORGANISM: Artificial Sequence
<220> FEATURE:
<223> OTHER INFORMATION: Synthetic

<400> SEQUENCE: 37
cttggcccca ggatttaga                                                  19

<210> SEQ ID NO 38
<211> LENGTH: 20
<212> TYPE: DNA
<213> ORGANISM: Artificial Sequence
<220> FEATURE:
<223> OTHER INFORMATION: Synthetic

<400> SEQUENCE: 38
ggagacaggt gtgagcctct                                                 20

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
tcccactcct atgagcaaca                                                 20

<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
tggagtccag cagagaggat                                                 20

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
gaagcattca gaccctctgc                                                 20

<210> SEQ ID NO 42
<211> LENGTH: 19
<212> TYPE: DNA
<213> ORGANISM: Artificial Sequence
<220> FEATURE:
<223> OTHER INFORMATION: Synthetic

<400> SEQUENCE: 42
gcgtgtgtct ctgcctctg                                                  19

<210> SEQ ID NO 43
<211> LENGTH: 20
<212> TYPE: DNA
<213> ORGANISM: Artificial Sequence
<220> FEATURE:
<223> OTHER INFORMATION: Synthetic
```

<400> SEQUENCE: 43
cgagacgcag agacactcag                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
ctgcatctca gctcagcaac                                               20

<210> SEQ ID NO 45
<211> LENGTH: 20
<212> TYPE: DNA
<213> ORGANISM: Artificial Sequence
<220> FEATURE:
<223> OTHER INFORMATION: Synthetic

<400> SEQUENCE: 45
gcaagagagt tcctggcagt                                               20

<210> SEQ ID NO 46
<211> LENGTH: 20
<212> TYPE: DNA
<213> ORGANISM: Artificial Sequence
<220> FEATURE:
<223> OTHER INFORMATION: Synthetic

<400> SEQUENCE: 46
gcccttcctc tctccagttt                                               20

<210> SEQ ID NO 47
<211> LENGTH: 20
<212> TYPE: DNA
<213> ORGANISM: Artificial Sequence
<220> FEATURE:
<223> OTHER INFORMATION: Synthetic

<400> SEQUENCE: 47
gcaagagagt tcctggcagt                                               20

<210> SEQ ID NO 48
<211> LENGTH: 20
<212> TYPE: DNA
<213> ORGANISM: Artificial Sequence
<220> FEATURE:
<223> OTHER INFORMATION: Synthetic

<400> SEQUENCE: 48
gcccttcctc tctccagttt                                               20

<210> SEQ ID NO 49
<211> LENGTH: 20
<212> TYPE: DNA
<213> ORGANISM: Artificial Sequence
<220> FEATURE:
<223> OTHER INFORMATION: Synthetic

<400> SEQUENCE: 49
agcactgttt gttccctgct                                               20

<210> SEQ ID NO 50
<211> LENGTH: 20

<212> TYPE: DNA
<213> ORGANISM: Artificial Sequence
<220> FEATURE:
<223> OTHER INFORMATION: Synthetic

<400> SEQUENCE: 50
ctcgggactc ctgtgttttg                                               20

<210> SEQ ID NO 51
<211> LENGTH: 20
<212> TYPE: DNA
<213> ORGANISM: Artificial Sequence
<220> FEATURE:
<223> OTHER INFORMATION: Synthetic

<400> SEQUENCE: 51
aaagctggag actggggagt                                               20

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
gtgcagatct gtgcaaatgg                                               20

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
aatttaacag gcaggcaagg                                               20

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
gtaaggcagg agagcaggtg                                               20

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
aagacctggc tcttgactgc                                               20

<210> SEQ ID NO 56
<211> LENGTH: 20
<212> TYPE: DNA
<213> ORGANISM: Artificial Sequence
<220> FEATURE:
<223> OTHER INFORMATION: Synthetic

<400> SEQUENCE: 56
ccaaaagatg gaaaggagca                                              20

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
ggctcaagat gaagctctgc                                              20

<210> SEQ ID NO 58
<211> LENGTH: 19
<212> TYPE: DNA
<213> ORGANISM: Artificial Sequence
<220> FEATURE:
<223> OTHER INFORMATION: Synthetic

<400> SEQUENCE: 58
ggcagagaat accccctca                                               19

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
agcatagcac cctgctcact                                              20

<210> SEQ ID NO 60
<211> LENGTH: 20
<212> TYPE: DNA
<213> ORGANISM: Artificial Sequence
<220> FEATURE:
<223> OTHER INFORMATION: Synthetic

<400> SEQUENCE: 60
tctgaggcct ggttctcatt                                              20

<210> SEQ ID NO 61
<211> LENGTH: 20
<212> TYPE: DNA
<213> ORGANISM: Artificial Sequence
<220> FEATURE:
<223> OTHER INFORMATION: Synthetic

<400> SEQUENCE: 61
ccctggaaag cttaacctca                                              20

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
gcttcccctg aaagaggagt                                              20

<210> SEQ ID NO 63
<211> LENGTH: 20
<212> TYPE: DNA
<213> ORGANISM: Artificial Sequence

```
<220> FEATURE:
<223> OTHER INFORMATION: Synthetic

<400> SEQUENCE: 63
ggaggattcc aagtcaccac                                              20

<210> SEQ ID NO 64
<211> LENGTH: 20
<212> TYPE: DNA
<213> ORGANISM: Artificial Sequence
<220> FEATURE:
<223> OTHER INFORMATION: Synthetic

<400> SEQUENCE: 64
gccaagagtc attgctggag                                              20

<210> SEQ ID NO 65
<211> LENGTH: 20
<212> TYPE: DNA
<213> ORGANISM: Artificial Sequence
<220> FEATURE:
<223> OTHER INFORMATION: Synthetic

<400> SEQUENCE: 65
gtaatggggc gtcctgatag                                              20

<210> SEQ ID NO 66
<211> LENGTH: 20
<212> TYPE: DNA
<213> ORGANISM: Artificial Sequence
<220> FEATURE:
<223> OTHER INFORMATION: Synthetic

<400> SEQUENCE: 66
tgtcagagcg gtacgaagaa                                              20

<210> SEQ ID NO 67
<211> LENGTH: 20
<212> TYPE: DNA
<213> ORGANISM: Artificial Sequence
<220> FEATURE:
<223> OTHER INFORMATION: Synthetic

<400> SEQUENCE: 67
aggctggaaa gaggaaggag                                              20

<210> SEQ ID NO 68
<211> LENGTH: 20
<212> TYPE: DNA
<213> ORGANISM: Artificial Sequence
<220> FEATURE:
<223> OTHER INFORMATION: Synthetic

<400> SEQUENCE: 68
cctgctccaa gttcttacgg                                              20

<210> SEQ ID NO 69
<211> LENGTH: 20
<212> TYPE: DNA
<213> ORGANISM: Artificial Sequence
<220> FEATURE:
<223> OTHER INFORMATION: Synthetic

<400> SEQUENCE: 69
agaggagagg tggcatcaga                                              20
```

<210> SEQ ID NO 70
<211> LENGTH: 19
<212> TYPE: DNA
<213> ORGANISM: Artificial Sequence
<220> FEATURE:
<223> OTHER INFORMATION: Synthetic

<400> SEQUENCE: 70
aaggatggga gccgagtct                                            19

<210> SEQ ID NO 71
<211> LENGTH: 20
<212> TYPE: DNA
<213> ORGANISM: Artificial Sequence
<220> FEATURE:
<223> OTHER INFORMATION: Synthetic

<400> SEQUENCE: 71
aagaccsctg tgcaaggtta                                           20

<210> SEQ ID NO 72
<211> LENGTH: 20
<212> TYPE: DNA
<213> ORGANISM: Artificial Sequence
<220> FEATURE:
<223> OTHER INFORMATION: Synthetic

<400> SEQUENCE: 72
caagataccc tggaggagca                                           20

<210> SEQ ID NO 73
<211> LENGTH: 20
<212> TYPE: DNA
<213> ORGANISM: Artificial Sequence
<220> FEATURE:
<223> OTHER INFORMATION: Synthetic

<400> SEQUENCE: 73
cttagcccct tgcagctcta                                           20

<210> SEQ ID NO 74
<211> LENGTH: 18
<212> TYPE: DNA
<213> ORGANISM: Artificial Sequence
<220> FEATURE:
<223> OTHER INFORMATION: Synthetic

<400> SEQUENCE: 74
gggatctggg ctggtctc                                             18

<210> SEQ ID NO 75
<211> LENGTH: 20
<212> TYPE: DNA
<213> ORGANISM: Artificial Sequence
<220> FEATURE:
<223> OTHER INFORMATION: Synthetic

<400> SEQUENCE: 75
ctgttctccg gtgctctgtc                                           20

<210> SEQ ID NO 76
<211> LENGTH: 20
<212> TYPE: DNA
<213> ORGANISM: Artificial Sequence
<220> FEATURE:
<223> OTHER INFORMATION: Synthetic

```
<400> SEQUENCE: 76
gggcatgttg ctctctgttt                                          20

<210> SEQ ID NO 77
<211> LENGTH: 20
<212> TYPE: DNA
<213> ORGANISM: Artificial Sequence
<220> FEATURE:
<223> OTHER INFORMATION: Synthetic

<400> SEQUENCE: 77
agagagagaa caggccacga                                          20

<210> SEQ ID NO 78
<211> LENGTH: 20
<212> TYPE: DNA
<213> ORGANISM: Artificial Sequence
<220> FEATURE:
<223> OTHER INFORMATION: Synthetic

<400> SEQUENCE: 78
tcttgttcca cagcaccatc                                          20

<210> SEQ ID NO 79
<211> LENGTH: 20
<212> TYPE: DNA
<213> ORGANISM: Artificial Sequence
<220> FEATURE:
<223> OTHER INFORMATION: Synthetic

<400> SEQUENCE: 79
agagaacagg ccacgaacat                                          20

<210> SEQ ID NO 80
<211> LENGTH: 20
<212> TYPE: DNA
<213> ORGANISM: Artificial Sequence
<220> FEATURE:
<223> OTHER INFORMATION: Synthetic

<400> SEQUENCE: 80
cccatctgtg ccttaagagg                                          20

<210> SEQ ID NO 81
<211> LENGTH: 20
<212> TYPE: DNA
<213> ORGANISM: Artificial Sequence
<220> FEATURE:
<223> OTHER INFORMATION: Synthetic

<400> SEQUENCE: 81
gccgttgtag gaggattcaa                                          20

<210> SEQ ID NO 82
<211> LENGTH: 20
<212> TYPE: DNA
<213> ORGANISM: Artificial Sequence
<220> FEATURE:
<223> OTHER INFORMATION: Synthetic

<400> SEQUENCE: 82
cagagcaatc tggtcctcca                                          20

<210> SEQ ID NO 83
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 83
cgtgtttgca cctttgtctg                                              20

<210> SEQ ID NO 84
<211> LENGTH: 20
<212> TYPE: DNA
<213> ORGANISM: Artificial Sequence
<220> FEATURE:
<223> OTHER INFORMATION: Synthetic

<400> SEQUENCE: 84
atacaaaggt cccccaggag                                              20

<210> SEQ ID NO 85
<211> LENGTH: 20
<212> TYPE: DNA
<213> ORGANISM: Artificial Sequence
<220> FEATURE:
<223> OTHER INFORMATION: Synthetic

<400> SEQUENCE: 85
aggtgttggg gtagaactgg                                              20

<210> SEQ ID NO 86
<211> LENGTH: 19
<212> TYPE: DNA
<213> ORGANISM: Artificial Sequence
<220> FEATURE:
<223> OTHER INFORMATION: Synthetic

<400> SEQUENCE: 86
ccctgctggt ggtaggtct                                               19

<210> SEQ ID NO 87
<211> LENGTH: 20
<212> TYPE: DNA
<213> ORGANISM: Artificial Sequence
<220> FEATURE:
<223> OTHER INFORMATION: Synthetic

<400> SEQUENCE: 87
gaggtgtcgg aggagaactg                                              20

<210> SEQ ID NO 88
<211> LENGTH: 20
<212> TYPE: DNA
<213> ORGANISM: Artificial Sequence
<220> FEATURE:
<223> OTHER INFORMATION: Synthetic

<400> SEQUENCE: 88
tattgcggca ctaacagagg                                              20

<210> SEQ ID NO 89
<211> LENGTH: 20
<212> TYPE: DNA
<213> ORGANISM: Artificial Sequence
<220> FEATURE:
<223> OTHER INFORMATION: Synthetic

<400> SEQUENCE: 89
```
agcacagaga ggctgagagg                                           20

<210> SEQ ID NO 90
<211> LENGTH: 20
<212> TYPE: DNA
<213> ORGANISM: Artificial Sequence
<220> FEATURE:
<223> OTHER INFORMATION: Synthetic

<400> SEQUENCE: 90
ccttcccctc tggatgagtc                                           20

<210> SEQ ID NO 91
<211> LENGTH: 20
<212> TYPE: DNA
<213> ORGANISM: Artificial Sequence
<220> FEATURE:
<223> OTHER INFORMATION: Synthetic

<400> SEQUENCE: 91
cagtcctggc ttctgtgtcc                                           20

<210> SEQ ID NO 92
<211> LENGTH: 20
<212> TYPE: DNA
<213> ORGANISM: Artificial Sequence
<220> FEATURE:
<223> OTHER INFORMATION: Synthetic

<400> SEQUENCE: 92
tcccttagaa ctgccacaca                                           20

<210> SEQ ID NO 93
<211> LENGTH: 19
<212> TYPE: DNA
<213> ORGANISM: Artificial Sequence
<220> FEATURE:
<223> OTHER INFORMATION: Synthetic

<400> SEQUENCE: 93
ctgtgtctcg ctccacacc                                            19

<210> SEQ ID NO 94
<211> LENGTH: 20
<212> TYPE: DNA
<213> ORGANISM: Artificial Sequence
<220> FEATURE:
<223> OTHER INFORMATION: Synthetic

<400> SEQUENCE: 94
cccctcccat ctctcttctc                                           20

<210> SEQ ID NO 95
<211> LENGTH: 20
<212> TYPE: DNA
<213> ORGANISM: Artificial Sequence
<220> FEATURE:
<223> OTHER INFORMATION: Synthetic

<400> SEQUENCE: 95
cagaccagaa cgagggagag                                           20

<210> SEQ ID NO 96
<211> LENGTH: 20
<212> TYPE: DNA

```
<213> ORGANISM: Artificial Sequence
<220> FEATURE:
<223> OTHER INFORMATION: Synthetic

<400> SEQUENCE: 96
gtgggcatgt gagatgagtg                                                 20

<210> SEQ ID NO 97
<211> LENGTH: 20
<212> TYPE: DNA
<213> ORGANISM: Artificial Sequence
<220> FEATURE:
<223> OTHER INFORMATION: Synthetic

<400> SEQUENCE: 97
gaaaccagac ccagccataa                                                 20

<210> SEQ ID NO 98
<211> LENGTH: 20
<212> TYPE: DNA
<213> ORGANISM: Artificial Sequence
<220> FEATURE:
<223> OTHER INFORMATION: Synthetic

<400> SEQUENCE: 98
ccagccttgg agtctgttct                                                 20

<210> SEQ ID NO 99
<211> LENGTH: 20
<212> TYPE: DNA
<213> ORGANISM: Artificial Sequence
<220> FEATURE:
<223> OTHER INFORMATION: Synthetic

<400> SEQUENCE: 99
gccctgaaag ggagtatggt                                                 20

<210> SEQ ID NO 100
<211> LENGTH: 20
<212> TYPE: DNA
<213> ORGANISM: Artificial Sequence
<220> FEATURE:
<223> OTHER INFORMATION: Synthetic

<400> SEQUENCE: 100
gatgatcctg gggtcagaga                                                 20

<210> SEQ ID NO 101
<211> LENGTH: 20
<212> TYPE: DNA
<213> ORGANISM: Artificial Sequence
<220> FEATURE:
<223> OTHER INFORMATION: Synthetic

<400> SEQUENCE: 101
ttgaggcaca cagctctgac                                                 20

<210> SEQ ID NO 102
<211> LENGTH: 20
<212> TYPE: DNA
<213> ORGANISM: Artificial Sequence
<220> FEATURE:
<223> OTHER INFORMATION: Synthetic

<400> SEQUENCE: 102
tctgtgcctc cactgtcatc                                                 20
```

<210> SEQ ID NO 103
<211> LENGTH: 19
<212> TYPE: DNA
<213> ORGANISM: Artificial Sequence
<220> FEATURE:
<223> OTHER INFORMATION: Synthetic

<400> SEQUENCE: 103
atccaggacc cagaagagc                                              19

<210> SEQ ID NO 104
<211> LENGTH: 20
<212> TYPE: DNA
<213> ORGANISM: Artificial Sequence
<220> FEATURE:
<223> OTHER INFORMATION: Synthetic

<400> SEQUENCE: 104
agcgtcccta aagccttgtt                                             20

<210> SEQ ID NO 105
<211> LENGTH: 20
<212> TYPE: DNA
<213> ORGANISM: Artificial Sequence
<220> FEATURE:
<223> OTHER INFORMATION: Synthetic

<400> SEQUENCE: 105
ccatactcct cccagtgctc                                             20

<210> SEQ ID NO 106
<211> LENGTH: 20
<212> TYPE: DNA
<213> ORGANISM: Artificial Sequence
<220> FEATURE:
<223> OTHER INFORMATION: Synthetic

<400> SEQUENCE: 106
ggccagtttt cctggtacat                                             20

<210> SEQ ID NO 107
<211> LENGTH: 20
<212> TYPE: DNA
<213> ORGANISM: Artificial Sequence
<220> FEATURE:
<223> OTHER INFORMATION: Synthetic

<400> SEQUENCE: 107
ggaggagtag agggcaggac                                             20

<210> SEQ ID NO 108
<211> LENGTH: 20
<212> TYPE: DNA
<213> ORGANISM: Artificial Sequence
<220> FEATURE:
<223> OTHER INFORMATION: Synthetic

<400> SEQUENCE: 108
ctcttctcac ctcccccttc                                             20

<210> SEQ ID NO 109
<211> LENGTH: 20
<212> TYPE: DNA
<213> ORGANISM: Artificial Sequence
<220> FEATURE:

<223> OTHER INFORMATION: Synthetic

<400> SEQUENCE: 109
tcgtgacaac caaaggaaca                                              20

<210> SEQ ID NO 110
<211> LENGTH: 20
<212> TYPE: DNA
<213> ORGANISM: Artificial Sequence
<220> FEATURE:
<223> OTHER INFORMATION: Synthetic

<400> SEQUENCE: 110
cctcccaaat ctgaggaaag                                              20

<210> SEQ ID NO 111
<211> LENGTH: 20
<212> TYPE: DNA
<213> ORGANISM: Artificial Sequence
<220> FEATURE:
<223> OTHER INFORMATION: Synthetic

<400> SEQUENCE: 111
ccccattgtt gttgttttcc                                              20

<210> SEQ ID NO 112
<211> LENGTH: 20
<212> TYPE: DNA
<213> ORGANISM: Artificial Sequence
<220> FEATURE:
<223> OTHER INFORMATION: Synthetic

<400> SEQUENCE: 112
gattccagtt gtgggcatct                                              20

<210> SEQ ID NO 113
<211> LENGTH: 20
<212> TYPE: DNA
<213> ORGANISM: Artificial Sequence
<220> FEATURE:
<223> OTHER INFORMATION: Synthetic

<400> SEQUENCE: 113
ccaggtgatt catctcacca                                              20

<210> SEQ ID NO 114
<211> LENGTH: 20
<212> TYPE: DNA
<213> ORGANISM: Artificial Sequence
<220> FEATURE:
<223> OTHER INFORMATION: Synthetic

<400> SEQUENCE: 114
ggcaggtagg tgagttccag                                              20

<210> SEQ ID NO 115
<211> LENGTH: 19
<212> TYPE: DNA
<213> ORGANISM: Artificial Sequence
<220> FEATURE:
<223> OTHER INFORMATION: Synthetic

<400> SEQUENCE: 115
gtcttgccct gaggaggtg                                               19

```
<210> SEQ ID NO 116
<211> LENGTH: 20
<212> TYPE: DNA
<213> ORGANISM: Artificial Sequence
<220> FEATURE:
<223> OTHER INFORMATION: Synthetic

<400> SEQUENCE: 116
tgatcatgct ggcaagagag                                          20

<210> SEQ ID NO 117
<211> LENGTH: 20
<212> TYPE: DNA
<213> ORGANISM: Artificial Sequence
<220> FEATURE:
<223> OTHER INFORMATION: Synthetic

<400> SEQUENCE: 117
agcatctgga cctagcatgg                                          20

<210> SEQ ID NO 118
<211> LENGTH: 20
<212> TYPE: DNA
<213> ORGANISM: Artificial Sequence
<220> FEATURE:
<223> OTHER INFORMATION: Synthetic

<400> SEQUENCE: 118
gcacaaagca gaggcacata                                          20

<210> SEQ ID NO 119
<211> LENGTH: 20
<212> TYPE: DNA
<213> ORGANISM: Artificial Sequence
<220> FEATURE:
<223> OTHER INFORMATION: Synthetic

<400> SEQUENCE: 119
cctgctgcct cttctctcag                                          20

<210> SEQ ID NO 120
<211> LENGTH: 20
<212> TYPE: DNA
<213> ORGANISM: Artificial Sequence
<220> FEATURE:
<223> OTHER INFORMATION: Synthetic

<400> SEQUENCE: 120
catgaccagc tctcaaagca                                          20

<210> SEQ ID NO 121
<211> LENGTH: 18
<212> TYPE: DNA
<213> ORGANISM: Artificial Sequence
<220> FEATURE:
<223> OTHER INFORMATION: Synthetic

<400> SEQUENCE: 121
ggctttgaag cccaggat                                            18

<210> SEQ ID NO 122
<211> LENGTH: 19
<212> TYPE: DNA
<213> ORGANISM: Artificial Sequence
<220> FEATURE:
<223> OTHER INFORMATION: Synthetic
```

```
<400> SEQUENCE: 122
gaccgcaggg gacttttag                                              19

<210> SEQ ID NO 123
<211> LENGTH: 20
<212> TYPE: DNA
<213> ORGANISM: Artificial Sequence
<220> FEATURE:
<223> OTHER INFORMATION: Synthetic

<400> SEQUENCE: 123
gcccaccttt ctcccatagt                                             20

<210> SEQ ID NO 124
<211> LENGTH: 20
<212> TYPE: DNA
<213> ORGANISM: Artificial Sequence
<220> FEATURE:
<223> OTHER INFORMATION: Synthetic

<400> SEQUENCE: 124
accctagcac agccacagtc                                             20

<210> SEQ ID NO 125
<211> LENGTH: 20
<212> TYPE: DNA
<213> ORGANISM: Artificial Sequence
<220> FEATURE:
<223> OTHER INFORMATION: Synthetic

<400> SEQUENCE: 125
gctgtggttt gtgatggttg                                             20

<210> SEQ ID NO 126
<211> LENGTH: 20
<212> TYPE: DNA
<213> ORGANISM: Artificial Sequence
<220> FEATURE:
<223> OTHER INFORMATION: Synthetic

<400> SEQUENCE: 126
gggatcccat cgtaaggttt                                             20

<210> SEQ ID NO 127
<211> LENGTH: 20
<212> TYPE: DNA
<213> ORGANISM: Artificial Sequence
<220> FEATURE:
<223> OTHER INFORMATION: Synthetic

<400> SEQUENCE: 127
aggacctgct gaactggtgt                                             20

<210> SEQ ID NO 128
<211> LENGTH: 20
<212> TYPE: DNA
<213> ORGANISM: Artificial Sequence
<220> FEATURE:
<223> OTHER INFORMATION: Synthetic

<400> SEQUENCE: 128
cctcaagagt ggctttggac                                             20

<210> SEQ ID NO 129
<211> LENGTH: 20
```

```
<212> TYPE: DNA
<213> ORGANISM: Artificial Sequence
<220> FEATURE:
<223> OTHER INFORMATION: Synthetic

<400> SEQUENCE: 129
ccaaaggttc tggctgaaga                                              20

<210> SEQ ID NO 130
<211> LENGTH: 20
<212> TYPE: DNA
<213> ORGANISM: Artificial Sequence
<220> FEATURE:
<223> OTHER INFORMATION: Synthetic

<400> SEQUENCE: 130
ggcaacgtag ccatcagtct                                              20

<210> SEQ ID NO 131
<211> LENGTH: 20
<212> TYPE: DNA
<213> ORGANISM: Artificial Sequence
<220> FEATURE:
<223> OTHER INFORMATION: Synthetic

<400> SEQUENCE: 131
cagctcatct accagggtca                                              20

<210> SEQ ID NO 132
<211> LENGTH: 20
<212> TYPE: DNA
<213> ORGANISM: Artificial Sequence
<220> FEATURE:
<223> OTHER INFORMATION: Synthetic

<400> SEQUENCE: 132
cttgatgcca gcagaagtca                                              20

<210> SEQ ID NO 133
<211> LENGTH: 20
<212> TYPE: DNA
<213> ORGANISM: Artificial Sequence
<220> FEATURE:
<223> OTHER INFORMATION: Synthetic

<400> SEQUENCE: 133
cttcccctaa tgggtcacct                                              20

<210> SEQ ID NO 134
<211> LENGTH: 20
<212> TYPE: DNA
<213> ORGANISM: Artificial Sequence
<220> FEATURE:
<223> OTHER INFORMATION: Synthetic

<400> SEQUENCE: 134
ctggatgtct ggctcctcat                                              20

<210> SEQ ID NO 135
<211> LENGTH: 20
<212> TYPE: DNA
<213> ORGANISM: Artificial Sequence
<220> FEATURE:
<223> OTHER INFORMATION: Synthetic

<400> SEQUENCE: 135
```
ctcgttggaa gaggaacagc 20

<210> SEQ ID NO 136
<211> LENGTH: 20
<212> TYPE: DNA
<213> ORGANISM: Artificial Sequence
<220> FEATURE:
<223> OTHER INFORMATION: Synthetic

<400> SEQUENCE: 136
tagaagattc cgtggccttg 20

<210> SEQ ID NO 137
<211> LENGTH: 20
<212> TYPE: DNA
<213> ORGANISM: Artificial Sequence
<220> FEATURE:
<223> OTHER INFORMATION: Synthetic

<400> SEQUENCE: 137
ccctttgacg accagatcat 20

<210> SEQ ID NO 138
<211> LENGTH: 20
<212> TYPE: DNA
<213> ORGANISM: Artificial Sequence
<220> FEATURE:
<223> OTHER INFORMATION: Synthetic

<400> SEQUENCE: 138
gcaatcgtgt agggttggag 20

<210> SEQ ID NO 139
<211> LENGTH: 20
<212> TYPE: DNA
<213> ORGANISM: Artificial Sequence
<220> FEATURE:
<223> OTHER INFORMATION: Synthetic

<400> SEQUENCE: 139
ttcctaaggc cactcaccag 20

<210> SEQ ID NO 140
<211> LENGTH: 20
<212> TYPE: DNA
<213> ORGANISM: Artificial Sequence
<220> FEATURE:
<223> OTHER INFORMATION: Synthetic

<400> SEQUENCE: 140
gcctgtgggg aaaaacctat 20

<210> SEQ ID NO 141
<211> LENGTH: 20
<212> TYPE: DNA
<213> ORGANISM: Artificial Sequence
<220> FEATURE:
<223> OTHER INFORMATION: Synthetic

<400> SEQUENCE: 141
ccagagcttt ctccaggtca 20

<210> SEQ ID NO 142
<211> LENGTH: 20
<212> TYPE: DNA
<213> ORGANISM: Artificial Sequence

```
<220> FEATURE:
<223> OTHER INFORMATION: Synthetic

<400> SEQUENCE: 142
gagacccagc ctttccctac                                                  20

<210> SEQ ID NO 143
<211> LENGTH: 20
<212> TYPE: DNA
<213> ORGANISM: Artificial Sequence
<220> FEATURE:
<223> OTHER INFORMATION: Synthetic

<400> SEQUENCE: 143
ccgcctctga cttctctgtc                                                  20

<210> SEQ ID NO 144
<211> LENGTH: 21
<212> TYPE: DNA
<213> ORGANISM: Artificial Sequence
<220> FEATURE:
<223> OTHER INFORMATION: Synthetic

<400> SEQUENCE: 144
tgcattcatt ctctgtcctc a                                                21

<210> SEQ ID NO 145
<211> LENGTH: 20
<212> TYPE: DNA
<213> ORGANISM: Artificial Sequence
<220> FEATURE:
<223> OTHER INFORMATION: Synthetic

<400> SEQUENCE: 145
ctctcctccg acttggcttt                                                  20

<210> SEQ ID NO 146
<211> LENGTH: 20
<212> TYPE: DNA
<213> ORGANISM: Artificial Sequence
<220> FEATURE:
<223> OTHER INFORMATION: Synthetic

<400> SEQUENCE: 146
atcagtttgt cccctcaacg                                                  20

<210> SEQ ID NO 147
<211> LENGTH: 20
<212> TYPE: DNA
<213> ORGANISM: Artificial Sequence
<220> FEATURE:
<223> OTHER INFORMATION: Synthetic

<400> SEQUENCE: 147
actgcagaga cactccagca                                                  20

<210> SEQ ID NO 148
<211> LENGTH: 20
<212> TYPE: DNA
<213> ORGANISM: Artificial Sequence
<220> FEATURE:
<223> OTHER INFORMATION: Synthetic

<400> SEQUENCE: 148
ccctgtgtgg atgaagttcc                                                  20
```

<210> SEQ ID NO 149
<211> LENGTH: 20
<212> TYPE: DNA
<213> ORGANISM: Artificial Sequence
<220> FEATURE:
<223> OTHER INFORMATION: Synthetic

<400> SEQUENCE: 149
ctggccctct ctgatctctg                                               20

<210> SEQ ID NO 150
<211> LENGTH: 20
<212> TYPE: DNA
<213> ORGANISM: Artificial Sequence
<220> FEATURE:
<223> OTHER INFORMATION: Synthetic

<400> SEQUENCE: 150
tcacttatag gggctgcaca                                               20

<210> SEQ ID NO 151
<211> LENGTH: 20
<212> TYPE: DNA
<213> ORGANISM: Artificial Sequence
<220> FEATURE:
<223> OTHER INFORMATION: Synthetic

<400> SEQUENCE: 151
ctaacccctt ccaagcactg                                               20

<210> SEQ ID NO 152
<211> LENGTH: 20
<212> TYPE: DNA
<213> ORGANISM: Artificial Sequence
<220> FEATURE:
<223> OTHER INFORMATION: Synthetic

<400> SEQUENCE: 152
atccacccat ttgtctgagg                                               20

<210> SEQ ID NO 153
<211> LENGTH: 20
<212> TYPE: DNA
<213> ORGANISM: Artificial Sequence
<220> FEATURE:
<223> OTHER INFORMATION: Synthetic

<400> SEQUENCE: 153
tcattctgtc cttccccaag                                               20

<210> SEQ ID NO 154
<211> LENGTH: 20
<212> TYPE: DNA
<213> ORGANISM: Artificial Sequence
<220> FEATURE:
<223> OTHER INFORMATION: Synthetic

<400> SEQUENCE: 154
gtttttccgg aagacgaagc                                               20

<210> SEQ ID NO 155
<211> LENGTH: 20
<212> TYPE: DNA
<213> ORGANISM: Artificial Sequence
<220> FEATURE:
<223> OTHER INFORMATION: Synthetic

<400> SEQUENCE: 155
cctctgcctg aggaggtaaa                                           20

<210> SEQ ID NO 156
<211> LENGTH: 20
<212> TYPE: DNA
<213> ORGANISM: Artificial Sequence
<220> FEATURE:
<223> OTHER INFORMATION: Synthetic

<400> SEQUENCE: 156
gcacaggact taagggtgga                                           20

<210> SEQ ID NO 157
<211> LENGTH: 20
<212> TYPE: DNA
<213> ORGANISM: Artificial Sequence
<220> FEATURE:
<223> OTHER INFORMATION: Synthetic

<400> SEQUENCE: 157
caagtcctgc tcactcatgc                                           20

<210> SEQ ID NO 158
<211> LENGTH: 20
<212> TYPE: DNA
<213> ORGANISM: Artificial Sequence
<220> FEATURE:
<223> OTHER INFORMATION: Synthetic

<400> SEQUENCE: 158
ccagcacctc aggaaggtag                                           20

<210> SEQ ID NO 159
<211> LENGTH: 20
<212> TYPE: DNA
<213> ORGANISM: Artificial Sequence
<220> FEATURE:
<223> OTHER INFORMATION: Synthetic

<400> SEQUENCE: 159
atcgaaggca gaaacacagc                                           20

<210> SEQ ID NO 160
<211> LENGTH: 20
<212> TYPE: DNA
<213> ORGANISM: Artificial Sequence
<220> FEATURE:
<223> OTHER INFORMATION: Synthetic

<400> SEQUENCE: 160
ctggtgagga ggacaggttg                                           20

<210> SEQ ID NO 161
<211> LENGTH: 20
<212> TYPE: DNA
<213> ORGANISM: Artificial Sequence
<220> FEATURE:
<223> OTHER INFORMATION: Synthetic

<400> SEQUENCE: 161
cctctcgacc tcaagctctc                                           20

<210> SEQ ID NO 162

```
<211> LENGTH: 20
<212> TYPE: DNA
<213> ORGANISM: Artificial Sequence
<220> FEATURE:
<223> OTHER INFORMATION: Synthetic

<400> SEQUENCE: 162
cttcttgtgc agggaaaagg                                               20

<210> SEQ ID NO 163
<211> LENGTH: 20
<212> TYPE: DNA
<213> ORGANISM: Artificial Sequence
<220> FEATURE:
<223> OTHER INFORMATION: Synthetic

<400> SEQUENCE: 163
ctggacaggt ggtgaaatgc                                               20

<210> SEQ ID NO 164
<211> LENGTH: 20
<212> TYPE: DNA
<213> ORGANISM: Artificial Sequence
<220> FEATURE:
<223> OTHER INFORMATION: Synthetic

<400> SEQUENCE: 164
gggctctggg aaggagttag                                               20

<210> SEQ ID NO 165
<211> LENGTH: 20
<212> TYPE: DNA
<213> ORGANISM: Artificial Sequence
<220> FEATURE:
<223> OTHER INFORMATION: Synthetic

<400> SEQUENCE: 165
gggctgggac ctcagatact                                               20

<210> SEQ ID NO 166
<211> LENGTH: 19
<212> TYPE: DNA
<213> ORGANISM: Artificial Sequence
<220> FEATURE:
<223> OTHER INFORMATION: Synthetic

<400> SEQUENCE: 166
ttcgagaacg cttgtggag                                                19

<210> SEQ ID NO 167
<211> LENGTH: 20
<212> TYPE: DNA
<213> ORGANISM: Artificial Sequence
<220> FEATURE:
<223> OTHER INFORMATION: Synthetic

<400> SEQUENCE: 167
gccccacaca tctactggag                                               20

<210> SEQ ID NO 168
<211> LENGTH: 19
<212> TYPE: DNA
<213> ORGANISM: Artificial Sequence
<220> FEATURE:
<223> OTHER INFORMATION: Synthetic

<400> SEQUENCE: 168
```
gcttcacagc tccctcctc                                                    19

<210> SEQ ID NO 169
<211> LENGTH: 20
<212> TYPE: DNA
<213> ORGANISM: Artificial Sequence
<220> FEATURE:
<223> OTHER INFORMATION: Synthetic

<400> SEQUENCE: 169
gttggggtag gggaggatac                                                   20

<210> SEQ ID NO 170
<211> LENGTH: 21
<212> TYPE: DNA
<213> ORGANISM: Artificial Sequence
<220> FEATURE:
<223> OTHER INFORMATION: Synthetic

<400> SEQUENCE: 170
cagctgcact tctgagaaac a                                                 21

<210> SEQ ID NO 171
<211> LENGTH: 20
<212> TYPE: DNA
<213> ORGANISM: Artificial Sequence
<220> FEATURE:
<223> OTHER INFORMATION: Synthetic

<400> SEQUENCE: 171
acaggcacac atggagacag                                                   20

<210> SEQ ID NO 172
<211> LENGTH: 20
<212> TYPE: DNA
<213> ORGANISM: Artificial Sequence
<220> FEATURE:
<223> OTHER INFORMATION: Synthetic

<400> SEQUENCE: 172
tttcagccct ggagagaaga                                                   20

<210> SEQ ID NO 173
<211> LENGTH: 20
<212> TYPE: DNA
<213> ORGANISM: Artificial Sequence
<220> FEATURE:
<223> OTHER INFORMATION: Synthetic

<400> SEQUENCE: 173
ggccagtgtt tctggtcttc                                                   20

<210> SEQ ID NO 174
<211> LENGTH: 20
<212> TYPE: DNA
<213> ORGANISM: Artificial Sequence
<220> FEATURE:
<223> OTHER INFORMATION: Synthetic

<400> SEQUENCE: 174
cctggttcca ctggtcctta                                                   20

<210> SEQ ID NO 175
<211> LENGTH: 20
<212> TYPE: DNA

<213> ORGANISM: Artificial Sequence
<220> FEATURE:
<223> OTHER INFORMATION: Synthetic

<400> SEQUENCE: 175
gcctagcccc acatttgtta                                              20

<210> SEQ ID NO 176
<211> LENGTH: 20
<212> TYPE: DNA
<213> ORGANISM: Artificial Sequence
<220> FEATURE:
<223> OTHER INFORMATION: Synthetic

<400> SEQUENCE: 176
acacgtgtgg tctgtggatg                                              20

<210> SEQ ID NO 177
<211> LENGTH: 20
<212> TYPE: DNA
<213> ORGANISM: Artificial Sequence
<220> FEATURE:
<223> OTHER INFORMATION: Synthetic

<400> SEQUENCE: 177
cgggatgaaa cccttctaca                                              20

<210> SEQ ID NO 178
<211> LENGTH: 20
<212> TYPE: DNA
<213> ORGANISM: Artificial Sequence
<220> FEATURE:
<223> OTHER INFORMATION: Synthetic

<400> SEQUENCE: 178
ttttaatgca caagggcaga                                              20

<210> SEQ ID NO 179
<211> LENGTH: 20
<212> TYPE: DNA
<213> ORGANISM: Artificial Sequence
<220> FEATURE:
<223> OTHER INFORMATION: Synthetic

<400> SEQUENCE: 179
cttacagggt tccagcaagg                                              20

<210> SEQ ID NO 180
<211> LENGTH: 20
<212> TYPE: DNA
<213> ORGANISM: Artificial Sequence
<220> FEATURE:
<223> OTHER INFORMATION: Synthetic

<400> SEQUENCE: 180
aggggtggtg tgcattatgt                                              20

<210> SEQ ID NO 181
<211> LENGTH: 20
<212> TYPE: DNA
<213> ORGANISM: Artificial Sequence
<220> FEATURE:
<223> OTHER INFORMATION: Synthetic

<400> SEQUENCE: 181
ccagcatttt gtgacctcct                                              20

<210> SEQ ID NO 182
<211> LENGTH: 20
<212> TYPE: DNA
<213> ORGANISM: Artificial Sequence
<220> FEATURE:
<223> OTHER INFORMATION: Synthetic

<400> SEQUENCE: 182
gctgtgttca caggggtagc                                           20

<210> SEQ ID NO 183
<211> LENGTH: 20
<212> TYPE: DNA
<213> ORGANISM: Artificial Sequence
<220> FEATURE:
<223> OTHER INFORMATION: Synthetic

<400> SEQUENCE: 183
tttcactgga gatgggaagg                                           20

<210> SEQ ID NO 184
<211> LENGTH: 20
<212> TYPE: DNA
<213> ORGANISM: Artificial Sequence
<220> FEATURE:
<223> OTHER INFORMATION: Synthetic

<400> SEQUENCE: 184
tgtatcccat agccctcacc                                           20

<210> SEQ ID NO 185
<211> LENGTH: 20
<212> TYPE: DNA
<213> ORGANISM: Artificial Sequence
<220> FEATURE:
<223> OTHER INFORMATION: Synthetic

<400> SEQUENCE: 185
ataccgatca tggcttcgat                                           20

<210> SEQ ID NO 186
<211> LENGTH: 20
<212> TYPE: DNA
<213> ORGANISM: Artificial Sequence
<220> FEATURE:
<223> OTHER INFORMATION: Synthetic

<400> SEQUENCE: 186
agtgtcccca ctctttgcag                                           20

<210> SEQ ID NO 187
<211> LENGTH: 20
<212> TYPE: DNA
<213> ORGANISM: Artificial Sequence
<220> FEATURE:
<223> OTHER INFORMATION: Synthetic

<400> SEQUENCE: 187
cgcttctcac ctggaacaag                                           20

<210> SEQ ID NO 188
<211> LENGTH: 20
<212> TYPE: DNA
<213> ORGANISM: Artificial Sequence
<220> FEATURE:

<223> OTHER INFORMATION: Synthetic

<400> SEQUENCE: 188
gggcagtgac aaattttgga                                                     20

<210> SEQ ID NO 189
<211> LENGTH: 20
<212> TYPE: DNA
<213> ORGANISM: Artificial Sequence
<220> FEATURE:
<223> OTHER INFORMATION: Synthetic

<400> SEQUENCE: 189
gttaagttgc ctgctgctca                                                     20

<210> SEQ ID NO 190
<211> LENGTH: 21
<212> TYPE: DNA
<213> ORGANISM: Artificial Sequence
<220> FEATURE:
<223> OTHER INFORMATION: Synthetic

<400> SEQUENCE: 190
tggagacacc tcaagaacag g                                                   21

<210> SEQ ID NO 191
<211> LENGTH: 20
<212> TYPE: DNA
<213> ORGANISM: Artificial Sequence
<220> FEATURE:
<223> OTHER INFORMATION: Synthetic

<400> SEQUENCE: 191
ctctaccatc gatcacagtg                                                     20

<210> SEQ ID NO 192
<211> LENGTH: 20
<212> TYPE: DNA
<213> ORGANISM: Artificial Sequence
<220> FEATURE:
<223> OTHER INFORMATION: Synthetic

<400> SEQUENCE: 192
ctctaccttc gaagaacgac                                                     20

<210> SEQ ID NO 193
<211> LENGTH: 24
<212> TYPE: DNA
<213> ORGANISM: Artificial Sequence
<220> FEATURE:
<223> OTHER INFORMATION: Synthetic

<400> SEQUENCE: 193
ccagctctac catcgatcac agtg                                                24

<210> SEQ ID NO 194
<211> LENGTH: 24
<212> TYPE: DNA
<213> ORGANISM: Artificial Sequence
<220> FEATURE:
<223> OTHER INFORMATION: Synthetic

<400> SEQUENCE: 194
ccagctctac cttcgaagaa cgac                                                24

```
<210> SEQ ID NO 195
<211> LENGTH: 7
<212> TYPE: DNA
<213> ORGANISM: Artificial Sequence
<220> FEATURE:
<223> OTHER INFORMATION: Synthetic

<400> SEQUENCE: 195 cacagtg                                                                   7

<210> SEQ ID NO 196
<211> LENGTH: 7
<212> TYPE: DNA
<213> ORGANISM: Artificial Sequence
<220> FEATURE:
<223> OTHER INFORMATION: Synthetic

<400> SEQUENCE: 196 gaacgac                                                                   7

<210> SEQ ID NO 197
<211> LENGTH: 20
<212> TYPE: DNA
<213> ORGANISM: Artificial Sequence
<220> FEATURE:
<223> OTHER INFORMATION: Synthetic

<400> SEQUENCE: 197
cactgtgatc gatggtagag                                                    20

<210> SEQ ID NO 198
<211> LENGTH: 20
<212> TYPE: DNA
<213> ORGANISM: Artificial Sequence
<220> FEATURE:
<223> OTHER INFORMATION: Synthetic

<400> SEQUENCE: 198
gtcgttcttc gaaggtagag                                                    20

<210> SEQ ID NO 199
<211> LENGTH: 10
<212> TYPE: DNA
<213> ORGANISM: Artificial Sequence
<220> FEATURE:
<223> OTHER INFORMATION: Synthetic

<400> SEQUENCE: 199
cacttctctc                                                               10

<210> SEQ ID NO 200
<211> LENGTH: 10
<212> TYPE: DNA
<213> ORGANISM: Artificial Sequence
<220> FEATURE:
<223> OTHER INFORMATION: Synthetic

<400> SEQUENCE: 200
cactcacatt                                                               10

<210> SEQ ID NO 201
<211> LENGTH: 26
<212> TYPE: DNA
<213> ORGANISM: Artificial Sequence
<220> FEATURE:
<223> OTHER INFORMATION: Synthetic
```

```
<400> SEQUENCE: 201
ggagatgagt ggatgggaga gaagtg                                            26

<210> SEQ ID NO 202
<211> LENGTH: 25
<212> TYPE: DNA
<213> ORGANISM: Artificial Sequence
<220> FEATURE:
<223> OTHER INFORMATION: Synthetic

<400> SEQUENCE: 202
gtggtaggag ggatgaatgt gagtg                                             25

<210> SEQ ID NO 203
<211> LENGTH: 25
<212> TYPE: DNA
<213> ORGANISM: Artificial Sequence
<220> FEATURE:
<223> OTHER INFORMATION: Synthetic

<400> SEQUENCE: 203
tcccctcacg cttctccttc agttc                                             25

<210> SEQ ID NO 204
<211> LENGTH: 25
<212> TYPE: DNA
<213> ORGANISM: Artificial Sequence
<220> FEATURE:
<223> OTHER INFORMATION: Synthetic

<400> SEQUENCE: 204
agggtcaggg attggggagc tagtg                                             25

<210> SEQ ID NO 205
<211> LENGTH: 26
<212> TYPE: DNA
<213> ORGANISM: Artificial Sequence
<220> FEATURE:
<223> OTHER INFORMATION: Synthetic

<400> SEQUENCE: 205
tgatgagggg aaggctgtct acctga                                            26

<210> SEQ ID NO 206
<211> LENGTH: 24
<212> TYPE: DNA
<213> ORGANISM: Artificial Sequence
<220> FEATURE:
<223> OTHER INFORMATION: Synthetic

<400> SEQUENCE: 206
gctgactctc agcccctcct ccag                                              24

<210> SEQ ID NO 207
<211> LENGTH: 25
<212> TYPE: DNA
<213> ORGANISM: Artificial Sequence
<220> FEATURE:
<223> OTHER INFORMATION: Synthetic

<400> SEQUENCE: 207
gtgaggggcg agaaacaaga caagc                                             25

<210> SEQ ID NO 208
<211> LENGTH: 26
```

```
<212> TYPE: DNA
<213> ORGANISM: Artificial Sequence
<220> FEATURE:
<223> OTHER INFORMATION: Synthetic

<400> SEQUENCE: 208
tgcagaaggg aagaaggttg ttacgc                                            26

<210> SEQ ID NO 209
<211> LENGTH: 25
<212> TYPE: DNA
<213> ORGANISM: Artificial Sequence
<220> FEATURE:
<223> OTHER INFORMATION: Synthetic

<400> SEQUENCE: 209
gcccagcctt aaccccagaa ctcag                                             25

<210> SEQ ID NO 210
<211> LENGTH: 25
<212> TYPE: DNA
<213> ORGANISM: Artificial Sequence
<220> FEATURE:
<223> OTHER INFORMATION: Synthetic

<400> SEQUENCE: 210
gcatcggaac tctgctcatg gaaag                                             25

<210> SEQ ID NO 211
<211> LENGTH: 25
<212> TYPE: DNA
<213> ORGANISM: Artificial Sequence
<220> FEATURE:
<223> OTHER INFORMATION: Synthetic

<400> SEQUENCE: 211
atggctctgc tgacccaaca aacag                                             25

<210> SEQ ID NO 212
<211> LENGTH: 25
<212> TYPE: DNA
<213> ORGANISM: Artificial Sequence
<220> FEATURE:
<223> OTHER INFORMATION: Synthetic

<400> SEQUENCE: 212
aaaacaggat ggcctggctc agttc                                             25

<210> SEQ ID NO 213
<211> LENGTH: 25
<212> TYPE: DNA
<213> ORGANISM: Artificial Sequence
<220> FEATURE:
<223> OTHER INFORMATION: Synthetic

<400> SEQUENCE: 213
tccccatttc ttggagtggg attga                                             25

<210> SEQ ID NO 214
<211> LENGTH: 25
<212> TYPE: DNA
<213> ORGANISM: Artificial Sequence
<220> FEATURE:
<223> OTHER INFORMATION: Synthetic

<400> SEQUENCE: 214
```
ttataagcca ctcggaagcc cctca                                              25

<210> SEQ ID NO 215
<211> LENGTH: 28
<212> TYPE: DNA
<213> ORGANISM: Artificial Sequence
<220> FEATURE:
<223> OTHER INFORMATION: Synthetic

<400> SEQUENCE: 215 ggagcccttaa agcaactagc ctctctcc                                          28

<210> SEQ ID NO 216
<211> LENGTH: 25
<212> TYPE: DNA
<213> ORGANISM: Artificial Sequence
<220> FEATURE:
<223> OTHER INFORMATION: Synthetic

<400> SEQUENCE: 216
gggctggcca tagcgaaaaa cacta                                              25

<210> SEQ ID NO 217
<211> LENGTH: 25
<212> TYPE: DNA
<213> ORGANISM: Artificial Sequence
<220> FEATURE:
<223> OTHER INFORMATION: Synthetic

<400> SEQUENCE: 217
aaagtgtgaa aagcgcctgc ccatc                                              25

<210> SEQ ID NO 218
<211> LENGTH: 25
<212> TYPE: DNA
<213> ORGANISM: Artificial Sequence
<220> FEATURE:
<223> OTHER INFORMATION: Synthetic

<400> SEQUENCE: 218
cctggggttc aaaaacagcc tgact                                              25

<210> SEQ ID NO 219
<211> LENGTH: 25
<212> TYPE: DNA
<213> ORGANISM: Artificial Sequence
<220> FEATURE:
<223> OTHER INFORMATION: Synthetic

<400> SEQUENCE: 219
gggcatcact ttcttttccc ccatc                                              25

<210> SEQ ID NO 220
<211> LENGTH: 25
<212> TYPE: DNA
<213> ORGANISM: Artificial Sequence
<220> FEATURE:
<223> OTHER INFORMATION: Synthetic

<400> SEQUENCE: 220
ttgaagatct ggcaggcagt gatcc                                              25

<210> SEQ ID NO 221
<211> LENGTH: 25
<212> TYPE: DNA
<213> ORGANISM: Artificial Sequence
<220> FEATURE:
<223> OTHER INFORMATION: Synthetic

<400> SEQUENCE: 221
cggtcctgct ctggtcaata aagga                                              25

<210> SEQ ID NO 222
<211> LENGTH: 23
<212> TYPE: DNA
<213> ORGANISM: Artificial Sequence
<220> FEATURE:
<223> OTHER INFORMATION: Synthetic

<400> SEQUENCE: 222
gaccctagcc gggctgtccc tac                                                23

<210> SEQ ID NO 223
<211> LENGTH: 25
<212> TYPE: DNA
<213> ORGANISM: Artificial Sequence
<220> FEATURE:
<223> OTHER INFORMATION: Synthetic

<400> SEQUENCE: 223
gggccttcac cttgataggc actcg                                              25

<210> SEQ ID NO 224
<211> LENGTH: 25
<212> TYPE: DNA
<213> ORGANISM: Artificial Sequence
<220> FEATURE:
<223> OTHER INFORMATION: Synthetic

<400> SEQUENCE: 224
agctagcaaa gggggagatt gcaca                                              25

<210> SEQ ID NO 225
<211> LENGTH: 25
<212> TYPE: DNA
<213> ORGANISM: Artificial Sequence
<220> FEATURE:
<223> OTHER INFORMATION: Synthetic

<400> SEQUENCE: 225
cagtcacttc gtcgcggcta aaaca                                              25

<210> SEQ ID NO 226
<211> LENGTH: 25
<212> TYPE: DNA
<213> ORGANISM: Artificial Sequence
<220> FEATURE:
<223> OTHER INFORMATION: Synthetic

<400> SEQUENCE: 226
ggagctgagc tgtagtctcc gagca                                              25

<210> SEQ ID NO 227
<211> LENGTH: 25
<212> TYPE: DNA
<213> ORGANISM: Artificial Sequence
<220> FEATURE:
<223> OTHER INFORMATION: Synthetic

<400> SEQUENCE: 227
cagaaagggt caccccctta tgtcg                                              25

<210> SEQ ID NO 228
<211> LENGTH: 25
<212> TYPE: DNA
<213> ORGANISM: Artificial Sequence
<220> FEATURE:
<223> OTHER INFORMATION: Synthetic

<400> SEQUENCE: 228
gaaccaagca tttcatggct cacaa                                  25

<210> SEQ ID NO 229
<211> LENGTH: 25
<212> TYPE: DNA
<213> ORGANISM: Artificial Sequence
<220> FEATURE:
<223> OTHER INFORMATION: Synthetic

<400> SEQUENCE: 229
ttgtggactg tccctgacct gggta                                  25

<210> SEQ ID NO 230
<211> LENGTH: 25
<212> TYPE: DNA
<213> ORGANISM: Artificial Sequence
<220> FEATURE:
<223> OTHER INFORMATION: Synthetic

<400> SEQUENCE: 230
ctcctgccat aggacccaag ctacg                                  25

<210> SEQ ID NO 231
<211> LENGTH: 25
<212> TYPE: DNA
<213> ORGANISM: Artificial Sequence
<220> FEATURE:
<223> OTHER INFORMATION: Synthetic

<400> SEQUENCE: 231
atgagcacct gcctctctct gctca                                  25

<210> SEQ ID NO 232
<211> LENGTH: 25
<212> TYPE: DNA
<213> ORGANISM: Artificial Sequence
<220> FEATURE:
<223> OTHER INFORMATION: Synthetic

<400> SEQUENCE: 232
catgcatctt ctcggtgagc cagtc                                  25

<210> SEQ ID NO 233
<211> LENGTH: 25
<212> TYPE: DNA
<213> ORGANISM: Artificial Sequence
<220> FEATURE:
<223> OTHER INFORMATION: Synthetic

<400> SEQUENCE: 233
tgttaagccg tggattcaag gacca                                  25

<210> SEQ ID NO 234
<211> LENGTH: 25
<212> TYPE: DNA
<213> ORGANISM: Artificial Sequence
<220> FEATURE:
<223> OTHER INFORMATION: Synthetic

<400> SEQUENCE: 234
gttttccctg ttggtgggaa ggtca                                              25

<210> SEQ ID NO 235
<211> LENGTH: 25
<212> TYPE: DNA
<213> ORGANISM: Artificial Sequence
<220> FEATURE:
<223> OTHER INFORMATION: Synthetic

<400> SEQUENCE: 235
ccatcaccca ggcagtcatc ttcat                                              25

<210> SEQ ID NO 236
<211> LENGTH: 25
<212> TYPE: DNA
<213> ORGANISM: Artificial Sequence
<220> FEATURE:
<223> OTHER INFORMATION: Synthetic

<400> SEQUENCE: 236
tgaggagagc ctctgggatc tggag                                              25

<210> SEQ ID NO 237
<211> LENGTH: 25
<212> TYPE: DNA
<213> ORGANISM: Artificial Sequence
<220> FEATURE:
<223> OTHER INFORMATION: Synthetic

<400> SEQUENCE: 237
tgaccttccc accaacaggg aaaac                                              25

<210> SEQ ID NO 238
<211> LENGTH: 25
<212> TYPE: DNA
<213> ORGANISM: Artificial Sequence
<220> FEATURE:
<223> OTHER INFORMATION: Synthetic

<400> SEQUENCE: 238
ttgcttggca gttgtggcaa gtagc                                              25

<210> SEQ ID NO 239
<211> LENGTH: 25
<212> TYPE: DNA
<213> ORGANISM: Artificial Sequence
<220> FEATURE:
<223> OTHER INFORMATION: Synthetic

<400> SEQUENCE: 239
aacctccaga tcccagaggc tctcc                                              25

<210> SEQ ID NO 240
<211> LENGTH: 25
<212> TYPE: DNA
<213> ORGANISM: Artificial Sequence
<220> FEATURE:
<223> OTHER INFORMATION: Synthetic

<400> SEQUENCE: 240
ggctcttggt agtcctgtgg ctggt                                              25

<210> SEQ ID NO 241

-continued

```
<211> LENGTH: 25
<212> TYPE: DNA
<213> ORGANISM: Artificial Sequence
<220> FEATURE:
<223> OTHER INFORMATION: Synthetic

<400> SEQUENCE: 241
cagtcgggag aagggaggga gagaa                                          25

<210> SEQ ID NO 242
<211> LENGTH: 23
<212> TYPE: DNA
<213> ORGANISM: Artificial Sequence
<220> FEATURE:
<223> OTHER INFORMATION: Synthetic

<400> SEQUENCE: 242
caccacgtgc tgggcagaga ctt                                            23

<210> SEQ ID NO 243
<211> LENGTH: 25
<212> TYPE: DNA
<213> ORGANISM: Artificial Sequence
<220> FEATURE:
<223> OTHER INFORMATION: Synthetic

<400> SEQUENCE: 243
aggccagcag aagagcccga ttaaa                                          25

<210> SEQ ID NO 244
<211> LENGTH: 25
<212> TYPE: DNA
<213> ORGANISM: Artificial Sequence
<220> FEATURE:
<223> OTHER INFORMATION: Synthetic

<400> SEQUENCE: 244
gcgctgttgg aattgtaaag cttgc                                          25

<210> SEQ ID NO 245
<211> LENGTH: 25
<212> TYPE: DNA
<213> ORGANISM: Artificial Sequence
<220> FEATURE:
<223> OTHER INFORMATION: Synthetic

<400> SEQUENCE: 245
ccaggtagtc caaggtgccc tttcc                                          25

<210> SEQ ID NO 246
<211> LENGTH: 25
<212> TYPE: DNA
<213> ORGANISM: Artificial Sequence
<220> FEATURE:
<223> OTHER INFORMATION: Synthetic

<400> SEQUENCE: 246
cggtgacttc cccactggca ctaat                                          25

<210> SEQ ID NO 247
<211> LENGTH: 25
<212> TYPE: DNA
<213> ORGANISM: Artificial Sequence
<220> FEATURE:
<223> OTHER INFORMATION: Synthetic

<400> SEQUENCE: 247
```
gcggagaaag gcaggggtgt aaatc                                        25

<210> SEQ ID NO 248
<211> LENGTH: 25
<212> TYPE: DNA
<213> ORGANISM: Artificial Sequence
<220> FEATURE:
<223> OTHER INFORMATION: Synthetic

<400> SEQUENCE: 248
acactctgac tgtccctggc cccta                                        25

<210> SEQ ID NO 249
<211> LENGTH: 25
<212> TYPE: DNA
<213> ORGANISM: Artificial Sequence
<220> FEATURE:
<223> OTHER INFORMATION: Synthetic

<400> SEQUENCE: 249
tggaggtgat cttgagaagg ggtga                                        25

<210> SEQ ID NO 250
<211> LENGTH: 25
<212> TYPE: DNA
<213> ORGANISM: Artificial Sequence
<220> FEATURE:
<223> OTHER INFORMATION: Synthetic

<400> SEQUENCE: 250
tcagatgggg agaaccctga ggttg                                        25

<210> SEQ ID NO 251
<211> LENGTH: 25
<212> TYPE: DNA
<213> ORGANISM: Artificial Sequence
<220> FEATURE:
<223> OTHER INFORMATION: Synthetic

<400> SEQUENCE: 251
gccagctctc agccatcaca gtctt                                        25

<210> SEQ ID NO 252
<211> LENGTH: 25
<212> TYPE: DNA
<213> ORGANISM: Artificial Sequence
<220> FEATURE:
<223> OTHER INFORMATION: Synthetic

<400> SEQUENCE: 252
cctctaaccc tcatggacgc agacc                                        25

<210> SEQ ID NO 253
<211> LENGTH: 25
<212> TYPE: DNA
<213> ORGANISM: Artificial Sequence
<220> FEATURE:
<223> OTHER INFORMATION: Synthetic

<400> SEQUENCE: 253
gactgagtct ggacggcaga gtgga                                        25

<210> SEQ ID NO 254
<211> LENGTH: 23
<212> TYPE: DNA

```
<213> ORGANISM: Artificial Sequence
<220> FEATURE:
<223> OTHER INFORMATION: Synthetic

<400> SEQUENCE: 254 gccctcttc tggagccttg gtg                                              23

<210> SEQ ID NO 255
<211> LENGTH: 25
<212> TYPE: DNA
<213> ORGANISM: Artificial Sequence
<220> FEATURE:
<223> OTHER INFORMATION: Synthetic

<400> SEQUENCE: 255
acggctgttt tcctcttggg gagtc                                           25

<210> SEQ ID NO 256
<211> LENGTH: 25
<212> TYPE: DNA
<213> ORGANISM: Artificial Sequence
<220> FEATURE:
<223> OTHER INFORMATION: Synthetic

<400> SEQUENCE: 256
gcaaaggctc cggtttaagc tctgg                                           25

<210> SEQ ID NO 257
<211> LENGTH: 24
<212> TYPE: DNA
<213> ORGANISM: Artificial Sequence
<220> FEATURE:
<223> OTHER INFORMATION: Synthetic

<400> SEQUENCE: 257
cttctcgtcc tcgtccagca gctt                                            24

<210> SEQ ID NO 258
<211> LENGTH: 24
<212> TYPE: DNA
<213> ORGANISM: Artificial Sequence
<220> FEATURE:
<223> OTHER INFORMATION: Synthetic

<400> SEQUENCE: 258
cccaagcacc tgctggaatg actc                                            24

<210> SEQ ID NO 259
<211> LENGTH: 26
<212> TYPE: DNA
<213> ORGANISM: Artificial Sequence
<220> FEATURE:
<223> OTHER INFORMATION: Synthetic

<400> SEQUENCE: 259
tggcaagttt tagcttcagt cgtcca                                          26

<210> SEQ ID NO 260
<211> LENGTH: 25
<212> TYPE: DNA
<213> ORGANISM: Artificial Sequence
<220> FEATURE:
<223> OTHER INFORMATION: Synthetic

<400> SEQUENCE: 260
gacctgcgct ggagctgctc ttatc                                           25
```

```
<210> SEQ ID NO 261
<211> LENGTH: 25
<212> TYPE: DNA
<213> ORGANISM: Artificial Sequence
<220> FEATURE:
<223> OTHER INFORMATION: Synthetic

<400> SEQUENCE: 261
aaagaaggca caggagccag acagc                                              25

<210> SEQ ID NO 262
<211> LENGTH: 26
<212> TYPE: DNA
<213> ORGANISM: Artificial Sequence
<220> FEATURE:
<223> OTHER INFORMATION: Synthetic

<400> SEQUENCE: 262
tcttaatctc ctgccttccc cagtga                                             26

<210> SEQ ID NO 263
<211> LENGTH: 25
<212> TYPE: DNA
<213> ORGANISM: Artificial Sequence
<220> FEATURE:
<223> OTHER INFORMATION: Synthetic

<400> SEQUENCE: 263
ggggtgcagg ttggaggttt tatga                                              25

<210> SEQ ID NO 264
<211> LENGTH: 25
<212> TYPE: DNA
<213> ORGANISM: Artificial Sequence
<220> FEATURE:
<223> OTHER INFORMATION: Synthetic

<400> SEQUENCE: 264
gctcaggtac cagacagctg ggttc                                              25

<210> SEQ ID NO 265
<211> LENGTH: 25
<212> TYPE: DNA
<213> ORGANISM: Artificial Sequence
<220> FEATURE:
<223> OTHER INFORMATION: Synthetic

<400> SEQUENCE: 265
cactgaaccc gaaccoctga ttttc                                              25

<210> SEQ ID NO 266
<211> LENGTH: 25
<212> TYPE: DNA
<213> ORGANISM: Artificial Sequence
<220> FEATURE:
<223> OTHER INFORMATION: Synthetic

<400> SEQUENCE: 266
attgatgagc agcttcggca gattg                                              25

<210> SEQ ID NO 267
<211> LENGTH: 25
<212> TYPE: DNA
<213> ORGANISM: Artificial Sequence
<220> FEATURE:
```

<223> OTHER INFORMATION: Synthetic

<400> SEQUENCE: 267
agctcggttg ggctcctctc tcttc 25

<210> SEQ ID NO 268
<211> LENGTH: 25
<212> TYPE: DNA
<213> ORGANISM: Artificial Sequence
<220> FEATURE:
<223> OTHER INFORMATION: Synthetic

<400> SEQUENCE: 268
gattgtcctc tgagggctgg gattg 25

<210> SEQ ID NO 269
<211> LENGTH: 25
<212> TYPE: DNA
<213> ORGANISM: Artificial Sequence
<220> FEATURE:
<223> OTHER INFORMATION: Synthetic

<400> SEQUENCE: 269
ccaagcgaag ctgctctacc tcctg 25

<210> SEQ ID NO 270
<211> LENGTH: 26
<212> TYPE: DNA
<213> ORGANISM: Artificial Sequence
<220> FEATURE:
<223> OTHER INFORMATION: Synthetic

<400> SEQUENCE: 270 tcttcctttasd gactcccgag gcttgc 26

<210> SEQ ID NO 271
<211> LENGTH: 25
<212> TYPE: DNA
<213> ORGANISM: Artificial Sequence
<220> FEATURE:
<223> OTHER INFORMATION: Synthetic

<400> SEQUENCE: 271
atggaaggca aatcgcctga aactg 25

<210> SEQ ID NO 272
<211> LENGTH: 25
<212> TYPE: DNA
<213> ORGANISM: Artificial Sequence
<220> FEATURE:
<223> OTHER INFORMATION: Synthetic

<400> SEQUENCE: 272
cggaggtagg cccttctctc tcgac 25

<210> SEQ ID NO 273
<211> LENGTH: 25
<212> TYPE: DNA
<213> ORGANISM: Artificial Sequence
<220> FEATURE:
<223> OTHER INFORMATION: Synthetic

<400> SEQUENCE: 273
aaccccaggc cctgctccat agtag 25

<210> SEQ ID NO 274
<211> LENGTH: 25
<212> TYPE: DNA
<213> ORGANISM: Artificial Sequence
<220> FEATURE:
<223> OTHER INFORMATION: Synthetic

<400> SEQUENCE: 274
atgcatggct ttggcctcct tagtg                                    25

<210> SEQ ID NO 275
<211> LENGTH: 27
<212> TYPE: DNA
<213> ORGANISM: Artificial Sequence
<220> FEATURE:
<223> OTHER INFORMATION: Synthetic

<400> SEQUENCE: 275
tgaagtacag gcagaaacca cccaaga                                  27

<210> SEQ ID NO 276
<211> LENGTH: 25
<212> TYPE: DNA
<213> ORGANISM: Artificial Sequence
<220> FEATURE:
<223> OTHER INFORMATION: Synthetic

<400> SEQUENCE: 276
tcaggccatt attgtccctg gcttg                                    25

<210> SEQ ID NO 277
<211> LENGTH: 25
<212> TYPE: DNA
<213> ORGANISM: Artificial Sequence
<220> FEATURE:
<223> OTHER INFORMATION: Synthetic

<400> SEQUENCE: 277
ctgggcaaag ggggaggtga aataa                                    25

<210> SEQ ID NO 278
<211> LENGTH: 22
<212> TYPE: DNA
<213> ORGANISM: Artificial Sequence
<220> FEATURE:
<223> OTHER INFORMATION: Synthetic

<400> SEQUENCE: 278
ggcccgcact cagactgctg ct                                       22

<210> SEQ ID NO 279
<211> LENGTH: 25
<212> TYPE: DNA
<213> ORGANISM: Artificial Sequence
<220> FEATURE:
<223> OTHER INFORMATION: Synthetic

<400> SEQUENCE: 279
cccaacacca catcaggaca tgtaa                                    25

<210> SEQ ID NO 280
<211> LENGTH: 26
<212> TYPE: DNA
<213> ORGANISM: Artificial Sequence
<220> FEATURE:
<223> OTHER INFORMATION: Synthetic

<400> SEQUENCE: 280
gccgaattcg aaaaactctc ggatca                                              26

<210> SEQ ID NO 281
<211> LENGTH: 27
<212> TYPE: DNA
<213> ORGANISM: Artificial Sequence
<220> FEATURE:
<223> OTHER INFORMATION: Synthetic

<400> SEQUENCE: 281 cccctccat ataccttgc ttcttca                                               27

<210> SEQ ID NO 282
<211> LENGTH: 25
<212> TYPE: DNA
<213> ORGANISM: Artificial Sequence
<220> FEATURE:
<223> OTHER INFORMATION: Synthetic

<400> SEQUENCE: 282
ccggaatccc agctccactt accag                                               25

<210> SEQ ID NO 283
<211> LENGTH: 25
<212> TYPE: DNA
<213> ORGANISM: Artificial Sequence
<220> FEATURE:
<223> OTHER INFORMATION: Synthetic

<400> SEQUENCE: 283
cttctggaag cctgtgggga gacct                                               25

<210> SEQ ID NO 284
<211> LENGTH: 25
<212> TYPE: DNA
<213> ORGANISM: Artificial Sequence
<220> FEATURE:
<223> OTHER INFORMATION: Synthetic

<400> SEQUENCE: 284
atgcaaatgc ccccaagagg taaca                                               25

<210> SEQ ID NO 285
<211> LENGTH: 26
<212> TYPE: DNA
<213> ORGANISM: Artificial Sequence
<220> FEATURE:
<223> OTHER INFORMATION: Synthetic

<400> SEQUENCE: 285
cacataagga ggtgagttcc gacgtg                                              26

<210> SEQ ID NO 286
<211> LENGTH: 25
<212> TYPE: DNA
<213> ORGANISM: Artificial Sequence
<220> FEATURE:
<223> OTHER INFORMATION: Synthetic

<400> SEQUENCE: 286
aactgcgatg aaaagggtg ctgtc                                                25

<210> SEQ ID NO 287
<211> LENGTH: 25

<212> TYPE: DNA
<213> ORGANISM: Artificial Sequence
<220> FEATURE:
<223> OTHER INFORMATION: Synthetic

<400> SEQUENCE: 287
gcgggcccaa cctctccata tttac                                              25

<210> SEQ ID NO 288
<211> LENGTH: 22
<212> TYPE: DNA
<213> ORGANISM: Artificial Sequence
<220> FEATURE:
<223> OTHER INFORMATION: Synthetic

<400> SEQUENCE: 288 aggcccccgag agggagtgtg ag                                                22

<210> SEQ ID NO 289
<211> LENGTH: 25
<212> TYPE: DNA
<213> ORGANISM: Artificial Sequence
<220> FEATURE:
<223> OTHER INFORMATION: Synthetic

<400> SEQUENCE: 289
cttttgggtg tgtggagggc ttcag                                              25

<210> SEQ ID NO 290
<211> LENGTH: 25
<212> TYPE: DNA
<213> ORGANISM: Artificial Sequence
<220> FEATURE:
<223> OTHER INFORMATION: Synthetic

<400> SEQUENCE: 290
atcccagggg ctggagtttg agttc                                              25

<210> SEQ ID NO 291
<211> LENGTH: 25
<212> TYPE: DNA
<213> ORGANISM: Artificial Sequence
<220> FEATURE:
<223> OTHER INFORMATION: Synthetic

<400> SEQUENCE: 291
ggttcttcac ggcggaagtt gtctg                                              25

<210> SEQ ID NO 292
<211> LENGTH: 25
<212> TYPE: DNA
<213> ORGANISM: Artificial Sequence
<220> FEATURE:
<223> OTHER INFORMATION: Synthetic

<400> SEQUENCE: 292
tcctggtcct agggcacagt gaagc                                              25

<210> SEQ ID NO 293
<211> LENGTH: 26
<212> TYPE: DNA
<213> ORGANISM: Artificial Sequence
<220> FEATURE:
<223> OTHER INFORMATION: Synthetic

<400> SEQUENCE: 293
tctgagatgg aaggattggg agtcca                                              26

<210> SEQ ID NO 294
<211> LENGTH: 25
<212> TYPE: DNA
<213> ORGANISM: Artificial Sequence
<220> FEATURE:
<223> OTHER INFORMATION: Synthetic

<400> SEQUENCE: 294
tgagggactg cacacagagg gaaga                                               25

<210> SEQ ID NO 295
<211> LENGTH: 25
<212> TYPE: DNA
<213> ORGANISM: Artificial Sequence
<220> FEATURE:
<223> OTHER INFORMATION: Synthetic

<400> SEQUENCE: 295
ggctctgtga tcagtcccag tgcag                                               25

<210> SEQ ID NO 296
<211> LENGTH: 25
<212> TYPE: DNA
<213> ORGANISM: Artificial Sequence
<220> FEATURE:
<223> OTHER INFORMATION: Synthetic

<400> SEQUENCE: 296
gcatccagcc ttctaactgc agagc                                               25

<210> SEQ ID NO 297
<211> LENGTH: 25
<212> TYPE: DNA
<213> ORGANISM: Artificial Sequence
<220> FEATURE:
<223> OTHER INFORMATION: Synthetic

<400> SEQUENCE: 297
tgggaagaaa ctgcggaatg aaaca                                               25

<210> SEQ ID NO 298
<211> LENGTH: 25
<212> TYPE: DNA
<213> ORGANISM: Artificial Sequence
<220> FEATURE:
<223> OTHER INFORMATION: Synthetic

<400> SEQUENCE: 298
aggagtggag ctttggggaa ccttg                                               25

<210> SEQ ID NO 299
<211> LENGTH: 25
<212> TYPE: DNA
<213> ORGANISM: Artificial Sequence
<220> FEATURE:
<223> OTHER INFORMATION: Synthetic

<400> SEQUENCE: 299
agtgagctgc tccggcaaaa agaaa                                               25

<210> SEQ ID NO 300
<211> LENGTH: 27
<212> TYPE: DNA
<213> ORGANISM: Artificial Sequence

```
<220> FEATURE:
<223> OTHER INFORMATION: Synthetic

<400> SEQUENCE: 300
gcaaaagctt tcttccttcc acccttc                                          27

<210> SEQ ID NO 301
<211> LENGTH: 26
<212> TYPE: DNA
<213> ORGANISM: Artificial Sequence
<220> FEATURE:
<223> OTHER INFORMATION: Synthetic

<400> SEQUENCE: 301
gggagacagg tctgaagcct ggagaa                                           26

<210> SEQ ID NO 302
<211> LENGTH: 25
<212> TYPE: DNA
<213> ORGANISM: Artificial Sequence
<220> FEATURE:
<223> OTHER INFORMATION: Synthetic

<400> SEQUENCE: 302
ttgggtgctg aactctgacc aggaa                                            25

<210> SEQ ID NO 303
<211> LENGTH: 25
<212> TYPE: DNA
<213> ORGANISM: Artificial Sequence
<220> FEATURE:
<223> OTHER INFORMATION: Synthetic

<400> SEQUENCE: 303
aaaaatgcgg actctgaact gatgc                                            25

<210> SEQ ID NO 304
<211> LENGTH: 28
<212> TYPE: DNA
<213> ORGANISM: Artificial Sequence
<220> FEATURE:
<223> OTHER INFORMATION: Synthetic

<400> SEQUENCE: 304
tgctgccaca agaaattcac tacttttt                                         28

<210> SEQ ID NO 305
<211> LENGTH: 22
<212> TYPE: DNA
<213> ORGANISM: Artificial Sequence
<220> FEATURE:
<223> OTHER INFORMATION: Synthetic

<400> SEQUENCE: 305
gtgcgcgagg tgagggaggt gt                                               22

<210> SEQ ID NO 306
<211> LENGTH: 25
<212> TYPE: DNA
<213> ORGANISM: Artificial Sequence
<220> FEATURE:
<223> OTHER INFORMATION: Synthetic

<400> SEQUENCE: 306
gctgtgggga agagttggga gacag                                            25
```

<210> SEQ ID NO 307
<211> LENGTH: 22
<212> TYPE: DNA
<213> ORGANISM: Artificial Sequence
<220> FEATURE:
<223> OTHER INFORMATION: Synthetic

<400> SEQUENCE: 307
cgggcacagc aggaagcagg tc                                         22

<210> SEQ ID NO 308
<211> LENGTH: 25
<212> TYPE: DNA
<213> ORGANISM: Artificial Sequence
<220> FEATURE:
<223> OTHER INFORMATION: Synthetic

<400> SEQUENCE: 308
gaagtgggat ccgcatgtag gcaag                                      25

<210> SEQ ID NO 309
<211> LENGTH: 25
<212> TYPE: DNA
<213> ORGANISM: Artificial Sequence
<220> FEATURE:
<223> OTHER INFORMATION: Synthetic

<400> SEQUENCE: 309
ccagcctccc tcacacttct ctgct                                      25

<210> SEQ ID NO 310
<211> LENGTH: 25
<212> TYPE: DNA
<213> ORGANISM: Artificial Sequence
<220> FEATURE:
<223> OTHER INFORMATION: Synthetic

<400> SEQUENCE: 310
cctggaacct atggggagga gggta                                      25

<210> SEQ ID NO 311
<211> LENGTH: 25
<212> TYPE: DNA
<213> ORGANISM: Artificial Sequence
<220> FEATURE:
<223> OTHER INFORMATION: Synthetic

<400> SEQUENCE: 311
actggtctgg accaccctcc acaca                                      25

<210> SEQ ID NO 312
<211> LENGTH: 25
<212> TYPE: DNA
<213> ORGANISM: Artificial Sequence
<220> FEATURE:
<223> OTHER INFORMATION: Synthetic

<400> SEQUENCE: 312
gaagacccag agaggggctg agaca                                      25

<210> SEQ ID NO 313
<211> LENGTH: 25
<212> TYPE: DNA
<213> ORGANISM: Artificial Sequence
<220> FEATURE:
<223> OTHER INFORMATION: Synthetic

```
<400> SEQUENCE: 313
tgccccaaac ctccttctca cttgt                                              25

<210> SEQ ID NO 314
<211> LENGTH: 22
<212> TYPE: DNA
<213> ORGANISM: Artificial Sequence
<220> FEATURE:
<223> OTHER INFORMATION: Synthetic

<400> SEQUENCE: 314
ctgccacgcc cagcaagagc ag                                                 22

<210> SEQ ID NO 315
<211> LENGTH: 25
<212> TYPE: DNA
<213> ORGANISM: Artificial Sequence
<220> FEATURE:
<223> OTHER INFORMATION: Synthetic

<400> SEQUENCE: 315
accctccctc cctcttcagt tttgg                                              25

<210> SEQ ID NO 316
<211> LENGTH: 23
<212> TYPE: DNA
<213> ORGANISM: Artificial Sequence
<220> FEATURE:
<223> OTHER INFORMATION: Synthetic

<400> SEQUENCE: 316
gccaaccaaa aggtgggctg ttc                                                23

<210> SEQ ID NO 317
<211> LENGTH: 24
<212> TYPE: DNA
<213> ORGANISM: Artificial Sequence
<220> FEATURE:
<223> OTHER INFORMATION: Synthetic

<400> SEQUENCE: 317
ccccttctgc ccccactatg agaa                                               24

<210> SEQ ID NO 318
<211> LENGTH: 25
<212> TYPE: DNA
<213> ORGANISM: Artificial Sequence
<220> FEATURE:
<223> OTHER INFORMATION: Synthetic

<400> SEQUENCE: 318
tgaaaggaag ttcttcccgc ccttc                                              25

<210> SEQ ID NO 319
<211> LENGTH: 25
<212> TYPE: DNA
<213> ORGANISM: Artificial Sequence
<220> FEATURE:
<223> OTHER INFORMATION: Synthetic

<400> SEQUENCE: 319
aaccactccc ctcagtctgc caaaa                                              25

<210> SEQ ID NO 320
```

```
<211> LENGTH: 25
<212> TYPE: DNA
<213> ORGANISM: Artificial Sequence
<220> FEATURE:
<223> OTHER INFORMATION: Synthetic

<400> SEQUENCE: 320
ccgccaccat ggcaatatca acttc                                          25

<210> SEQ ID NO 321
<211> LENGTH: 26
<212> TYPE: DNA
<213> ORGANISM: Artificial Sequence
<220> FEATURE:
<223> OTHER INFORMATION: Synthetic

<400> SEQUENCE: 321
tggacttgaa ttgggacaaa ggcttg                                         26

<210> SEQ ID NO 322
<211> LENGTH: 25
<212> TYPE: DNA
<213> ORGANISM: Artificial Sequence
<220> FEATURE:
<223> OTHER INFORMATION: Synthetic

<400> SEQUENCE: 322
ttccctcttg tctctccacc tgtgc                                          25

<210> SEQ ID NO 323
<211> LENGTH: 25
<212> TYPE: DNA
<213> ORGANISM: Artificial Sequence
<220> FEATURE:
<223> OTHER INFORMATION: Synthetic

<400> SEQUENCE: 323
gaagggatgt ggctgatcag aagga                                          25

<210> SEQ ID NO 324
<211> LENGTH: 25
<212> TYPE: DNA
<213> ORGANISM: Artificial Sequence
<220> FEATURE:
<223> OTHER INFORMATION: Synthetic

<400> SEQUENCE: 324
tcctgtgcct gtagtcgttt tgctg                                          25

<210> SEQ ID NO 325
<211> LENGTH: 25
<212> TYPE: DNA
<213> ORGANISM: Artificial Sequence
<220> FEATURE:
<223> OTHER INFORMATION: Synthetic

<400> SEQUENCE: 325
agtgggaatt tctgatgcgg aatgg                                          25

<210> SEQ ID NO 326
<211> LENGTH: 25
<212> TYPE: DNA
<213> ORGANISM: Artificial Sequence
<220> FEATURE:
<223> OTHER INFORMATION: Synthetic

<400> SEQUENCE: 326
```
gggaaaggga gccagaggct aaggt                                              25

<210> SEQ ID NO 327
<211> LENGTH: 24
<212> TYPE: DNA
<213> ORGANISM: Artificial Sequence
<220> FEATURE:
<223> OTHER INFORMATION: Synthetic

<400> SEQUENCE: 327
gtggctgcct cctccctcat caat                                               24

<210> SEQ ID NO 328
<211> LENGTH: 25
<212> TYPE: DNA
<213> ORGANISM: Artificial Sequence
<220> FEATURE:
<223> OTHER INFORMATION: Synthetic

<400> SEQUENCE: 328
tgctcaatcc gattaaacgc tgctg                                              25

<210> SEQ ID NO 329
<211> LENGTH: 25
<212> TYPE: DNA
<213> ORGANISM: Artificial Sequence
<220> FEATURE:
<223> OTHER INFORMATION: Synthetic

<400> SEQUENCE: 329
ccagctcacc ccaaatctgc tgttc                                              25

<210> SEQ ID NO 330
<211> LENGTH: 25
<212> TYPE: DNA
<213> ORGANISM: Artificial Sequence
<220> FEATURE:
<223> OTHER INFORMATION: Synthetic

<400> SEQUENCE: 330
tggcagtccc tggtactcct gaaga                                              25

<210> SEQ ID NO 331
<211> LENGTH: 25
<212> TYPE: DNA
<213> ORGANISM: Artificial Sequence
<220> FEATURE:
<223> OTHER INFORMATION: Synthetic

<400> SEQUENCE: 331
tgcaaccctg gctgtttctc tagcc                                              25

<210> SEQ ID NO 332
<211> LENGTH: 25
<212> TYPE: DNA
<213> ORGANISM: Artificial Sequence
<220> FEATURE:
<223> OTHER INFORMATION: Synthetic

<400> SEQUENCE: 332
gggaagacgg gaactggagt tttgg                                              25

<210> SEQ ID NO 333
<211> LENGTH: 25
<212> TYPE: DNA

```
<213> ORGANISM: Artificial Sequence
<220> FEATURE:
<223> OTHER INFORMATION: Synthetic

<400> SEQUENCE: 333
atttttagcc cagtgccccg aagac                                             25

<210> SEQ ID NO 334
<211> LENGTH: 25
<212> TYPE: DNA
<213> ORGANISM: Artificial Sequence
<220> FEATURE:
<223> OTHER INFORMATION: Synthetic

<400> SEQUENCE: 334
gtgctctcag ggagatccca gcaat                                             25

<210> SEQ ID NO 335
<211> LENGTH: 25
<212> TYPE: DNA
<213> ORGANISM: Artificial Sequence
<220> FEATURE:
<223> OTHER INFORMATION: Synthetic

<400> SEQUENCE: 335
caaggaggag cctggtgggt acttg                                             25

<210> SEQ ID NO 336
<211> LENGTH: 25
<212> TYPE: DNA
<213> ORGANISM: Artificial Sequence
<220> FEATURE:
<223> OTHER INFORMATION: Synthetic

<400> SEQUENCE: 336
ggagctggga gaggcagaaa tcctt                                             25

<210> SEQ ID NO 337
<211> LENGTH: 25
<212> TYPE: DNA
<213> ORGANISM: Artificial Sequence
<220> FEATURE:
<223> OTHER INFORMATION: Synthetic

<400> SEQUENCE: 337
gccatggaaa cgtcacagtt catcc                                             25

<210> SEQ ID NO 338
<211> LENGTH: 25
<212> TYPE: DNA
<213> ORGANISM: Artificial Sequence
<220> FEATURE:
<223> OTHER INFORMATION: Synthetic

<400> SEQUENCE: 338
ctgcgtgggg gaaggacaca ttgta                                             25

<210> SEQ ID NO 339
<211> LENGTH: 25
<212> TYPE: DNA
<213> ORGANISM: Artificial Sequence
<220> FEATURE:
<223> OTHER INFORMATION: Synthetic

<400> SEQUENCE: 339
tccacctcca agcccagatt cagat                                             25
```

<210> SEQ ID NO 340
<211> LENGTH: 24
<212> TYPE: DNA
<213> ORGANISM: Artificial Sequence
<220> FEATURE:
<223> OTHER INFORMATION: Synthetic

<400> SEQUENCE: 340
actttgccca agacccctg tgtg                                            24

<210> SEQ ID NO 341
<211> LENGTH: 25
<212> TYPE: DNA
<213> ORGANISM: Artificial Sequence
<220> FEATURE:
<223> OTHER INFORMATION: Synthetic

<400> SEQUENCE: 341
attccaacca gcctcttccg ctgac                                          25

<210> SEQ ID NO 342
<211> LENGTH: 25
<212> TYPE: DNA
<213> ORGANISM: Artificial Sequence
<220> FEATURE:
<223> OTHER INFORMATION: Synthetic

<400> SEQUENCE: 342
agacggtgaa ggtggggacc aattt                                          25

<210> SEQ ID NO 343
<211> LENGTH: 25
<212> TYPE: DNA
<213> ORGANISM: Artificial Sequence
<220> FEATURE:
<223> OTHER INFORMATION: Synthetic

<400> SEQUENCE: 343
ttctcctcca ccatgttagg cttgg                                          25

<210> SEQ ID NO 344
<211> LENGTH: 25
<212> TYPE: DNA
<213> ORGANISM: Artificial Sequence
<220> FEATURE:
<223> OTHER INFORMATION: Synthetic

<400> SEQUENCE: 344
cagggcgcaa tcttcctact ccaaa                                          25

<210> SEQ ID NO 345
<211> LENGTH: 25
<212> TYPE: DNA
<213> ORGANISM: Artificial Sequence
<220> FEATURE:
<223> OTHER INFORMATION: Synthetic

<400> SEQUENCE: 345
caacagggcc caattctgag agagg                                          25

<210> SEQ ID NO 346
<211> LENGTH: 27
<212> TYPE: DNA
<213> ORGANISM: Artificial Sequence
<220> FEATURE:

<223> OTHER INFORMATION: Synthetic

<400> SEQUENCE: 346
gggacttttt cttctagcct gcctcca                                           27

<210> SEQ ID NO 347
<211> LENGTH: 25
<212> TYPE: DNA
<213> ORGANISM: Artificial Sequence
<220> FEATURE:
<223> OTHER INFORMATION: Synthetic

<400> SEQUENCE: 347
ggcagaaaat gctaacctgc ccaga                                             25

<210> SEQ ID NO 348
<211> LENGTH: 27
<212> TYPE: DNA
<213> ORGANISM: Artificial Sequence
<220> FEATURE:
<223> OTHER INFORMATION: Synthetic

<400> SEQUENCE: 348 cccattttttg ccttacttcc ctcatca                                          27

<210> SEQ ID NO 349
<211> LENGTH: 25
<212> TYPE: DNA
<213> ORGANISM: Artificial Sequence
<220> FEATURE:
<223> OTHER INFORMATION: Synthetic

<400> SEQUENCE: 349
ggcctctgat tttgcttccc acctt                                             25

<210> SEQ ID NO 350
<211> LENGTH: 25
<212> TYPE: DNA
<213> ORGANISM: Artificial Sequence
<220> FEATURE:
<223> OTHER INFORMATION: Synthetic

<400> SEQUENCE: 350
cctgcttgag tcccaggtcc aaaga                                             25

<210> SEQ ID NO 351
<211> LENGTH: 25
<212> TYPE: DNA
<213> ORGANISM: Artificial Sequence
<220> FEATURE:
<223> OTHER INFORMATION: Synthetic

<400> SEQUENCE: 351
caggggtgga accctagcca agact                                             25

<210> SEQ ID NO 352
<211> LENGTH: 25
<212> TYPE: DNA
<213> ORGANISM: Artificial Sequence
<220> FEATURE:
<223> OTHER INFORMATION: Synthetic

<400> SEQUENCE: 352
gttccctggg ctggaaacct tccta                                             25

```
<210> SEQ ID NO 353
<211> LENGTH: 25
<212> TYPE: DNA
<213> ORGANISM: Artificial Sequence
<220> FEATURE:
<223> OTHER INFORMATION: Synthetic

<400> SEQUENCE: 353
acagaggcaa ggacagggac tgagc                                      25

<210> SEQ ID NO 354
<211> LENGTH: 25
<212> TYPE: DNA
<213> ORGANISM: Artificial Sequence
<220> FEATURE:
<223> OTHER INFORMATION: Synthetic

<400> SEQUENCE: 354
tggccatctg ctccatcaga aagtg                                      25

<210> SEQ ID NO 355
<211> LENGTH: 23
<212> TYPE: DNA
<213> ORGANISM: Artificial Sequence
<220> FEATURE:
<223> OTHER INFORMATION: Synthetic

<400> SEQUENCE: 355
aaggggctcc tgcttgcacc ttc                                        23

<210> SEQ ID NO 356
<211> LENGTH: 25
<212> TYPE: DNA
<213> ORGANISM: Artificial Sequence
<220> FEATURE:
<223> OTHER INFORMATION: Synthetic

<400> SEQUENCE: 356
ggaacaaagg ctggagactg ggtca                                      25

<210> SEQ ID NO 357
<211> LENGTH: 25
<212> TYPE: DNA
<213> ORGANISM: Artificial Sequence
<220> FEATURE:
<223> OTHER INFORMATION: Synthetic

<400> SEQUENCE: 357
tgagctcctc aacccgactc tcctc                                      25

<210> SEQ ID NO 358
<211> LENGTH: 25
<212> TYPE: DNA
<213> ORGANISM: Artificial Sequence
<220> FEATURE:
<223> OTHER INFORMATION: Synthetic

<400> SEQUENCE: 358
catctgcatt ttcaccccac ccttc                                      25

<210> SEQ ID NO 359
<211> LENGTH: 27
<212> TYPE: DNA
<213> ORGANISM: Artificial Sequence
<220> FEATURE:
<223> OTHER INFORMATION: Synthetic
```

<400> SEQUENCE: 359
tcaggcaaag tcatagaacc attttca                                              27

<210> SEQ ID NO 360
<211> LENGTH: 25
<212> TYPE: DNA
<213> ORGANISM: Artificial Sequence
<220> FEATURE:
<223> OTHER INFORMATION: Synthetic

<400> SEQUENCE: 360
ttaacctgtg gcttctcctc cacct                                                25

<210> SEQ ID NO 361
<211> LENGTH: 25
<212> TYPE: DNA
<213> ORGANISM: Artificial Sequence
<220> FEATURE:
<223> OTHER INFORMATION: Synthetic

<400> SEQUENCE: 361
ggtttcttct ttggctgggg agagg                                                25

<210> SEQ ID NO 362
<211> LENGTH: 25
<212> TYPE: DNA
<213> ORGANISM: Artificial Sequence
<220> FEATURE:
<223> OTHER INFORMATION: Synthetic

<400> SEQUENCE: 362
tggcctcatc ttgggcctgt gttat                                                25

<210> SEQ ID NO 363
<211> LENGTH: 25
<212> TYPE: DNA
<213> ORGANISM: Artificial Sequence
<220> FEATURE:
<223> OTHER INFORMATION: Synthetic

<400> SEQUENCE: 363
accctgtcag ctgtggagct tttgg                                                25

<210> SEQ ID NO 364
<211> LENGTH: 25
<212> TYPE: DNA
<213> ORGANISM: Artificial Sequence
<220> FEATURE:
<223> OTHER INFORMATION: Synthetic

<400> SEQUENCE: 364
agatcccagc acaggagctc agcat                                                25

<210> SEQ ID NO 365
<211> LENGTH: 25
<212> TYPE: DNA
<213> ORGANISM: Artificial Sequence
<220> FEATURE:
<223> OTHER INFORMATION: Synthetic

<400> SEQUENCE: 365
cagagcggca tcatctcctg catag                                                25

<210> SEQ ID NO 366
<211> LENGTH: 25

```
<212> TYPE: DNA
<213> ORGANISM: Artificial Sequence
<220> FEATURE:
<223> OTHER INFORMATION: Synthetic

<400> SEQUENCE: 366
tccttctggg gcagaaaact caaca                                        25

<210> SEQ ID NO 367
<211> LENGTH: 24
<212> TYPE: DNA
<213> ORGANISM: Artificial Sequence
<220> FEATURE:
<223> OTHER INFORMATION: Synthetic

<400> SEQUENCE: 367 ctgcaccta gcctgcctct cctg                                          24

<210> SEQ ID NO 368
<211> LENGTH: 25
<212> TYPE: DNA
<213> ORGANISM: Artificial Sequence
<220> FEATURE:
<223> OTHER INFORMATION: Synthetic

<400> SEQUENCE: 368
aggagagtgc tcctgctccc ctcag                                        25

<210> SEQ ID NO 369
<211> LENGTH: 25
<212> TYPE: DNA
<213> ORGANISM: Artificial Sequence
<220> FEATURE:
<223> OTHER INFORMATION: Synthetic

<400> SEQUENCE: 369
gcatatgagt gaggtgggggg accag                                       25

<210> SEQ ID NO 370
<211> LENGTH: 25
<212> TYPE: DNA
<213> ORGANISM: Artificial Sequence
<220> FEATURE:
<223> OTHER INFORMATION: Synthetic

<400> SEQUENCE: 370
tcgtcccttc cctttgattg tgagg                                        25

<210> SEQ ID NO 371
<211> LENGTH: 25
<212> TYPE: DNA
<213> ORGANISM: Artificial Sequence
<220> FEATURE:
<223> OTHER INFORMATION: Synthetic

<400> SEQUENCE: 371
tgagcaggag ctgggtcaga ctgtt                                        25

<210> SEQ ID NO 372
<211> LENGTH: 27
<212> TYPE: DNA
<213> ORGANISM: Artificial Sequence
<220> FEATURE:
<223> OTHER INFORMATION: Synthetic

<400> SEQUENCE: 372
```

```
ccaagtgctg ttgttacctg ggggtta                                              27

<210> SEQ ID NO 373
<211> LENGTH: 23
<212> TYPE: DNA
<213> ORGANISM: Artificial Sequence
<220> FEATURE:
<223> OTHER INFORMATION: Synthetic

<400> SEQUENCE: 373
agggatgggc cctgagacct gtt                                                  23

<210> SEQ ID NO 374
<211> LENGTH: 25
<212> TYPE: DNA
<213> ORGANISM: Artificial Sequence
<220> FEATURE:
<223> OTHER INFORMATION: Synthetic

<400> SEQUENCE: 374
gcccagtgat tgtgcagttg gatct                                                25

<210> SEQ ID NO 375
<211> LENGTH: 29
<212> TYPE: DNA
<213> ORGANISM: Artificial Sequence
<220> FEATURE:
<223> OTHER INFORMATION: Synthetic

<400> SEQUENCE: 375
tgtctgtctc tgacatgtcc ctactcagc                                            29

<210> SEQ ID NO 376
<211> LENGTH: 25
<212> TYPE: DNA
<213> ORGANISM: Artificial Sequence
<220> FEATURE:
<223> OTHER INFORMATION: Synthetic

<400> SEQUENCE: 376
gttccctttc ctcagaccag ctcca                                                25

<210> SEQ ID NO 377
<211> LENGTH: 24
<212> TYPE: DNA
<213> ORGANISM: Artificial Sequence
<220> FEATURE:
<223> OTHER INFORMATION: Synthetic

<400> SEQUENCE: 377
ggatggcact caggtgggtg gtag                                                 24

<210> SEQ ID NO 378
<211> LENGTH: 25
<212> TYPE: DNA
<213> ORGANISM: Artificial Sequence
<220> FEATURE:
<223> OTHER INFORMATION: Synthetic

<400> SEQUENCE: 378
cccagaggtt tccttcccct caaaa                                                25

<210> SEQ ID NO 379
<211> LENGTH: 25
<212> TYPE: DNA
<213> ORGANISM: Artificial Sequence
```

<220> FEATURE:
<223> OTHER INFORMATION: Synthetic

<400> SEQUENCE: 379
gccagtaggt ggaggcatag cgaag                                          25

<210> SEQ ID NO 380
<211> LENGTH: 26
<212> TYPE: DNA
<213> ORGANISM: Artificial Sequence
<220> FEATURE:
<223> OTHER INFORMATION: Synthetic

<400> SEQUENCE: 380
gagggaggta gtgcaaaggt ggcatt                                         26

<210> SEQ ID NO 381
<211> LENGTH: 25
<212> TYPE: DNA
<213> ORGANISM: Artificial Sequence
<220> FEATURE:
<223> OTHER INFORMATION: Synthetic

<400> SEQUENCE: 381
ctggtcttgg gactccctct tcagc                                          25

<210> SEQ ID NO 382
<211> LENGTH: 25
<212> TYPE: DNA
<213> ORGANISM: Artificial Sequence
<220> FEATURE:
<223> OTHER INFORMATION: Synthetic

<400> SEQUENCE: 382
ggtggagctt taatgggaag cgtca                                          25

<210> SEQ ID NO 383
<211> LENGTH: 25
<212> TYPE: DNA
<213> ORGANISM: Artificial Sequence
<220> FEATURE:
<223> OTHER INFORMATION: Synthetic

<400> SEQUENCE: 383
cagcaaaaac cccgacagac agaca                                          25

<210> SEQ ID NO 384
<211> LENGTH: 25
<212> TYPE: DNA
<213> ORGANISM: Artificial Sequence
<220> FEATURE:
<223> OTHER INFORMATION: Synthetic

<400> SEQUENCE: 384
ggtaggggct atgggcttgg atacg                                          25

<210> SEQ ID NO 385
<211> LENGTH: 25
<212> TYPE: DNA
<213> ORGANISM: Artificial Sequence
<220> FEATURE:
<223> OTHER INFORMATION: Synthetic

<400> SEQUENCE: 385
tgagaccagt ttcctgcctc tgtgg                                          25

<210> SEQ ID NO 386
<211> LENGTH: 25
<212> TYPE: DNA
<213> ORGANISM: Artificial Sequence
<220> FEATURE:
<223> OTHER INFORMATION: Synthetic

<400> SEQUENCE: 386
ggctttagcc ccagggctcc ttagt                                              25

<210> SEQ ID NO 387
<211> LENGTH: 25
<212> TYPE: DNA
<213> ORGANISM: Artificial Sequence
<220> FEATURE:
<223> OTHER INFORMATION: Synthetic

<400> SEQUENCE: 387
ggtctggatg cccatcttcg acaac                                              25

<210> SEQ ID NO 388
<211> LENGTH: 25
<212> TYPE: DNA
<213> ORGANISM: Artificial Sequence
<220> FEATURE:
<223> OTHER INFORMATION: Synthetic

<400> SEQUENCE: 388
gaacagggtc ccaaggacaa cgaac                                              25

<210> SEQ ID NO 389
<211> LENGTH: 25
<212> TYPE: DNA
<213> ORGANISM: Artificial Sequence
<220> FEATURE:
<223> OTHER INFORMATION: Synthetic

<400> SEQUENCE: 389
ttctttgctc ctagaggccc catca                                              25

<210> SEQ ID NO 390
<211> LENGTH: 25
<212> TYPE: DNA
<213> ORGANISM: Artificial Sequence
<220> FEATURE:
<223> OTHER INFORMATION: Synthetic

<400> SEQUENCE: 390
gatgagggga tggtctgtcc ctgtc                                              25

<210> SEQ ID NO 391
<211> LENGTH: 25
<212> TYPE: DNA
<213> ORGANISM: Artificial Sequence
<220> FEATURE:
<223> OTHER INFORMATION: Synthetic

<400> SEQUENCE: 391
tccagggagg cagacttgag acagg                                              25

<210> SEQ ID NO 392
<211> LENGTH: 26
<212> TYPE: DNA
<213> ORGANISM: Artificial Sequence
<220> FEATURE:
<223> OTHER INFORMATION: Synthetic

<400> SEQUENCE: 392
caaaaatacc tttggggtgg gtgagg                                          26

<210> SEQ ID NO 393
<211> LENGTH: 23
<212> TYPE: DNA
<213> ORGANISM: Artificial Sequence
<220> FEATURE:
<223> OTHER INFORMATION: Synthetic

<400> SEQUENCE: 393
gtgcgggtgg tgagctaggg aag                                             23

<210> SEQ ID NO 394
<211> LENGTH: 25
<212> TYPE: DNA
<213> ORGANISM: Artificial Sequence
<220> FEATURE:
<223> OTHER INFORMATION: Synthetic

<400> SEQUENCE: 394
actctcaggg gatatgcagg cagga                                           25

<210> SEQ ID NO 395
<211> LENGTH: 190
<212> TYPE: DNA
<213> ORGANISM: Artificial Sequence
<220> FEATURE:
<223> OTHER INFORMATION: Synthetic

<400> SEQUENCE: 395
tatacgcagt gctaccatcg atcacttgca gtgggaattt ctgatgcgga atggttgaca     60
tcatatctgg aattttaatt agaatgaaaa atggcccttc ctaaggggct atatgggcca    120
ccgtggacat ggggcttggg agagttttga gacctgggag aaatggactt cgaaagacgc    180
tccacgatat                                                          190

<210> SEQ ID NO 396
<211> LENGTH: 190
<212> TYPE: DNA
<213> ORGANISM: Artificial Sequence
<220> FEATURE:
<223> OTHER INFORMATION: Synthetic

<400> SEQUENCE: 396
tatacgcagt gctaccatcg atcacaagga aagggacac agaatgaatg ggaatgacaa      60
ctgggcagcc agagagctac ttgaaaggta gcagggaaag tggagttctg aagggagttc    120 tgagggggacc aggccccagg taccccaatt cccacaggga atcgagactt cgaaagacgc   180
tccacgatat                                                          190

<210> SEQ ID NO 397
<211> LENGTH: 190
<212> TYPE: DNA
<213> ORGANISM: Artificial Sequence
<220> FEATURE:
<223> OTHER INFORMATION: Synthetic

<400> SEQUENCE: 397
tatacgcagt gctaccatcg atcacagaag gatgagtcag gctgtagagt aatctactct     60
ggttctcacg ggaccagccc agggcacagc cggcagggag gctgctggca tagaggccct    120

| | |
|---|---|
| gtctcccctg gcctctgtct ctgatgaatg atccggacag caggcgactt cgaaagacgc | 180 |
| tccacgatat | 190 |

<210> SEQ ID NO 398
<211> LENGTH: 190
<212> TYPE: DNA
<213> ORGANISM: Artificial Sequence
<220> FEATURE:
<223> OTHER INFORMATION: Synthetic

<400> SEQUENCE: 398

| | |
|---|---|
| tatacgcagt gctaccatcg atcacctctc cgtggagatg gctctgagaa atcaaatatt | 60 |
| gacaatgagg gaacagaact tattaaatct gggacaggga tgtgtgtggg gagctgtggg | 120 |
| aatggccgga tgcctgggtt cggagggtaa tgaaggttct gggaggactt cgaaagacgc | 180 |
| tccacgatat | 190 |

<210> SEQ ID NO 399
<211> LENGTH: 190
<212> TYPE: DNA
<213> ORGANISM: Artificial Sequence
<220> FEATURE:
<223> OTHER INFORMATION: Synthetic

<400> SEQUENCE: 399

| | |
|---|---|
| tatacgcagt gctaccatcg atcacgttta agaaaagaaa tggggtctgt gcaaagttcc | 60 |
| tttccccgag ggacccatga accttgcccc tgaggctccc caccccacgc ctccagcaaa | 120 |
| ttttcactcc tttgggactt ttccctaggg gttctggcca accacgactt cgaaagacgc | 180 |
| tccacgatat | 190 |

<210> SEQ ID NO 400
<211> LENGTH: 190
<212> TYPE: DNA
<213> ORGANISM: Artificial Sequence
<220> FEATURE:
<223> OTHER INFORMATION: Synthetic

<400> SEQUENCE: 400

| | |
|---|---|
| tatacgcagt gctaccatcg atcactcacc tctgtctgcc acccatggcc tatctggcta | 60 |
| gaggaacacc tccacgttcc atcttagctg tgctagctgt gcagctggtt ttggggtggg | 120 |
| cggtactcct ctccttccat tcctgctgtc agcaacagga gtctggactt cgaaagacgc | 180 |
| tccacgatat | 190 |

<210> SEQ ID NO 401
<211> LENGTH: 190
<212> TYPE: DNA
<213> ORGANISM: Artificial Sequence
<220> FEATURE:
<223> OTHER INFORMATION: Synthetic

<400> SEQUENCE: 401

| | |
|---|---|
| tatacgcagt gctaccatcg atcacgaggg aaagggttga cacttctggg aataaagata | 60 |
| cggtaggtgg gagggtgagg tcagcgctgg gatagggtgt ggttaatcca cttgctcttc | 120 |
| aggagtacca gggactgcca ctcctggtag tgccaggctg gcatagactt cgaaagacgc | 180 |
| tccacgatat | 190 |

<210> SEQ ID NO 402
<211> LENGTH: 190

```
<212> TYPE: DNA
<213> ORGANISM: Artificial Sequence
<220> FEATURE:
<223> OTHER INFORMATION: Synthetic

<400> SEQUENCE: 402
tatacgcagt gctaccatcg atcacaactg aggtgccagc ttctcttctc ctcatccagc      60
aaagaaaatg tcataaattt cgctcctcat ggaaatgtaa tcagtgggct cgctgctggc     120
tttgtcttaa ttaggcacta ttgatggaaa cagggagggc gccttgactt cgaaagacgc     180
tccacgatat                                                            190

<210> SEQ ID NO 403
<211> LENGTH: 190
<212> TYPE: DNA
<213> ORGANISM: Artificial Sequence
<220> FEATURE:
<223> OTHER INFORMATION: Synthetic

<400> SEQUENCE: 403
tatacgcagt gctaccatcg atcacggaag agccattctg aggggaaatt tgcctgctgg      60
taaccagttt aaggatacca gctgctggta taaatactgc tggataaata ctgctggatt     120
tatactgcag gataaatact gctggcccct gcggtatttc ctagtgactt cgaaagacgc     180
tccacgatat                                                            190

<210> SEQ ID NO 404
<211> LENGTH: 190
<212> TYPE: DNA
<213> ORGANISM: Artificial Sequence
<220> FEATURE:
<223> OTHER INFORMATION: Synthetic

<400> SEQUENCE: 404
tatacgcagt gctaccatcg atcacctaga gtgagccccg acttagcaga gcagttcctc      60
ctggggcctg cggtgtggga tcgcgtggtg aaccccacgg tgcatgcgcc tcaggctcta     120
gtttgaggca ggaaagcgca gcttgatgct tctctggaga ctgatgactt cgaaagacgc     180
tccacgatat                                                            190

<210> SEQ ID NO 405
<211> LENGTH: 190
<212> TYPE: DNA
<213> ORGANISM: Artificial Sequence
<220> FEATURE:
<223> OTHER INFORMATION: Synthetic

<400> SEQUENCE: 405
tatacgcagt gctaccatcg atcacgctgt agttggtttt attgatttgc tggcctaaca      60
gaacgttttt ccttggagca agtacaaat ccttcaagtt tgaaattcat aacctgagat      120
caatgcctgt ggcagcctgt ggggatgagg aaggagagcc acagggactt cgaaagacgc     180
tccacgatat                                                            190

<210> SEQ ID NO 406
<211> LENGTH: 190
<212> TYPE: DNA
<213> ORGANISM: Artificial Sequence
<220> FEATURE:
<223> OTHER INFORMATION: Synthetic

<400> SEQUENCE: 406
```

-continued

| | |
|---|---|
| tatacgcagt gctaccatcg atcacgccgt taggctgcag cctaatgaaa agagagtgcc | 60 |
| cagcgcctca gactttgcgc ctgggattct gagcacctgt ccgagatccc cgcttcctgc | 120 |
| catcctacct ttctgagaga ggcaccactg tgaccttcct cgtgcgactt cgaaagacgc | 180 |
| tccacgatat | 190 |

<210> SEQ ID NO 407
<211> LENGTH: 190
<212> TYPE: DNA
<213> ORGANISM: Artificial Sequence
<220> FEATURE:
<223> OTHER INFORMATION: Synthetic

<400> SEQUENCE: 407

| | |
|---|---|
| tatacgcagt gctaccatcg atcacccaat ctgttctcag ggcattttga gtcaaataaa | 60 |
| tgatcctgac tgatcttaac cattagcaca gagttcctca gccaactctg ctaagagacc | 120 |
| tcagtacaca caaaacagtg ttcctgcccc tcaggacttc aaagcgactt cgaaagacgc | 180 |
| tccacgatat | 190 |

<210> SEQ ID NO 408
<211> LENGTH: 190
<212> TYPE: DNA
<213> ORGANISM: Artificial Sequence
<220> FEATURE:
<223> OTHER INFORMATION: Synthetic

<400> SEQUENCE: 408

| | |
|---|---|
| tatacgcagt gctaccatcg atcacatgtg caccccttcc ttgatcctct ctcactcact | 60 |
| catggtcctg gagggtagag tggatgaggg tttgggcaac cacacttcag cttgatagat | 120 |
| cttttcctga ttatcttatg ttctcatacc ccggggcaga gataggactt cgaaagacgc | 180 |
| tccacgatat | 190 |

<210> SEQ ID NO 409
<211> LENGTH: 190
<212> TYPE: DNA
<213> ORGANISM: Artificial Sequence
<220> FEATURE:
<223> OTHER INFORMATION: Synthetic

<400> SEQUENCE: 409

| | |
|---|---|
| tatacgcagt gctaccatcg atcactggcc atcatcttta actcccattt gttcctagtg | 60 |
| ccttgaggga ctgactttga tttttagccc agtgccccga agacagtagg atatcctagg | 120 |
| gaaaaacagc aaggcctccc aggcccctgt ggagtacaga gccctgactt cgaaagacgc | 180 |
| tccacgatat | 190 |

<210> SEQ ID NO 410
<211> LENGTH: 190
<212> TYPE: DNA
<213> ORGANISM: Artificial Sequence
<220> FEATURE:
<223> OTHER INFORMATION: Synthetic

<400> SEQUENCE: 410

| | |
|---|---|
| tatacgcagt gctaccatcg atcacctggt tcaggggtgg tatctgcttg tagactctcc | 60 |
| actcctgtat acctgtaggt tttgcctgca cgatgtccag caaagctgag aagaagcagc | 120 |
| gattgagtgg ccgaggaagc tcccaggcaa gctggtcagg gcggggactt cgaaagacgc | 180 |
| tccacgatat | 190 |

<210> SEQ ID NO 411
<211> LENGTH: 190
<212> TYPE: DNA
<213> ORGANISM: Artificial Sequence
<220> FEATURE:
<223> OTHER INFORMATION: Synthetic

<400> SEQUENCE: 411
tatacgcagt gctaccatcg atcactcccc aaggaggagc tggtgggta cttgctgggg      60 cagaggatgc ttagcaatgg agggtgggga aagtcagagg ggcttggagg cattttaggg    120
ctggggagca ggcgctgttg cttctgggca ggaaacgggc taagtgactt cgaaagacgc    180
tccacgatat                                                           190

<210> SEQ ID NO 412
<211> LENGTH: 190
<212> TYPE: DNA
<213> ORGANISM: Artificial Sequence
<220> FEATURE:
<223> OTHER INFORMATION: Synthetic

<400> SEQUENCE: 412
tatacgcagt gctaccatcg atcacagcca tggaggttca gcagccctgc cactgagtcc      60 ttttttgta tgtcttcctc ctggccagcc tcatccttgt tctttctgtc ttaaaatttc     120
ccacaatata ccaggagttc accaaccagt cctttctcta gcctcgactt cgaaagacgc    180
tccacgatat                                                           190

<210> SEQ ID NO 413
<211> LENGTH: 190
<212> TYPE: DNA
<213> ORGANISM: Artificial Sequence
<220> FEATURE:
<223> OTHER INFORMATION: Synthetic

<400> SEQUENCE: 413
tatacgcagt gctaccatcg atcactcctc cttatttcaa gtgttcctgg ttgctcctac      60
cccactgaag agggtttgat ctcttccttt ttcccatttt caccctgggt ggcaaaacaa    120
ataatgtttt tctcccatta agcccatcac catggagact cagccgactt cgaaagacgc    180
tccacgatat                                                           190

<210> SEQ ID NO 414
<211> LENGTH: 190
<212> TYPE: DNA
<213> ORGANISM: Artificial Sequence
<220> FEATURE:
<223> OTHER INFORMATION: Synthetic

<400> SEQUENCE: 414
tatacgcagt gctaccatcg atcacgtttt gccacccttt gaatccaaag cccggctgat      60
gctttctacc atctgttgag ggctgttcta tctccgccct cattttggca gggacttggt    120
agactgcgga ggttcaggtt caggatgaca ggaaagaagt ctagagactt cgaaagacgc    180
tccacgatat                                                           190

<210> SEQ ID NO 415
<211> LENGTH: 190
<212> TYPE: DNA
<213> ORGANISM: Artificial Sequence
<220> FEATURE:

<223> OTHER INFORMATION: Synthetic

<400> SEQUENCE: 415
tatacgcagt gctaccatcg atcacctagg gaggaaagag tttaacgagg cagcctcttg      60 tggcttttgac ctgagggatt cctttcctgt gggtgagccg gagccagtaa ggttggaagg    120 ttttttggtag ttgttgctat tgctgggatc tccctgagag cactggactt cgaaagacgc   180
tccacgatat                                                            190

<210> SEQ ID NO 416
<211> LENGTH: 190
<212> TYPE: DNA
<213> ORGANISM: Artificial Sequence
<220> FEATURE:
<223> OTHER INFORMATION: Synthetic

<400> SEQUENCE: 416
tatacgcagt gctaccatcg atcacagaca ggactatgag ctaagtgtag acctccttct      60
ttacctggag ctcctttaca ctgatagtag cttgtgaaat agaatcccct tctaaaatta    120
aaggttgaga ggttaagcgt gggcatggga gaaaagtccc tgggcgactt cgaaagacgc   180
tccacgatat                                                            190

<210> SEQ ID NO 417
<211> LENGTH: 190
<212> TYPE: DNA
<213> ORGANISM: Artificial Sequence
<220> FEATURE:
<223> OTHER INFORMATION: Synthetic

<400> SEQUENCE: 417
tatacgcagt gctaccatcg atcacataag aacttgcatt aggttccagg atcttagaaa      60
tgtgcagaat gtatccttct gagttctgaa gtgctcaggt gaaagcagtt aaaatgggat    120
tgctcgctgc taggaggagt aggggaagat gggagggaag acagtgactt cgaaagacgc   180
tccacgatat                                                            190

<210> SEQ ID NO 418
<211> LENGTH: 190
<212> TYPE: DNA
<213> ORGANISM: Artificial Sequence
<220> FEATURE:
<223> OTHER INFORMATION: Synthetic

<400> SEQUENCE: 418
tatacgcagt gctaccatcg atcactcccc tggcctagtt cttgcctgga acctgaatgc      60
cagcagtttt cccaagggag ttggatcatc tcacctactc acctactact aagctccgga    120
atcgcctgtt ccatcttttc acgccttcct gcctcggcct ctgtggactt cgaaagacgc   180
tccacgatat                                                            190

<210> SEQ ID NO 419
<211> LENGTH: 190
<212> TYPE: DNA
<213> ORGANISM: Artificial Sequence
<220> FEATURE:
<223> OTHER INFORMATION: Synthetic

<400> SEQUENCE: 419
tatacgcagt gctaccatcg atcacctcat tcccctctta gttttccttt ctggaagcca      60
gagggagttt cctgttcctc atggtctttt ggttatatct catttgttcc ttcctccttt    120

```
cagcccctgg ggaatgggaa agccaccagt tttactccaa tctccgactt cgaaagacgc    180
tccacgatat                                                          190

<210> SEQ ID NO 420
<211> LENGTH: 190
<212> TYPE: DNA
<213> ORGANISM: Artificial Sequence
<220> FEATURE:
<223> OTHER INFORMATION: Synthetic

<400> SEQUENCE: 420
tatacgcagt gctaccatcg atcacgtgtg actagtagat caggaggcag agaaacagag     60
ccgctgggtt ttatgggagt cagagtgggt gtggcagaac tgaatgctca gcaggccagt    120
ggtttggaga agggctgatt cctatgagcc ccaacttctc catgtgactt cgaaagacgc    180
tccacgatat                                                          190

<210> SEQ ID NO 421
<211> LENGTH: 190
<212> TYPE: DNA
<213> ORGANISM: Artificial Sequence
<220> FEATURE:
<223> OTHER INFORMATION: Synthetic

<400> SEQUENCE: 421
tatacgcagt gctaccatcg atcacgactg tgtttaactt ccaagaaat gccttccttt      60 ttgtatgttt attcttccta gagccacggt tggaggacc tcaagcacag agtgaagaat    120
cagtggagcc cgaggcagat gtggtaggct tgggtcttcc ctgtggactt cgaaagacgc    180
tccacgatat                                                          190

<210> SEQ ID NO 422
<211> LENGTH: 190
<212> TYPE: DNA
<213> ORGANISM: Artificial Sequence
<220> FEATURE:
<223> OTHER INFORMATION: Synthetic

<400> SEQUENCE: 422
tatacgcagt gctaccatcg atcacctggt gaatcaaagg atcagttgtg gatggcacat     60
gaggaattct ctcttgtctg ccacttcttc tacttgctct ctgctgttag cctactcacc    120
acaaatccag ttcactgagt aaaagacaaa gtcatctgtg ccttcgactt cgaaagacgc    180
tccacgatat                                                          190

<210> SEQ ID NO 423
<211> LENGTH: 190
<212> TYPE: DNA
<213> ORGANISM: Artificial Sequence
<220> FEATURE:
<223> OTHER INFORMATION: Synthetic

<400> SEQUENCE: 423
tatacgcagt gctaccatcg atcacccagg acagaggagg gctttaagta aggcgcaggt     60
ctctcttgtc tccccacctt gggtcaaact gtgatgagct tattcatcat gcgggtgaac    120
acctgaacaa gttgaatgag ctgggaagat attgtcctaa ttggagactt cgaaagacgc    180
tccacgatat                                                          190

<210> SEQ ID NO 424
```

```
<211> LENGTH: 190
<212> TYPE: DNA
<213> ORGANISM: Artificial Sequence
<220> FEATURE:
<223> OTHER INFORMATION: Synthetic

<400> SEQUENCE: 424
tatacgcagt gctaccatcg atcactcttt tggactccat cgtgaagaaa ttgctcctat      60
accctctccc ttttccagct tgtggtctcc ctgctcctaa ttgcttgatc taggctaata     120
tcctacacat tcccttaatt caccttttacc tttgagatcg agggcgactt cgaaagacgc    180
tccacgatat                                                            190

<210> SEQ ID NO 425
<211> LENGTH: 190
<212> TYPE: DNA
<213> ORGANISM: Artificial Sequence
<220> FEATURE:
<223> OTHER INFORMATION: Synthetic

<400> SEQUENCE: 425
tatacgcagt gctaccatcg atcacctgtt tcttccaaag ctggaaagct atctttcagt      60
ttctcctaac cattctgaac ctgtctggct tctctcatct cccatgtcct cacttgtgat     120
tgtggatggg aggaatgact catcctggca gttgtagtta ctttggactt cgaaagacgc    180
tccacgatat                                                            190

<210> SEQ ID NO 426
<211> LENGTH: 190
<212> TYPE: DNA
<213> ORGANISM: Artificial Sequence
<220> FEATURE:
<223> OTHER INFORMATION: Synthetic

<400> SEQUENCE: 426
tatacgcagt gctaccatcg atcacccctc tgctctcctt ctgtagaagc ccctcttcct      60
ttcccgagct gcgctgacag gactggcgga tgcagtgtgg acacaggagc atgatgccat     120
tctggaacac tttgcccagg accctacaga atccatcctc accatgactt cgaaagacgc    180
tccacgatat                                                            190

<210> SEQ ID NO 427
<211> LENGTH: 190
<212> TYPE: DNA
<213> ORGANISM: Artificial Sequence
<220> FEATURE:
<223> OTHER INFORMATION: Synthetic

<400> SEQUENCE: 427
tatacgcagt gctaccatcg atcacttcat tgacccttgt tttgggctga agctagagct      60
gggcatgcct gtacaggtgc gtaccctaca ttcccagatc aaaggtggtc ctacagagag    120
ccgagggctc tcagttcctt catcatcctt aagtcttgtc atctcgactt cgaaagacgc   180
tccacgatat                                                            190

<210> SEQ ID NO 428
<211> LENGTH: 190
<212> TYPE: DNA
<213> ORGANISM: Artificial Sequence
<220> FEATURE:
<223> OTHER INFORMATION: Synthetic

<400> SEQUENCE: 428
```

```
tatacgcagt gctaccatcg atcaccatac tctctgcatt tcctccccac atctctggat    60
atggaatcat atccgtgaaa agaacaggaa gcacttcatg gcacttccat ttagagaagg   120
atcaggatac cctgagggac gtgagaaaga actcagccgg gctttgactt cgaaagacgc   180
tccacgatat                                                          190

<210> SEQ ID NO 429
<211> LENGTH: 190
<212> TYPE: DNA
<213> ORGANISM: Artificial Sequence
<220> FEATURE:
<223> OTHER INFORMATION: Synthetic

<400> SEQUENCE: 429
tatacgcagt gctaccatcg atcacgtgac tgggtgtcat ggctgggcct ggagactgaa    60
ctctgatctg ctgtcttcca tgcagaccca gaaccagctt gtctacttca ttcgccaagc   120
accagttccc atcacctggg agaacttcga ggcaactgtg cagttgactt cgaaagacgc   180
tccacgatat                                                          190

<210> SEQ ID NO 430
<211> LENGTH: 190
<212> TYPE: DNA
<213> ORGANISM: Artificial Sequence
<220> FEATURE:
<223> OTHER INFORMATION: Synthetic

<400> SEQUENCE: 430
tatacgcagt gctaccatcg atcacgggac ggtgcggggc ccctatatcc cggccctgct    60
tcggctgctc ggtggagtct ttgcccctca gatctttgca aacacaggct ggcctgagag   120
cattagaaat cattttgctt ctcatctgca caagttcttg gcctggactt cgaaagacgc   180
tccacgatat                                                          190

<210> SEQ ID NO 431
<211> LENGTH: 190
<212> TYPE: DNA
<213> ORGANISM: Artificial Sequence
<220> FEATURE:
<223> OTHER INFORMATION: Synthetic

<400> SEQUENCE: 431
tatacgcagt gctaccatcg atcacaaagg gaaatatagg tgctgtgggg acactgggag    60
gactcacatg tctcgtggta gagagtgttg aaggcgcgat acagatcttt gaccttattt   120
tatggcaatt tcttgttata actccatgag gtttccctct tgcctgactt cgaaagacgc   180
tccacgatat                                                          190

<210> SEQ ID NO 432
<211> LENGTH: 190
<212> TYPE: DNA
<213> ORGANISM: Artificial Sequence
<220> FEATURE:
<223> OTHER INFORMATION: Synthetic

<400> SEQUENCE: 432
tatacgcagt gctaccatcg atcactggtc atttcttgat atcaaaaaag catgagtcac    60
catttcttct acctgctctc ctgaaatgca tatgcttcct ggtccccTac cgatcatcaa   120
ccgtgattcc tacgggggcca gcaagaactc atcccctctg tccacgactt cgaaagacgc   180
```

```
tccacgatat                                                              190

<210> SEQ ID NO 433
<211> LENGTH: 190
<212> TYPE: DNA
<213> ORGANISM: Artificial Sequence
<220> FEATURE:
<223> OTHER INFORMATION: Synthetic

<400> SEQUENCE: 433
tatacgcagt gctaccatcg atcactccac aaactttcct ttccttagac actcggtaca        60
aactggaggg gcacacggtc ctctacatcc ctgcagaggc catgaacatg aagcctgaga       120
tggtgataaa ggacaaagag ctggtgcaac ggctagagag tgagtgactt cgaaagacgc       180
tccacgatat                                                              190

<210> SEQ ID NO 434
<211> LENGTH: 190
<212> TYPE: DNA
<213> ORGANISM: Artificial Sequence
<220> FEATURE:
<223> OTHER INFORMATION: Synthetic

<400> SEQUENCE: 434
tatacgcagt gctaccatcg atcacgctgg cactgctagc atcacctggc gatcacaggg        60
gagagggaaa ggggaggctc ggatgctgac aatgagttg ggttaggagg tctctgtcgg       120
ggttgcgggg agtgaaggat gctgttggga agcagtgtga agaaagactt cgaaagacgc       180
tccacgatat                                                              190

<210> SEQ ID NO 435
<211> LENGTH: 190
<212> TYPE: DNA
<213> ORGANISM: Artificial Sequence
<220> FEATURE:
<223> OTHER INFORMATION: Synthetic

<400> SEQUENCE: 435
tatacgcagt gctaccatcg atcacgaagg agattttgta ctctcccctg cagcctccat        60
gatccactgg acccggcaga taaggagat gctcagtgcc caggagactg tggagacagg       120
agaaaattta ggtcctctgg aggagattga gttctggcgc aaccggactt cgaaagacgc       180
tccacgatat                                                              190

<210> SEQ ID NO 436
<211> LENGTH: 190
<212> TYPE: DNA
<213> ORGANISM: Artificial Sequence
<220> FEATURE:
<223> OTHER INFORMATION: Synthetic

<400> SEQUENCE: 436
tatacgcagt gctaccatcg atcactgcat ggacctgtct ggcatcagta agcagctggt        60
gaagaaggga gtgaagcacg ttgaatccat cctgcacctt gccaagtcgt cctacttggc       120 gcccttatg aaactggcac agcagatcca ggtttgtgag cgaatgactt cgaaagacgc       180
tccacgatat                                                              190

<210> SEQ ID NO 437
<211> LENGTH: 190
<212> TYPE: DNA
<213> ORGANISM: Artificial Sequence
```

```
<220> FEATURE:
<223> OTHER INFORMATION: Synthetic

<400> SEQUENCE: 437
tatacgcagt gctaccatcg atcacaaagg attcaggctc agcaagaagt gggcaatggt    60
tgggatgata cagggagcta agtaaggaga gggagccaag gcaatcttcg atagcacaga   120
ctgacccacc cagggttcgg ccttgtactt gcaggagagt ataaagactt cgaaagacgc   180
tccacgatat                                                          190

<210> SEQ ID NO 438
<211> LENGTH: 190
<212> TYPE: DNA
<213> ORGANISM: Artificial Sequence
<220> FEATURE:
<223> OTHER INFORMATION: Synthetic

<400> SEQUENCE: 438
tatacgcagt gctaccatcg atcacgtaga atagagggtc cctaaggaga gagacatcaa    60
gttaaccaat aaatatacat caagtacctt ctgtgagcac aaccectgcc acccagctgg   120 gaaaataaga ttacccaaaa caggattact agacagcgtg ggagcgactt cgaaagacgc   180
tccacgatat                                                          190

<210> SEQ ID NO 439
<211> LENGTH: 190
<212> TYPE: DNA
<213> ORGANISM: Artificial Sequence
<220> FEATURE:
<223> OTHER INFORMATION: Synthetic

<400> SEQUENCE: 439
tatacgcagt gctaccatcg atcacatgat gtgacaggct gattatgtta gtgctaggtc    60
acacaggagg taagagtggc ctgtagaata cagatagaag acctgtcttc ctaggtgaaa   120
atttcagctg ggcattaagg gaattgagcc agaactaact ggagggactt cgaaagacgc   180
tccacgatat                                                          190

<210> SEQ ID NO 440
<211> LENGTH: 190
<212> TYPE: DNA
<213> ORGANISM: Artificial Sequence
<220> FEATURE:
<223> OTHER INFORMATION: Synthetic

<400> SEQUENCE: 440
tatacgcagt gctaccatcg atcacgccta aagccctggc tgagaacagg gcagtgaaag    60
ggaactgggt gacaactatg gggacgaatg agagtgatat gcggccagtt gatccgacag   120
caacagagta tccacttagt gcggagtcct gaattcaact ggagagactt cgaaagacgc   180
tccacgatat                                                          190

<210> SEQ ID NO 441
<211> LENGTH: 190
<212> TYPE: DNA
<213> ORGANISM: Artificial Sequence
<220> FEATURE:
<223> OTHER INFORMATION: Synthetic

<400> SEQUENCE: 441
tatacgcagt gctaccatcg atcaccagac acaaaatcta gaaaaatcta gactcgaggg    60
```

```
aattcttagt ctggtagggg agctagggca cacacatgag aaaagaaaag ttgacatgtg    120
ctaactctgg tccgaaggct cacagagacc tgaaatgatc gctacgactt cgaaagacgc    180
tccacgatat                                                           190

<210> SEQ ID NO 442
<211> LENGTH: 190
<212> TYPE: DNA
<213> ORGANISM: Artificial Sequence
<220> FEATURE:
<223> OTHER INFORMATION: Synthetic

<400> SEQUENCE: 442
tatacgcagt gctaccatcg atcactcagt gctttctagt gcataaatct atttctcatc    60
tctctttact gccaggatgg ctctcgtcaa gcacagtcaa acctgacctt tttgtcaatc    120
ctgaaggaac cttaccagga gttggctttc atgaagccca aggacgactt cgaaagacgc    180
tccacgatat                                                           190

<210> SEQ ID NO 443
<211> LENGTH: 190
<212> TYPE: DNA
<213> ORGANISM: Artificial Sequence
<220> FEATURE:
<223> OTHER INFORMATION: Synthetic

<400> SEQUENCE: 443
tatacgcagt gctaccatcg atcactctct agcaagctcc ctaagctgat cagtctcatc    60
cgcatcatct gggtcaactc tccccactac aacactcggg agagactgac ctcgctcttc    120
cgaaaggtgt gcatatgctg agggtgggat ggagggggttt atgaggactt cgaaagacgc    180
tccacgatat                                                           190

<210> SEQ ID NO 444
<211> LENGTH: 190
<212> TYPE: DNA
<213> ORGANISM: Artificial Sequence
<220> FEATURE:
<223> OTHER INFORMATION: Synthetic

<400> SEQUENCE: 444
tatacgcagt gctaccatcg atcacaatgc attcggcaga ggatctgtgg ttgaaaaggt    60
agtgaagatt gcccttctgc tcagagactg agctcagaag gcttctaccg gcatgatctg    120
ctttagggtt gctcagcatt ggagcctggg ctggactttc tgtttgactt cgaaagacgc    180
tccacgatat                                                           190

<210> SEQ ID NO 445
<211> LENGTH: 190
<212> TYPE: DNA
<213> ORGANISM: Artificial Sequence
<220> FEATURE:
<223> OTHER INFORMATION: Synthetic

<400> SEQUENCE: 445
tatacgcagt gctaccatcg atcaccaggg tggctgcaga gctgggctga ggcagagtaa    60
ggggccacct aggacaagga gtgggcatgg aacccagagg tgtcggcctg gccaggggtg    120
gagaaccagg ggtgggatga gtttcaggag tcaaattaag gagtagactt cgaaagacgc    180
tccacgatat                                                           190
```

```
<210> SEQ ID NO 446
<211> LENGTH: 190
<212> TYPE: DNA
<213> ORGANISM: Artificial Sequence
<220> FEATURE:
<223> OTHER INFORMATION: Synthetic

<400> SEQUENCE: 446
tatacgcagt gctaccatcg atcacatgca gagaaggagt tgggtgtcaa ggaggtgggg      60
acagaggctg tggggactcc ttctgcagat gagcaatgag atcatccgct tatgctgcca     120
cgccatctcc ctggaccgga tctttgaggg atatgtctct tccaggactt cgaaagacgc     180
tccacgatat                                                            190

<210> SEQ ID NO 447
<211> LENGTH: 190
<212> TYPE: DNA
<213> ORGANISM: Artificial Sequence
<220> FEATURE:
<223> OTHER INFORMATION: Synthetic

<400> SEQUENCE: 447
tatacgcagt gctaccatcg atcacaagga ggacctgcaa ggctgcattc tctgttgtca      60
cgcttggaaa gatcactacg tacaggctgt gcagatgcac atccagtatg atacgcctcc     120
cctaacatcc catgtctcaa ctcccttgtc agccctgtaa gagggacttc gaaagacgc      180 tccacgatat                                                            190

<210> SEQ ID NO 448
<211> LENGTH: 190
<212> TYPE: DNA
<213> ORGANISM: Artificial Sequence
<220> FEATURE:
<223> OTHER INFORMATION: Synthetic

<400> SEQUENCE: 448
tatacgcagt gctaccatcg atcactaatc tctcctccct gatcccagga accctacctg      60
gtcttttcct cctatcttga ccccatcgtc taaaattcta ttatgtatga atctgctcct     120
agaacttaga tgctctgtct cctgtctggt tcttctcacc ttgaggactt cgaaagacgc     180
tccacgatat                                                            190

<210> SEQ ID NO 449
<211> LENGTH: 190
<212> TYPE: DNA
<213> ORGANISM: Artificial Sequence
<220> FEATURE:
<223> OTHER INFORMATION: Synthetic

<400> SEQUENCE: 449
tatacgcagt gctaccatcg atcaccttgt cctttgggat tcaggagggt tgtttctcgg      60
ggtctgattt ttctagggct ttccctgaat gcagggctcc tggtctaggt ttgcatagcc     120
agactgctct tgccttccaa ttcagtcggc ctttctcctg acacagactt cgaaagacgc     180
tccacgatat                                                            190

<210> SEQ ID NO 450
<211> LENGTH: 190
<212> TYPE: DNA
<213> ORGANISM: Artificial Sequence
<220> FEATURE:
<223> OTHER INFORMATION: Synthetic
```

```
<400> SEQUENCE: 450
tatacgcagt gctaccatcg atcacgttct ccagtcgggg ctgggtccta gatcagacca    60
gcatctttgc tcaggttgat gcctttgtgc agcgctgcaa ggaccttatt gaggtgggaa   120
gactgaagaa ccaaaagcta acagcagacc ctccagaatc cctccgactt cgaaagacgc   180
tccacgatat                                                          190

<210> SEQ ID NO 451
<211> LENGTH: 190
<212> TYPE: DNA
<213> ORGANISM: Artificial Sequence
<220> FEATURE:
<223> OTHER INFORMATION: Synthetic

<400> SEQUENCE: 451
tatacgcagt gctaccatcg atcacttttta gacatttgaa gctaaaccaa atagcttagg    60
actttggagt ttggaaggaa agcaggaacc ctcatgctgt cttctttttt aggtatgtga   120
ctgtcagtat cacttcgccc gctgggaaga tggcaagcag ggtccgactt cgaaagacgc   180
tccacgatat                                                          190

<210> SEQ ID NO 452
<211> LENGTH: 190
<212> TYPE: DNA
<213> ORGANISM: Artificial Sequence
<220> FEATURE:
<223> OTHER INFORMATION: Synthetic

<400> SEQUENCE: 452
tatacgcagt gctaccatcg atcactatcc tggatgtcaa gaacacctgt tggcatgaag    60
actacaataa gtgagggaac cacaggctga tgccaggcgt gggcagggaa ggcagatcag   120
gcagccaaga gtgggaggag tggcgagagt atgcaaagga aatgggactt cgaaagacgc   180
tccacgatat                                                          190

<210> SEQ ID NO 453
<211> LENGTH: 190
<212> TYPE: DNA
<213> ORGANISM: Artificial Sequence
<220> FEATURE:
<223> OTHER INFORMATION: Synthetic

<400> SEQUENCE: 453
tatacgcagt gctaccatcg atcacactcc cgcagcgggg tgcagctttc ctctgggatg    60
agtgaccgga gggaacccgc cttcccgggc acgtcgccag cctcttcctc ttcttcccta   120
ggctatcaag cggacttatg acaagaaggc ggtggatctc tacatgactt cgaaagacgc   180
tccacgatat                                                          190

<210> SEQ ID NO 454
<211> LENGTH: 190
<212> TYPE: DNA
<213> ORGANISM: Artificial Sequence
<220> FEATURE:
<223> OTHER INFORMATION: Synthetic

<400> SEQUENCE: 454
tatacgcagt gctaccatcg atcacctgtt caatagcgag ctggccctgg tgaaccgtga    60
acggaacaag aaatggccag acctggagcc tacgtggcc cagtattccg gaaaggcgcg    120
ctgggtgcac atcctccggc gtcgcatcga cagagtcatg accgtgactt cgaaagacgc   180
```

```
tccacgatat                                                                    190

<210> SEQ ID NO 455
<211> LENGTH: 190
<212> TYPE: DNA
<213> ORGANISM: Artificial Sequence
<220> FEATURE:
<223> OTHER INFORMATION: Synthetic

<400> SEQUENCE: 455
tatacgcagt gctaccatcg atcacatggc tcctgagagg ttccccaaag agtcttcagg    60
accagcacct atgtcggtga ggggagtggc aggtccagtt cagtgaggtc agtcgtgggt   120
taagatctgc agaggtggtg tgtgaggctg gtagaacatg cgccagactt cgaaagacgc   180
tccacgatat                                                                    190

<210> SEQ ID NO 456
<211> LENGTH: 190
<212> TYPE: DNA
<213> ORGANISM: Artificial Sequence
<220> FEATURE:
<223> OTHER INFORMATION: Synthetic

<400> SEQUENCE: 456
tatacgcagt gctaccatcg atcactcatt ttaggaattt catatcaggc tgcagaggag    60
gaatagggcc ggtatctggg gtgttgggtc agtagaagat acagcctcat gatccagaga   120
cctggacagg tgacaccctt acagagcctg gtctctctgg aaagagactt cgaaagacgc   180
tccacgatat                                                                    190

<210> SEQ ID NO 457
<211> LENGTH: 190
<212> TYPE: DNA
<213> ORGANISM: Artificial Sequence
<220> FEATURE:
<223> OTHER INFORMATION: Synthetic

<400> SEQUENCE: 457
tatacgcagt gctaccatcg atcactgaac acacacaccc tttgggaata aaggttgaaa    60
gctgttgagg tagtgacctg ccatcatgca gctggtgctg gtagagagtt aggcagcctg   120
cagatagctg gaggctggtt tgggcctggt ggactacgcc caggcgactt cgaaagacgc   180
tccacgatat                                                                    190

<210> SEQ ID NO 458
<211> LENGTH: 190
<212> TYPE: DNA
<213> ORGANISM: Artificial Sequence
<220> FEATURE:
<223> OTHER INFORMATION: Synthetic

<400> SEQUENCE: 458
tatacgcagt gctaccatcg atcacgactc cttttctcat tgcgccttgg tctcttccta    60
tcaccttcct tttgactct accttccttc taagttatca aaactcaatc catctccata   120
gcaagcctta tgcatattgt tggggtatgt gcgcatgcgc gcatggactt cgaaagacgc   180
tccacgatat                                                                    190

<210> SEQ ID NO 459
<211> LENGTH: 190
<212> TYPE: DNA
```

<213> ORGANISM: Artificial Sequence
<220> FEATURE:
<223> OTHER INFORMATION: Synthetic

<400> SEQUENCE: 459

```
tatacgcagt gctaccatcg atcacgtagg tctcagggag atggtggccc ctggaggaag    60
gtggcaggcc gactccaccc acctgttctt cttcccctca gtgccttgct ggtgctcatt   120
tcctgccccg tattgggact ggaaaggaga gtgtgcacac ctatcgactt cgaaagacgc   180
tccacgatat                                                          190
```

<210> SEQ ID NO 460
<211> LENGTH: 190
<212> TYPE: DNA
<213> ORGANISM: Artificial Sequence
<220> FEATURE:
<223> OTHER INFORMATION: Synthetic

<400> SEQUENCE: 460

```
tatacgcagt gctaccatcg atcacgcaga tggtccaggc cattgatgag ctggttcgaa    60
aaaccttcca agagtggaca tcaagtctgg acaaggattg cattcggcgg ttggataccc   120
cattgctgcg aatcagccag gagaaggcgg gcatgctgga tgtcagactt cgaaagacgc   180
tccacgatat                                                          190
```

<210> SEQ ID NO 461
<211> LENGTH: 190
<212> TYPE: DNA
<213> ORGANISM: Artificial Sequence
<220> FEATURE:
<223> OTHER INFORMATION: Synthetic

<400> SEQUENCE: 461

```
tatacgcagt gctaccatcg atcacccact ccactatctg actaaaccag tgatgtcgct    60
gttctgccac tagatggcca taatggctca gctaagtcac ccaaaccctg tccctttcct   120
gactgttggt ggggctgtca gaccatgcct tcttctacag cttcagactt cgaaagacgc   180
tccacgatat                                                          190
```

<210> SEQ ID NO 462
<211> LENGTH: 190
<212> TYPE: DNA
<213> ORGANISM: Artificial Sequence
<220> FEATURE:
<223> OTHER INFORMATION: Synthetic

<400> SEQUENCE: 462

```
tatacgcagt gctaccatcg atcactgctt gtggggccaa atgtaggagg ggctttgcca    60
gagaagtgct gtgtggagac ggagtcccag ggacagatga gactgtgagt gtttgtcctg   120
ggcagcaaaa ggtggcccaa ccaggggaag agggcacatt ctggcgactt cgaaagacgc   180
tccacgatat                                                          190
```

<210> SEQ ID NO 463
<211> LENGTH: 190
<212> TYPE: DNA
<213> ORGANISM: Artificial Sequence
<220> FEATURE:
<223> OTHER INFORMATION: Synthetic

<400> SEQUENCE: 463

```
tatacgcagt gctaccatcg atcacgagaa aggaagcaaa agaaccagga tggagaagca    60
```

```
gagcggagtg tcaggtgaga ggggtgaggc agaggcatca gtgaggagga cagggatgtt      120
gggagctgca gggatgagga agccgttgag gagcagagtg tgcacgactt cgaaagacgc      180
tccacgatat                                                              190
```

<210> SEQ ID NO 464
<211> LENGTH: 190
<212> TYPE: DNA
<213> ORGANISM: Artificial Sequence
<220> FEATURE:
<223> OTHER INFORMATION: Synthetic

<400> SEQUENCE: 464

```
tatacgcagt gctaccatcg atcactggct aggtcgagag gtttgagaaa aggcttcgag      60
tagtgagagt tgttggagat tggctttgct gagcttcctg gttttgtgag ttatggccaa      120
gcacagccac gtaaacattg cctcataaat caacgataag attctgactt cgaaagacgc      180
tccacgatat                                                              190
```

<210> SEQ ID NO 465
<211> LENGTH: 190
<212> TYPE: DNA
<213> ORGANISM: Artificial Sequence
<220> FEATURE:
<223> OTHER INFORMATION: Synthetic

<400> SEQUENCE: 465

```
tatacgcagt gctaccatcg atcacacagt ttctgtaagg ttcttgacta ttccgtgctg      60
gtggatttca actgtgattc ccgcactttg ttcccttccc tctgcagcac tgtgtttact      120
gaaatttgaa cacagtgtcc ctctagttag gataaaccag gagacgactt cgaaagacgc      180
tccacgatat                                                              190
```

<210> SEQ ID NO 466
<211> LENGTH: 190
<212> TYPE: DNA
<213> ORGANISM: Artificial Sequence
<220> FEATURE:
<223> OTHER INFORMATION: Synthetic

<400> SEQUENCE: 466

```
tatacgcagt gctaccatcg atcactgctc tttgtgttca agctccagtt aagatcttga      60
aataagcaga ctgtccaaat gttctgatgt tcctcggaat tacctggctc tcttagtcct      120
ggagccttcc agtccctaat agcactgatt taatcccaca aggggacttt cgaaagacgc      180
tccacgatat                                                              190
```

<210> SEQ ID NO 467
<211> LENGTH: 190
<212> TYPE: DNA
<213> ORGANISM: Artificial Sequence
<220> FEATURE:
<223> OTHER INFORMATION: Synthetic

<400> SEQUENCE: 467

```
tatacgcagt gctaccatcg atcactggct tttatcacgt tttacggaca gaacagcttc      60
acagattgca cttaacacaa acatattcca gatgtcatcc acaccctggc tgaaggagct      120
gtattatcac cctgtgtgga gcagagtaga atttcctgag aggaggactt cgaaagacgc      180
tccacgatat                                                              190
```

<210> SEQ ID NO 468
<211> LENGTH: 190
<212> TYPE: DNA
<213> ORGANISM: Artificial Sequence
<220> FEATURE:
<223> OTHER INFORMATION: Synthetic

<400> SEQUENCE: 468
tatacgcagt gctaccatcg atcactctgc ttcatttctc atctcgacat ttccctgtgc    60
ttcccagcct ctccacctgt tcgattgttg ctctagttta tccctcgtg cggtcccctc   120 actgcctggc tgctctctct caaaggtccc ttctgattct ctttggactt cgaaagacgc   180
tccacgatat                                                           190

<210> SEQ ID NO 469
<211> LENGTH: 190
<212> TYPE: DNA
<213> ORGANISM: Artificial Sequence
<220> FEATURE:
<223> OTHER INFORMATION: Synthetic

<400> SEQUENCE: 469
tatacgcagt gctaccatcg atcacggaaa ttgactactg ggagcggctg ctgtttgaga    60
cgccccatta cgtggtgaac gtagctgagc gagccgagga cctgcgcatt ctgcgtgaaa   120
atctgctact cgttgctaga gactacaata ggtagggctt cagtcgactt cgaaagacgc   180
tccacgatat                                                           190

<210> SEQ ID NO 470
<211> LENGTH: 190
<212> TYPE: DNA
<213> ORGANISM: Artificial Sequence
<220> FEATURE:
<223> OTHER INFORMATION: Synthetic

<400> SEQUENCE: 470
tatacgcagt gctaccatcg atcactctgt cctctacatc ttttccatct caaaaaaaaa    60
aaattgtctc ccactcttac ggccctatca ttattcctac cccttgtagt tttattttct   120
agctgcaggg tggagagtaa agccaaccag gtcccctccc accccgactt cgaaagacgc   180
tccacgatat                                                           190

<210> SEQ ID NO 471
<211> LENGTH: 190
<212> TYPE: DNA
<213> ORGANISM: Artificial Sequence
<220> FEATURE:
<223> OTHER INFORMATION: Synthetic

<400> SEQUENCE: 471
tatacgcagt gctaccatcg atcactggtc tagaaatgtt cacatttctc cactgtttcc    60
tgaagtggag gaaagatctt cagggcttgt ccctctgga taccaggcct ctcttatgca   120
caggattatt gccatgctgt ccccagatga gcaggccta ttcaagactt cgaaagacgc   180
tccacgatat                                                           190

<210> SEQ ID NO 472
<211> LENGTH: 190
<212> TYPE: DNA
<213> ORGANISM: Artificial Sequence
<220> FEATURE:
<223> OTHER INFORMATION: Synthetic -continued

<400> SEQUENCE: 472
tatacgcagt gctaccatcg atcacatgac ggggcctgac tctaggtgca gatgattgtg    60
aatgagttca aggcatccac tctgaccatt ggctggcgag cccaagagat gtcagagaag   120
ctgctggtac gcattagtgg caaacgggta tacagggacc tggaagactt cgaaagacgc   180
tccacgatat                                                          190

<210> SEQ ID NO 473
<211> LENGTH: 190
<212> TYPE: DNA
<213> ORGANISM: Artificial Sequence
<220> FEATURE:
<223> OTHER INFORMATION: Synthetic

<400> SEQUENCE: 473
tatacgcagt gctaccatcg atcacttgaa gaggaccaaa gagagcatcg ggcagctgta    60
cagcagaaat tgatgaacct gcaccaggat gtggtgacca tcatgaccaa ctcctatgag   120
gtcttcaaga atgatggtcc tgaggtaggg ttcctgtggc caggagactt cgaaagacgc   180
tccacgatat                                                          190

<210> SEQ ID NO 474
<211> LENGTH: 190
<212> TYPE: DNA
<213> ORGANISM: Artificial Sequence
<220> FEATURE:
<223> OTHER INFORMATION: Synthetic

<400> SEQUENCE: 474
tatacgcagt gctaccatcg atcacagttc catcaggcca ttctcttgct ccccgaccct    60
tttttctttt ttaccagtgt gtacttctca aacatcgtgc tctagtcttg gactcagcca   120
accttcagtc ctcacacctc ttcctccagg actcagcgtc ctgcggactt cgaaagacgc   180
tccacgatat                                                          190

<210> SEQ ID NO 475
<211> LENGTH: 190
<212> TYPE: DNA
<213> ORGANISM: Artificial Sequence
<220> FEATURE:
<223> OTHER INFORMATION: Synthetic

<400> SEQUENCE: 475
tatacgcagt gctaccatcg atcacttcca ttaaaccaac ttgtttcctt ccctgttggc    60
tggttctcac ttcccaggat gtgccctgtc ttccctgaaa agttctcttt ttcctccctc   120
catcccatca gattcagcag cagtggatgc tgtacatgat tcggcgactt cgaaagacgc   180
tccacgatat                                                          190

<210> SEQ ID NO 476
<211> LENGTH: 190
<212> TYPE: DNA
<213> ORGANISM: Artificial Sequence
<220> FEATURE:
<223> OTHER INFORMATION: Synthetic

<400> SEQUENCE: 476
tatacgcagt gctaccatcg atcacggacc gcatgatgga ggatgccctg cgcctgaatg    60
tgaagtggtc actgctagaa ctatccaagg ctatcaacgg ggatggaaag accagcccaa   120

| | |
|---|---|
| acccactctt ccaagtcctt gtcattttga agaatgatct gcaaggactt cgaaagacgc | 180 |
| tccacgatat | 190 |

<210> SEQ ID NO 477
<211> LENGTH: 190
<212> TYPE: DNA
<213> ORGANISM: Artificial Sequence
<220> FEATURE:
<223> OTHER INFORMATION: Synthetic

<400> SEQUENCE: 477

| | |
|---|---|
| tatacgcagt gctaccatcg atcactctca aaaccattgc atcttatttg tcagtttccc | 60 |
| ttaattccta aacttggtcc ttggccttga ctttatccta tggccttcag acctgctgct | 120 |
| gaagtgtgtg accttcccag tcctaaggct tttctctcca tctccgactt cgaaagacgc | 180 |
| tccacgatat | 190 |

<210> SEQ ID NO 478
<211> LENGTH: 190
<212> TYPE: DNA
<213> ORGANISM: Artificial Sequence
<220> FEATURE:
<223> OTHER INFORMATION: Synthetic

<400> SEQUENCE: 478

| | |
|---|---|
| tatacgcagt gctaccatcg atcacctggg ttcctcacag gtggaattct cacccactct | 60 |
| gcagactttg gcaggtgtgg tcaatgacat tggcaaccac ctcttttcca ccatctctgt | 120 |
| cttctgccac ctccctgaca ttctcaccaa gcgcaagtta catcggactt cgaaagacgc | 180 |
| tccacgatat | 190 |

<210> SEQ ID NO 479
<211> LENGTH: 190
<212> TYPE: DNA
<213> ORGANISM: Artificial Sequence
<220> FEATURE:
<223> OTHER INFORMATION: Synthetic

<400> SEQUENCE: 479

| | |
|---|---|
| tatacgcagt gctaccatcg atcacttgag attaggtgac tgatgctcat gggttttggg | 60 |
| atttgggatg ggagatgagg aaagacaagc ttgggactgg gactgggact ggcctgtaag | 120 |
| aggcctagat accaacagac aagacatcac atcctatgaa ggagagactt cgaaagacgc | 180 |
| tccacgatat | 190 |

<210> SEQ ID NO 480
<211> LENGTH: 190
<212> TYPE: DNA
<213> ORGANISM: Artificial Sequence
<220> FEATURE:
<223> OTHER INFORMATION: Synthetic

<400> SEQUENCE: 480

| | |
|---|---|
| tatacgcagt gctaccatcg atcacactaa gagtcacatt ttcactttct gcctactcct | 60 |
| ttaccttcta atgtgcatgt ttgagctgta tttctctggg aagctggttt tagagtggaa | 120 |
| ggtctggagc agtgggcagg gctcaggcag aagttgggtt ggggtgactt cgaaagacgc | 180 |
| tccacgatat | 190 |

<210> SEQ ID NO 481
<211> LENGTH: 190

```
<212> TYPE: DNA
<213> ORGANISM: Artificial Sequence
<220> FEATURE:
<223> OTHER INFORMATION: Synthetic

<400> SEQUENCE: 481
tatacgcagt gctaccatcg atcacgaagt cagtgagaag catctttctt ggtcctttga      60
agagcaagat gaggacatca agaagatcca gacccaaatc agcagcggca tgactaacaa     120
cgcaagcctg ctgcagaact acctcaagac ctgggacatg taccggactt cgaaagacgc     180
tccacgatat                                                            190

<210> SEQ ID NO 482
<211> LENGTH: 190
<212> TYPE: DNA
<213> ORGANISM: Artificial Sequence
<220> FEATURE:
<223> OTHER INFORMATION: Synthetic

<400> SEQUENCE: 482
tatacgcagt gctaccatcg atcacgagat ctgggagatc aacaaggact ccttcattca      60
tcgctaccag cgcctcaacc ctcctgtctc ttcttttgtt gccgacattg cccggtgagt     120
ggtgagggtg gattgaaagt ctgtctgtag gaggcacagc actgcgactt cgaaagacgc     180
tccacgatat                                                            190

<210> SEQ ID NO 483
<211> LENGTH: 150
<212> TYPE: DNA
<213> ORGANISM: Artificial Sequence
<220> FEATURE:
<223> OTHER INFORMATION: Synthetic

<400> SEQUENCE: 483
tgcgtaagtg catcagtcca tcatgcatcc gtcgctacat gagtgactag atgaatccgt      60
cagtcaatgc ctggatgagt agatcgctga ctgcatacgt gttcagtcag tcagtcaggc     120
atctatatac gcagtgctac catcgatcac                                      150

<210> SEQ ID NO 484
<211> LENGTH: 150
<212> TYPE: DNA
<213> ORGANISM: Artificial Sequence
<220> FEATURE:
<223> OTHER INFORMATION: Synthetic

<400> SEQUENCE: 484
tagatgcctg actgactgac tgaacacgta tgcagtcagc gatctactca tccaggcatt      60
gactgacgga ttcatctagt cactcatgta gcgacggatg catgatggac tgatgcactt     120
acgcaatatc gtggagcgtc tttcgaagtc                                      150

<210> SEQ ID NO 485
<211> LENGTH: 175
<212> TYPE: DNA
<213> ORGANISM: Artificial Sequence
<220> FEATURE:
<223> OTHER INFORMATION: Synthetic

<400> SEQUENCE: 485
tgcgtaagtg catcagtcca tcatgaccta gctacatgac tcagtccata cctgcgtcag      60
tcaatggatg gctaactgga tccgtcgatc agtagatgag taactgagtc gctgcgtcag     120
```
tgactgttca gtcagtcagt caggcatcta tatacgcagt gctaccatcg atcac   175

<210> SEQ ID NO 486
<211> LENGTH: 175
<212> TYPE: DNA
<213> ORGANISM: Artificial Sequence
<220> FEATURE:
<223> OTHER INFORMATION: Synthetic

<400> SEQUENCE: 486
tagatgcctg actgactgac tgaacagtca ctgacgcagc gactcagtta ctcatctact   60
gatcgacgga tccagttagc catccattga ctgacgcagg tatggactga gtcatgtagc   120
taggtcatga tggactgatg cacttacgca atatcgtgga gcgtctttcg aagtc   175

<210> SEQ ID NO 487
<211> LENGTH: 115
<212> TYPE: DNA
<213> ORGANISM: Artificial Sequence
<220> FEATURE:
<223> OTHER INFORMATION: Synthetic

<400> SEQUENCE: 487
tgcgtaagtg catcagtcca tcatggcatc aatgcatgcc tgagtagatc cgtaactgag   60
tcgctgttca gtcagtcagt caggcatcta tatacgcagt gctaccatcg atcac   115

<210> SEQ ID NO 488
<211> LENGTH: 115
<212> TYPE: DNA
<213> ORGANISM: Artificial Sequence
<220> FEATURE:
<223> OTHER INFORMATION: Synthetic

<400> SEQUENCE: 488
tagatgcctg actgactgac tgaacagcga ctcagttacg gatctactca ggcatgcatt   60
gatgccatga tggactgatg cacttacgca atatcgtgga gcgtctttcg aagtc   115

<210> SEQ ID NO 489
<211> LENGTH: 175
<212> TYPE: DNA
<213> ORGANISM: Artificial Sequence
<220> FEATURE:
<223> OTHER INFORMATION: Synthetic

<400> SEQUENCE: 489
tgcgtaagtg catcagtcca tcatgaacta gatacataaa tcaatcagtg cgtcaatgag   60
taaataggta agtagatgac tagctccatc gatgcatcac tgcgtagcta gctacatgac   120
tgcatgttca gtcagtcagt caggcatcta tatacgcagt gctaccatcg atcac   175

<210> SEQ ID NO 490
<211> LENGTH: 175
<212> TYPE: DNA
<213> ORGANISM: Artificial Sequence
<220> FEATURE:
<223> OTHER INFORMATION: Synthetic

<400> SEQUENCE: 490
tagatgcctg actgactgac tgaacatgca gtcatgtagc tagctacgca gtgatgcatc   60
gatggagcta gtcatctact tacctattta ctcattgacg cactgattga tttatgtatc   120
tagttcatga tggactgatg cacttacgca atatcgtgga gcgtctttcg aagtc   175

```
<210> SEQ ID NO 491
<211> LENGTH: 190
<212> TYPE: DNA
<213> ORGANISM: Artificial Sequence
<220> FEATURE:
<223> OTHER INFORMATION: Synthetic

<400> SEQUENCE: 491
tatacgcagt gctaccatcg atcacaattc ccagaagtaa gaccatcttt gggacaagag      60
acaatgaaga gaagtcagat gtggaggaac agaaaacaag agccaggggc cagggcaggt     120
cagtcctaga gaaacaaatg gaccaaactg gggacaaaga aggcagactt cgaaagacgc     180
tccacgatat                                                            190

<210> SEQ ID NO 492
<211> LENGTH: 190
<212> TYPE: DNA
<213> ORGANISM: Artificial Sequence
<220> FEATURE:
<223> OTHER INFORMATION: Synthetic

<400> SEQUENCE: 492
tatacgcagt gctaccatcg atcaccggag agctccccat tctccgaggg gcccttagga      60
agcttgctga cagagtcacc ctgaggggaa agtgggaaag aaaacagaaa agcaagaagc     120
ggtgagtaga aattcaggtg ggagacattc cctaccatcc aagccgactt cgaaagacgc     180
tccacgatat                                                            190

<210> SEQ ID NO 493
<211> LENGTH: 190
<212> TYPE: DNA
<213> ORGANISM: Artificial Sequence
<220> FEATURE:
<223> OTHER INFORMATION: Synthetic

<400> SEQUENCE: 493
tatacgcagt gctaccatcg atcactggtg atccagaggt tggttccctg atctcatgat      60
ccagtctctc ttacttggga tccagaaaat gtgaaccaca ctttcttctc tatcctattc     120
aaagtttaca ctggtctaaa ctccatcaga cacagctgcc tctgcgactt cgaaagacgc     180
tccacgatat                                                            190

<210> SEQ ID NO 494
<211> LENGTH: 190
<212> TYPE: DNA
<213> ORGANISM: Artificial Sequence
<220> FEATURE:
<223> OTHER INFORMATION: Synthetic

<400> SEQUENCE: 494
tatacgcagt gctaccatcg atcactgccc cagagtaaca acaaaaaagg gatggggtaa      60
agcacatctt gcctgcctac cttctgtcct gaaagagagt cttctgaggg tttagtgcgt     120 tccagggggtg gcctctggcg gctctgagac tctgctcgtg agatagactt cgaaagacgc    180
tccacgatat                                                            190

<210> SEQ ID NO 495
<211> LENGTH: 190
<212> TYPE: DNA
<213> ORGANISM: Artificial Sequence
<220> FEATURE:
<223> OTHER INFORMATION: Synthetic
```

```
<400> SEQUENCE: 495
tatacgcagt gctaccatcg atcacagtca gccacagtca ctggggaagg caggagatta      60
agactttcag atggaattct ggtagccagc ctaagacacc cactgaaccc gaacccctga     120
ttttcacagg ggtgagcatc ccattctctc agctctgagg aaggagactt cgaaagacgc     180
tccacgatat                                                            190

<210> SEQ ID NO 496
<211> LENGTH: 190
<212> TYPE: DNA
<213> ORGANISM: Artificial Sequence
<220> FEATURE:
<223> OTHER INFORMATION: Synthetic

<400> SEQUENCE: 496
tatacgcagt gctaccatcg atcactctgg tgtccagagt tggctgacct ggctggcggt      60
ctccactgat agagccatca gtccgattac cacggttacg cggcggcgg ctgcgattac      120 gacgttgagg tcttgattca tcttctgtag ggtaggaaaa aaccagactt cgaaagacgc     180
tccacgatat                                                            190

<210> SEQ ID NO 497
<211> LENGTH: 190
<212> TYPE: DNA
<213> ORGANISM: Artificial Sequence
<220> FEATURE:
<223> OTHER INFORMATION: Synthetic

<400> SEQUENCE: 497
tatacgcagt gctaccatcg atcacagtca cacatccaac ctcccaccct cgattcctac      60
ccatctctaa ctttccagac cccaggcaca ccctcaccca ggccattctc tgtcatgttg     120
ggcccatctg attccaggcc tccatccatg acggtcctgt cttcagactt cgaaagacgc     180
tccacgatat                                                            190

<210> SEQ ID NO 498
<211> LENGTH: 190
<212> TYPE: DNA
<213> ORGANISM: Artificial Sequence
<220> FEATURE:
<223> OTHER INFORMATION: Synthetic

<400> SEQUENCE: 498
tatacgcagt gctaccatcg atcacctctg gttcagacgt gtccaatagg ctgtagggat      60
tactgtctgg atccttcagc actggtcaga ggaagaagag gaggagttgg cagtcaggtg     120
cccatcatct ttccttttgg cccatattca tgaacccagc tgtctgactt cgaaagacgc     180
tccacgatat                                                            190

<210> SEQ ID NO 499
<211> LENGTH: 190
<212> TYPE: DNA
<213> ORGANISM: Artificial Sequence
<220> FEATURE:
<223> OTHER INFORMATION: Synthetic

<400> SEQUENCE: 499
tatacgcagt gctaccatcg atcacatccc tgtcgccagg cccagctcgg ttgggctcct      60
ctctcttctc tgactcagtc tctgaagctg tagacacatc tgagctgggg cctgaagaac     120
acaatgggat ttattcacgg ccattcatcc cacctcagga tccatgactt cgaaagacgc     180
```

```
tccacgatat                                                              190

<210> SEQ ID NO 500
<211> LENGTH: 190
<212> TYPE: DNA
<213> ORGANISM: Artificial Sequence
<220> FEATURE:
<223> OTHER INFORMATION: Synthetic

<400> SEQUENCE: 500
tatacgcagt gctaccatcg atcacaaact ggaagaattc tccttctcac tcacaagcct        60
cccagccaat caatcacttt ttcatcatct ccattccaga tttccccaaa cttccatcca       120
gacctctgcc tctacccaca agccctgcca ctccttgcct cctgtgactt cgaaagacgc       180
tccacgatat                                                              190

<210> SEQ ID NO 501
<211> LENGTH: 190
<212> TYPE: DNA
<213> ORGANISM: Artificial Sequence
<220> FEATURE:
<223> OTHER INFORMATION: Synthetic

<400> SEQUENCE: 501
tatacgcagt gctaccatcg atcacatagg ttcgagtcgc atggagggag gaggaggagc        60
tctcatcagt gctatatcca gccttgtcgc tgccaccgct gccccgccca ctcccaggag       120
ggcgaaagcc cagcccaatc tgccgaagct gctcatcaat ttgtagactt cgaaagacgc       180
tccacgatat                                                              190

<210> SEQ ID NO 502
<211> LENGTH: 190
<212> TYPE: DNA
<213> ORGANISM: Artificial Sequence
<220> FEATURE:
<223> OTHER INFORMATION: Synthetic

<400> SEQUENCE: 502
tatacgcagt gctaccatcg atcaccctct ccaagcgaag ctgctctacc tcctggttgg        60
gtaaaagatg gaagaagggg aaggagaaat aagatcagtg ccttgcttca tgcttctgca       120
ccctgactgt ccctctatat ctaacctctc aggaatgcag ggagagactt cgaaagacgc       180
tccacgatat                                                              190

<210> SEQ ID NO 503
<211> LENGTH: 190
<212> TYPE: DNA
<213> ORGANISM: Artificial Sequence
<220> FEATURE:
<223> OTHER INFORMATION: Synthetic

<400> SEQUENCE: 503
tatacgcagt gctaccatcg atcacacagc agtcttagtt cccttttcac acccagcatt        60
tttctctccc ggcctgggta cctgcaggta ggagaggtga tactccagca aagcctgggc       120
attgctgatg ttctctcggg tgccaacaaa aatgaaggga accatgactt cgaaagacgc       180
tccacgatat                                                              190

<210> SEQ ID NO 504
<211> LENGTH: 190
<212> TYPE: DNA
```

<213> ORGANISM: Artificial Sequence
<220> FEATURE:
<223> OTHER INFORMATION: Synthetic

<400> SEQUENCE: 504

```
tatacgcagt gctaccatcg atcaccccta gagaacagag agcagaaacg atggatcaga      60
aaggaaaatg aaatggaagg attaacgccg cccagtctcc taggggagcc tgcccagtgg     120
gatcattctg ggctctaaat ctactagtgt taaacaactt tccgtgactt cgaaagacgc     180
tccacgatat                                                            190
```

<210> SEQ ID NO 505
<211> LENGTH: 190
<212> TYPE: DNA
<213> ORGANISM: Artificial Sequence
<220> FEATURE:
<223> OTHER INFORMATION: Synthetic

<400> SEQUENCE: 505

```
tatacgcagt gctaccatcg atcacctcca ccctctcaaa gaacaatccc agccctcaga      60
ggacaatccc atttacttct ggaaaccaat ctctatgccc acttgccccg tacccatacc     120
tcctccctgg ggttcttctt gtcattatca ccttccactc gaaccgactt cgaaagacgc     180
tccacgatat                                                            190
```

<210> SEQ ID NO 506
<211> LENGTH: 190
<212> TYPE: DNA
<213> ORGANISM: Artificial Sequence
<220> FEATURE:
<223> OTHER INFORMATION: Synthetic

<400> SEQUENCE: 506

```
tatacgcagt gctaccatcg atcactcact cccattacag actgtttctc tgtccttgtg      60
aaactgggag tccacaggga ggtgccaatc ctggataaaa gctcagaatc actgtagaga     120
atcttgattc tgacctctaa ctgtatatac acaccaccaa ctcacgactt cgaaagacgc     180
tccacgatat                                                            190
```

<210> SEQ ID NO 507
<211> LENGTH: 190
<212> TYPE: DNA
<213> ORGANISM: Artificial Sequence
<220> FEATURE:
<223> OTHER INFORMATION: Synthetic

<400> SEQUENCE: 507

```
tatacgcagt gctaccatcg atcactttc gggcctgctg gatgttggca ccgtgagtcc       60
caattgccag tcccatcagg tcctctcgca ctgtgaactc ctcttggaag gctgctgcca     120
actgcttgct tgtctgaaag gaaaagtcac tgtaggaatc atggtgactt cgaaagacgc     180
tccacgatat                                                            190
```

<210> SEQ ID NO 508
<211> LENGTH: 190
<212> TYPE: DNA
<213> ORGANISM: Artificial Sequence
<220> FEATURE:
<223> OTHER INFORMATION: Synthetic

<400> SEQUENCE: 508

```
tatacgcagt gctaccatcg atcacgtgag gggttaagaa aaacagaaaa catgcctcta      60
```

```
gaacaccagg ctttcacttc atttctcaat cagtccttag aggaacccct gggttcaggg      120
gcaggaagac aggaaaggtt ttagaggagt gaatcccatg ttgtagactt cgaaagacgc      180
tccacgatat                                                              190
```

<210> SEQ ID NO 509
<211> LENGTH: 190
<212> TYPE: DNA
<213> ORGANISM: Artificial Sequence
<220> FEATURE:
<223> OTHER INFORMATION: Synthetic

<400> SEQUENCE: 509

```
tatacgcagt gctaccatcg atcaccaggg gcttctgtgg ttgactggga ggaaaccagt      60
gggaaagtca ttaaaactgg cttggaataa acactaaggg agagccaggg actagaaatc      120
aggatgccta agtcccggga aaagggttaa gaaatgaagc taggagactt cgaaagacgc      180
tccacgatat                                                              190
```

<210> SEQ ID NO 510
<211> LENGTH: 190
<212> TYPE: DNA
<213> ORGANISM: Artificial Sequence
<220> FEATURE:
<223> OTHER INFORMATION: Synthetic

<400> SEQUENCE: 510

```
tatacgcagt gctaccatcg atcacttcag gcagaataaa ctcaccagaa tgaagagctc      60
actgtttgtg atgttgagaa agatgcagtt ggctcccagg gctttcttga actctttatg      120
gacgttttca ttggagcagc tgcagaggaa aaaagtactc agcgggactt cgaaagacgc      180
tccacgatat                                                              190
```

<210> SEQ ID NO 511
<211> LENGTH: 190
<212> TYPE: DNA
<213> ORGANISM: Artificial Sequence
<220> FEATURE:
<223> OTHER INFORMATION: Synthetic

<400> SEQUENCE: 511

```
tatacgcagt gctaccatcg atcacgaaga gggaccacag ttaaagaaca aggatgggaa      60
aataaagaaa ctaagtgtct tcttagcaag aagggctcta gtagagggcc aggggaacaa      120
cagagaaaac tgcaaagtgg gagtgatgcc tgggagaaat aaagcgactt cgaaagacgc      180
tccacgatat                                                              190
```

<210> SEQ ID NO 512
<211> LENGTH: 190
<212> TYPE: DNA
<213> ORGANISM: Artificial Sequence
<220> FEATURE:
<223> OTHER INFORMATION: Synthetic

<400> SEQUENCE: 512

```
tatacgcagt gctaccatcg atcacgacat agaactggca catggtaaaa aaggagaagt      60
tgtggatgac ctgagcaact ttctatgaat aacatatttg tttcagtagt tctccaaagg      120
cattcccagt cactcacatc tcccttcatc atccgcaccc gggccgactt cgaaagacgc      180
tccacgatat                                                              190
```

<210> SEQ ID NO 513
<211> LENGTH: 190
<212> TYPE: DNA
<213> ORGANISM: Artificial Sequence
<220> FEATURE:
<223> OTHER INFORMATION: Synthetic

<400> SEQUENCE: 513
tatacgcagt gctaccatcg atcacgttac cataaatgga aggcaaatcg cctgaaactg    60
gggatgttcc tgagagtttg gctgatcaca acagtgataa aaggggaact gttgcatttt   120
acatttccat aggctacatg gctggatatg gcttagttgg ggagggactt cgaaagacgc   180
tccacgatat                                                          190

<210> SEQ ID NO 514
<211> LENGTH: 190
<212> TYPE: DNA
<213> ORGANISM: Artificial Sequence
<220> FEATURE:
<223> OTHER INFORMATION: Synthetic

<400> SEQUENCE: 514
tatacgcagt gctaccatcg atcacaggaa catgaaccaa ccagagaaaa gcctagaatc    60
ctggggaaaa gtgacattta gaaaggtgta ctccacagcc cttacctcca cttcatcccc   120
ttctgtgatc tccttattat agtcagctgg aggtggtagc cggacgactt cgaaagacgc   180
tccacgatat                                                          190

<210> SEQ ID NO 515
<211> LENGTH: 190
<212> TYPE: DNA
<213> ORGANISM: Artificial Sequence
<220> FEATURE:
<223> OTHER INFORMATION: Synthetic

<400> SEQUENCE: 515
tatacgcagt gctaccatcg atcacaatat gaaaagcta ctctgactga tatggttgcc    60
catttcttta caaagggtt attgcctcag ctgggcgagt ccacctatc tggataatta   120 gaggctaaac cccaggccct gctccatagt agtgtcttcc atctcgactt cgaaagacgc   180
tccacgatat                                                          190

<210> SEQ ID NO 516
<211> LENGTH: 190
<212> TYPE: DNA
<213> ORGANISM: Artificial Sequence
<220> FEATURE:
<223> OTHER INFORMATION: Synthetic

<400> SEQUENCE: 516
tatacgcagt gctaccatcg atcaccttga gttttagata gggacacaag tggtgtaatg    60
agacagcctg aaaggctgca ctggggaaag aatatgggca gtcaaacaga gaaaggaaat   120
gatattgtca tggagaggtg tatgtaccac ctgcatcaga acagcgactt cgaaagacgc   180
tccacgatat                                                          190

<210> SEQ ID NO 517
<211> LENGTH: 190
<212> TYPE: DNA
<213> ORGANISM: Artificial Sequence
<220> FEATURE:
<223> OTHER INFORMATION: Synthetic

```
<400> SEQUENCE: 517
tatacgcagt gctaccatcg atcactggaa accaatgatc tactcaggct cccacagggg      60
cctccctatc tgtctgcctc ctgttgtgct aagcagcctg ccagagttca attaaaatac     120
caacaacatt cagcaaggct aagaatatcc catgagacag tgtgagactt cgaaagacgc     180
tccacgatat                                                            190

<210> SEQ ID NO 518
<211> LENGTH: 190
<212> TYPE: DNA
<213> ORGANISM: Artificial Sequence
<220> FEATURE:
<223> OTHER INFORMATION: Synthetic

<400> SEQUENCE: 518
tatacgcagt gctaccatcg atcacgctgt cctggaacac ctagaggaca tgaggatctg      60
tcgagagaga agggcctacc tccgcaatac agcaagagat ctgagcagac tcgctgccct     120
gatgcatggg tcctaagaca ataatcggaa cactagacaa gttcagactt cgaaagacgc     180
tccacgatat                                                            190

<210> SEQ ID NO 519
<211> LENGTH: 190
<212> TYPE: DNA
<213> ORGANISM: Artificial Sequence
<220> FEATURE:
<223> OTHER INFORMATION: Synthetic

<400> SEQUENCE: 519
tatacgcagt gctaccatcg atcacaaagg ataataaaat ttatggaaga ctccaatctt      60 gatatttga caagagcaag agggatgact gaacagctga tccacctcct gtggtctgtg     120
tcctcactaa ggaggccaaa gccatgcatt caccccctatg ctcccgactt cgaaagacgc    180
tccacgatat                                                            190

<210> SEQ ID NO 520
<211> LENGTH: 190
<212> TYPE: DNA
<213> ORGANISM: Artificial Sequence
<220> FEATURE:
<223> OTHER INFORMATION: Synthetic

<400> SEQUENCE: 520
tatacgcagt gctaccatcg atcacagaac ctgagttatg agcatgttca ttcaggttta      60
atgccaactc ctactgttct ccattcaagt cttctgaggc acttttactt ctacttgcct     120
gggtctctct tccctttttgg gttcttccct tagctcctgc tcaaggactt cgaaagacgc    180
tccacgatat                                                            190

<210> SEQ ID NO 521
<211> LENGTH: 190
<212> TYPE: DNA
<213> ORGANISM: Artificial Sequence
<220> FEATURE:
<223> OTHER INFORMATION: Synthetic

<400> SEQUENCE: 521
tatacgcagt gctaccatcg atcactactg cttttgtgga gagatttcta ctcctagata      60
tattcaaatc ggctatgcct atggtgtaat ccaattctcc tccaccatgt taggcttggc     120
```

```
cccagggtga gcagcaatat accctagtt ttcccagcta ccatggactt cgaaagacgc    180
tccacgatat                                                          190

<210> SEQ ID NO 522
<211> LENGTH: 190
<212> TYPE: DNA
<213> ORGANISM: Artificial Sequence
<220> FEATURE:
<223> OTHER INFORMATION: Synthetic

<400> SEQUENCE: 522
tatacgcagt gctaccatcg atcacccttc aattagtctc caaaactagc tctgtcccca    60
acttcatatt ccaatcctgt ctctgctcct aaattccacc cattcatccc atactagttt   120
ttttctccaa gggtatctgt ggtggaagtg agccccaagt tctgcgactt cgaaagacgc   180
tccacgatat                                                          190

<210> SEQ ID NO 523
<211> LENGTH: 190
<212> TYPE: DNA
<213> ORGANISM: Artificial Sequence
<220> FEATURE:
<223> OTHER INFORMATION: Synthetic

<400> SEQUENCE: 523
tatacgcagt gctaccatcg atcaccagtc tacgctcatt gtgaaaataa gcaggtgaag    60
gcaagagcag gtgggtggaa tgtattaggg agccacctag atccagagga taacttgatt   120
cagtggccat agcatcacct ggctttggct tctggagcct ggcacgactt cgaaagacgc   180
tccacgatat                                                          190

<210> SEQ ID NO 524
<211> LENGTH: 190
<212> TYPE: DNA
<213> ORGANISM: Artificial Sequence
<220> FEATURE:
<223> OTHER INFORMATION: Synthetic

<400> SEQUENCE: 524
tatacgcagt gctaccatcg atcacttcta ggagaagagc aggaacagtc tgagtaaaaa    60
ccaagtactg aagctgagga tgccatgttg attaagaaag gaatgggdat taggatatcc   120
agatgaggtt tggagtagga agattgcgcc ctggacggtg aatacgactt cgaaagacgc   180
tccacgatat                                                          190

<210> SEQ ID NO 525
<211> LENGTH: 190
<212> TYPE: DNA
<213> ORGANISM: Artificial Sequence
<220> FEATURE:
<223> OTHER INFORMATION: Synthetic

<400> SEQUENCE: 525
tatacgcagt gctaccatcg atcacaactg acaacagggc ccaattctga gagaggagaa    60
agggaccttc ccaaatgtac aattccagaa gcagtgtaaa tactccctga cccatcccaa   120
gtttgctgag tcatgaatat taaatcagca gcaaggtcaa aacgggactt cgaaagacgc   180
tccacgatat                                                          190

<210> SEQ ID NO 526
<211> LENGTH: 190
```

```
<212> TYPE: DNA
<213> ORGANISM: Artificial Sequence
<220> FEATURE:
<223> OTHER INFORMATION: Synthetic

<400> SEQUENCE: 526
tatacgcagt gctaccatcg atcacgtatc tgtagggtac tgagagtgga agattagcct      60
gaatttaggg atttgtggtt tttaactcag gaacagggca gaaaatgcta acctgcccag     120
atccacatta ccacattacc tggctttcag ctcaaccccca aactcgactt cgaaagacgc    180
tccacgatat                                                            190

<210> SEQ ID NO 527
<211> LENGTH: 190
<212> TYPE: DNA
<213> ORGANISM: Artificial Sequence
<220> FEATURE:
<223> OTHER INFORMATION: Synthetic

<400> SEQUENCE: 527
tatacgcagt gctaccatcg atcacactct ctgaatcaca gtatcctggt ccccatctat      60
tcaagtctat cactgccaca gcacacagga gaaagggaaa agattcagag agactttctg     120
ctggacactt atatgtggga cagaaaacgt gtcccttccc agccagactt cgaaagacgc    180
tccacgatat                                                            190

<210> SEQ ID NO 528
<211> LENGTH: 190
<212> TYPE: DNA
<213> ORGANISM: Artificial Sequence
<220> FEATURE:
<223> OTHER INFORMATION: Synthetic

<400> SEQUENCE: 528
tatacgcagt gctaccatcg atcacatcca ctcttaacaa gtgatgccat gggaaggtat      60
ctcttcccca gctccccagg gtgaaatcaa agaatgagac agaaatcagg agagtctcta    120
ggacaattcc aggcatcaaa tccaagaggt tcagaatacc aacaggactt cgaaagacgc    180
tccacgatat                                                            190

<210> SEQ ID NO 529
<211> LENGTH: 190
<212> TYPE: DNA
<213> ORGANISM: Artificial Sequence
<220> FEATURE:
<223> OTHER INFORMATION: Synthetic

<400> SEQUENCE: 529
tatacgcagt gctaccatcg atcactgact atgaagctta catgcctcaa gacgaagaaa      60
ctatatgaat gacctgaagg tatctgaggt ctaagtgaga cctcaaatcc attcctgagt     120
agaatggtag agcagtgggt cttgagatca aggtgtggtg gggaggactt cgaaagacgc    180
tccacgatat                                                            190

<210> SEQ ID NO 530
<211> LENGTH: 190
<212> TYPE: DNA
<213> ORGANISM: Artificial Sequence
<220> FEATURE:
<223> OTHER INFORMATION: Synthetic

<400> SEQUENCE: 530
```

```
tatacgcagt gctaccatcg atcacgagac ttgcgaaaga tgccacctta  tggctggctg    60
ggaagcaact tgactgatcc aacccagggt tcctgaggtc aaagatgcca  aacgtcgtaa   120
atggatctga ccatttctcc ttggcttggg aaccggaata taagagactt  cgaaagacgc   180
tccacgatat                                                           190

<210> SEQ ID NO 531
<211> LENGTH: 190
<212> TYPE: DNA
<213> ORGANISM: Artificial Sequence
<220> FEATURE:
<223> OTHER INFORMATION: Synthetic

<400> SEQUENCE: 531
tatacgcagt gctaccatcg atcacgaaag tggggtgagt gttccagagc  cagtaggcag    60
aggcctctct gaggaagatg aaaggatctt ttacgggaca gagggccttc  ccaaagggac   120
cgtgtggaag aaagacaatt ctccatgtgc ttggatcgtg gggaagactt  cgaaagacgc   180
tccacgatat                                                           190

<210> SEQ ID NO 532
<211> LENGTH: 190
<212> TYPE: DNA
<213> ORGANISM: Artificial Sequence
<220> FEATURE:
<223> OTHER INFORMATION: Synthetic

<400> SEQUENCE: 532
tatacgcagt gctaccatcg atcacatgtg attaaggtct aaggtatgtc  ttccaccaga    60
caacggacac agtcaattag aagctgggta aagggtctc  tcctgcggag  cggggagcgc   120
caagccaggg acaataatgg cctgaagttc attctcccgg agattgactt  cgaaagacgc   180
tccacgatat                                                           190

<210> SEQ ID NO 533
<211> LENGTH: 190
<212> TYPE: DNA
<213> ORGANISM: Artificial Sequence
<220> FEATURE:
<223> OTHER INFORMATION: Synthetic

<400> SEQUENCE: 533
tatacgcagt gctaccatcg atcactagaa gcaggtgcag gtgccttaga  ggggtcaaaa    60
ataagaggaa cagggttcac tctaagcggt ctcccaggga aggctgcggg  ttggagcaag   120
ggtccaagat tctaagggcc aggactcagc tccagaagct cgatcgactt  cgaaagacgc   180
tccacgatat                                                           190

<210> SEQ ID NO 534
<211> LENGTH: 190
<212> TYPE: DNA
<213> ORGANISM: Artificial Sequence
<220> FEATURE:
<223> OTHER INFORMATION: Synthetic

<400> SEQUENCE: 534
tatacgcagt gctaccatcg atcacacagc gctcaggcca cacccactcc  gccgccgctg    60
gccccaccgg gcttggacaa gttagggatg ggcatgcgcc tgaacgactg  cttggtcact   120
ttccccacct ttgtctttct tggtgcgcac gctccaaaaa gaaagacttt  cgaaagacgc   180
tccacgatat                                                           190
```

<210> SEQ ID NO 535
<211> LENGTH: 190
<212> TYPE: DNA
<213> ORGANISM: Artificial Sequence
<220> FEATURE:
<223> OTHER INFORMATION: Synthetic

<400> SEQUENCE: 535

```
tatacgcagt gctaccatcg atcacaaaaa gaagaggagt cgccgcaagg aaaaaggtgc    60
ttggtgcgca cgcgctgagc tttaccctct tcgcgtatgc atcgccgata ttttaagaat   120
ctgtaactct ctactgtagt agatttaaca gtcatggctc ttaccgactt cgaaagacgc   180
tccacgatat                                                          190
```

<210> SEQ ID NO 536
<211> LENGTH: 190
<212> TYPE: DNA
<213> ORGANISM: Artificial Sequence
<220> FEATURE:
<223> OTHER INFORMATION: Synthetic

<400> SEQUENCE: 536

```
tatacgcagt gctaccatcg atcacgaccc aacaccacat caggacatgt aattcttatt    60
tatttttcac cctcaacaag gaagaaaggt ctctccctca attctgctct tccaatactt   120
gaggataggc acccctaacc ctccttcctc cagggaggcc tcagcgactt cgaaagacgc   180
tccacgatat                                                          190
```

<210> SEQ ID NO 537
<211> LENGTH: 190
<212> TYPE: DNA
<213> ORGANISM: Artificial Sequence
<220> FEATURE:
<223> OTHER INFORMATION: Synthetic

<400> SEQUENCE: 537

```
tatacgcagt gctaccatcg atcactcagt gtctgtggac gtagtctctg aagagtgctt    60
cagctgatgg ggaaggagaa actcaagaca gagatcctcc tagggatggc gtcactttcc   120
tgccaacttt ctcgttgcct ctccttgaaa gcagaagaag tgccagactt cgaaagacgc   180
tccacgatat                                                          190
```

<210> SEQ ID NO 538
<211> LENGTH: 190
<212> TYPE: DNA
<213> ORGANISM: Artificial Sequence
<220> FEATURE:
<223> OTHER INFORMATION: Synthetic

<400> SEQUENCE: 538

```
tatacgcagt gctaccatcg atcaccccctc agcttccgtc agatcttggg ctcctagggc    60
cttgtacaag tccatggccc tctggttcca gtccaggacg gccaggcgga attgggagca   120
gcccttatcc aaggccacct gtgggagaag acaacactaa cttttgactt cgaaagacgc   180
tccacgatat                                                          190
```

<210> SEQ ID NO 539
<211> LENGTH: 190
<212> TYPE: DNA
<213> ORGANISM: Artificial Sequence
<220> FEATURE:

<223> OTHER INFORMATION: Synthetic

<400> SEQUENCE: 539

| tatacgcagt gctaccatcg atcacctcca tatacccttg cttcttcagg tcctcacttg | 60 |
| tcgccccacc catctcctca cctcagccac cttttttgatt attttggaac caatcccttg | 120 |
| acctgttgtg gagagaaaga ggcaaaaaat agctattgtt tgagcgactt cgaaagacgc | 180 |
| tccacgatat | 190 |

<210> SEQ ID NO 540
<211> LENGTH: 190
<212> TYPE: DNA
<213> ORGANISM: Artificial Sequence
<220> FEATURE:
<223> OTHER INFORMATION: Synthetic

<400> SEQUENCE: 540

| tatacgcagt gctaccatcg atcacgaagg ggatcagaaa atgacaccgg ctgggctctg | 60 |
| gggacagggg ataacagtgg ggtctgtggg gtgctttgct cccacccag cctcagcttc | 120 |
| tgcccagtac cccgatattc cggcatcaca tagatatcct ccagagactt cgaaagacgc | 180 |
| tccacgatat | 190 |

<210> SEQ ID NO 541
<211> LENGTH: 190
<212> TYPE: DNA
<213> ORGANISM: Artificial Sequence
<220> FEATURE:
<223> OTHER INFORMATION: Synthetic

<400> SEQUENCE: 541

| tatacgcagt gctaccatcg atcacaaatg gtgcgtccct tccatgtact gtagatgaaa | 60 |
| tagtatatcc catagcccac cacgcagggc cctgagagag agaaaagggg agtaaggctt | 120 |
| ctggaagcct gtggggagac ctctgaggcc ggctggagag gtggagactt cgaaagacgc | 180 |
| tccacgatat | 190 |

<210> SEQ ID NO 542
<211> LENGTH: 190
<212> TYPE: DNA
<213> ORGANISM: Artificial Sequence
<220> FEATURE:
<223> OTHER INFORMATION: Synthetic

<400> SEQUENCE: 542

| tatacgcagt gctaccatcg atcacttcta agggccaggt gctcttaccc agtagcttcc | 60 |
| cgggcgctgg aagaatctct gctaccaaac agtgatagaa aggattgtct ccaaagccat | 120 |
| ctgctctcag ggctgccgag attggagttg tgacaaagag atagagactt cgaaagacgc | 180 |
| tccacgatat | 190 |

<210> SEQ ID NO 543
<211> LENGTH: 190
<212> TYPE: DNA
<213> ORGANISM: Artificial Sequence
<220> FEATURE:
<223> OTHER INFORMATION: Synthetic

<400> SEQUENCE: 543

| tatacgcagt gctaccatcg atcactgcag tcttcacccg aatcagcctc aggatatctc | 60 |
| cacagtctcc ctccttggcc tctcggatcc gcacggaagc catccggatc cccgctgtct | 120 |

```
gggaccaaag tcccagggcc tcgcaaacgg caactagacc ccttagactt cgaaagacgc    180
tccacgatat                                                           190

<210> SEQ ID NO 544
<211> LENGTH: 190
<212> TYPE: DNA
<213> ORGANISM: Artificial Sequence
<220> FEATURE:
<223> OTHER INFORMATION: Synthetic

<400> SEQUENCE: 544
tatacgcagt gctaccatcg atcacgcagt gcttttaaa ttgacatatg cagtgataac     60
ctgctttagc ctcaggctca ctcacccgcc cagaccctgg gtaagcctta agaccctcag    120
ctctgaaagc tgtttcctgc agctcttgag tagcatgaag tgttagactt cgaaagacgc    180
tccacgatat                                                           190

<210> SEQ ID NO 545
<211> LENGTH: 190
<212> TYPE: DNA
<213> ORGANISM: Artificial Sequence
<220> FEATURE:
<223> OTHER INFORMATION: Synthetic

<400> SEQUENCE: 545
tatacgcagt gctaccatcg atcactttag gattccatta tctcatttct agtcctgata    60
caggatgcta cttgggacgc aggggaggac tgtttctaga cctcaggcct gtgaatgcag    120
gctccccgag tggacagaaa tcttggagga cctagatcag gccctgactt cgaaagacgc    180
tccacgatat                                                           190

<210> SEQ ID NO 546
<211> LENGTH: 190
<212> TYPE: DNA
<213> ORGANISM: Artificial Sequence
<220> FEATURE:
<223> OTHER INFORMATION: Synthetic

<400> SEQUENCE: 546
tatacgcagt gctaccatcg atcacgagga ggagagggga gatggaatat cctctcccag    60
ttcagaaact ttctcggcag tggaggatga tagtggaggg gactctgtcc ttcaccccat    120
tgatccccag agggtgata gctgagtctt gtgactgggc ccctggactt cgaaagacgc     180
tccacgatat                                                           190

<210> SEQ ID NO 547
<211> LENGTH: 190
<212> TYPE: DNA
<213> ORGANISM: Artificial Sequence
<220> FEATURE:
<223> OTHER INFORMATION: Synthetic

<400> SEQUENCE: 547
tatacgcagt gctaccatcg atcacgccct gagacctgtt ctccccaccc aggtgcagga    60
gcgggacagg gcactcagct catgcagtct tcccttctct cctctggccc tgtagcaggg    120
cctctccctc tgtctgtctc tgacatgtcc ctactcagct ttgttgactt cgaaagacgc    180
tccacgatat                                                           190

<210> SEQ ID NO 548
```

<211> LENGTH: 190
<212> TYPE: DNA
<213> ORGANISM: Artificial Sequence
<220> FEATURE:
<223> OTHER INFORMATION: Synthetic

<400> SEQUENCE: 548
tatacgcagt gctaccatcg atcacgtttt ctctttctga tagagtgccc acgaccctcc    60
ggctgtccac ctcagcaatg gcccaggaca agagcctatc gctgtcatga cctttgacct   120
caccaagatc acaaagtatg gggttggcct agcccttgac ccagtgactt cgaaagacgc   180
tccacgatat                                                          190

<210> SEQ ID NO 549
<211> LENGTH: 190
<212> TYPE: DNA
<213> ORGANISM: Artificial Sequence
<220> FEATURE:
<223> OTHER INFORMATION: Synthetic

<400> SEQUENCE: 549
tatacgcagt gctaccatcg atcacaaacc cacactggtt ctcaaaggac acatgacata    60
cacaatcttt ccttctgtgt ccttccagaa cctcctcctc ctttgaggtt cgaacctggg   120
acccagaggg agtgattttt tatggggata ccaaccctaa ggatggactt cgaaagacgc   180
tccacgatat                                                          190

<210> SEQ ID NO 550
<211> LENGTH: 190
<212> TYPE: DNA
<213> ORGANISM: Artificial Sequence
<220> FEATURE:
<223> OTHER INFORMATION: Synthetic

<400> SEQUENCE: 550
tatacgcagt gctaccatcg atcacctggt ttatgctggg acttcgagac ggcaggcctg    60
agatccaact gcacaatcac tgggcccagc ttacggtggg tgctggacca cggctggatg   120
atgggagatg gcaccaggta agctagctct ggtcctcagg ggagggactt cgaaagacgc   180
tccacgatat                                                          190

<210> SEQ ID NO 551
<211> LENGTH: 190
<212> TYPE: DNA
<213> ORGANISM: Artificial Sequence
<220> FEATURE:
<223> OTHER INFORMATION: Synthetic

<400> SEQUENCE: 551
tatacgcagt gctaccatcg atcacgctgc tcttccccgc ttccaacctt cggttgccgg    60
taactacacc ccaggggtgg aaccctagcc aagacttggt aaagcactgc tgggtggctg   120
gccgtgggaa tctaagtcca cacttttagg gagaagggaa gggttgactt cgaaagacgc   180
tccacgatat                                                          190

<210> SEQ ID NO 552
<211> LENGTH: 190
<212> TYPE: DNA
<213> ORGANISM: Artificial Sequence
<220> FEATURE:
<223> OTHER INFORMATION: Synthetic

<400> SEQUENCE: 552

```
tatacgcagt gctaccatcg atcacgccaa atgctcagag gggagtcaac tgagggcagg    60
gaggtcggga ctgcggctcc gatgccctga tttctacatc cccgtatctt atctctgtca   120
cactccagct ggttcctgcc ctggatggct gcctgcgccg ggattgactt cgaaagacgc   180
tccacgatat                                                          190

<210> SEQ ID NO 553
<211> LENGTH: 190
<212> TYPE: DNA
<213> ORGANISM: Artificial Sequence
<220> FEATURE:
<223> OTHER INFORMATION: Synthetic

<400> SEQUENCE: 553
tatacgcagt gctaccatcg atcactctac cactggcccc tttcctcctt gagacccag    60 ctttgaggcc tcaggataat catttctccc cacagacatt ccccagcctc atgcagagcc   120
ctgggccttc tctttggacc tgggactcaa gcaggcagca ggctcgactt cgaaagacgc   180
tccacgatat                                                          190

<210> SEQ ID NO 554
<211> LENGTH: 190
<212> TYPE: DNA
<213> ORGANISM: Artificial Sequence
<220> FEATURE:
<223> OTHER INFORMATION: Synthetic

<400> SEQUENCE: 554
tatacgcagt gctaccatcg atcacacagt ggggcattgc ctgtattcag tggagcctgg    60
agcaatgagg gaagagggga gtccaacatg tcaatattag gaaggtttcc agcccaggga   120
acataacaag actggctcca cagaattgtt tttcattaat aatttgactt cgaaagacgc   180
tccacgatat                                                          190

<210> SEQ ID NO 555
<211> LENGTH: 190
<212> TYPE: DNA
<213> ORGANISM: Artificial Sequence
<220> FEATURE:
<223> OTHER INFORMATION: Synthetic

<400> SEQUENCE: 555
tatacgcagt gctaccatcg atcacggctt atggatggca ctcaggtggg tggtaggggc    60
gagggacata tcttgaagct ccccacagca agcaaacagt tttgacttag actgcatatt   120
tacttggggc aggtgtggtt tcaaaaaggg tcaagccaaa aaaaagactt cgaaagacgc   180
tccacgatat                                                          190

<210> SEQ ID NO 556
<211> LENGTH: 190
<212> TYPE: DNA
<213> ORGANISM: Artificial Sequence
<220> FEATURE:
<223> OTHER INFORMATION: Synthetic

<400> SEQUENCE: 556
tatacgcagt gctaccatcg atcactgggg caggatttaa gtggtgagaa tggccagtag    60
gtggaggcat agcgaagagg cagaattaag gcagctaggg gtgaggccac aggcagtagg   120
cccggctcat tcttccctct ctctctaccg tcccttcccc acacagactt cgaaagacgc   180
```

```
tccacgatat                                                               190

<210> SEQ ID NO 557
<211> LENGTH: 190
<212> TYPE: DNA
<213> ORGANISM: Artificial Sequence
<220> FEATURE:
<223> OTHER INFORMATION: Synthetic

<400> SEQUENCE: 557
tatacgcagt gctaccatcg atcactctgc agaaggtggt gttgtcttct gggtcggggc         60
cagggctgga tctgcccctg tcttgggac tccctcttca gctgaagctg agtatgtcca         120
gggtggtctt gagccaaggg tcgaagatga aggcccttgc cctgcgactt cgaaagacgc        180
tccacgatat                                                               190

<210> SEQ ID NO 558
<211> LENGTH: 190
<212> TYPE: DNA
<213> ORGANISM: Artificial Sequence
<220> FEATURE:
<223> OTHER INFORMATION: Synthetic

<400> SEQUENCE: 558
tatacgcagt gctaccatcg atcaccagtg gaaggtagtg cttttgcaaa ctcaggttgg         60
aggagtggaa aagtggggag aagattctgg atccgagcca ccttaatgct ctaatgccac        120
ctttgcacta cctccctcta ggagaagact cttccacctc tttttgactt cgaaagacgc       180
tccacgatat                                                               190

<210> SEQ ID NO 559
<211> LENGTH: 190
<212> TYPE: DNA
<213> ORGANISM: Artificial Sequence
<220> FEATURE:
<223> OTHER INFORMATION: Synthetic

<400> SEQUENCE: 559
tatacgcagt gctaccatcg atcacggaaa tgaggacttc ttaggctgag atcccagcaa         60
aaaccccgac agacagacat actctggata caggtcactt tctggaagcc aggacccacc        120
tggttccgca gaagctactc cctttgagac cagtttcctg cctctgactt cgaaagacgc       180
tccacgatat                                                               190

<210> SEQ ID NO 560
<211> LENGTH: 190
<212> TYPE: DNA
<213> ORGANISM: Artificial Sequence
<220> FEATURE:
<223> OTHER INFORMATION: Synthetic

<400> SEQUENCE: 560
tatacgcagt gctaccatcg atcaccgtga gagggtcaca gagagatgtg ggtaggggtt         60
ctggaaaaag gggtggaggc agggagaaag aaaaagggag gagagcagag ggagaaagtc        120
gcgtctctct ctctctctcc tagtcttggt ccacttgctg ccttcgactt cgaaagacgc       180
tccacgatat                                                               190

<210> SEQ ID NO 561
<211> LENGTH: 190
<212> TYPE: DNA
<213> ORGANISM: Artificial Sequence
```

<220> FEATURE:
<223> OTHER INFORMATION: Synthetic

<400> SEQUENCE: 561
tatacgcagt gctaccatcg atcaccagac aaatttgtct ctactccatt aagcaagaac    60
tggcttgtgc tggtcccagc tgggaaaaac agacagattt gggaatatct ctcccctcaa   120
agaatacggt gacccagctc tcaaccacag acctctagag aatgcgactt cgaaagacgc   180
tccacgatat                                                         190

<210> SEQ ID NO 562
<211> LENGTH: 190
<212> TYPE: DNA
<213> ORGANISM: Artificial Sequence
<220> FEATURE:
<223> OTHER INFORMATION: Synthetic

<400> SEQUENCE: 562
tatacgcagt gctaccatcg atcactgccc agcatccctc cctggggaac cctcgtatcc    60
aagcccatag cccctacccc tcagctccca gtcttctgcc ctcttaggaa cccttgtgtc   120
ctagcccaaa gctcccagcc tactaaggag ccctggggct aaagtgactt cgaaagacgc   180
tccacgatat                                                         190

<210> SEQ ID NO 563
<211> LENGTH: 190
<212> TYPE: DNA
<213> ORGANISM: Artificial Sequence
<220> FEATURE:
<223> OTHER INFORMATION: Synthetic

<400> SEQUENCE: 563
tatacgcagt gctaccatcg atcacttaaa aagaaccatt aggttaaagc atcctccatc    60
tccagacccc atgagaatcc cagtgtccaa gactcctaat ttcttacaag aatcttttca   120
ccagtaaccc aggcagcagg ctgagtcact cactggagct gctgtgactt cgaaagacgc   180
tccacgatat                                                         190

<210> SEQ ID NO 564
<211> LENGTH: 190
<212> TYPE: DNA
<213> ORGANISM: Artificial Sequence
<220> FEATURE:
<223> OTHER INFORMATION: Synthetic

<400> SEQUENCE: 564
tatacgcagt gctaccatcg atcacccctt ctgcagagat cagccgggac ctaaatgact    60
ccagggtaag gaggccctgg ggagtctgta gggtagaaga cacaaatccc aagcccacc   120 ttctacctct cctaatcttg accctataga ccctctcagg atctagactt cgaaagacgc   180
tccacgatat                                                         190

<210> SEQ ID NO 565
<211> LENGTH: 190
<212> TYPE: DNA
<213> ORGANISM: Artificial Sequence
<220> FEATURE:
<223> OTHER INFORMATION: Synthetic

<400> SEQUENCE: 565
tatacgcagt gctaccatcg atcacttgtt ccgagtgcca atatcctgac cttttgtccc    60
tggaatctcc tcggagctgg cttttctctc ctccctccac cccaccttct ccaggacact    120
gtgccaccaa cctctctttc cccagcctgc cctagattcc aggatgactt cgaaagacgc    180
tccacgatat                                                           190

<210> SEQ ID NO 566
<211> LENGTH: 190
<212> TYPE: DNA
<213> ORGANISM: Artificial Sequence
<220> FEATURE:
<223> OTHER INFORMATION: Synthetic

<400> SEQUENCE: 566
tatacgcagt gctaccatcg atcacatgtt gttcttatta atctcacaca gttcctgaca    60
tattagttct cacatagttc ctgacatact agtctgagcc tgctgggtat caaagatctg    120
ggagggcgtg tgacatggat gaaccatgga gaggctgaga tggaggactt cgaaagacgc    180
tccacgatat                                                           190

<210> SEQ ID NO 567
<211> LENGTH: 190
<212> TYPE: DNA
<213> ORGANISM: Artificial Sequence
<220> FEATURE:
<223> OTHER INFORMATION: Synthetic

<400> SEQUENCE: 567
tatacgcagt gctaccatcg atcactgtga aggctttcat gccctggttt ctttctggag    60
atgctggtgg gaaaggtggg ctccaggaaa aggctggagg tttgtaacag ctcttctcct    120
ggaaattttt cagatctccc ctctctcagc gtgtttccct cagaagactt cgaaagacgc    180
tccacgatat                                                           190

<210> SEQ ID NO 568
<211> LENGTH: 190
<212> TYPE: DNA
<213> ORGANISM: Artificial Sequence
<220> FEATURE:
<223> OTHER INFORMATION: Synthetic

<400> SEQUENCE: 568
tatacgcagt gctaccatcg atcactacag tgcagagaag acatttcttt ctttccaagt    60
gaacatgggg tacaagggta gagactgagc cgggaatccg gaggccaccc ctggctgtgt    120
ttgctaagct ttacgttttg aggataggac caggtttcat ctttagactt cgaaagacgc    180
tccacgatat                                                           190

<210> SEQ ID NO 569
<211> LENGTH: 190
<212> TYPE: DNA
<213> ORGANISM: Artificial Sequence
<220> FEATURE:
<223> OTHER INFORMATION: Synthetic

<400> SEQUENCE: 569
tatacgcagt gctaccatcg atcacaaaca gaggctgtat cacttccgtg ctgcttgcct    60
gaggaaggaa agagcaagtt gcctctgagg tcccttgcag aaggagcctt ccatgttca    120 tgccaattta accaggcact atctttggta gctctatggg tttctgactt cgaaagacgc    180
tccacgatat                                                           190

```
<210> SEQ ID NO 570
<211> LENGTH: 190
<212> TYPE: DNA
<213> ORGANISM: Artificial Sequence
<220> FEATURE:
<223> OTHER INFORMATION: Synthetic

<400> SEQUENCE: 570
tatacgcagt gctaccatcg atcacaccac atccactaga tgagatagga ggtcaaaaat      60
atccagccat tctctagggt ctacaaggac cctttatggt ttggcccctg cctaggtctt     120
caatctcttg ctgtattcat cttgtctttg ctcattaaag cccaggactt cgaaagacgc     180
tccacgatat                                                             190

<210> SEQ ID NO 571
<211> LENGTH: 190
<212> TYPE: DNA
<213> ORGANISM: Artificial Sequence
<220> FEATURE:
<223> OTHER INFORMATION: Synthetic

<400> SEQUENCE: 571
tatacgcagt gctaccatcg atcacttaat ctttcttcaa atcttgccgg ttttccttgg      60
agaggttttt cttctccttt caactgtcac cttaaatcct tagcccagtt tctcaacacc     120
tcacatccaa actgccgtcc acatcctcaa acccactccc tccaggactt cgaaagacgc     180
tccacgatat                                                             190

<210> SEQ ID NO 572
<211> LENGTH: 190
<212> TYPE: DNA
<213> ORGANISM: Artificial Sequence
<220> FEATURE:
<223> OTHER INFORMATION: Synthetic

<400> SEQUENCE: 572
tatacgcagt gctaccatcg atcacagaga accgaagtag acctggctgc agggctggga      60
tctcagggca gtgctgggga ctgggaatgt ggtgttgaga gggcttcagg gagacgtgat     120
gggaagatgg ggaagcctct gcacgtggac agagccaggt ggtgtgactt cgaaagacgc     180
tccacgatat                                                             190

<210> SEQ ID NO 573
<211> LENGTH: 190
<212> TYPE: DNA
<213> ORGANISM: Artificial Sequence
<220> FEATURE:
<223> OTHER INFORMATION: Synthetic

<400> SEQUENCE: 573
tatacgcagt gctaccatcg atcactggcc tttatccatc tctgcgggc ctgtcctagc       60 ttccctcctg gctcggccag cctcccggct ggtctcttcg ctctctttct tgatctctag     120
ctctttattc ctctgacatt ctgccccatc tgctcccgga ctcttgactt cgaaagacgc     180
tccacgatat                                                             190

<210> SEQ ID NO 574
<211> LENGTH: 190
<212> TYPE: DNA
<213> ORGANISM: Artificial Sequence
<220> FEATURE:
<223> OTHER INFORMATION: Synthetic
```

```
<400> SEQUENCE: 574
tatacgcagt gctaccatcg atcacgctgc tgatagtatg agttttaccg aggctgcagg      60
ttttgctccc atgtcggtga cggagggagg agtggtcgct gtggtgattt gtgtgcatca     120
gccagccagg tgtctgtgac agtcggatga cttggaagcc tccccgactt cgaaagacgc     180
tccacgatat                                                            190

<210> SEQ ID NO 575
<211> LENGTH: 190
<212> TYPE: DNA
<213> ORGANISM: Artificial Sequence
<220> FEATURE:
<223> OTHER INFORMATION: Synthetic

<400> SEQUENCE: 575
tatacgcagt gctaccatcg atcactctgg tgaccggcac aggtgcaggt gaggggtgga      60
attcttccaa gagggatggt caagctggga cgttgagaca caggggacag aggacactgt     120
gtgacacgat ttacaatctt tccacactgg gcaccgtccc catcagactt cgaaagacgc     180
tccacgatat                                                            190

<210> SEQ ID NO 576
<211> LENGTH: 190
<212> TYPE: DNA
<213> ORGANISM: Artificial Sequence
<220> FEATURE:
<223> OTHER INFORMATION: Synthetic

<400> SEQUENCE: 576
tatacgcagt gctaccatcg atcactccac ccattcgggg cctacacgaa gtgggtccca      60
tgcaatccat tcctcaggg aactcaaact ccagcccctg ggatgagaag aatccagcaa      120
tgcttgggag agccagagga cttcatggaa gaagtgtcct ctgaggactt cgaaagacgc     180
tccacgatat                                                            190

<210> SEQ ID NO 577
<211> LENGTH: 190
<212> TYPE: DNA
<213> ORGANISM: Artificial Sequence
<220> FEATURE:
<223> OTHER INFORMATION: Synthetic

<400> SEQUENCE: 577
tatacgcagt gctaccatcg atcacagcca tggagagatc ccaccaaggg aaggctgtgg      60
gagattctgc ctttcctccc tgcctctgcc cagggtgctg ggtgtgaact gagggtgggg     120
tgactgttga aggttctaac aagccgtctc tgagagattt gtagcgactt cgaaagacgc     180
tccacgatat                                                            190

<210> SEQ ID NO 578
<211> LENGTH: 190
<212> TYPE: DNA
<213> ORGANISM: Artificial Sequence
<220> FEATURE:
<223> OTHER INFORMATION: Synthetic

<400> SEQUENCE: 578
tatacgcagt gctaccatcg atcacaggct agtgttaggt ctttcatttc aggaactgtg      60
ttcaaagttt ggcttctgaa gggcaccagg agagagatgt tgctattcaa atctgagggt     120
ccagtctctg cggggtggta tgagggtttg cttgtgaatg gtggcgactt cgaaagacgc     180
```
tccacgatat                                                             190

<210> SEQ ID NO 579
<211> LENGTH: 190
<212> TYPE: DNA
<213> ORGANISM: Artificial Sequence
<220> FEATURE:
<223> OTHER INFORMATION: Synthetic

<400> SEQUENCE: 579
tatacgcagt gctaccatcg atcacgtacc cgctttaaaa ggcaccatgc tagcacagct    60
ttaagcatga gtacgaatgc agaggtaaca gatgtgtgcc ttgtcaggac tatgcatggt   120
tgagaagttg gaaatgtaat tggaggcaaa ataacagacc tccacgactt cgaaagacgc   180
tccacgatat                                                           190

<210> SEQ ID NO 580
<211> LENGTH: 190
<212> TYPE: DNA
<213> ORGANISM: Artificial Sequence
<220> FEATURE:
<223> OTHER INFORMATION: Synthetic

<400> SEQUENCE: 580
tatacgcagt gctaccatcg atcacctggg agtcatggct agaagccaga cacaactgcc    60
tgtttccagt ttgtctcatt ttgcctccag aggaaggctc taagacatcc ctgtggctct   120
gtgatcagtc ccagtgcaga acttcagagt gggtagaggg gtgtggactt cgaaagacgc   180
tccacgatat                                                           190

<210> SEQ ID NO 581
<211> LENGTH: 190
<212> TYPE: DNA
<213> ORGANISM: Artificial Sequence
<220> FEATURE:
<223> OTHER INFORMATION: Synthetic

<400> SEQUENCE: 581
tatacgcagt gctaccatcg atcacgggga tagttgaggt tatggtggga accttgggcc    60
ctgctgaccc tgtttcctcc tccctagcct ttatcctcct cttctacctc gttttttatg   120
ggttcctcac cgccatgttc accctcacca tgtgggtgat gctgcgactt cgaaagacgc   180
tccacgatat                                                           190

<210> SEQ ID NO 582
<211> LENGTH: 190
<212> TYPE: DNA
<213> ORGANISM: Artificial Sequence
<220> FEATURE:
<223> OTHER INFORMATION: Synthetic

<400> SEQUENCE: 582
tatacgcagt gctaccatcg atcacaaacc tccagaagga actcatagtt ccttccagga    60
gtttgatttt gatgacccaa tccccacgtg cttggaagtt cttgaaatct gtccaccttc   120
ccatttactg cagttgggag ctgtgtgatt tgggcatgtg gcagagactt cgaaagacgc   180
tccacgatat                                                           190

<210> SEQ ID NO 583
<211> LENGTH: 190
<212> TYPE: DNA

```
<213> ORGANISM: Artificial Sequence
<220> FEATURE:
<223> OTHER INFORMATION: Synthetic

<400> SEQUENCE: 583
tatacgcagt gctaccatcg atcacaactt ctgcctttgt tggctgtagg cttgatgatt      60
cgccccaaga ctgagaacct tgatgtcatt gtcaatgtca gtgacactga aagctgggac     120
cagcatgttc agaagctcaa caagttcttg gagcgtgagt gtggggactt cgaaagacgc     180
tccacgatat                                                            190

<210> SEQ ID NO 584
<211> LENGTH: 190
<212> TYPE: DNA
<213> ORGANISM: Artificial Sequence
<220> FEATURE:
<223> OTHER INFORMATION: Synthetic

<400> SEQUENCE: 584
tatacgcagt gctaccatcg atcacctggt tatgtgtcag ttcaagactt cgggcagggg      60
actggggacc ttggaagtgg aacatctggc ccctgagtct ctccctccca cctctttagc    120
ttacaacgac tctatccaag cccaaaagaa tgatgtctgc cgcccgactt cgaaagacgc    180
tccacgatat                                                            190

<210> SEQ ID NO 585
<211> LENGTH: 190
<212> TYPE: DNA
<213> ORGANISM: Artificial Sequence
<220> FEATURE:
<223> OTHER INFORMATION: Synthetic

<400> SEQUENCE: 585
tatacgcagt gctaccatcg atcacggacg ctattacgaa cagccagata atggagtcct      60
caactacccc aaacgtgcct gccaattcaa ccggacccag ctgggcaact gctccggcat    120
tggggactcc acccactatg gttacagcac tgggcagccc tgtgtgactt cgaaagacgc    180
tccacgatat                                                            190

<210> SEQ ID NO 586
<211> LENGTH: 190
<212> TYPE: DNA
<213> ORGANISM: Artificial Sequence
<220> FEATURE:
<223> OTHER INFORMATION: Synthetic

<400> SEQUENCE: 586
tatacgcagt gctaccatcg atcacttcat caagatgaac cgggtatcta tgaccttggt      60
ccccagggtg aatggaggaa ggatctgggg acaccacctg cagacaattg catcctttca    120
ctggggctaa tgggcatgag aaagacttgg atgtttgtgt agctggactt cgaaagacgc    180
tccacgatat                                                            190

<210> SEQ ID NO 587
<211> LENGTH: 190
<212> TYPE: DNA
<213> ORGANISM: Artificial Sequence
<220> FEATURE:
<223> OTHER INFORMATION: Synthetic

<400> SEQUENCE: 587
tatacgcagt gctaccatcg atcactcccc ggcttagctt ggtctggatg cccatcttcg      60
```
acaacttctt cctctgactc tcttcacctt ccaccctcac tccaggtcat caacttctat    120
gcaggagcaa accagagcat gaatgttacc tgtgctggga aggtggactt cgaaagacgc    180
tccacgatat                                                          190

<210> SEQ ID NO 588
<211> LENGTH: 190
<212> TYPE: DNA
<213> ORGANISM: Artificial Sequence
<220> FEATURE:
<223> OTHER INFORMATION: Synthetic

<400> SEQUENCE: 588
tatacgcagt gctaccatcg atcaccgcac tcctcttgct tctctctggg atgcagaggc     60
ctgctctcct aggggccaga cacacgcccc cctccaccaa cgccctggcc tctggcttct    120
ctccctaacg cttccacctt ctccttcatt cccagattgt ccgtagactt cgaaagacgc    180
tccacgatat                                                          190

<210> SEQ ID NO 589
<211> LENGTH: 190
<212> TYPE: DNA
<213> ORGANISM: Artificial Sequence
<220> FEATURE:
<223> OTHER INFORMATION: Synthetic

<400> SEQUENCE: 589
tatacgcagt gctaccatcg atcacccggt ctgtcctttc tagaaactgg ctgctccctc     60
cacatcccct tccttgcttc ctattcaacc cttaatcatg tatctcttct ttcttggctc    120
tgctccagaa actgattcct gaggatgggg taagaacttg gggtagactt cgaaagacgc    180
tccacgatat                                                          190

<210> SEQ ID NO 590
<211> LENGTH: 190
<212> TYPE: DNA
<213> ORGANISM: Artificial Sequence
<220> FEATURE:
<223> OTHER INFORMATION: Synthetic

<400> SEQUENCE: 590
tatacgcagt gctaccatcg atcacacagc gagatgaaga tgctgagaat ctcggcaact     60
tcgtcatgtt ccccgccaac ggcaacatcg acctcatgta cttcccctac tatggcaaaa    120
agttccacgt aagtcccagg ggaggcccag gctgatggcg ggtgcgactt cgaaagacgc    180
tccacgatat                                                          190

<210> SEQ ID NO 591
<211> LENGTH: 190
<212> TYPE: DNA
<213> ORGANISM: Artificial Sequence
<220> FEATURE:
<223> OTHER INFORMATION: Synthetic

<400> SEQUENCE: 591
tatacgcagt gctaccatcg atcacaacgt ggaggtgaat gtagaatgtc gcatcaacgc     60
cgccaacatc gccacagacg atgagcgaga caagttcgcc ggccgcgtgg ccttcaaact    120
ccgcatcaac aaaacctgag gccccttcct cccaccccat ctctcgactt cgaaagacgc    180
tccacgatat                                                          190

<210> SEQ ID NO 592
<211> LENGTH: 190
<212> TYPE: DNA
<213> ORGANISM: Artificial Sequence
<220> FEATURE:
<223> OTHER INFORMATION: Synthetic

<400> SEQUENCE: 592
tatacgcagt gctaccatcg atcaccctgt ggatgctcct ggaatgtccc tgaccctgcc        60
tgatccctcc ctcacccacc ccaaaggtat ttttgataac agagctatga cttgtctgag       120
cctcacatcc ttttccttga cttctcaacc cagcctgaag tccatgactt cgaaagacgc       180
tccacgatat                                                              190

<210> SEQ ID NO 593
<211> LENGTH: 190
<212> TYPE: DNA
<213> ORGANISM: Artificial Sequence
<220> FEATURE:
<223> OTHER INFORMATION: Synthetic

<400> SEQUENCE: 593
tatacgcagt gctaccatcg atcacgcggt tccgtcactc gcctttccca ccaacttctc        60
ccaacctcag atcagtcaga cagggagctg ggctaagatg gccacggagg agttaggagc       120
ctttctagtt ctggtttagc tgtgagagct atccactctc ctgccgactt cgaaagacgc       180
tccacgatat                                                              190

<210> SEQ ID NO 594
<211> LENGTH: 190
<212> TYPE: DNA
<213> ORGANISM: Artificial Sequence
<220> FEATURE:
<223> OTHER INFORMATION: Synthetic

<400> SEQUENCE: 594
tatacgcagt gctaccatcg atcacaacgt gcacacgcgt ctcatttgac cccttttgctt       60 ccagagatga atgtggcact ccctccttcc attcctaagc tctggccacc gtcccttgat      120
ctctcatact ttctccctgt ctacacagtc gccatcttgg tgactgactt cgaaagacgc      180
tccacgatat                                                              190

<210> SEQ ID NO 595
<211> LENGTH: 190
<212> TYPE: DNA
<213> ORGANISM: Artificial Sequence
<220> FEATURE:
<223> OTHER INFORMATION: Synthetic

<400> SEQUENCE: 595
tatacgcagt gctaccatcg atcactgaat ttatctggct cctgggcagg tcttctcctc        60
ctctccatcc ctattccctc ctctgaaatg caccccttg taattgagga caaggtggtt       120
ctgtggcctt ttccctcttt gctggcacgt tctgcttctc accctgactt cgaaagacgc      180
tccacgatat                                                              190

<210> SEQ ID NO 596
<211> LENGTH: 190
<212> TYPE: DNA
<213> ORGANISM: Artificial Sequence
<220> FEATURE:
<223> OTHER INFORMATION: Synthetic

```
<400> SEQUENCE: 596
tatacgcagt gctaccatcg atcacaaccc ataatgccca cagaatgtca aatgaggggc      60
ctcctgcctc ctgctctgaa tattctgtag ctgtagaggc atttaaccc tttgtcctcc     120 agcatccctt cacttcctca tcctctctaa cctccttttt cttttgactt cgaaagacgc    180
tccacgatat                                                           190

<210> SEQ ID NO 597
<211> LENGTH: 190
<212> TYPE: DNA
<213> ORGANISM: Artificial Sequence
<220> FEATURE:
<223> OTHER INFORMATION: Synthetic

<400> SEQUENCE: 597
tatacgcagt gctaccatcg atcacggaag ctcatcaagg tgacctgtct acagaggcaa    60
ggacagggac tgagcttcag gagctctagt ttgcctgctg ggtagggaca gatgtttaag   120
ttaaaagtct ctgaaagagg cgggtctgga tctcctgggg agagtgactt cgaaagacgc   180
tccacgatat                                                          190

<210> SEQ ID NO 598
<211> LENGTH: 190
<212> TYPE: DNA
<213> ORGANISM: Artificial Sequence
<220> FEATURE:
<223> OTHER INFORMATION: Synthetic

<400> SEQUENCE: 598
tatacgcagt gctaccatcg atcactttgg cattccctag taagaaagag aaaaaaaaaa    60
ggtggtcttg aggtcaggaa ggctggtggc ttcatagctg tctgggatcc ttggggcaag   120
gcaaggggct cctgcttgca ccttcagcct ggttgatgag ctgacgactt cgaaagacgc   180
tccacgatat                                                          190

<210> SEQ ID NO 599
<211> LENGTH: 190
<212> TYPE: DNA
<213> ORGANISM: Artificial Sequence
<220> FEATURE:
<223> OTHER INFORMATION: Synthetic

<400> SEQUENCE: 599
tatacgcagt gctaccatcg atcacctccc tgggagccag cagccctgag gagcatgggc    60
aggcagtact gagctcctca acccgactct cctccctatc ccaagaagcc ctttgaaagg   120
ttttcctggc agagtttaaa gcttcaattc attcagctac ctggcgactt cgaaagacgc   180
tccacgatat                                                          190

<210> SEQ ID NO 600
<211> LENGTH: 190
<212> TYPE: DNA
<213> ORGANISM: Artificial Sequence
<220> FEATURE:
<223> OTHER INFORMATION: Synthetic

<400> SEQUENCE: 600
tatacgcagt gctaccatcg atcacgaccc tggctagcag gcctcccact ggcctctctc    60
catccagtag cacccacccc tgttcccctt gggaacccag gtatcctgcc actttctgat   120
```

```
ggagcagatg gccaccctgg aggctcagcc ttgctaaatc agacagactt cgaaagacgc    180
tccacgatat                                                           190

<210> SEQ ID NO 601
<211> LENGTH: 190
<212> TYPE: DNA
<213> ORGANISM: Artificial Sequence
<220> FEATURE:
<223> OTHER INFORMATION: Synthetic

<400> SEQUENCE: 601
tatacgcagt gctaccatcg atcaccagcc cacactcatt gcagactcag gtggctgctt    60
cccagcacct cctcactcac ccctgcacct gctgaccccca gtagcctgca ctggcgttca   120
cccctcagac acacaggtgg cagcaaagtt ttattgtaaa ataaggactt cgaaagacgc    180
tccacgatat                                                           190

<210> SEQ ID NO 602
<211> LENGTH: 190
<212> TYPE: DNA
<213> ORGANISM: Artificial Sequence
<220> FEATURE:
<223> OTHER INFORMATION: Synthetic

<400> SEQUENCE: 602
tatacgcagt gctaccatcg atcacaattg accctgagca taaaacaagt cttggtggat    60
ccagatcatc atatacaaga gatgaaatcc tccagggtgt gggatggggt gagatttcct    120
tttaggtact aaggttcacc aagaggttgt cagacagggt ttggcgactt cgaaagacgc    180
tccacgatat                                                           190

<210> SEQ ID NO 603
<211> LENGTH: 190
<212> TYPE: DNA
<213> ORGANISM: Artificial Sequence
<220> FEATURE:
<223> OTHER INFORMATION: Synthetic

<400> SEQUENCE: 603
tatacgcagt gctaccatcg atcacgaagt gggcccctac ctagaatgtg gctgattgta    60
aactaaccct taactgcaag aacatttctt acatctccca acatccctc acagtaaaaa    120 ccttaaaatc taagctggta tgtcctactc cccatcctcc tccccgactt cgaaagacgc    180
tccacgatat                                                           190

<210> SEQ ID NO 604
<211> LENGTH: 190
<212> TYPE: DNA
<213> ORGANISM: Artificial Sequence
<220> FEATURE:
<223> OTHER INFORMATION: Synthetic

<400> SEQUENCE: 604
tatacgcagt gctaccatcg atcaccaaca aaacaccagt gcaggccaac ttgttcagtg    60
gagccccggg acaaagcaaa tggaagtcct gggtgcttct gacgcacacc tattgcaagc   120
aagggttcaa agacccaaaa cccaaaatgg caggggaggg agagagactt cgaaagacgc    180
tccacgatat                                                           190

<210> SEQ ID NO 605
<211> LENGTH: 190
```

```
<212> TYPE: DNA
<213> ORGANISM: Artificial Sequence
<220> FEATURE:
<223> OTHER INFORMATION: Synthetic

<400> SEQUENCE: 605
tatacgcagt gctaccatcg atcactggga ggctgtcagt ggggaacaag aagtggagaa    60
tgtcagtctg agtcaggccc ttctgtcttg aacatgagtt ttttatggcg ggaggtagac   120
tgaccctttt tggacttcag gtggctgtag gagacagaag caggggactt cgaaagacgc   180
tccacgatat                                                          190

<210> SEQ ID NO 606
<211> LENGTH: 190
<212> TYPE: DNA
<213> ORGANISM: Artificial Sequence
<220> FEATURE:
<223> OTHER INFORMATION: Synthetic

<400> SEQUENCE: 606
tatacgcagt gctaccatcg atcacggaga gatgacatca catgagtgag agggtctgtg    60 cccctttttcc ctgaccaatg ctttgaaggg cctaaggctg gacaacggg aattcaaatc   120 aagatggtgg ccacacccca tgcaaatatg tttactgagc acctcgactt cgaaagacgc   180
tccacgatat                                                          190

<210> SEQ ID NO 607
<211> LENGTH: 190
<212> TYPE: DNA
<213> ORGANISM: Artificial Sequence
<220> FEATURE:
<223> OTHER INFORMATION: Synthetic

<400> SEQUENCE: 607
tatacgcagt gctaccatcg atcacggtgc atggcagggc tgagtatatg acctgaaact    60
ctggctgtat tcagtattac acaattatta ggcccctcct tgagaccctc cagctctggg   120
ctgggagttg cggagaatgg caaagaagta tccacactcg tccctgactt cgaaagacgc   180
tccacgatat                                                          190

<210> SEQ ID NO 608
<211> LENGTH: 190
<212> TYPE: DNA
<213> ORGANISM: Artificial Sequence
<220> FEATURE:
<223> OTHER INFORMATION: Synthetic

<400> SEQUENCE: 608
tatacgcagt gctaccatcg atcacggttt ggatgttctg tggatacact gaggcaagaa    60
tgtggttata ggattcaacc ggaggaagac taaaaaaatg tctgtgcagg gctgggaccc   120
aatgagatgg ggtcagctgc ctttgaccat gaaggcagga tgagagactt cgaaagacgc   180
tccacgatat                                                          190

<210> SEQ ID NO 609
<211> LENGTH: 190
<212> TYPE: DNA
<213> ORGANISM: Artificial Sequence
<220> FEATURE:
<223> OTHER INFORMATION: Synthetic

<400> SEQUENCE: 609
```

```
tatacgcagt gctaccatcg atcaccagtc aagaagaaaa cggcattttg agtgttagac      60
tggaaacttt ccacttgata agaggtccca agacttagta cctgaagggt gaaatattct     120
ccatccagtg gtttcttctt tggctgggga gaggagctgg tgttggactt cgaaagacgc     180
tccacgatat                                                             190

<210> SEQ ID NO 610
<211> LENGTH: 190
<212> TYPE: DNA
<213> ORGANISM: Artificial Sequence
<220> FEATURE:
<223> OTHER INFORMATION: Synthetic

<400> SEQUENCE: 610
tatacgcagt gctaccatcg atcaccagct cgtggtgagg ctccccttc ttgcggagat      60 tctcttcctc tgtgcgccgg tctctcccag gacaggcaca aacacgcacc tcaaagctgt    120
tccgtcccag tagattacca ctactcagga taggaaaaga gaagcgactt cgaaagacgc    180
tccacgatat                                                             190

<210> SEQ ID NO 611
<211> LENGTH: 190
<212> TYPE: DNA
<213> ORGANISM: Artificial Sequence
<220> FEATURE:
<223> OTHER INFORMATION: Synthetic

<400> SEQUENCE: 611
tatacgcagt gctaccatcg atcacagagg cagtaaggaa atcaggtcct acctgtccca     60
tttaaaaaac caggctccat ctactcccaa ccaccttgt cctttctgga gcctaagctc    120
cagctccagg taggtggagg agaagccaca ggttaagagg tcccagactt cgaaagacgc    180
tccacgatat                                                             190

<210> SEQ ID NO 612
<211> LENGTH: 190
<212> TYPE: DNA
<213> ORGANISM: Artificial Sequence
<220> FEATURE:
<223> OTHER INFORMATION: Synthetic

<400> SEQUENCE: 612
tatacgcagt gctaccatcg atcacagcca gagaaaagaa aactgagtgg gagcagtaag     60
gagattcccc gccggggatg tgatgagagg tggatgggta gtagtatgga agaaatcggt    120
aagaggtggg cccaggggtc agaggcaagc agaggctggg gcacagactt cgaaagacgc    180
tccacgatat                                                             190

<210> SEQ ID NO 613
<211> LENGTH: 190
<212> TYPE: DNA
<213> ORGANISM: Artificial Sequence
<220> FEATURE:
<223> OTHER INFORMATION: Synthetic

<400> SEQUENCE: 613
tatacgcagt gctaccatcg atcaccaggc cagtgtgcag ggtggcaagt ggctcctgac     60
ctggagtctt ccagtgtgat gatggtgagg atgggcctcc ggttcatgcc gcccatgcag    120
gaactgttac acatgtagtt gtagtggatg gtggtacagt cagaggactt cgaaagacgc    180
tccacgatat                                                             190
```

<210> SEQ ID NO 614
<211> LENGTH: 190
<212> TYPE: DNA
<213> ORGANISM: Artificial Sequence
<220> FEATURE:
<223> OTHER INFORMATION: Synthetic

<400> SEQUENCE: 614

```
tatacgcagt gctaccatcg atcacctact gctcacctgg agggccactg acaaccaccc      60
ttaacccctc ctcccagaga ccccagttgc aaaccagacc tcaggcggct catagggcac     120
caccacacta tgtcgaaaag tgtttctgtc atccaaatac tccacgactt cgaaagacgc     180
tccacgatat                                                             190
```

<210> SEQ ID NO 615
<211> LENGTH: 190
<212> TYPE: DNA
<213> ORGANISM: Artificial Sequence
<220> FEATURE:
<223> OTHER INFORMATION: Synthetic

<400> SEQUENCE: 615

```
tatacgcagt gctaccatcg atcaccgcaa atttccttcc actcggataa gatgctgagg      60
aggggccaga cctaagagca atcagtgagg aatcagaggc ctggggaccc tgggcaacca     120
gccctgtcgt ctctccagcc ccagctgctc accatcgcta tctgagactt cgaaagacgc     180
tccacgatat                                                             190
```

<210> SEQ ID NO 616
<211> LENGTH: 190
<212> TYPE: DNA
<213> ORGANISM: Artificial Sequence
<220> FEATURE:
<223> OTHER INFORMATION: Synthetic

<400> SEQUENCE: 616

```
tatacgcagt gctaccatcg atcactgtgg aatcaaccca cagctgcaca gggcaggtct      60
tggccagttg gcaaaacatc ttgttgaggg caggggagta ctgtaggaag aggaaggaga     120
cagagttgaa agtcagggca caagtgaaca gataaagcaa ctggagactt cgaaagacgc     180
tccacgatat                                                             190
```

<210> SEQ ID NO 617
<211> LENGTH: 190
<212> TYPE: DNA
<213> ORGANISM: Artificial Sequence
<220> FEATURE:
<223> OTHER INFORMATION: Synthetic

<400> SEQUENCE: 617

```
tatacgcagt gctaccatcg atcacatacg gccaggcatt gaagtctcat ggaagccagc      60
ccctcagggc aactgaccgt gcaagtcaca gacttggctg tcccagaatg caagaagccc     120
agacggaaac cgtagctgcc ctggtaggtt ttctgggaag ggacagactt cgaaagacgc     180
tccacgatat                                                             190
```

<210> SEQ ID NO 618
<211> LENGTH: 190
<212> TYPE: DNA
<213> ORGANISM: Artificial Sequence
<220> FEATURE:

<223> OTHER INFORMATION: Synthetic

<400> SEQUENCE: 618

| | |
|---|---|
| tatacgcagt gctaccatcg atcacaccct tccccacctg atacacggct ccatttcttt | 60 |
| gattcctttc actgcaaagc ttctggaaga acaactgtct caccgctcac ctgcccattc | 120 |
| tcttcggaca ctcctcagcc ctgcattaca aaccctcac gaatggactt cgaaagacgc | 180 |
| tccacgatat | 190 |

<210> SEQ ID NO 619
<211> LENGTH: 190
<212> TYPE: DNA
<213> ORGANISM: Artificial Sequence
<220> FEATURE:
<223> OTHER INFORMATION: Synthetic

<400> SEQUENCE: 619

| | |
|---|---|
| tatacgcagt gctaccatcg atcacgaata acacacaagc ctgttatatg agaggttaag | 60 |
| agagcgagaa agagcaaggg gcagcccctg tgtggaccag catcttgcac gaagttatgc | 120 |
| aactatcatc gcaccttctc ccagacaagc tttcaaaggc tttgcgactt cgaaagacgc | 180 |
| tccacgatat | 190 |

<210> SEQ ID NO 620
<211> LENGTH: 190
<212> TYPE: DNA
<213> ORGANISM: Artificial Sequence
<220> FEATURE:
<223> OTHER INFORMATION: Synthetic

<400> SEQUENCE: 620

| | |
|---|---|
| tatacgcagt gctaccatcg atcacgccca aagtctcaat cccacttgga gggacacagg | 60 |
| tctacagaca ggtctccctg tctttatctc tcaaatcttc agtagcaact aaaatctccg | 120 |
| tgttttcag agcaggacct tcccaggggt accagcatca gtgggacttt cgaaagacgc | 180 |
| tccacgatat | 190 |

<210> SEQ ID NO 621
<211> LENGTH: 190
<212> TYPE: DNA
<213> ORGANISM: Artificial Sequence
<220> FEATURE:
<223> OTHER INFORMATION: Synthetic

<400> SEQUENCE: 621

| | |
|---|---|
| tatacgcagt gctaccatcg atcaccagga tacaaatgtg ccaggctgaa ctaggccttc | 60 |
| caaatggcca gggagccaag agaaatgcag gtgcccttgg ctgggtggga aggcaatgag | 120 |
| atcaactgag accccaaaca ggggcaggcc tgaccagaat cttaagactt cgaaagacgc | 180 |
| tccacgatat | 190 |

<210> SEQ ID NO 622
<211> LENGTH: 190
<212> TYPE: DNA
<213> ORGANISM: Artificial Sequence
<220> FEATURE:
<223> OTHER INFORMATION: Synthetic

<400> SEQUENCE: 622

| | |
|---|---|
| tatacgcagt gctaccatcg atcacagatg acgtaagtac ggcacaaagt ggccggtacg | 60 |
| cggcaggtgc atgggaagaa actgcggaat gaaacaaccg cgagctaaga gatggggcag | 120 | cgggagaaat gaattcgagt tccgcctcct accaggaaga accgggactt cgaaagacgc    180 tccacgatat                                                            190

<210> SEQ ID NO 623
<211> LENGTH: 190
<212> TYPE: DNA
<213> ORGANISM: Artificial Sequence
<220> FEATURE:
<223> OTHER INFORMATION: Synthetic

<400> SEQUENCE: 623
tatacgcagt gctaccatcg atcactcggg ccggagggct gcacggagga ccacacggac    60
gcctgcgggc ccgccccttc cgcttcacga cgttcagcct gcgtctggaa ctggaatggc   120
ctagcccaaa gctagataac aggtagattg tttttccgac aaattgactt cgaaagacgc   180
tccacgatat                                                            190

<210> SEQ ID NO 624
<211> LENGTH: 190
<212> TYPE: DNA
<213> ORGANISM: Artificial Sequence
<220> FEATURE:
<223> OTHER INFORMATION: Synthetic

<400> SEQUENCE: 624
tatacgcagt gctaccatcg atcacttcaa aatttgattc tcagacgtac ccattctttt    60
tttttttcct ccgggaagat gagatatact cattcttgaa ataccteeg ggcttgcctt   120 ctgcacactt ctttccctcc ctgtctcacg ccatggtagc gtccggactt cgaaagacgc   180
tccacgatat                                                            190

<210> SEQ ID NO 625
<211> LENGTH: 190
<212> TYPE: DNA
<213> ORGANISM: Artificial Sequence
<220> FEATURE:
<223> OTHER INFORMATION: Synthetic

<400> SEQUENCE: 625
tatacgcagt gctaccatcg atcacctagg ttgcaggcga cccgcggggt ggggcacacc    60
attcaaagaa ggggagggat tgaggtttgc atcaaaacaa atacccctgc ctttgcaaag   120
gccataacta agtaatccag aaaaagaaat gcaggcggag aataggactt cgaaagacgc   180
tccacgatat                                                            190

<210> SEQ ID NO 626
<211> LENGTH: 190
<212> TYPE: DNA
<213> ORGANISM: Artificial Sequence
<220> FEATURE:
<223> OTHER INFORMATION: Synthetic

<400> SEQUENCE: 626
tatacgcagt gctaccatcg atcacagcct ccctctgcca agtaagagga accggcctaa    60
aggacatttt ctctctctct cctcccctct catcgggtga atagtgagct gctccggcaa   120
aaagaaaccg gaaatgctgc tgcaagaggc agaaatgtaa atgtggactt cgaaagacgc   180
tccacgatat                                                            190

<210> SEQ ID NO 627

```
<211> LENGTH: 190
<212> TYPE: DNA
<213> ORGANISM: Artificial Sequence
<220> FEATURE:
<223> OTHER INFORMATION: Synthetic

<400> SEQUENCE: 627
tatacgcagt gctaccatcg atcactcgga atggagcccc agttttcact aggatgccat      60
gggctctaaa atatacagct atgagttctc aatgtttcga gatccaaaag tctcagacct     120
caatgctttg tgcatctttt atttcaggga ttccctacgc ccagcgactt cgaaagacgc     180
tccacgatat                                                            190

<210> SEQ ID NO 628
<211> LENGTH: 190
<212> TYPE: DNA
<213> ORGANISM: Artificial Sequence
<220> FEATURE:
<223> OTHER INFORMATION: Synthetic

<400> SEQUENCE: 628
tatacgcagt gctaccatcg atcacccggg tggatgtgca aagaagtacg ctttaggccg      60
gctcaaggtt ccccaaagct ccactcctct gcctaggcgt tcaactttga gttcggatgg     120
tcctaacatc cccatcatct acacccaggt ctcccaacaa tgcaagactt cgaaagacgc     180
tccacgatat                                                            190

<210> SEQ ID NO 629
<211> LENGTH: 190
<212> TYPE: DNA
<213> ORGANISM: Artificial Sequence
<220> FEATURE:
<223> OTHER INFORMATION: Synthetic

<400> SEQUENCE: 629
tatacgcagt gctaccatcg atcacagccc cagcgatttt cccgagctga aaatacacgg      60
agccgagagc ccgtgactca gagaggactc atcaagttca gtcaggagct tacccaatcc     120
agggaagcgt gtcaccgtcg tggaaagcac gctcccagcc cgaacgactt cgaaagacgc     180
tccacgatat                                                            190

<210> SEQ ID NO 630
<211> LENGTH: 190
<212> TYPE: DNA
<213> ORGANISM: Artificial Sequence
<220> FEATURE:
<223> OTHER INFORMATION: Synthetic

<400> SEQUENCE: 630
tatacgcagt gctaccatcg atcaccaaag tgtccccgga gcccagcagc tacctgctcc      60
ctggacggtg gctctagact tttgagaagc tcaaaacttt tagcgccagt cttgagcaca     120
tgggagggga aaaccccaat cccatcaacc cctgcgaggc tcctggactt cgaaagacgc     180
tccacgatat                                                            190

<210> SEQ ID NO 631
<211> LENGTH: 190
<212> TYPE: DNA
<213> ORGANISM: Artificial Sequence
<220> FEATURE:
<223> OTHER INFORMATION: Synthetic

<400> SEQUENCE: 631
```

| | | |
|---|---|---|
| tatacgcagt gctaccatcg atcaccacaa agctggacag tcgccatgac aagtaagggc | 60 | |
| aagtaatccg cctgccggag gaagcaaagg aaatggagtt ggggaggagg gtgcagagtc | 120 | |
| aggattctcg ccgacctggt gccgtagata ctaacatttt ggggtgactt cgaaagacgc | 180 | |
| tccacgatat | 190 | |

<210> SEQ ID NO 632
<211> LENGTH: 190
<212> TYPE: DNA
<213> ORGANISM: Artificial Sequence
<220> FEATURE:
<223> OTHER INFORMATION: Synthetic

<400> SEQUENCE: 632

| | | |
|---|---|---|
| tatacgcagt gctaccatcg atcacgtagg cgcttctcgc caagatagaa gcgttcagac | 60 | |
| tacaactccc agcagccacg aggagcccta gggcttgatg ggaacgggaa accttctaac | 120 | |
| ctttcacgtc ccggctccgc gggttccgtg ggtcgcccgc gaaatgactt cgaaagacgc | 180 | |
| tccacgatat | 190 | |

<210> SEQ ID NO 633
<211> LENGTH: 190
<212> TYPE: DNA
<213> ORGANISM: Artificial Sequence
<220> FEATURE:
<223> OTHER INFORMATION: Synthetic

<400> SEQUENCE: 633

| | | |
|---|---|---|
| tatacgcagt gctaccatcg atcacgccca atcggaaggt ggaccgaaat cccgcgacag | 60 | |
| caagaggccc gtagcgaccc gcggtgctaa ggaacacagt gctttcaaaa gaattggcgt | 120 | |
| ccgctgttcg cctctcctcc cgggagtctt ctgcctactc ccagagactt cgaaagacgc | 180 | |
| tccacgatat | 190 | |

<210> SEQ ID NO 634
<211> LENGTH: 190
<212> TYPE: DNA
<213> ORGANISM: Artificial Sequence
<220> FEATURE:
<223> OTHER INFORMATION: Synthetic

<400> SEQUENCE: 634

| | | |
|---|---|---|
| tatacgcagt gctaccatcg atcacgagga gggaagcaca ggtgggtttc tttagctctg | 60 | |
| cgtcggatcc ctgagaactt cgaagccatc ctggctgagg ctaatctccg ctgtgcttcc | 120 | |
| tctgcagtat gaagactttg gagactcaac cgttagctcc ggactgactt cgaaagacgc | 180 | |
| tccacgatat | 190 | |

<210> SEQ ID NO 635
<211> LENGTH: 190
<212> TYPE: DNA
<213> ORGANISM: Artificial Sequence
<220> FEATURE:
<223> OTHER INFORMATION: Synthetic

<400> SEQUENCE: 635

| | | |
|---|---|---|
| tatacgcagt gctaccatcg atcacaccca gtttctctct ccactcccct ggaaacagag | 60 | |
| tttggttccc ctagtgagtt gagtcctcga atcgaggagc aagaactttc tgaaaataca | 120 | |
| agccttcctg cagaagaagc aaacgggagc ctttctgaag aagaagactt cgaaagacgc | 180 | | tccacgatat                                                                  190

<210> SEQ ID NO 636
<211> LENGTH: 190
<212> TYPE: DNA
<213> ORGANISM: Artificial Sequence
<220> FEATURE:
<223> OTHER INFORMATION: Synthetic

<400> SEQUENCE: 636
tatacgcagt gctaccatcg atcaccgaac gggccagagt tggggtctgg aaaagccatg      60
gaagatacct ctggggaacc cgctgcagag gacgagggag acacgtaagt ggtgatggca     120
gtggagtgtg gagtctgggg agatgaagtg tgaggtcgat ctgtcgactt cgaaagacgc     180
tccacgatat                                                            190

<210> SEQ ID NO 637
<211> LENGTH: 190
<212> TYPE: DNA
<213> ORGANISM: Artificial Sequence
<220> FEATURE:
<223> OTHER INFORMATION: Synthetic

<400> SEQUENCE: 637
tatacgcagt gctaccatcg atcacatctt cctttcagcg cttggaacta cagcttctcc      60
cagctgcctc gatttctcag tggttcctgg tcagagttca gcaccaacc tgagaacttc     120 ttgaaaggct gtaagtggta aggataacaa cggggcaggg agctggactt cgaaagacgc     180
tccacgatat                                                            190

<210> SEQ ID NO 638
<211> LENGTH: 190
<212> TYPE: DNA
<213> ORGANISM: Artificial Sequence
<220> FEATURE:
<223> OTHER INFORMATION: Synthetic

<400> SEQUENCE: 638
tatacgcagt gctaccatcg atcacgctta cctaccccag aggcaggctc agccctagcc      60
ctacacttga aaagcatagg tctggccagc tttctaactc tcccctgttt ctagggctcc     120
tgacggttcc tgcatcttga ccaatagtgc tgataacatc ttgcggactt cgaaagacgc     180
tccacgatat                                                            190

<210> SEQ ID NO 639
<211> LENGTH: 190
<212> TYPE: DNA
<213> ORGANISM: Artificial Sequence
<220> FEATURE:
<223> OTHER INFORMATION: Synthetic

<400> SEQUENCE: 639
tatacgcagt gctaccatcg atcacagcag gtggaatatg cagaaatggt aaggactggg      60
gctaactgcc tcttcatcaa tgctgcacat ttaagtcctt cgtggagatg gaaaaagtgt     120
agtccaagtg tttcctgttc acaaacggga ctgtttttca agacggactt cgaaagacgc     180
tccacgatat                                                            190

<210> SEQ ID NO 640
<211> LENGTH: 190
<212> TYPE: DNA
<213> ORGANISM: Artificial Sequence

```
<220> FEATURE:
<223> OTHER INFORMATION: Synthetic

<400> SEQUENCE: 640
tatacgcagt gctaccatcg atcacttcca tatacttgtg tgtactgagt cttcttccca    60
atatagtttc tcgggttttc tcctttcttt tccacctttt cacagaactt tctgcaagtc   120
tcatttccag ctccccagcg tctttcctga gtacttgccc tgcccgactt cgaaagacgc   180
tccacgatat                                                           190

<210> SEQ ID NO 641
<211> LENGTH: 190
<212> TYPE: DNA
<213> ORGANISM: Artificial Sequence
<220> FEATURE:
<223> OTHER INFORMATION: Synthetic

<400> SEQUENCE: 641
tatacgcagt gctaccatcg atcacgtggg tcttgcagga agcctttact cctcgtcttg    60
ccctctccag gagacacttt gcatcctctg tacccttat ctctcagggt ggggacgggg    120
aatgtcctca ttcccaaatg ctgtagccac acaattgctc tttcggactt cgaaagacgc   180
tccacgatat                                                           190

<210> SEQ ID NO 642
<211> LENGTH: 190
<212> TYPE: DNA
<213> ORGANISM: Artificial Sequence
<220> FEATURE:
<223> OTHER INFORMATION: Synthetic

<400> SEQUENCE: 642
tatacgcagt gctaccatcg atcaccccttt tgctcattaa aaccgtattt gttgactctg   60
cttattctgc accacgtgtt ggggaagcag tggtgagagc gaggcagatg tgattccctc   120
cttctctgat aggtatgacg aaggggagt gaggagcacc aggggacttt cgaaagacgc   180
tccacgatat                                                           190

<210> SEQ ID NO 643
<211> LENGTH: 190
<212> TYPE: DNA
<213> ORGANISM: Artificial Sequence
<220> FEATURE:
<223> OTHER INFORMATION: Synthetic

<400> SEQUENCE: 643
tatacgcagt gctaccatcg atcacaaagt atgaatctat atggcttttg gtggctaaat   60
ttgacattaa agtctgagct cacccttgaa cattgagaca gagtctgtgc tccatatata   120
caccccatct gccacaacac tgctagaggc acgcgcctca gactcgactt cgaaagacgc   180
tccacgatat                                                           190

<210> SEQ ID NO 644
<211> LENGTH: 190
<212> TYPE: DNA
<213> ORGANISM: Artificial Sequence
<220> FEATURE:
<223> OTHER INFORMATION: Synthetic

<400> SEQUENCE: 644
tatacgcagt gctaccatcg atcacgtctc tgtataggtc cctgtccttc gaatggtgga   60
```

```
aggtgatacc atctatgatt actgctggta ttctctgatg tcctcagccc agccagacac        120
ctcctagtaa gtaatgtttg cctccctgct cgccgcccca ccaccgactt cgaaagacgc        180
tccacgatat                                                                190

<210> SEQ ID NO 645
<211> LENGTH: 190
<212> TYPE: DNA
<213> ORGANISM: Artificial Sequence
<220> FEATURE:
<223> OTHER INFORMATION: Synthetic

<400> SEQUENCE: 645
tatacgcagt gctaccatcg atcacattcc tccccttcct ttgacagcac cggggtttca        60
gtgtccatgt ctctctcagc gtggccagca gcagccggga gaacccgatt catatctggg        120
acgcattcac tggagagctc cgggcttcct ttcgcgccta caaccgactt cgaaagacgc        180
tccacgatat                                                                190

<210> SEQ ID NO 646
<211> LENGTH: 190
<212> TYPE: DNA
<213> ORGANISM: Artificial Sequence
<220> FEATURE:
<223> OTHER INFORMATION: Synthetic

<400> SEQUENCE: 646
tatacgcagt gctaccatcg atcaccatac cctgtcagct gtggagcttt tggtctctga        60
aatctttcta gaaaattgtt gataaagctg attccgtttt cctgtaggcc ttcaacttgc        120
atctctccaa ggaagaactg ggatttgaga gggatgaagt ggggcgactt cgaaagacgc        180
tccacgatat                                                                190

<210> SEQ ID NO 647
<211> LENGTH: 190
<212> TYPE: DNA
<213> ORGANISM: Artificial Sequence
<220> FEATURE:
<223> OTHER INFORMATION: Synthetic

<400> SEQUENCE: 647
tatacgcagt gctaccatcg atcacacttt gttccttccc tctctagcaa aaaagcaggg        60
ccagagcggc atcatctcct gcatagcctt cagcccagcc cagcccctct atgcctgtgg        120
ctcctacggc cgctccctgg gtctgtatgc ctgggatgat ggctcgactt cgaaagacgc        180
tccacgatat                                                                190

<210> SEQ ID NO 648
<211> LENGTH: 190
<212> TYPE: DNA
<213> ORGANISM: Artificial Sequence
<220> FEATURE:
<223> OTHER INFORMATION: Synthetic

<400> SEQUENCE: 648
tatacgcagt gctaccatcg atcactttca tcccgatggc aaccgcttct tctcaggagc        60
ccgcaaggta ggggtcacac cctgagagcc caaagcagct gggcagcggg gcaggagcag        120
ggatgtagtc tgcagtgtag gggaatgggt ggggatgggg aaaaagactt cgaaagacgc        180
tccacgatat                                                                190
```

<210> SEQ ID NO 649
<211> LENGTH: 190
<212> TYPE: DNA
<213> ORGANISM: Artificial Sequence
<220> FEATURE:
<223> OTHER INFORMATION: Synthetic

<400> SEQUENCE: 649

```
tatacgcagt gctaccatcg atcactgact ccaggtcctg ttccttgtct ccaggatgct    60
gagctcctgt gctgggatct ccggcagtct ggttacccac tgtggtccct gggtcgagag   120
gtgaccacca atcagcgcat ctacttcgat ctggacccgt gagtggactt cgaaagacgc   180
tccacgatat                                                          190
```

<210> SEQ ID NO 650
<211> LENGTH: 190
<212> TYPE: DNA
<213> ORGANISM: Artificial Sequence
<220> FEATURE:
<223> OTHER INFORMATION: Synthetic

<400> SEQUENCE: 650

```
tatacgcagt gctaccatcg atcacagttc ctagtgagtg gcagcacgag cggggctgtc    60
tctgtgtggg acacggacgg gcctggcaat gatgggaagc cggagcccgt gttgagtttt   120
ctgccccaga aggactgcac caatggcgtg aggtcctcag ttcaagactt cgaaagacgc   180
tccacgatat                                                          190
```

<210> SEQ ID NO 651
<211> LENGTH: 190
<212> TYPE: DNA
<213> ORGANISM: Artificial Sequence
<220> FEATURE:
<223> OTHER INFORMATION: Synthetic

<400> SEQUENCE: 651

```
tatacgcagt gctaccatcg atcactcagg gtgagcgggg ctgagcagga gctgggtcag    60
actgttgggt gtgaccgtgt gagactgtgc agacagtgac agggcgcctg tcgcccacac   120
tccacactgt ttgccattct ccagcagcat ggggaccatt actcagactt cgaaagacgc   180
tccacgatat                                                          190
```

<210> SEQ ID NO 652
<211> LENGTH: 190
<212> TYPE: DNA
<213> ORGANISM: Artificial Sequence
<220> FEATURE:
<223> OTHER INFORMATION: Synthetic

<400> SEQUENCE: 652

```
tatacgcagt gctaccatcg atcacctctg aggggagcag gagcactctc ctccgctccc    60
cggggctccc caggaggcag acaacccagt tgccagagtc aaggacacac ataaaagagt   120
aaaggtgttg aaaaatacag tcgtcacctt tgatattgct gttccgactt cgaaagacgc   180
tccacgatat                                                          190
```

<210> SEQ ID NO 653
<211> LENGTH: 190
<212> TYPE: DNA
<213> ORGANISM: Artificial Sequence
<220> FEATURE:
<223> OTHER INFORMATION: Synthetic

```
<400> SEQUENCE: 653
tatacgcagt gctaccatcg atcacgactt tgaagaaata ctgccagcag gggatgtgat      60
tttggacctc acaatcaaag ggaagggacg aaaggcctgg ggaggcttga gagggagagg     120
aatgtcaccc ctgcccagag gtgctgaaag ccagggctct tacacgactt cgaaagacgc    180
tccacgatat                                                           190

<210> SEQ ID NO 654
<211> LENGTH: 190
<212> TYPE: DNA
<213> ORGANISM: Artificial Sequence
<220> FEATURE:
<223> OTHER INFORMATION: Synthetic

<400> SEQUENCE: 654
tatacgcagt gctaccatcg atcaccttca aggttattat tattctctcc aaacctgccg     60
ggagcagcgg tgttgttttg ggatggagga ggaggctgcg ggagcgaaag gggtgggttc    120
ctcggggtgg agagggcgag agcctttctg gattcgagag aggaagactt cgaaagacgc    180
tccacgatat                                                           190

<210> SEQ ID NO 655
<211> LENGTH: 190
<212> TYPE: DNA
<213> ORGANISM: Artificial Sequence
<220> FEATURE:
<223> OTHER INFORMATION: Synthetic

<400> SEQUENCE: 655
tatacgcagt gctaccatcg atcaccttct gtgggcaggg aggaggcggg agggaaggtg     60
ctggtgctct gatgtgtgat gggttactag acaggtgatc ttgggagcca gactccgggt    120
cccacgcaga gctggatgcg ggtggtgcta tggatgtcag gagttgactt cgaaagacgc    180
tccacgatat                                                           190

<210> SEQ ID NO 656
<211> LENGTH: 190
<212> TYPE: DNA
<213> ORGANISM: Artificial Sequence
<220> FEATURE:
<223> OTHER INFORMATION: Synthetic

<400> SEQUENCE: 656
tatacgcagt gctaccatcg atccctctg gggacaactt ccccaaggct ccttgactct      60
cttcacagtc tgtctcccaa ctcttcccca cagccagagg gtcagtgaac tgttggctga   120
acgatttccc agccagaaca tattcctgcc ttcctggctt gccgggactt cgaaagacgc   180
tccacgatat                                                          190

<210> SEQ ID NO 657
<211> LENGTH: 190
<212> TYPE: DNA
<213> ORGANISM: Artificial Sequence
<220> FEATURE:
<223> OTHER INFORMATION: Synthetic

<400> SEQUENCE: 657
tatacgcagt gctaccatcg atcacaatct ttgctgcaaa ctcttccatc agaccctctg     60
ttccatggca tgccagcttt gctctgaaaa gaggccaggg gtcagatgaa acttcaagcc   120
acgctgggta ggacagaacc ttcgggaggt cacctgggtc ccttggactt cgaaagacgc   180
```

```
tccacgatat                                                              190

<210> SEQ ID NO 658
<211> LENGTH: 190
<212> TYPE: DNA
<213> ORGANISM: Artificial Sequence
<220> FEATURE:
<223> OTHER INFORMATION: Synthetic

<400> SEQUENCE: 658
tatacgcagt gctaccatcg atcacgcggt aaggtgtttg aatgtattat gtgctcatta      60
aaggagagct aggattattg ttcctctctt tacttcccag cctccctcac acttctctgc     120
tctgccatcc ctccctctct tttccctgga tctctttggg tataagactt cgaaagacgc     180
tccacgatat                                                              190

<210> SEQ ID NO 659
<211> LENGTH: 190
<212> TYPE: DNA
<213> ORGANISM: Artificial Sequence
<220> FEATURE:
<223> OTHER INFORMATION: Synthetic

<400> SEQUENCE: 659
tatacgcagt gctaccatcg atcacctctt tcggatgtgg ggtgggagtg ggacacttgg      60
gagtctggga agatatcaag tagcagtccc ctgggaccca gtcctgagac cctgtctcag     120
cagctattga tgtccaggaa ggggctgcag gggttggcaa gttgtgactt cgaaagacgc     180
tccacgatat                                                              190

<210> SEQ ID NO 660
<211> LENGTH: 190
<212> TYPE: DNA
<213> ORGANISM: Artificial Sequence
<220> FEATURE:
<223> OTHER INFORMATION: Synthetic

<400> SEQUENCE: 660
tatacgcagt gctaccatcg atcacgctgt gctgggacag tggatgcctg ggtgcactgg      60
ccaaggagat ggtgaagtgt gttggttgtg gttagaaaag tcaactcctt tcctttccaa     120
agcaatagag cacttgcccc agaagtctaa gacccagtgt gggatgactt cgaaagacgc     180
tccacgatat                                                              190

<210> SEQ ID NO 661
<211> LENGTH: 190
<212> TYPE: DNA
<213> ORGANISM: Artificial Sequence
<220> FEATURE:
<223> OTHER INFORMATION: Synthetic

<400> SEQUENCE: 661
tatacgcagt gctaccatcg atcacctgag tgggagaatg actcaggcag caggttccta      60
gaccctggtt cccatcagcc ccaatgatgg tcgtggccaa accaggcatt tgccttctgt     120
gctattagct ggctaactta ggacactggt ctggaccacc tccagacttc gaaagacgc      180 tccacgatat                                                              190

<210> SEQ ID NO 662
<211> LENGTH: 190
<212> TYPE: DNA
```

<213> ORGANISM: Artificial Sequence
<220> FEATURE:
<223> OTHER INFORMATION: Synthetic

<400> SEQUENCE: 662

```
tatacgcagt gctaccatcg atcactttgc ccggaaatcc ctgaaattca gtggtggcct      60
gaaggagggg aggctctgcc cgcatggttg gctgccatgg aatagtgaaa tcacctggga     120
ggggtgggct gtgtggttcc agagaggcca gctccttggt aactggactt cgaaagacgc     180
tccacgatat                                                            190
```

<210> SEQ ID NO 663
<211> LENGTH: 190
<212> TYPE: DNA
<213> ORGANISM: Artificial Sequence
<220> FEATURE:
<223> OTHER INFORMATION: Synthetic

<400> SEQUENCE: 663

```
tatacgcagt gctaccatcg atcactggtg atggagcggg agatggcggt gtgcatgtgg      60
tgagggcggg ctgaagagtg gagtgcattt gggcacacca aggggcagga gaccctgag     120
cctggcttcc tgctgcttcc aatgtgaatg cacagagtcc ttggtgactt cgaaagacgc     180
tccacgatat                                                            190
```

<210> SEQ ID NO 664
<211> LENGTH: 190
<212> TYPE: DNA
<213> ORGANISM: Artificial Sequence
<220> FEATURE:
<223> OTHER INFORMATION: Synthetic

<400> SEQUENCE: 664

```
tatacgcagt gctaccatcg atcactgccc caaacctcct tctcacttgt gatcgcccag      60
acctggatct ccgcttcacc atcaagttcc aggagtatag ccctaatctc tggggccacg     120
agttccgctc gcaccacgat tactacatca ttggtactgc tgggcgactt cgaaagacgc     180
tccacgatat                                                            190
```

<210> SEQ ID NO 665
<211> LENGTH: 190
<212> TYPE: DNA
<213> ORGANISM: Artificial Sequence
<220> FEATURE:
<223> OTHER INFORMATION: Synthetic

<400> SEQUENCE: 665

```
tatacgcagt gctaccatcg atcactgggg ccagaatcag ggctagattc tggagtgcca      60
acctcttcct ctggcttttc tctcccagcc acatcggatg ggacccggga gggcctggag     120
agcctgcagg gaggtgtgtg cctaaccaga ggcatgaagg tgcttgactt cgaaagacgc     180
tccacgatat                                                            190
```

<210> SEQ ID NO 666
<211> LENGTH: 190
<212> TYPE: DNA
<213> ORGANISM: Artificial Sequence
<220> FEATURE:
<223> OTHER INFORMATION: Synthetic

<400> SEQUENCE: 666

```
tatacgcagt gctaccatcg atcaccggtg atacaggaaa gaggagaaga gaggatggga      60
```
gggtgggagg ggaatggaaa ccaaatgagg aaaagactca attagaacta attagccaag        120
tcagtgcttc aatcagtgct gtcagagaag tggggaggac tccgtgactt cgaaagacgc        180
tccacgatat                                                               190

<210> SEQ ID NO 667
<211> LENGTH: 190
<212> TYPE: DNA
<213> ORGANISM: Artificial Sequence
<220> FEATURE:
<223> OTHER INFORMATION: Synthetic

<400> SEQUENCE: 667
tatacgcagt gctaccatcg atcactcacc cacccagagc tagggcggg aacagcccac         60 cttttggttg gcaccgcctt ctttctgcct ctcactggtt ttctcttctc tatctcttat       120
tctttccctc tcttccgtct ctaggtctgt tcttcttccc tagcagactt cgaaagacgc       180
tccacgatat                                                               190

<210> SEQ ID NO 668
<211> LENGTH: 190
<212> TYPE: DNA
<213> ORGANISM: Artificial Sequence
<220> FEATURE:
<223> OTHER INFORMATION: Synthetic

<400> SEQUENCE: 668
tatacgcagt gctaccatcg atcaccctta tggggaaggc tctgacactc caccccagct        60
caggccatgg gcagcagggc tccattctct ggcctggccc aggcctctac atacttactc       120
cagccatttg gggtggttgg gtcatgacag ctaccatgag aagaagactt cgaaagacgc       180
tccacgatat                                                               190

<210> SEQ ID NO 669
<211> LENGTH: 190
<212> TYPE: DNA
<213> ORGANISM: Artificial Sequence
<220> FEATURE:
<223> OTHER INFORMATION: Synthetic

<400> SEQUENCE: 669
tatacgcagt gctaccatcg atcactgtcc cgttttgtcc agtggccaat agcaagatat        60
gaaccggtcg ggacatgtat ggacttggtc tgatgctgaa tgggccactt gggaccggaa      120
gtgacttgct ccagacaaga ggtgaccagg cccggacaga aatgggactt cgaaagacgc      180
tccacgatat                                                               190

<210> SEQ ID NO 670
<211> LENGTH: 190
<212> TYPE: DNA
<213> ORGANISM: Artificial Sequence
<220> FEATURE:
<223> OTHER INFORMATION: Synthetic

<400> SEQUENCE: 670
tatacgcagt gctaccatcg atcacatcag gaggtgggag gtggatggtt cttattctgt        60
ggagaagaag ggcgggaaga acttcctttc aggaggaagc tggaacttac tgactgtaag      120
aggttagagg tggaccgaga aggactttc ccagtcttca gtggcgactt cgaaagacgc       180
tccacgatat                                                               190

<210> SEQ ID NO 671
<211> LENGTH: 190
<212> TYPE: DNA
<213> ORGANISM: Artificial Sequence
<220> FEATURE:
<223> OTHER INFORMATION: Synthetic

<400> SEQUENCE: 671

```
tatacgcagt gctaccatcg atcactccca agatctccct tcccttgtgc tctgtgctga    60
ttttaggaca gctaagatga ctgccatgtg ctgtggcagg cctaatttgt cttgttcttt   120
cctttccata tcccagtata atctctgtta atcaacagga ctaccgactt cgaaagacgc   180
tccacgatat                                                          190
```

<210> SEQ ID NO 672
<211> LENGTH: 190
<212> TYPE: DNA
<213> ORGANISM: Artificial Sequence
<220> FEATURE:
<223> OTHER INFORMATION: Synthetic

<400> SEQUENCE: 672

```
tatacgcagt gctaccatcg atcaccaaga acccatgtgc tctcccgagt aacccagatg    60
gctgtcttgt tcattccatc ctacatttct gactcctttc agactcaaca cagttcccct   120
cttagtgacc aaaatggtgg cctactggct ggtctagctg acagtgactt cgaaagacgc   180
tccacgatat                                                          190
```

<210> SEQ ID NO 673
<211> LENGTH: 190
<212> TYPE: DNA
<213> ORGANISM: Artificial Sequence
<220> FEATURE:
<223> OTHER INFORMATION: Synthetic

<400> SEQUENCE: 673

```
tatacgcagt gctaccatcg atcacgtact tagcaaaggc cactgtttcc atagtgacca    60
gctgatacct cttcctgccc tctagtgtgc aattgggtgt tgcctcagtt tcctcccagc   120
tcagttttat tagatcaaag ctgttgttgg gcaccaggtt ggccagactt cgaaagacgc   180
tccacgatat                                                          190
```

<210> SEQ ID NO 674
<211> LENGTH: 190
<212> TYPE: DNA
<213> ORGANISM: Artificial Sequence
<220> FEATURE:
<223> OTHER INFORMATION: Synthetic

<400> SEQUENCE: 674

```
tatacgcagt gctaccatcg atcacctcaa tcaccagcca agatggttgc tttgtccacc    60
agaggtcaag ttcacctctc tggtgctgta gttcccagct ccttcctgat tttctaatc   120
gctccttctg gggaacagga agttgatatt gccatggtgg cggggacttt cgaaagacgc   180
tccacgatat                                                          190
```

<210> SEQ ID NO 675
<211> LENGTH: 190
<212> TYPE: DNA
<213> ORGANISM: Artificial Sequence
<220> FEATURE:
<223> OTHER INFORMATION: Synthetic

<400> SEQUENCE: 675

| tatacgcagt gctaccatcg atcacgtggg tagggatagg gctagtttgg agtggtgagg | 60 |
| ttggcagtgc ttggggaggc gaaaatgggc tgggcgagaa ggcagaggaa ggtgtcacct | 120 |
| ctagggagg gagagagtaa tgcaggcagg agtggggtcg ccaatgactt cgaaagacgc | 180 |
| tccacgatat | 190 |

<210> SEQ ID NO 676
<211> LENGTH: 190
<212> TYPE: DNA
<213> ORGANISM: Artificial Sequence
<220> FEATURE:
<223> OTHER INFORMATION: Synthetic

<400> SEQUENCE: 676

| tatacgcagt gctaccatcg atcaccatcc atggggacag tctgagtgtc ttgctaagcc | 60 |
| aaagcaccag agacagggta agacgcaatt aggatcaaag tggtaaaaac atgttcacat | 120 |
| gttaaagtct attccctacc atccctaccc aaggcacttg agaaggactt cgaaagacgc | 180 |
| tccacgatat | 190 |

<210> SEQ ID NO 677
<211> LENGTH: 190
<212> TYPE: DNA
<213> ORGANISM: Artificial Sequence
<220> FEATURE:
<223> OTHER INFORMATION: Synthetic

<400> SEQUENCE: 677

| tatacgcagt gctaccatcg atcacaaaaa gcccaggtgc ccagtcccct agacttagcc | 60 |
| ccattctcca accacaaaag cagccgtcag gagcatcact ggagcgagtc agcagggtc | 120 |
| acaacctctg ccctccctgc ccctccctg actttaggtc ccctcgactt cgaaagacgc | 180 |
| tccacgatat | 190 |

<210> SEQ ID NO 678
<211> LENGTH: 190
<212> TYPE: DNA
<213> ORGANISM: Artificial Sequence
<220> FEATURE:
<223> OTHER INFORMATION: Synthetic

<400> SEQUENCE: 678

| tatacgcagt gctaccatcg atcacagcaa gatgcctggg tcttgagagg tgcgggcacc | 60 |
| gcaggagggg agttgaaagc tgggaggcca ggtactgggc tgtctggaat ttactcttgc | 120 |
| cttctgagcc cacactggag ctgcccgaag tggggaggct cgtatgactt cgaaagacgc | 180 |
| tccacgatat | 190 |

<210> SEQ ID NO 679
<211> LENGTH: 190
<212> TYPE: DNA
<213> ORGANISM: Artificial Sequence
<220> FEATURE:
<223> OTHER INFORMATION: Synthetic

<400> SEQUENCE: 679

| tatacgcagt gctaccatcg atcactccac ctacatctag aggcacaggt ggagagacaa | 60 |
| gagggaagag acgtggggat aaatagtctc cgtgacagac aagcacctcg ccaaagcagc | 120 |

```
caagacatca taacatgctg agagacagga agacacctgg ggacagactt cgaaagacgc    180
tccacgatat                                                           190

<210> SEQ ID NO 680
<211> LENGTH: 190
<212> TYPE: DNA
<213> ORGANISM: Artificial Sequence
<220> FEATURE:
<223> OTHER INFORMATION: Synthetic

<400> SEQUENCE: 680
tatacgcagt gctaccatcg atcactcaga gcgctggcat ccagagactc cccgcagccc    60
cgctcgaata gcacaagacc aacagccttt cacatgtgta gtgacttggg tgtctggagc    120
tatttgaaaa tgctggtgac ttccacgcag aataacacag gccgtgactt cgaaagacgc    180
tccacgatat                                                           190

<210> SEQ ID NO 681
<211> LENGTH: 190
<212> TYPE: DNA
<213> ORGANISM: Artificial Sequence
<220> FEATURE:
<223> OTHER INFORMATION: Synthetic

<400> SEQUENCE: 681
tatacgcagt gctaccatcg atcactcacc accacatgca tgtttcggat gtgtcctgtt    60
cttccctagc ctcggcctgg aggggagtaa gtcacttagg gtcttggatc cacattaagg    120
aagttgatct cactcagtct cccatcccct tgccttttgt ttcttgactt cgaaagacgc    180
tccacgatat                                                           190

<210> SEQ ID NO 682
<211> LENGTH: 190
<212> TYPE: DNA
<213> ORGANISM: Artificial Sequence
<220> FEATURE:
<223> OTHER INFORMATION: Synthetic

<400> SEQUENCE: 682
tatacgcagt gctaccatcg atcacctgtg gcacagctgc tggcagagtc cagagcagga    60
aggcagagcg gaagtaaagg aaccgagagg gctgggacca cagaagctag agctgtcgcc    120
ctgccatccc caaaccgcat aggattgagg ctgtcttggg gctgagactt cgaaagacgc    180
tccacgatat                                                           190

<210> SEQ ID NO 683
<211> LENGTH: 25
<212> TYPE: DNA
<213> ORGANISM: Artificial Sequence
<220> FEATURE:
<223> OTHER INFORMATION: Synthetic

<400> SEQUENCE: 683
aatgagacac gtgagatctg gaagg                                          25

<210> SEQ ID NO 684
<211> LENGTH: 25
<212> TYPE: DNA
<213> ORGANISM: Artificial Sequence
<220> FEATURE:
<223> OTHER INFORMATION: Synthetic

<400> SEQUENCE: 684
```

```
caatttgttt tgttttaggg cagga                                           25

<210> SEQ ID NO 685
<211> LENGTH: 25
<212> TYPE: DNA
<213> ORGANISM: Artificial Sequence
<220> FEATURE:
<223> OTHER INFORMATION: Synthetic

<400> SEQUENCE: 685
atttacggta gtgggggaag gcata                                           25

<210> SEQ ID NO 686
<211> LENGTH: 25
<212> TYPE: DNA
<213> ORGANISM: Artificial Sequence
<220> FEATURE:
<223> OTHER INFORMATION: Synthetic

<400> SEQUENCE: 686
aatgcaagct acgggagaaa gaaac                                           25

<210> SEQ ID NO 687
<211> LENGTH: 25
<212> TYPE: DNA
<213> ORGANISM: Artificial Sequence
<220> FEATURE:
<223> OTHER INFORMATION: Synthetic

<400> SEQUENCE: 687
ttaattgtgc ttgaagaggg ggtgt                                           25

<210> SEQ ID NO 688
<211> LENGTH: 25
<212> TYPE: DNA
<213> ORGANISM: Artificial Sequence
<220> FEATURE:
<223> OTHER INFORMATION: Synthetic

<400> SEQUENCE: 688
ttatacttcc caaagcatac cacca                                           25

<210> SEQ ID NO 689
<211> LENGTH: 26
<212> TYPE: DNA
<213> ORGANISM: Artificial Sequence
<220> FEATURE:
<223> OTHER INFORMATION: Synthetic

<400> SEQUENCE: 689
cgtgttaatt cccgtgtact gtttca                                          26

<210> SEQ ID NO 690
<211> LENGTH: 18
<212> TYPE: DNA
<213> ORGANISM: Artificial Sequence
<220> FEATURE:
<223> OTHER INFORMATION: Synthetic

<400> SEQUENCE: 690
cgagtggcgg agctgctg                                                   18

<210> SEQ ID NO 691
<211> LENGTH: 26
<212> TYPE: DNA
```

```
<213> ORGANISM: Artificial Sequence
<220> FEATURE:
<223> OTHER INFORMATION: Synthetic

<400> SEQUENCE: 691
cctctagcct cttgagtctt cattgc                                          26

<210> SEQ ID NO 692
<211> LENGTH: 26
<212> TYPE: DNA
<213> ORGANISM: Artificial Sequence
<220> FEATURE:
<223> OTHER INFORMATION: Synthetic

<400> SEQUENCE: 692
tgaagttcaa cattcccaga agctaa                                          26

<210> SEQ ID NO 693
<211> LENGTH: 26
<212> TYPE: DNA
<213> ORGANISM: Artificial Sequence
<220> FEATURE:
<223> OTHER INFORMATION: Synthetic

<400> SEQUENCE: 693
tcccaggttt atgatttgag agttca                                          26

<210> SEQ ID NO 694
<211> LENGTH: 25
<212> TYPE: DNA
<213> ORGANISM: Artificial Sequence
<220> FEATURE:
<223> OTHER INFORMATION: Synthetic

<400> SEQUENCE: 694
ggaacttagg aaataatgag ccaca                                           25

<210> SEQ ID NO 695
<211> LENGTH: 25
<212> TYPE: DNA
<213> ORGANISM: Artificial Sequence
<220> FEATURE:
<223> OTHER INFORMATION: Synthetic

<400> SEQUENCE: 695
ttccaacata caccacagat ttcca                                           25

<210> SEQ ID NO 696
<211> LENGTH: 25
<212> TYPE: DNA
<213> ORGANISM: Artificial Sequence
<220> FEATURE:
<223> OTHER INFORMATION: Synthetic

<400> SEQUENCE: 696
gccatacttt ccctatgaca ccaaa                                           25

<210> SEQ ID NO 697
<211> LENGTH: 23
<212> TYPE: DNA
<213> ORGANISM: Artificial Sequence
<220> FEATURE:
<223> OTHER INFORMATION: Synthetic

<400> SEQUENCE: 697
gaccgtaact attcggtgcg ttg                                             23
```

<210> SEQ ID NO 698
<211> LENGTH: 25
<212> TYPE: DNA
<213> ORGANISM: Artificial Sequence
<220> FEATURE:
<223> OTHER INFORMATION: Synthetic

<400> SEQUENCE: 698
tgtgagaagt gtgaaggaga cagga                                    25

<210> SEQ ID NO 699
<211> LENGTH: 25
<212> TYPE: DNA
<213> ORGANISM: Artificial Sequence
<220> FEATURE:
<223> OTHER INFORMATION: Synthetic

<400> SEQUENCE: 699
ttattcctga aaccagcct gtgaa                                     25

<210> SEQ ID NO 700
<211> LENGTH: 26
<212> TYPE: DNA
<213> ORGANISM: Artificial Sequence
<220> FEATURE:
<223> OTHER INFORMATION: Synthetic

<400> SEQUENCE: 700
ttgatggttg ttaccaatac atgctc                                   26

<210> SEQ ID NO 701
<211> LENGTH: 25
<212> TYPE: DNA
<213> ORGANISM: Artificial Sequence
<220> FEATURE:
<223> OTHER INFORMATION: Synthetic

<400> SEQUENCE: 701
acagattgtg gtttagcccc gaagt                                    25

<210> SEQ ID NO 702
<211> LENGTH: 28
<212> TYPE: DNA
<213> ORGANISM: Artificial Sequence
<220> FEATURE:
<223> OTHER INFORMATION: Synthetic

<400> SEQUENCE: 702
tgttctcagc tgatcaaata gctacaaa                                 28

<210> SEQ ID NO 703
<211> LENGTH: 25
<212> TYPE: DNA
<213> ORGANISM: Artificial Sequence
<220> FEATURE:
<223> OTHER INFORMATION: Synthetic

<400> SEQUENCE: 703
tgaagttatt catttaggtc atcaa                                    25

<210> SEQ ID NO 704
<211> LENGTH: 25
<212> TYPE: DNA
<213> ORGANISM: Artificial Sequence
<220> FEATURE:

<223> OTHER INFORMATION: Synthetic

<400> SEQUENCE: 704
attctgttat cattgccttt ttgaa                                          25

<210> SEQ ID NO 705
<211> LENGTH: 25
<212> TYPE: DNA
<213> ORGANISM: Artificial Sequence
<220> FEATURE:
<223> OTHER INFORMATION: Synthetic

<400> SEQUENCE: 705
ggttttcact actgggagtg gaggt                                          25

<210> SEQ ID NO 706
<211> LENGTH: 25
<212> TYPE: DNA
<213> ORGANISM: Artificial Sequence
<220> FEATURE:
<223> OTHER INFORMATION: Synthetic

<400> SEQUENCE: 706
tcctggtatg ttccaaggtg ttagg                                          25

<210> SEQ ID NO 707
<211> LENGTH: 26
<212> TYPE: DNA
<213> ORGANISM: Artificial Sequence
<220> FEATURE:
<223> OTHER INFORMATION: Synthetic

<400> SEQUENCE: 707
tcagttttag ttcggcctag aatgtt                                         26

<210> SEQ ID NO 708
<211> LENGTH: 27
<212> TYPE: DNA
<213> ORGANISM: Artificial Sequence
<220> FEATURE:
<223> OTHER INFORMATION: Synthetic

<400> SEQUENCE: 708
ttgcctctga aaatctgtag taacaaa                                        27

<210> SEQ ID NO 709
<211> LENGTH: 25
<212> TYPE: DNA
<213> ORGANISM: Artificial Sequence
<220> FEATURE:
<223> OTHER INFORMATION: Synthetic

<400> SEQUENCE: 709
cagttaccgg tcacagtggc taaac                                          25

<210> SEQ ID NO 710
<211> LENGTH: 25
<212> TYPE: DNA
<213> ORGANISM: Artificial Sequence
<220> FEATURE:
<223> OTHER INFORMATION: Synthetic

<400> SEQUENCE: 710
tcaagcacac tttctttctc cttgg                                          25

```
<210> SEQ ID NO 711
<211> LENGTH: 21
<212> TYPE: DNA
<213> ORGANISM: Artificial Sequence
<220> FEATURE:
<223> OTHER INFORMATION: Synthetic

<400> SEQUENCE: 711
ccaagatctc ggaacggctc t                                          21

<210> SEQ ID NO 712
<211> LENGTH: 22
<212> TYPE: DNA
<213> ORGANISM: Artificial Sequence
<220> FEATURE:
<223> OTHER INFORMATION: Synthetic

<400> SEQUENCE: 712
gtcctcgact caccccctcct tt                                        22

<210> SEQ ID NO 713
<211> LENGTH: 25
<212> TYPE: DNA
<213> ORGANISM: Artificial Sequence
<220> FEATURE:
<223> OTHER INFORMATION: Synthetic

<400> SEQUENCE: 713
acaagcaccg agtcctttgt gtcta                                      25

<210> SEQ ID NO 714
<211> LENGTH: 25
<212> TYPE: DNA
<213> ORGANISM: Artificial Sequence
<220> FEATURE:
<223> OTHER INFORMATION: Synthetic

<400> SEQUENCE: 714
acggtgttgg gtaaattctg agtga                                      25

<210> SEQ ID NO 715
<211> LENGTH: 25
<212> TYPE: DNA
<213> ORGANISM: Artificial Sequence
<220> FEATURE:
<223> OTHER INFORMATION: Synthetic

<400> SEQUENCE: 715
aagagagaaa cccgaagaac aatgg                                      25

<210> SEQ ID NO 716
<211> LENGTH: 27
<212> TYPE: DNA
<213> ORGANISM: Artificial Sequence
<220> FEATURE:
<223> OTHER INFORMATION: Synthetic

<400> SEQUENCE: 716
cgtttctcaa tttcagctat ccaaatg                                    27

<210> SEQ ID NO 717
<211> LENGTH: 25
<212> TYPE: DNA
<213> ORGANISM: Artificial Sequence
<220> FEATURE:
<223> OTHER INFORMATION: Synthetic
```

<400> SEQUENCE: 717
ctcaactgtt gttgcccctt taagt                                              25

<210> SEQ ID NO 718
<211> LENGTH: 26
<212> TYPE: DNA
<213> ORGANISM: Artificial Sequence
<220> FEATURE:
<223> OTHER INFORMATION: Synthetic

<400> SEQUENCE: 718
cattcatttg gcttcatttt tatctt                                             26

<210> SEQ ID NO 719
<211> LENGTH: 27
<212> TYPE: DNA
<213> ORGANISM: Artificial Sequence
<220> FEATURE:
<223> OTHER INFORMATION: Synthetic

<400> SEQUENCE: 719
ccagatcttc ttggaataaa tgtcagg                                            27

<210> SEQ ID NO 720
<211> LENGTH: 26
<212> TYPE: DNA
<213> ORGANISM: Artificial Sequence
<220> FEATURE:
<223> OTHER INFORMATION: Synthetic

<400> SEQUENCE: 720
cacaatgatc tcccttgtaa gctcct                                             26

<210> SEQ ID NO 721
<211> LENGTH: 26
<212> TYPE: DNA
<213> ORGANISM: Artificial Sequence
<220> FEATURE:
<223> OTHER INFORMATION: Synthetic

<400> SEQUENCE: 721
cctttcccca ataacatatg ctctga                                             26

<210> SEQ ID NO 722
<211> LENGTH: 25
<212> TYPE: DNA
<213> ORGANISM: Artificial Sequence
<220> FEATURE:
<223> OTHER INFORMATION: Synthetic

<400> SEQUENCE: 722
cggaaatccc cttatgactt gctac                                              25

<210> SEQ ID NO 723
<211> LENGTH: 25
<212> TYPE: DNA
<213> ORGANISM: Artificial Sequence
<220> FEATURE:
<223> OTHER INFORMATION: Synthetic

<400> SEQUENCE: 723
aaccgttaca attgctctca ctcca                                              25

<210> SEQ ID NO 724
<211> LENGTH: 25

```
<212> TYPE: DNA
<213> ORGANISM: Artificial Sequence
<220> FEATURE:
<223> OTHER INFORMATION: Synthetic

<400> SEQUENCE: 724
ggtgtttctt taaatggctc cacct                                              25

<210> SEQ ID NO 725
<211> LENGTH: 25
<212> TYPE: DNA
<213> ORGANISM: Artificial Sequence
<220> FEATURE:
<223> OTHER INFORMATION: Synthetic

<400> SEQUENCE: 725
gggtgggaaa ttgggtaaga aaata                                              25

<210> SEQ ID NO 726
<211> LENGTH: 28
<212> TYPE: DNA
<213> ORGANISM: Artificial Sequence
<220> FEATURE:
<223> OTHER INFORMATION: Synthetic

<400> SEQUENCE: 726
aaaatgatga actgttaagg aaaaatca                                           28

<210> SEQ ID NO 727
<211> LENGTH: 25
<212> TYPE: DNA
<213> ORGANISM: Artificial Sequence
<220> FEATURE:
<223> OTHER INFORMATION: Synthetic

<400> SEQUENCE: 727
tgctccttta aaatccctc atttg                                               25

<210> SEQ ID NO 728
<211> LENGTH: 25
<212> TYPE: DNA
<213> ORGANISM: Artificial Sequence
<220> FEATURE:
<223> OTHER INFORMATION: Synthetic

<400> SEQUENCE: 728
gagtgtcgtt aagtttacgg ccaac                                              25

<210> SEQ ID NO 729
<211> LENGTH: 25
<212> TYPE: DNA
<213> ORGANISM: Artificial Sequence
<220> FEATURE:
<223> OTHER INFORMATION: Synthetic

<400> SEQUENCE: 729 ggattttgc tgggtaaaag cctgt                                               25

<210> SEQ ID NO 730
<211> LENGTH: 25
<212> TYPE: DNA
<213> ORGANISM: Artificial Sequence
<220> FEATURE:
<223> OTHER INFORMATION: Synthetic

<400> SEQUENCE: 730
```
gaaacttgtg aagcccaagt actgc                                              25

<210> SEQ ID NO 731
<211> LENGTH: 24
<212> TYPE: DNA
<213> ORGANISM: Artificial Sequence
<220> FEATURE:
<223> OTHER INFORMATION: Synthetic

<400> SEQUENCE: 731
aagcctgccc aaagatgcta ggac                                               24

<210> SEQ ID NO 732
<211> LENGTH: 25
<212> TYPE: DNA
<213> ORGANISM: Artificial Sequence
<220> FEATURE:
<223> OTHER INFORMATION: Synthetic

<400> SEQUENCE: 732
taattctaca gggatttggg ggatg                                              25

<210> SEQ ID NO 733
<211> LENGTH: 25
<212> TYPE: DNA
<213> ORGANISM: Artificial Sequence
<220> FEATURE:
<223> OTHER INFORMATION: Synthetic

<400> SEQUENCE: 733
gggcttgtca ttaaacaggc tgaac                                              25

<210> SEQ ID NO 734
<211> LENGTH: 26
<212> TYPE: DNA
<213> ORGANISM: Artificial Sequence
<220> FEATURE:
<223> OTHER INFORMATION: Synthetic

<400> SEQUENCE: 734
tcatatttga aaaccaggtt gagcag                                             26

<210> SEQ ID NO 735
<211> LENGTH: 25
<212> TYPE: DNA
<213> ORGANISM: Artificial Sequence
<220> FEATURE:
<223> OTHER INFORMATION: Synthetic

<400> SEQUENCE: 735
aataggagag cctgatcatg tgtgg                                              25

<210> SEQ ID NO 736
<211> LENGTH: 25
<212> TYPE: DNA
<213> ORGANISM: Artificial Sequence
<220> FEATURE:
<223> OTHER INFORMATION: Synthetic

<400> SEQUENCE: 736
tctgccagta gttttaaagg gctga                                              25

<210> SEQ ID NO 737
<211> LENGTH: 26
<212> TYPE: DNA
<213> ORGANISM: Artificial Sequence
<220> FEATURE:
<223> OTHER INFORMATION: Synthetic

<400> SEQUENCE: 737
tttagagaaa ataagtgctg ctgagg        26

<210> SEQ ID NO 738
<211> LENGTH: 27
<212> TYPE: DNA
<213> ORGANISM: Artificial Sequence
<220> FEATURE:
<223> OTHER INFORMATION: Synthetic

<400> SEQUENCE: 738
gcactactgg ttgttttagg cttttc        27

<210> SEQ ID NO 739
<211> LENGTH: 26
<212> TYPE: DNA
<213> ORGANISM: Artificial Sequence
<220> FEATURE:
<223> OTHER INFORMATION: Synthetic

<400> SEQUENCE: 739
tgcctgatag aagtcagact ctgtgg        26

<210> SEQ ID NO 740
<211> LENGTH: 25
<212> TYPE: DNA
<213> ORGANISM: Artificial Sequence
<220> FEATURE:
<223> OTHER INFORMATION: Synthetic

<400> SEQUENCE: 740
gagccacctt tcaatcccat tctac         25

<210> SEQ ID NO 741
<211> LENGTH: 25
<212> TYPE: DNA
<213> ORGANISM: Artificial Sequence
<220> FEATURE:
<223> OTHER INFORMATION: Synthetic

<400> SEQUENCE: 741
tagcaattct catttggatt cctgt         25

<210> SEQ ID NO 742
<211> LENGTH: 25
<212> TYPE: DNA
<213> ORGANISM: Artificial Sequence
<220> FEATURE:
<223> OTHER INFORMATION: Synthetic

<400> SEQUENCE: 742
cctctctcct ctaggtggca aactc         25

<210> SEQ ID NO 743
<211> LENGTH: 25
<212> TYPE: DNA
<213> ORGANISM: Artificial Sequence
<220> FEATURE:
<223> OTHER INFORMATION: Synthetic

<400> SEQUENCE: 743
ctattttgcc agcgcagatt tgata         25

<210> SEQ ID NO 744
<211> LENGTH: 26
<212> TYPE: DNA
<213> ORGANISM: Artificial Sequence
<220> FEATURE:
<223> OTHER INFORMATION: Synthetic

<400> SEQUENCE: 744
caacaacaat gctatccaca cagatg                                              26

<210> SEQ ID NO 745
<211> LENGTH: 25
<212> TYPE: DNA
<213> ORGANISM: Artificial Sequence
<220> FEATURE:
<223> OTHER INFORMATION: Synthetic

<400> SEQUENCE: 745
tggttttgta ccactccctc tctca                                               25

<210> SEQ ID NO 746
<211> LENGTH: 25
<212> TYPE: DNA
<213> ORGANISM: Artificial Sequence
<220> FEATURE:
<223> OTHER INFORMATION: Synthetic

<400> SEQUENCE: 746
agcccctaga cagctggtag aagaa                                               25

<210> SEQ ID NO 747
<211> LENGTH: 25
<212> TYPE: DNA
<213> ORGANISM: Artificial Sequence
<220> FEATURE:
<223> OTHER INFORMATION: Synthetic

<400> SEQUENCE: 747
atattcaagc atgaggaatg gcaaa                                               25

<210> SEQ ID NO 748
<211> LENGTH: 27
<212> TYPE: DNA
<213> ORGANISM: Artificial Sequence
<220> FEATURE:
<223> OTHER INFORMATION: Synthetic

<400> SEQUENCE: 748
tttccaaaag aaaaatactt ctcctca                                             27

<210> SEQ ID NO 749
<211> LENGTH: 25
<212> TYPE: DNA
<213> ORGANISM: Artificial Sequence
<220> FEATURE:
<223> OTHER INFORMATION: Synthetic

<400> SEQUENCE: 749
aagtcccagc tgaaaggtaa ccaaa                                               25

<210> SEQ ID NO 750
<211> LENGTH: 25
<212> TYPE: DNA
<213> ORGANISM: Artificial Sequence
<220> FEATURE:
<223> OTHER INFORMATION: Synthetic

```
<400> SEQUENCE: 750
aactgccttt ggaagaaaat tcagg                                          25

<210> SEQ ID NO 751
<211> LENGTH: 25
<212> TYPE: DNA
<213> ORGANISM: Artificial Sequence
<220> FEATURE:
<223> OTHER INFORMATION: Synthetic

<400> SEQUENCE: 751
ggttttcatg aacctcacat ggact                                          25

<210> SEQ ID NO 752
<211> LENGTH: 25
<212> TYPE: DNA
<213> ORGANISM: Artificial Sequence
<220> FEATURE:
<223> OTHER INFORMATION: Synthetic

<400> SEQUENCE: 752
ctcgaaattc caagggcact gaaaa                                          25

<210> SEQ ID NO 753
<211> LENGTH: 28
<212> TYPE: DNA
<213> ORGANISM: Artificial Sequence
<220> FEATURE:
<223> OTHER INFORMATION: Synthetic

<400> SEQUENCE: 753
gaaaagctag agtcacattt tagtgacc                                       28

<210> SEQ ID NO 754
<211> LENGTH: 25
<212> TYPE: DNA
<213> ORGANISM: Artificial Sequence
<220> FEATURE:
<223> OTHER INFORMATION: Synthetic

<400> SEQUENCE: 754
aaaccaaaca gaatttccac agacc                                          25

<210> SEQ ID NO 755
<211> LENGTH: 25
<212> TYPE: DNA
<213> ORGANISM: Artificial Sequence
<220> FEATURE:
<223> OTHER INFORMATION: Synthetic

<400> SEQUENCE: 755
tcagtccaga gcaagtgaat actgc                                          25

<210> SEQ ID NO 756
<211> LENGTH: 25
<212> TYPE: DNA
<213> ORGANISM: Artificial Sequence
<220> FEATURE:
<223> OTHER INFORMATION: Synthetic

<400> SEQUENCE: 756
tttttccttc gatggctgta acaat                                          25

<210> SEQ ID NO 757
```

<211> LENGTH: 25
<212> TYPE: DNA
<213> ORGANISM: Artificial Sequence
<220> FEATURE:
<223> OTHER INFORMATION: Synthetic

<400> SEQUENCE: 757
atgtaggctt gtgcctgaca ttaaa                                 25

<210> SEQ ID NO 758
<211> LENGTH: 25
<212> TYPE: DNA
<213> ORGANISM: Artificial Sequence
<220> FEATURE:
<223> OTHER INFORMATION: Synthetic

<400> SEQUENCE: 758
ttaggggaaa ttttagagcc aacga                                 25

<210> SEQ ID NO 759
<211> LENGTH: 26
<212> TYPE: DNA
<213> ORGANISM: Artificial Sequence
<220> FEATURE:
<223> OTHER INFORMATION: Synthetic

<400> SEQUENCE: 759
tgctgatgag tgaccagttt agatga                                26

<210> SEQ ID NO 760
<211> LENGTH: 25
<212> TYPE: DNA
<213> ORGANISM: Artificial Sequence
<220> FEATURE:
<223> OTHER INFORMATION: Synthetic

<400> SEQUENCE: 760
gcccaccttt taggtttgtc gttag                                 25

<210> SEQ ID NO 761
<211> LENGTH: 27
<212> TYPE: DNA
<213> ORGANISM: Artificial Sequence
<220> FEATURE:
<223> OTHER INFORMATION: Synthetic

<400> SEQUENCE: 761
cccacacctt tgatgtattt ctctttg                               27

<210> SEQ ID NO 762
<211> LENGTH: 25
<212> TYPE: DNA
<213> ORGANISM: Artificial Sequence
<220> FEATURE:
<223> OTHER INFORMATION: Synthetic

<400> SEQUENCE: 762
gatttcagct cttcatcacc cacat                                 25

<210> SEQ ID NO 763
<211> LENGTH: 25
<212> TYPE: DNA
<213> ORGANISM: Artificial Sequence
<220> FEATURE:
<223> OTHER INFORMATION: Synthetic

<400> SEQUENCE: 763

-continued tcttttccag tgacgtagtg tgtgg                                                 25

<210> SEQ ID NO 764
<211> LENGTH: 29
<212> TYPE: DNA
<213> ORGANISM: Artificial Sequence
<220> FEATURE:
<223> OTHER INFORMATION: Synthetic

<400> SEQUENCE: 764
tctctcagtg aatcattttc ctaggagtt                                             29

<210> SEQ ID NO 765
<211> LENGTH: 26
<212> TYPE: DNA
<213> ORGANISM: Artificial Sequence
<220> FEATURE:
<223> OTHER INFORMATION: Synthetic

<400> SEQUENCE: 765
tgctattatg gcacaattga tgttga                                                26

<210> SEQ ID NO 766
<211> LENGTH: 28
<212> TYPE: DNA
<213> ORGANISM: Artificial Sequence
<220> FEATURE:
<223> OTHER INFORMATION: Synthetic

<400> SEQUENCE: 766
catgatctta tttcaaccaa ctctcaaa                                              28

<210> SEQ ID NO 767
<211> LENGTH: 25
<212> TYPE: DNA
<213> ORGANISM: Artificial Sequence
<220> FEATURE:
<223> OTHER INFORMATION: Synthetic

<400> SEQUENCE: 767
gagggaacaa cttgtggaaa agtga                                                 25

<210> SEQ ID NO 768
<211> LENGTH: 25
<212> TYPE: DNA
<213> ORGANISM: Artificial Sequence
<220> FEATURE:
<223> OTHER INFORMATION: Synthetic

<400> SEQUENCE: 768
gaagcatagg ctaattctca tgcaa                                                 25

<210> SEQ ID NO 769
<211> LENGTH: 25
<212> TYPE: DNA
<213> ORGANISM: Artificial Sequence
<220> FEATURE:
<223> OTHER INFORMATION: Synthetic

<400> SEQUENCE: 769
tagggctatt tcacaaaagg gctgt                                                 25

<210> SEQ ID NO 770
<211> LENGTH: 25
<212> TYPE: DNA

<213> ORGANISM: Artificial Sequence
<220> FEATURE:
<223> OTHER INFORMATION: Synthetic

<400> SEQUENCE: 770
gtgtggctag gtccttggga taaac                                            25

<210> SEQ ID NO 771
<211> LENGTH: 25
<212> TYPE: DNA
<213> ORGANISM: Artificial Sequence
<220> FEATURE:
<223> OTHER INFORMATION: Synthetic

<400> SEQUENCE: 771
aaggtcagta ggttcacagg cccta                                            25

<210> SEQ ID NO 772
<211> LENGTH: 28
<212> TYPE: DNA
<213> ORGANISM: Artificial Sequence
<220> FEATURE:
<223> OTHER INFORMATION: Synthetic

<400> SEQUENCE: 772
ttcacttgaa gataatgaac atcttacc                                         28

<210> SEQ ID NO 773
<211> LENGTH: 25
<212> TYPE: DNA
<213> ORGANISM: Artificial Sequence
<220> FEATURE:
<223> OTHER INFORMATION: Synthetic

<400> SEQUENCE: 773
ctggatttgc agtgttgtgt cctat                                            25

<210> SEQ ID NO 774
<211> LENGTH: 25
<212> TYPE: DNA
<213> ORGANISM: Artificial Sequence
<220> FEATURE:
<223> OTHER INFORMATION: Synthetic

<400> SEQUENCE: 774
caacattctg ttctgagtgc tggtg                                            25

<210> SEQ ID NO 775
<211> LENGTH: 25
<212> TYPE: DNA
<213> ORGANISM: Artificial Sequence
<220> FEATURE:
<223> OTHER INFORMATION: Synthetic

<400> SEQUENCE: 775
gagtagacag ccaaccccct gtatt                                            25

<210> SEQ ID NO 776
<211> LENGTH: 25
<212> TYPE: DNA
<213> ORGANISM: Artificial Sequence
<220> FEATURE:
<223> OTHER INFORMATION: Synthetic

<400> SEQUENCE: 776
agcatgtagg agaggtacgg tggta                                            25

<210> SEQ ID NO 777
<211> LENGTH: 25
<212> TYPE: DNA
<213> ORGANISM: Artificial Sequence
<220> FEATURE:
<223> OTHER INFORMATION: Synthetic

<400> SEQUENCE: 777
agccgttagt caactctgag tgcag                                      25

<210> SEQ ID NO 778
<211> LENGTH: 25
<212> TYPE: DNA
<213> ORGANISM: Artificial Sequence
<220> FEATURE:
<223> OTHER INFORMATION: Synthetic

<400> SEQUENCE: 778
tgaccaagca atgtgcatag acaag                                      25

<210> SEQ ID NO 779
<211> LENGTH: 25
<212> TYPE: DNA
<213> ORGANISM: Artificial Sequence
<220> FEATURE:
<223> OTHER INFORMATION: Synthetic

<400> SEQUENCE: 779
cccaaaactg aaagatgaaa acata                                      25

<210> SEQ ID NO 780
<211> LENGTH: 25
<212> TYPE: DNA
<213> ORGANISM: Artificial Sequence
<220> FEATURE:
<223> OTHER INFORMATION: Synthetic

<400> SEQUENCE: 780
tgcagaaagg atcctattgt tggtg                                      25

<210> SEQ ID NO 781
<211> LENGTH: 25
<212> TYPE: DNA
<213> ORGANISM: Artificial Sequence
<220> FEATURE:
<223> OTHER INFORMATION: Synthetic

<400> SEQUENCE: 781
ctcagaagcg agggagactt aaacc                                      25

<210> SEQ ID NO 782
<211> LENGTH: 25
<212> TYPE: DNA
<213> ORGANISM: Artificial Sequence
<220> FEATURE:
<223> OTHER INFORMATION: Synthetic

<400> SEQUENCE: 782
ccctggctca tctccatacc tactc                                      25

<210> SEQ ID NO 783
<211> LENGTH: 25
<212> TYPE: DNA
<213> ORGANISM: Artificial Sequence
<220> FEATURE:

<223> OTHER INFORMATION: Synthetic

<400> SEQUENCE: 783
ccattcttcc tgaataactt ggcta                                      25

<210> SEQ ID NO 784
<211> LENGTH: 25
<212> TYPE: DNA
<213> ORGANISM: Artificial Sequence
<220> FEATURE:
<223> OTHER INFORMATION: Synthetic

<400> SEQUENCE: 784
tcaaaggttt gaacttgcct ctcac                                      25

<210> SEQ ID NO 785
<211> LENGTH: 25
<212> TYPE: DNA
<213> ORGANISM: Artificial Sequence
<220> FEATURE:
<223> OTHER INFORMATION: Synthetic

<400> SEQUENCE: 785
aacaaagcaa attgcaggca ataaa                                      25

<210> SEQ ID NO 786
<211> LENGTH: 25
<212> TYPE: DNA
<213> ORGANISM: Artificial Sequence
<220> FEATURE:
<223> OTHER INFORMATION: Synthetic

<400> SEQUENCE: 786
agcctgtggt cataaaacac ctcac                                      25

<210> SEQ ID NO 787
<211> LENGTH: 25
<212> TYPE: DNA
<213> ORGANISM: Artificial Sequence
<220> FEATURE:
<223> OTHER INFORMATION: Synthetic

<400> SEQUENCE: 787
gaagcataaa gcaatggacc aggtt                                      25

<210> SEQ ID NO 788
<211> LENGTH: 26
<212> TYPE: DNA
<213> ORGANISM: Artificial Sequence
<220> FEATURE:
<223> OTHER INFORMATION: Synthetic

<400> SEQUENCE: 788
ttttcctcac cttatgtcaa caagga                                     26

<210> SEQ ID NO 789
<211> LENGTH: 25
<212> TYPE: DNA
<213> ORGANISM: Artificial Sequence
<220> FEATURE:
<223> OTHER INFORMATION: Synthetic

<400> SEQUENCE: 789
cttggggttt caggagagaa attgt                                      25

```
<210> SEQ ID NO 790
<211> LENGTH: 25
<212> TYPE: DNA
<213> ORGANISM: Artificial Sequence
<220> FEATURE:
<223> OTHER INFORMATION: Synthetic

<400> SEQUENCE: 790
tgacacagac aaacaggtga ctcaa                                   25

<210> SEQ ID NO 791
<211> LENGTH: 25
<212> TYPE: DNA
<213> ORGANISM: Artificial Sequence
<220> FEATURE:
<223> OTHER INFORMATION: Synthetic

<400> SEQUENCE: 791
aatttgttct ttcaatttgg catgg                                   25

<210> SEQ ID NO 792
<211> LENGTH: 25
<212> TYPE: DNA
<213> ORGANISM: Artificial Sequence
<220> FEATURE:
<223> OTHER INFORMATION: Synthetic

<400> SEQUENCE: 792
tcaattttct gcatgaattt ccact                                   25

<210> SEQ ID NO 793
<211> LENGTH: 25
<212> TYPE: DNA
<213> ORGANISM: Artificial Sequence
<220> FEATURE:
<223> OTHER INFORMATION: Synthetic

<400> SEQUENCE: 793
cataatgggc cacatgattt ttacc                                   25

<210> SEQ ID NO 794
<211> LENGTH: 25
<212> TYPE: DNA
<213> ORGANISM: Artificial Sequence
<220> FEATURE:
<223> OTHER INFORMATION: Synthetic

<400> SEQUENCE: 794
gtaaagtcaa aaaccttccc catcc                                   25

<210> SEQ ID NO 795
<211> LENGTH: 24
<212> TYPE: DNA
<213> ORGANISM: Artificial Sequence
<220> FEATURE:
<223> OTHER INFORMATION: Synthetic

<400> SEQUENCE: 795
caactgctga acatagaccc aagg                                    24

<210> SEQ ID NO 796
<211> LENGTH: 25
<212> TYPE: DNA
<213> ORGANISM: Artificial Sequence
<220> FEATURE:
<223> OTHER INFORMATION: Synthetic
```

```
<400> SEQUENCE: 796
aaattcataa cattttcct ttgaa                                          25

<210> SEQ ID NO 797
<211> LENGTH: 25
<212> TYPE: DNA
<213> ORGANISM: Artificial Sequence
<220> FEATURE:
<223> OTHER INFORMATION: Synthetic

<400> SEQUENCE: 797
ttgttggaaa gcacattagg tgtgt                                         25

<210> SEQ ID NO 798
<211> LENGTH: 25
<212> TYPE: DNA
<213> ORGANISM: Artificial Sequence
<220> FEATURE:
<223> OTHER INFORMATION: Synthetic

<400> SEQUENCE: 798
tcctgtgaag aaagctatgc agttg                                         25

<210> SEQ ID NO 799
<211> LENGTH: 25
<212> TYPE: DNA
<213> ORGANISM: Artificial Sequence
<220> FEATURE:
<223> OTHER INFORMATION: Synthetic

<400> SEQUENCE: 799
aaaatcttgg tctttcccac agagg                                         25

<210> SEQ ID NO 800
<211> LENGTH: 25
<212> TYPE: DNA
<213> ORGANISM: Artificial Sequence
<220> FEATURE:
<223> OTHER INFORMATION: Synthetic

<400> SEQUENCE: 800
agactcttat tggtggtttg tggaa                                         25

<210> SEQ ID NO 801
<211> LENGTH: 25
<212> TYPE: DNA
<213> ORGANISM: Artificial Sequence
<220> FEATURE:
<223> OTHER INFORMATION: Synthetic

<400> SEQUENCE: 801
gccagcattg agctgataaa gacct                                         25

<210> SEQ ID NO 802
<211> LENGTH: 27
<212> TYPE: DNA
<213> ORGANISM: Artificial Sequence
<220> FEATURE:
<223> OTHER INFORMATION: Synthetic

<400> SEQUENCE: 802
caaaagtgaa agaaaatgaa tgaaaca                                       27

<210> SEQ ID NO 803
<211> LENGTH: 26
```

```
<212> TYPE: DNA
<213> ORGANISM: Artificial Sequence
<220> FEATURE:
<223> OTHER INFORMATION: Synthetic

<400> SEQUENCE: 803
ccggatttat ttattgttcc tggttg                                          26

<210> SEQ ID NO 804
<211> LENGTH: 25
<212> TYPE: DNA
<213> ORGANISM: Artificial Sequence
<220> FEATURE:
<223> OTHER INFORMATION: Synthetic

<400> SEQUENCE: 804
tgccaggctc tatatgtgtt ttgtg                                           25

<210> SEQ ID NO 805
<211> LENGTH: 27
<212> TYPE: DNA
<213> ORGANISM: Artificial Sequence
<220> FEATURE:
<223> OTHER INFORMATION: Synthetic

<400> SEQUENCE: 805
tgaaaagagt ggtgctagat acttgga                                         27

<210> SEQ ID NO 806
<211> LENGTH: 25
<212> TYPE: DNA
<213> ORGANISM: Artificial Sequence
<220> FEATURE:
<223> OTHER INFORMATION: Synthetic

<400> SEQUENCE: 806
tcacctacaa ctgattggca gtgtc                                           25

<210> SEQ ID NO 807
<211> LENGTH: 27
<212> TYPE: DNA
<213> ORGANISM: Artificial Sequence
<220> FEATURE:
<223> OTHER INFORMATION: Synthetic

<400> SEQUENCE: 807
ggcctaagaa ttagtgaaaa tcccaac                                         27

<210> SEQ ID NO 808
<211> LENGTH: 25
<212> TYPE: DNA
<213> ORGANISM: Artificial Sequence
<220> FEATURE:
<223> OTHER INFORMATION: Synthetic

<400> SEQUENCE: 808
tcatccttca cagatcaacc tcctc                                           25

<210> SEQ ID NO 809
<211> LENGTH: 25
<212> TYPE: DNA
<213> ORGANISM: Artificial Sequence
<220> FEATURE:
<223> OTHER INFORMATION: Synthetic

<400> SEQUENCE: 809
```

```
ctgaactcag aaggtgaacc acacc                                              25

<210> SEQ ID NO 810
<211> LENGTH: 26
<212> TYPE: DNA
<213> ORGANISM: Artificial Sequence
<220> FEATURE:
<223> OTHER INFORMATION: Synthetic

<400> SEQUENCE: 810
cctgtaaaag tcctcaggtc aactca                                             26

<210> SEQ ID NO 811
<211> LENGTH: 26
<212> TYPE: DNA
<213> ORGANISM: Artificial Sequence
<220> FEATURE:
<223> OTHER INFORMATION: Synthetic

<400> SEQUENCE: 811
tgagaatttg tgatttcctg gtgttg                                             26

<210> SEQ ID NO 812
<211> LENGTH: 27
<212> TYPE: DNA
<213> ORGANISM: Artificial Sequence
<220> FEATURE:
<223> OTHER INFORMATION: Synthetic

<400> SEQUENCE: 812
gaaatcctat agatagaaaa gcattca                                            27

<210> SEQ ID NO 813
<211> LENGTH: 24
<212> TYPE: DNA
<213> ORGANISM: Artificial Sequence
<220> FEATURE:
<223> OTHER INFORMATION: Synthetic

<400> SEQUENCE: 813
atatctctct ttggttccct tttt                                               24

<210> SEQ ID NO 814
<211> LENGTH: 29
<212> TYPE: DNA
<213> ORGANISM: Artificial Sequence
<220> FEATURE:
<223> OTHER INFORMATION: Synthetic

<400> SEQUENCE: 814
tccttaagaa atcagtattc caatgcaaa                                          29

<210> SEQ ID NO 815
<211> LENGTH: 25
<212> TYPE: DNA
<213> ORGANISM: Artificial Sequence
<220> FEATURE:
<223> OTHER INFORMATION: Synthetic

<400> SEQUENCE: 815
catccaaaag gagagtttgg atttg                                              25

<210> SEQ ID NO 816
<211> LENGTH: 25
<212> TYPE: DNA
<213> ORGANISM: Artificial Sequence
```

```
<220> FEATURE:
<223> OTHER INFORMATION: Synthetic

<400> SEQUENCE: 816
catgcctaga aaatcgtggc tgata                                      25

<210> SEQ ID NO 817
<211> LENGTH: 25
<212> TYPE: DNA
<213> ORGANISM: Artificial Sequence
<220> FEATURE:
<223> OTHER INFORMATION: Synthetic

<400> SEQUENCE: 817
aaaaagggtg tggctttatt tattt                                      25

<210> SEQ ID NO 818
<211> LENGTH: 25
<212> TYPE: DNA
<213> ORGANISM: Artificial Sequence
<220> FEATURE:
<223> OTHER INFORMATION: Synthetic

<400> SEQUENCE: 818
ccaacaaatc tgtagattgc tgaca                                      25

<210> SEQ ID NO 819
<211> LENGTH: 26
<212> TYPE: DNA
<213> ORGANISM: Artificial Sequence
<220> FEATURE:
<223> OTHER INFORMATION: Synthetic

<400> SEQUENCE: 819
aaagaaagcc aagttaggtt cagaca                                     26

<210> SEQ ID NO 820
<211> LENGTH: 25
<212> TYPE: DNA
<213> ORGANISM: Artificial Sequence
<220> FEATURE:
<223> OTHER INFORMATION: Synthetic

<400> SEQUENCE: 820
tgagaggttg ctgaggaatt cttgt                                      25

<210> SEQ ID NO 821
<211> LENGTH: 25
<212> TYPE: DNA
<213> ORGANISM: Artificial Sequence
<220> FEATURE:
<223> OTHER INFORMATION: Synthetic

<400> SEQUENCE: 821
gcctagtgga aaacatttc caagc                                       25

<210> SEQ ID NO 822
<211> LENGTH: 25
<212> TYPE: DNA
<213> ORGANISM: Artificial Sequence
<220> FEATURE:
<223> OTHER INFORMATION: Synthetic

<400> SEQUENCE: 822
acagctggac atgcatgctc ttaat                                      25
```

<210> SEQ ID NO 823
<211> LENGTH: 26
<212> TYPE: DNA
<213> ORGANISM: Artificial Sequence
<220> FEATURE:
<223> OTHER INFORMATION: Synthetic

<400> SEQUENCE: 823
ttgcaacttt ccagacattt attttc                                              26

<210> SEQ ID NO 824
<211> LENGTH: 25
<212> TYPE: DNA
<213> ORGANISM: Artificial Sequence
<220> FEATURE:
<223> OTHER INFORMATION: Synthetic

<400> SEQUENCE: 824
agggtttcca aagttttggt gaatg                                               25

<210> SEQ ID NO 825
<211> LENGTH: 25
<212> TYPE: DNA
<213> ORGANISM: Artificial Sequence
<220> FEATURE:
<223> OTHER INFORMATION: Synthetic

<400> SEQUENCE: 825
taaaatttgt ttggaggtgg ggtct                                               25

<210> SEQ ID NO 826
<211> LENGTH: 25
<212> TYPE: DNA
<213> ORGANISM: Artificial Sequence
<220> FEATURE:
<223> OTHER INFORMATION: Synthetic

<400> SEQUENCE: 826
acccacagaa acttccattt cactg                                               25

<210> SEQ ID NO 827
<211> LENGTH: 26
<212> TYPE: DNA
<213> ORGANISM: Artificial Sequence
<220> FEATURE:
<223> OTHER INFORMATION: Synthetic

<400> SEQUENCE: 827
cacaagaaaa ggtttcatga gatagg                                              26

<210> SEQ ID NO 828
<211> LENGTH: 26
<212> TYPE: DNA
<213> ORGANISM: Artificial Sequence
<220> FEATURE:
<223> OTHER INFORMATION: Synthetic

<400> SEQUENCE: 828
tgccatctaa aatattgctc ctacca                                              26

<210> SEQ ID NO 829
<211> LENGTH: 23040
<212> TYPE: DNA
<213> ORGANISM: Homo sapiens
<220> FEATURE:
<221> NAME/KEY: misc_feature

```
<222> LOCATION: (5120)..(5120)
<223> OTHER INFORMATION: n is a, c, g, or t
<220> FEATURE:
<221> NAME/KEY: misc_feature
<222> LOCATION: (14080)..(14080)
<223> OTHER INFORMATION: n is a, c, g, or t
<220> FEATURE:
<221> NAME/KEY: misc_feature
<222> LOCATION: (15360)..(15360)
<223> OTHER INFORMATION: n is a, c, g, or t
<220> FEATURE:
<221> NAME/KEY: misc_feature
<222> LOCATION: (15760)..(15760)
<223> OTHER INFORMATION: n is a, c, g, or t
<220> FEATURE:
<221> NAME/KEY: misc_feature
<222> LOCATION: (23040)..(23040)
<223> OTHER INFORMATION: n is a, c, g, or t

<400> SEQUENCE: 829
ctggaatgca aagcgaatac cccatgataa gaaaagtcta gggtacaggt cactgagttt      60
tcccaccaga ggctgtcacg ggccccaccc aagcctgtgt gggtttgggt catttcttcc     120
agactcctct tccaatccca attccttctc ttcattcact agtggaggag gagagagatg     180
gcttggaaag aaaggagact tagtgccttt tatgcctctc tcttcccagc agaagagcag     240
tcccacccct ctataagaac aaagagtcag ggtgagtgtg agggcaatgt gtgcgcctat     300
gcacttgggt atccgaatgt gatggagtgg gaaaggggcc agttatgcag acttgcgtgc     360
gttcacagga attggagatt ctatccgag tgtgtcctga accgcgtcta cgaagatcct      420
ctacacggac cctcacactt cacgacagaa actcctcctg caactttgg aggaattctt      480
gagtagggat tgagattagg gaggtggaga agaccgggtt ggccctggct gagagacacc     540
caaattttct aatcactgct caggagcgat tggcaggttc gagcagcaca gtcattccgc     600
acacagatgt ccctgcgttc actcttctga tatgaattct ttcaaaattc cagaactccc     660
atgaattgca aatcgtgctg agtgcccagt tcttatattg ccctcttcgt gggtgcgcgg     720
agaaccttgg ccaccagcca aaagtgcagc ctgccctttg atttaggaac acagaaaggt     780
caagtctccc tggctactgt gggttggcca ggagggagct tttccgtggt ggtaccaggg     840
agaagtgtct gcgggatttt tctgtctttt tctacaagat agagatgaag ggaagagaga     900
aagccccagt gccctcactc ccattctcgg gctgttccca agggagaagg aaaaaactat     960
cagagcagaa cagccctccc aaggcagctg cgcccttcct taccacttct cacccaggga    1020
aactttgtcg agaattttta agctgcagga cagaaaggca gaagctgctt caggattcag    1080
aaccggggca gggttttaag gtttctcaca gttcaggtgt gtaggtcagg ctaaagctgc    1140
tcagtcctgg cgtctgcctt ctctttctcc tcaggtgcct taaggactaa actgcagaat    1200
caatggctct cctcagagca gatgaattcc tgtcaatgat tctggggaag aggaggaagc    1260
aaaggttgcc aagagagaac ctctgacctc tgcccagaaa ttcttgtatc caccagcttg    1320
tggactttcc catgaaaggg aaaaagagaa gcaggcacag gagtcatggc tggaacgcag    1380
ctcaacaatg aagggacagg aatggagctc aacagtgaag ggacagggag taactgcttt    1440
cttcccttcc ccgccagatg ggcaaatggc ctggactcgg agatacctct ttttctctgt    1500
catcttccaa atgctggact aaacagaatt gagccacgta gggtagctga agaacaatgc    1560
atagaaagaa gtctgtggtc tggccaggag agccacatgg agctctggac ttctgagcgg    1620
gttctaggaa actgactgag taggggagaa gcccaattaa ccttgttctc agggcaggat    1680
ataagtgcca agttcctttt ctctgcaatt gcccctgcca ggccttgctc cacgccatga    1740
```

```
gtgcagatca gacttttgca aggccctagt ctgtgatctc actctagaga ggcgatgccg      1800
ggagaattcc agagaaggca gtgaaatttt gaaagaatgc taaatgttct gaaaactgct      1860
ggagaattcc agtgcagcat tggaaagggc ctcctgctcc atgttcccct gggtcaggca      1920
gcctttgcat gcctgacctt aatcctcaac cccaacacta caaacccac ttcagcccta       1980
aaatgagtca cagtgtttgg agtaggaggg actctatcag ggaagtcagt taagagctgc      2040
ccctgcctct caggttcaga gaaaaaagaa ttgtgaggcc agatgctcac ccagtgccct      2100
tcctcccttc taagccctta gggttccctc tgttcagaac tgtaccagac aggaagaaat      2160
tttcaaggga ggtgcctgtg catgttcagg aatgaagaag tgtaaggata tcagtgcttt      2220
agtgctggga aggtgcgagc tggttaggga gagaatacta cccaagaatg tccagggtcc      2280
ctctgtttgg cctctgcaca gtcacttgac actctgcctt actgaacaga aacacgcaat      2340
gcacttcggg tgtccgacgg gagtttcatc ttcgctacaa gaggaaggta aaattgcgtg      2400
caaattgtct tggcctctct ctttcctctc aatccacttc ccctcccgcc aaaattaaaa      2460
tcgcaaaacg cggagactgg gcgggcaaag gcaaagaaa agaagggag ccggcgcgaa        2520
gtctcagtta tgaaaaaacg cattgagctc ctcgtacatg gagtagtgca tagagtagtg      2580
gtagcttttc tcgtggtcgg gcgaggagtc ctgcttgagt gagaagttgc cattgagaca      2640
atccaaattt gtttgtttgc ttcccttttt tcggtggtgg ggaaaggtgg caggcttttt      2700
gggacaacca tggaggggtc tgtggctaaa cgaaattcaa accaagggaa agacagagaa      2760
agggaaagat gtgcctggat gtctgtgcct ctgcatgggc gactcaagca ttctcctccc      2820
cttctgaaaa atctgaaaat actgaagcca accccagtaa tcccaagagt ggccaagggg      2880
gataacatac ccctactcag atagacacat gtatgtgagc aggtaatcac agcctggtgt      2940
agacagaccc ttgcccacac tctccctcta ggaggctccc cagggacctt gggctggtaa      3000
gacactgatc tgatgttggg taggttggat taagttctaa tcagtggtct ctaaaaataa      3060
gcctaccatg cttcccttca ttcacgaatc tgggtctgc aaggcgaatc ccatctctgg       3120
agatacaata aaaaccaggg gaaaattgga acagagggag gtgtgggatg ggcctgcttc      3180
agacatgggc ttgaaagagg tccgaattgt ttccttgctc taaaggtggc gtgacctttg      3240
ctcccgtaac ctttgacttc tggcctctga accctgtttt gctcttttccc tgatgggcac     3300
tggtctctga gttccccttt ggtcaaatgc attctcattc ctcactaaga tgcttcctgg      3360
ggagcttacc accctttgtt agaaggaccc atttacccat ctgtctcctt gcctggaccc      3420
tggtgacgac ttgttctgta cttgctcctc tggcttacct cacggaccca aggctaccca     3480
ccctgcacat cctatccaaa atgcaaatac catgcaaaca ctggatttac aagcctcatg      3540
cctagtaatc tttgttcagg ctgttctgtc ttcctgaggt gtccagtcca gcttcctcac      3600
tctgggcagc acatttcacg aaggcaggaa ctggacccag agcctggcac acagaatatc      3660
ctcaatatat agctgtggca aaaatggaag gctgcaagcc agcacaggac ctctacccac      3720
aggaagtccc tcctcaaaat cttccctctt ttctcttcag ccaaaggtc actggggcag       3780
aatgtatggt gtgtgcagga cactgtggtc agggcaggag gtcacaattt aaccagagat      3840
ctggatctat caagttctgc tcatgggtgg gtaggtgggt ggaggctgct tctaaacaca      3900
gagagggagc agtcacatta ttggatggga gcgaggaagc tggagacctg gcccattttc      3960
attctgcata aaattttaat ggtctctctg gctgatccgg gatctctgcc tcctggaaga      4020
gcaagagggc gttgtggtag cccctgatga ctagagaaat ggaagggctt tcagttagat      4080
cgggtgcctg ggcaggagga cggggcagag cagctgctgg cgatttatta agcagtcacg      4140
```

```
gaaaaattgg tttataaatt acagctgttt taactttagg gcctcttctt cagggaatgg   4200
aagcagccga ctggaccggg attggagtgt gtgtaaggct gtattcatct attcattcac   4260
ttctcaaacc atcctctcgg cgtcatgcag tgcctgctgt attctgggta ctgtggcagg   4320
ccgcggcagg catccagcaa tggcgtgaag atacatgatg ggaaagaaac gcctcaaaat   4380
agtgtgctca gacctatggt cagtccaagc agagagaccc acagttcaat cagagttacg   4440
tcaaatgagg tcttgaattt gttccttgga cccaaccgcc accacctggc cgcccacctg   4500
aaaaactttt ccccaagttc ttgagaagtc gcgtaggatc caggagagaa aaatcaaagt   4560
agagaggacg ccaacacaaa cagagcccca ggaaaacatg catgtacacg tctacacaca   4620
ccctctcagt gctagacaga attagatccg gagaggaaag acaggagcca cgtgaatcta   4680
cagtacatca tggcagggca cattccccctt ctccctcaca ttggctgggg aggtggcagt   4740
ttcagcttaa ctcacctggt tctctttgtg catttccctg gagctcaaca gggacctaat   4800
ctgccaaagt cccatgaaca ggagtcaaag ctggagactg gggagtggat aaggtctggg   4860
aacccaactc tattggcttt cctcccctcc catttgcatc ccatttgcac agatctgcac   4920
actggtctcc tctttcctgc ttcccttct ccatggaaaa aagcttggat ttgaaggatc   4980
ataggaattt aacaggcagg caagggcatc ccaggtccaa gaagagggaa gaaggtgtgc   5040
tttctagtca gggagctggg gagatatacc tgaaggacat aggagggcct cttcctgact   5100
aagccctgtt gcctaccaan ctggagctct cacacttggc tcaagatgaa gctctgccgc   5160
gtccccaagg tcagggtagg gtgatttatt gtgctttat tcagcatctt gtctgtggcc   5220
tgtgaacttt gtgtcgcata tgttctaaga tcctgccagc tcctgcagcc tctcctcagt   5280
cctttctcta acccccttgct cctttccatc ttttggaaac ttgtctccag ctgcccacac   5340
tgttcccttc ccagccctat agactattat gtcctcagcc tcggaattgt tctgtccctt   5400
ggagcccggg gcaggagtat gtggattggc atctatgact ctagcatctt aggacagctt   5460
aagagccaaa catgatcaaa tctacccctg gctgcctctg ccctggtctg acacccatca   5520
ttgctttcct cggtctcctc tgtgccagct gtgcagcgca ttgctgagtc tcacctgcag   5580
tctatcagca atttgaatga cctgtgacat gtggattagc tgtgggtcct ccttgagtat   5640
acgaggacgt cccctttctag ttcagtgtct catacacgca ccgaactcag ccctacctga   5700
gacatgggtt tcctccatcc ttggctcagt ccctctccca atcaggtttt ccctaataat   5760
tctcttccct gagaattaag gccaaggccg tttggggttt gaggctagag ccaaaagagg   5820
acttcccacc tatggcagta cgtgaggaca ttcaggatg gaggaccagg agagtccaac   5880
acccctgtca cctgcatttc acctacattt ttgaacctag atgcagaagg gcaccgggtc   5940
aaatgatagt cctatgatgg agcaatataa accaccacga ctcctagtgg ctcctgggtg   6000
tggaaagctt aacctcagcc atcagacact tagctcacac tccaggacag ccggatggat   6060
acgcagagcc tgtgttctta tatggaggat tccaagtcac cacttctctc accggcttct   6120
accagggtcc aggactaagg cgttttctc catagcctca agctgctctg cccctttccc   6180
cttcttccct gactccaggc ctgaacccct cccgtgctgt aataaatctt tgtaaataac   6240
gggaagtcct tctcgaataa ctggattcct ccaaagattt cccatcccc acaggactcc   6300
cctcgggaaa ttcccctttt gggccctttg aagtcttgag ttcttagagg tgcatagtac   6360
cattgacact catttctaat gacacgttcc ctcaccccgc ttttgggtta gtcaatgtct   6420
cctggttttc ttcgtaccgc tctgacagtc ggtcaaagtc ccgcttcacg ttttcctctg   6480
```

```
ctgtgtgcac cctaaggtcc aataatacgg cactgcagca tgcgccatgc ctacccttgc   6540
tgttcgtatc ttcatgactt tctagagaaa tgtatagatc tgggaactag agggagaaaa   6600
agaccagggg cggcttctga ggagctgaca gttaatgggg tataaagcga tgggaggatt   6660
ttatcagagg gaggcagagg ctggagtggg ctcagagatc agaaagctgg gtcctctgaa   6720 cctttcttg agagggctga gatctctcct ggaagatgac tagccgtttc cagactaacc    6780
ttgggaactt gacctcactg gtgtgtggtg gtgagtcttg tttctatttg gcttaactct   6840
tccccttccg cttcctcaga aggaaaggag aaacagagcc gctttggctt tgggtcttat   6900
ttgtcactgt agctgtgtcc tcctctccct acactcccac ttctccaggg gatttcccaa   6960
acctactccc aagtttttga ctccaggatt gatgtccaac cccaaaccca cacccttttct  7020 cctgttccag ggtggacatt acagactagc taacttacta gacatgtacc gtggccaggc   7080
actgtggctg tgacttggac ctcaagggct taggacagat gacattatgg atccacaggc   7140
taacttacta gacatgtatc atggccaggc actgtgactg tgacttggac ctcaagggct   7200
ttctggcctg gggtatgacg aagggctagc aaggaaccct gtctgtggct ctgcagcctg   7260
agatttgtgg aaattgaaaa ccactgctcc tagccccatc ttacccgaaa agtcttgcca   7320
gctacttaat ctatctcaac caccactgac caagcggtta cagttccacg ccacggtggg   7380
ttttcatcac ttagactggc aggtggtctg atggagctca aaggcctttc aaagtcatct   7440
cattttcaaa ccctagccaa cgaggcctca ctcagggtga tgctggagtt tgaggaaagg   7500
ctgacaggtg ggattcagta gtgaaacaga tacaaaagat gaggagagat ggagagagtg   7560
aggaagggag acaggtctgg ctgcaaacaa aagggctgtc ctccccatca gacttccgga   7620
tggcaagggc ccttcctcca ggtctcatgc ttatgtgaca agaaaacaat gtcttgttaa   7680
ggcaaagaga ttaagtttga ttctgggcat gttgagctgg agggagagac agggctctga   7740
gggtgactgt cgattgtgca tgggagcata tattttagt tcgctgacag actgtgtctg   7800
tgttgcccag tggttacaag gactcagtag gtcgtgctg gacaggggca aggacacatc   7860
cactccgtct ccacttcacc ctctcaagca gcgtgatgga ttttgcccat taagcataaa   7920
aggcagagag ggagcaggga aatgacttct gctgggttct cttttggcag catatatcca   7980
gtctgatcag agactcggct ccaggtggga gagggaagat aagacccctg tgcaaggtta   8040
catccaaatt gtcccagaga catgctgact cagtcgttgt agagggaatc ctgtcctttg   8100
gtatctataa ggaatcatcc ttcacccgct tccctgactt agccccttgc agctctagga   8160
agaaggttct ttctccagcc taaccccagt ttatcctgct gcagacttga gagggttccc   8220
aagcagctgc taccaggaat ggtaggctgg gtctgttctt tctattcctt ctatcaggct   8280
ccctggggaa agccagcaac cctctcccac acacttttat tccccacact ctctccccac   8340
cccttgccat tgtcatctgt gcctgttttc tgcagggtct gacaatgaat cagatgaaga   8400
aggggaagga ggcacggca gtggtggacc agatcttggc ccaggaagag aactggaagt    8460
ttgagaagaa taatgtaaga gccctctccc acctgacctt cccatgcgtg ttaggagttt   8520
ctgttctctt ttctgaggcc tgaggaagaa acccaaagat cattatctac aaagatcgta   8580
gagagcttgg aaaacagaga gcaacatgcc ccagtccctc tctctggcca gttcttgtgg   8640
actcgacatc aaaagcctct ctcctgccag tgccataggt ttgttagagc tactgttttg   8700
taacagctgc tcaggtgtcc tctctgccat gcctgggcct cccctttgtc agccacctt    8760 cttacttgaa aatttgggtc agggtccaga tggtctctta cttggctttg cctcggggtg   8820
tgaacggggt cagtgaccctc taaaactaac ctgcctctca gttctgaatc cagacagaat  8880
```

```
gagatagctg agaggtgcaa acagaagaga aaaagagca acatcccta ggagagggc      8940
agaggagaga gaggtggaga aaatggaggc agatgtggga caggggtgag aaactgccag    9000
gatttcctcg ctgagcctgg ctggtaggta tagttgtttt acccacctgg attccctgtt    9060
ctttgaagtg gcacctaata aagaaataat accctgccgc tgcggtcagt gctgtgtgtg    9120
cccagagatc tgagtgtccg ggtaggggag acattcaccc taggcttttt ttccagaagc    9180
ttccttgagg ctagcattct tgttatgatt gaagcacaat ggccgaggga agtgaaaggg    9240
aaagaactgg ctccagctcc ctctcacaac tggacttgag tattaagcac atcccttgcc    9300
accctcccac cttaaaagtt ttcagtatca aagaagcta gcgcaggcca cccgagtccc     9360
aaagagggac aaggggtcag gggcagagca aaaatccagt ctgcttcaac cacggagact    9420
gcctttggga tggaaagttt cagagctggc gctccacaag tgattattga tggtgacagg    9480
attccctcat cctgctccaa cctctcaact gtggacacat ctgggcccac atccttcatg    9540
tccaagttca agaagttgaa aagagaaaat catctcaagg gttgagggga aagggaggc     9600
cagactcgct ccaaggtctt cagtccagct tgaacttgtc ctctgattcc ttcagcaggt    9660
acaggctgtc atcttccaga cagcctcctc tctctcccac ctcaaattct tctccattcc    9720
tctaccccaa gagtctctct agaacctcct tctccaggaa gccagggccc aggggaatgt    9780
ttgaggcctt cttcctggaa attagctgcg tggagagagc acaaaagtta tctagcgaat    9840
tgaaacatga gtgttctctc cacttgcctg accagcacag aaccccgtca gcttcccata    9900
gaactgaggc ctaagaggat acctcagcta taggaagagc ccctcctcct tcctctggag    9960
ccatgttccc atcaatgtga accgaacaga tccatttctc tcactcagag tttgtcatca   10020
agagcaagca aaggggaaag atgggctctg gaaggaagga gagttccaag atgccaaggc   10080
gaaaatcgag acaaaaatat cacagccgtg aaactggttg gatgccaagt gagccagatc   10140
tgtcaggaat tcgacccggc gctgagttgc agataccatt gaggtgaaaa atccaagaat   10200
cagggatgac aagaccagat ctgtgaagtg acccctggcc ctggcacatg ttataaagac   10260
aagggggtggg accctccgat ctaagaaggc tctaagcttc ttcagagttc aggcagggct   10320
tggaagaacc ccaaaggaaa gcagacaggt gtaacgtcct cagcttccct gcccttcctg   10380
ctttcttagc caggactaaa actcaggggc ctctctgctc catctactct tctactccta   10440
ttcacacagc tacaatgggg ccaaggtttc ctggaatgct caatcccctg tccccacaca   10500
tgtatgtgtc taagccttgc cccacacatg tatgtgtcta agtcccagat taaacctctc   10560
gttgttgaat aggaagtatt aaggagggtc catatttccc agaggtttaa cagcctcctt   10620
ccctgacctc cttcccacgc gcttctgtga gagcaggaag gtgagtgaat ggaaattttt   10680
tccttaaggc ttacagggc agctccgacc tagagacatc gttgcaacct ttcattctca    10740
cacccttccc aaggccgtca cggtccatat ctgcaccca gtctgtgctt atcacacaat    10800
aggccctgaa tacagctctt tagaccagcc gtactgtgaa gctgacagcc ctttctgcac   10860
ctgcagatgt aaccatacct gggtcttta gtggcttcct tcttcaggac aagaaaaatg    10920
cccttctttc ctctctcctt cccaaacagc ctgacctagg ctttaccacc ctgcagctgc   10980
aactttagcc ctgggaaaca gagggaagc tggtaagtag aagccctgtt gggtgttaat    11040
tcttgaaaga acaggaaccg ggagaagggc cactgaaaaa ggagcagatg aaggaggttt   11100
gaagggcagg caaccctcaa gaaaggtacc agcaaactgt gcctcgctag acaagctgaa   11160
gcatattact gtgaatccag acccctactg gagaagcaac tctggggaga ctccaaagcc   11220
```

```
ttccagatat tgctactcca aatccagagg caggacacat gggtcctatc caattctatg   11280
tatattactc ctaccacgct actaccatat gcctaccctg accctccaac tcaccttgcc   11340
atggaactga ggcactttgt aacggtgacc cacatacact catacttaca gtcgtcccga   11400
caggtccagc ctgaaacaga caaatgtggc ctggtgaact agaggaaaga gagagcatga   11460
atggggtcca agcgcaaatg taggccaaga gggcctgtaa gttggagaga accaggagaa   11520
cttcaacctg acttttgagg ctccaaattg cctttccaac cgtattggtc actactcctg   11580
ttcatgtacc ctgctccctg atgcttccta atcaaagagt ctttcagggg ctcaaatcat   11640
tctctgcctt gcacttgaaa aggctcatgt ccccgtgggg tgctgtgtcc atatatcgag   11700
gcgatagggt taagggaagg cggacgcctg atgggttaat gagcaaactg aagtgttttc   11760
agggctatgt ccctcaagct tcctgactgc ctggcctggt ctgaatcact cactcttctt   11820
ttttcttcta gtcgcaattg gtaatatttc taggaaaatt aggaaccctg ggaacaggac   11880
gcttgcttta gtatcctctc cctgctcacc tcccctgcac gaatagtgtc ccctggagtt   11940
gaccacccaa ctgatactga ctgagaagct gaaatgaaca aaacaacccc ttagccctcc   12000
cctaggttaa tggtggaagt gggagtagag acttctgttc tgttgacttc ttggaagatg   12060
gggtactgtc tctctgggac gctcttgaga atttccctgc cagcacagcc ccagataaca   12120
atctctagat ggcgattacc tggcctctct tcccaacttt tagcctggag cccctagttc   12180
tcccctgagc ctccttagct tgtccttctt cctaacttgt atttggcttc agatgtgatc   12240
gttgtatgct tctcaaaggt tcctcgtctc ctcttccttg gaccaaaagt cagaggcaag   12300
aatgccctca ttcatacccc gagtgagcaa gtgatgtcct gaaaggccca gtggatcagt   12360
ggaatgaagc gggcaggaag acttagtgct cctgaaacaa gagtggcctc cccatggtta   12420
ggatacaagt gctcatcaag ggccacccct aggaaggacc aattttccta tcagaagctt   12480
acgactcctc ccgatttctg tttgttttca gtcctctgac cccaagctgg ctggtgaagt   12540
aggtagaggg aggagacttt cttcctctcc tcttgtcaga caccagacga ggttttttcc   12600
tctggcttcc cagctctgaa tgggctcatt cttttttcaga aagcaggat ctttgtagag    12660 ggagggacct acagttacct ggacttcttt cctctgtctc ccctcttggt acccttgact   12720
gcaggttgac caggtcctgg gctggatgat ggggtgagag taagggtca gttttgatac    12780 atgcccaact tttctctcta ccctaagaca tcctgggcaa attgcttacc tcagttcccc   12840
tgatcctcac cctaacccta acaccagctc aagagaaaat ccctaggatg gcatagcaac   12900
ctgtcccaca agaggtgcct gctttaagtg tgctcagcac atggaagcaa gtttagaaat   12960
ggagggaaga gagaaagaga tgctggtgtc cttcattctc cagtccctga taggtgcctt   13020
tgatcccttc ttgaccagta aaaaaaagtc ttccttccat ccccaccct accactaggc    13080 ctaaggaata gggtcagggg ctccaaatag aatgtggttg cctctgtgag tgagtgcatg   13140
gccgtgttat ctctgcaggt ctacgccagg gtgttcctca gttgtgtggt ctttgtattt   13200
gaggaggcat taagaggtgg ttagagtctt attccagcca acaataatgg gttgaacaaa   13260
gccttagggg caggcaggtg ttgggtgatg gaatgatctg gaaagagatt ccttccctgc   13320
cctccacctg tgagaagccc ctctagagtg acatctccat gagagccgag gtggggtaag   13380
ggatgtgtac tctttcaagg agtgggagaa ttattctagc gaatgtttgt gttgtcccag   13440
tgttagccag caagcctcca gttccctggg aacgttctc agggtaccaa ttttaccacc    13500
tgtctgcaaa cactttaaga ctccgtagag cctgtggtgt ttatcggtgg cattgggaga   13560
attagtgtgt atttatgttg gcgtgggtg tggggtggat ctccctcagg gacatggacc    13620
```

```
cttgagttct atttctgttc ctccctcctg ttcctccctc tttgtcctta tctgcctaga    13680
acccttccga tctcctgggc aagacacgcc aggtgattca tctcaccaga gcagaaaaac    13740
aagttcaact gggcactttt aagggtgggcc tagtcagaag aagcctttcc cctgaaatcc    13800
ctctacttcc caagcacgca agctttctcc tgctgttaaa ctctgtttac aggtgggtgg    13860
cagaagaagg tgccctgccc ttctgttttcc tctcttgttg tggtttctca accaggaagt    13920
cattttactg cagaatcagt tgactctctc tataacgtgg ctggccgagg tcatgtctgg    13980
atgggatgcg tctgtgtttc gctttgttct tgttgcgggt gtggtggtgg tgggactcaa    14040
agacggtaaa gatagctttc tctcctccct ggggaatctn gaagcagaag gtgacagaag    14100
gggaaagggt cctctgatca ttgctcaccc cacagagatc ttgaaaggag gggtcttgat    14160
tctgctgctg tttgtgcctc tctctgttac taacccgtcc tctcgctgtt agacatctct    14220
ctcactgcct gtctctggtt gagcatatgg ggagcactgt ctgcatcttg ctttgagagc    14280
tggtcatgac agttcctgcc gagctgcctt gttctttcaa atttaacaga tcacctattt    14340
actgatgggc gtttatggac tgggctcaga cctggggaac ctcttttcctc ctctcacagg    14400 acggtaatgc tgctcatggt ggtgcacgaa gggccagggt atgtggctac atgttcctga    14460
tctccttaga caactacctt cagttaccag tgccaatatc caggagtttg ctggctgcaa    14520
gaagatcttt gggagcctgg catttctgcc ggagagcttt gtgtgtgttc acctagaccg    14580
tttatgcatc tgtagacaca cacacagtga agtgtggttt tcgtcgtttt ggtggggagg    14640
tttgggcctg agggagtact cctgtagcag taacctttcc atgaaagtct gcagagtgtg    14700
ctggggatgg aggaagatga cagtagggtg tgctatctgg taaaatatcc ctggagaggg    14760
ctcagcgctc agacctgaac agcaacagag tggcagaaaa agcacgggaa aggctttcta    14820
cagagcagtg actgttgtta ctcgctgtta caccttaggt aatgcgtttt cctctctggg    14880
ttgccccatc aactgcaccc actcgtgagt ccaacggtct tttctgcaga aaggaggact    14940
ttcctttcag gggtctttct aaagtataaa tgttacaaag ccaacgtgcc ctttcactca    15000
actccctgtc cacccagtct ctcctgtctg ctgggagaac tgacatatgt cccttcccac    15060
ccactcttcc actgtggaac ctcctgtcat tttccacttc accaagtgac agaggacctg    15120
actgcaagga aagatggcta ggaaacccag tccctccaca ccctagagta acttgatgcc    15180
ttgtgaggga cacaggcaaa ttacaccatg aattgttgaa gccctaagcc agagccaagg    15240
gcaagagtat agagaatctg gagatgcgga gagggttctg aggttttaga gtaggagagg    15300
gtccaagcct gtgggtcacc cttccgactt ccctttccga atgccaaaca ccttcatgtn    15360
ccacaagggg catgaaaggg gaccaggatg tatgtagacc caggagccct agtatgttag    15420
gagcctcaaa accttcttgt ttaaaaggga aactagaaga gatgccaaag gttctggctg    15480
aagaccccag agtctggtgc tacttctcta ccacctgagg aaccccggtg gactagggtc    15540
cctttctctg atgttccctc aactgtcacc tctcaaggaa accccattat ccctacaaaa    15600
attcttactg ccttccaacc cctgtgaccc cattctctcc acggtgactg tgtcataccc    15660
caaaggtgac ctctgttttt tgagagggga agcggcccta agggagtgtc taagaacaaa    15720
agcgacccat tcagagactg tccctgaaac ctagtactgn tggctctgtg ccatcccttc    15780
ctgctcacct tacactcaat tcctctttc ctggagggag tggctgggaa tcttcagaaa    15840
ttagaacgaa ctaattccta aggccactca ccagaatggg gttatttcct ccttgtgagt    15900
gaggagagtg gtgggtaggg agggtctact gtggactca ttttccttgc cttggctatg    15960
```

```
ccagaggagc tcactgacct aaggagtagc tgtccagaaa gctgacattg ccctgggtta   16020
ggggagaata aataaaatct gtggcatcag acaggtatta ccgaggcgaa gagtggactg   16080
aggagtggaa tgacaggatg atgcactgtt ggggtagggt gaccaagagg tcctcccaac   16140
gctgtaaata ctcacatctt tcgcctgtgt gcccctcgca acactcaata aaggactccc   16200 tccctccaa ccctacacga ttgcagtcta ataggttttt cccactcccc actccggtg    16260 tccgctggac ttcatggctt catttactct aatggactat cttagactgc aaagcgcttt   16320
aaatgtgccc tctcctctgt gcttctactt aagtctaaat acaacttgca gggtctggtc   16380
tttgaccgct actcctgccc acttctttgc tgggcccact cataccggtt ttcctaggaa   16440
aactctggag aaaattgagg caggagccac tcattcgtgc cacctcctaa cccctctccc   16500
aagtaccctg tgtttgccca gcactgaatg agacagctaa agtgatccct gagagaacta   16560
agtcctgggt cctcccttat actaggagtc atccaggggt ttctcacctt ctcacctggg   16620
ccctgcaccc taaaaaatta aagggtggag cagggctgt ttttgtttct cctaagccag    16680
gaagttgtgt ggatgagtca aggttgaatg gagagcccta cacctccacc tctagtgctc   16740
gtctttgcct gctgtcctgt ctttacttgt cttgagtgtc tgtgcagccc ctataagtga   16800
tggataatac acagaggctt gcaggccact gctccttcc ccacacctct ctccctttt     16860 cttcttgcca caggaaactt atccctgaca cttgtctacc cacagcactc cctgttccca   16920
gaaaaaatgg tctccagctg tctcgatgca cacactggta ttcaggacgg aagctttgga   16980
aacgcttttt ctgcttcttg cgccgatctg gcctctatta ctccaccaag ggcacctcta   17040
cagcccaggc ggtttcacgc cccacacttt gtacagaccg agaggccagt tgatctgctc   17100
tgttttatac tagtgacaat catcccagag agattttctg acagtctaag tctagagagg   17160
taattaacag ggcctgggag ttggagatga gtccgacagc taaatatgtc agatcgactg   17220
catctgaact tgctgcttaa ctcaggagac agaccctcct gcagacctgt gaaccccaac   17280
ccagagttcc aggctggagt gagagtaaag gggtcaagat gagtcacctc ttcagcatgt   17340
ccaggggttc agactgtaaa atctggccac ctgagaccag cagcagccca ttcttggtga   17400
gtgtctgaga tttctggctt tttggagacg tagctgctaa aaaaaacttg agggcaaagg   17460
ggaaattcct catcatcttt ccatgcagag gaggacccag tactgagaga gggtgacagg   17520
cctgatgagg gatgaagaga ggaaggacag gacacagaca ggggagccca aagccacttg   17580
gaaggattct ttcttccaaa attcaggaaa aaggcttgaa ccagtgaagt actgatctgg   17640
tccaacagat agaaagaggg cccagagagg tcagggcttg ttgcggagaa gggaggcagc   17700
tgcctacttc acaggtcaag acagagttaa aaacaaaacc acagcaaatt caacaccccg   17760
ggagggattt ggggatgggg aaggccatat aatcttctct ccagggctga aaaccagcta   17820
ctgaggggcc gttttgaat atgggaggga gatgatgctg atcatggagc cagaggacgc     17880
tggtgccagc ctagccccac atttgttagt cttaaaactt agacaatctt tctcatgcct   17940
cttccacaga agacggaaaa tggagggtgc tttagatgag gctgagcaga aggccagact   18000
taagaagaat ctctgttgag ggaggaaggc agagcagtga cttggaatag gggtgcacca   18060
tgctgaatgt gctgatcatg ggggccagca gcaggatcac agtggtaggc tcagcaaggc   18120
gtcaggtgag aacctttatt tcagtgataa ttcatttttc aaaccatctt tacagaggag   18180
taaacttcac agttccacac atggctgggc tccaggtaga actccatagg agtgacgagg   18240
tgagccccaa accacattct gttccttcct cgtcattctg cagacaatgg tcatccacag   18300
accacacgtg tggtggcttt ttccagtagc caaaatgatc ctgcaccaaa gctcatagac   18360
```

```
tgagaacctg agcatgcaaa accacagtct gggtgaaggg gtgttctcag tcttttcaag    18420
agaggaagaa gcaaagcggc acttacagag tgtgagatag acacagatct gtggcgaggg    18480
aaggtgggtg gcatcttggg actctctcca ggctttctgg agtggggtca gtggagagat    18540
gaacagtgag aaacatttga tcaaactgca aaaccctgtg tatcttcata acaatggtgg    18600
ggcaaagact atctacagct ggggcaaggg agaggcacag cattcagtcg tgctgccttg    18660
gagaacagag tccttttcct gaggtggccc aggtccagct gctggtttca gatcaaaatt    18720
ggacaaagtt tcaccactcc ctttctctt cttgagctca caagtcccga tgctgactct    18780
ttgagtcctc agatagccag aagtcctgac tctgcccttc tgctaagatt ctccttcacc    18840
ctcacctccc cagccctggc aaggggtttg ttaattagta agacaactgg tttagcccaa    18900
agcagctcag cttttcactg gagatgggaa ggtaaaggac agaagcagaa gtgccatcag    18960
acgatgctga atacatagga gcaatcctg agaccagata ttcacttcag cagggctctg    19020
tgttctcctc tggctatgtg agaactcata ccgatcatgg cttcgatatc cacacatgtt    19080
acactcgaaa gggtcacgga agccgtggca gcccatgtga atcacatagt ccaggaagag    19140
gacgcggcag tggtcacacc gatacacatc catcacctcc ccttccttgt tgatcacttt    19200
aacctccttc agaagtggca tcccattgcg ggcccgagac aggaccatgt gattttgctg    19260
atagatgtga ttctggcgtt atagttgaca tcaaagcagt ggcgcttctc acctggaaca    19320
agtgacagaa agggttacaa agggaacact gccaaggcag ttctagagac ctcaaaaagg    19380
gaggagagtt aagttgcctg ctgctcaaga agaccaagcc tggcagaatg gtttcccatg    19440
gacactggtc ggcagcaacg tgtttggatg gttaaaataa agccagcagg cagaagagag    19500
gggcagagat gtggttcagt gccacatggt aaggtatgcc cactgtgcat gttagaggag    19560
agccctcaag aaaggaggga aagaagcagg acactaggat gagccaccag cccacaggag    19620
cctgggactt ctgctatagt tcatgatctc ttaagacaca gtcggctccc aactcttatt    19680
cagactccaa ctggctactc cccaaactca cccgtcctgg ctgactgaga ctgaagtgaa    19740
agagcttcaa atgtagaaag tgaaaacaga gtttagccac cttcagagtg tgtgggtgtt    19800
gtgtgttaga aaacagaggc tctctggtca cagggaaggc cacagaccat tgttcattgt    19860
taaggagatg gggcagcctc agatgttcac gtgcatgcaa cttgcaatca tcagatcccc    19920
agtcaaacca caaaagtgta actgcttcca aacctgcacg gagcatctgg tccagcttct    19980
agtcaaaatc acaccacgcc ccaacaaaaa tacacacggc aacagcaagt cctaagttta    20040
gaaactaagg ctgcctggtt gggccattcc ctacctgtgg cagaggtggt ggtagtgacg    20100
gtggtggaga cagtcatatc tataataaga agcagactag taaactcgcc tggagtgcag    20160
ccaaccatca tcatggctct gatctcaacc taagtgaaac taacacttct tgcaggaggt    20220
ggaaaacaga ggggagccag ggaaagctga gctggagacc acatttggtt gctgcagaag    20280
tctttgtcct ctgtgagaca ctgggaagtg ctgtgtggat tcacctgcca gctgtgtcac    20340
tccacctctc tgatcctcct tccttccatg gtaaaagagc ctcactggtg gttcctaata    20400
cttgatccaa tctgtccctc ttccccagtt catctctaat ggatgcaaaa tgctccctac    20460
tggtaattat cgccagcccg ctgagatagc agcgggctga cctgatggtc tattttcacc    20520
tttaccctca cagttcaaga ggtcagggaa gtcaaggctg gagtgctgtg caactgtcag    20580
caaggattaa agggaatgac tcactcttcc ttcacacctt acccattgcc attaccctgg    20640
ctgggccctg aagccctgaa gttgctacct caatcaagag ctaactctac taggtttctg    20700
```

```
attccagcac agagagaatg tttgccacat tgcttgctaa tctgtccagt acgagagctc   20760
tttcacttcc catctctgct ttgatgtgtc ttgcctccgc tggatgcaca ctctattgtt   20820
gttacctgtt ataactgctc agattcttgc ctggggtacc tgctgtggtc agtgaagccg   20880
caccagggca cattcaaatc ttgcagtctt atgccgagat gggaaagctc gacccatccc   20940
caaccagtac cttcattagc cctgagtggc ttttgggcta gtgcaaaagt actcgactga   21000
ctctggctga ccagcagttg taaataacgg gcacttcagc cacacaaaac caccaccaga   21060
tgtggcacta cccaaagccc caagagcaga gagatgaaag acaaagcttg gaatttgcag   21120
agtctattgt ggtccctcct ctcactgcca aatcattacc caggaattac cccaagcacg   21180
gtgctaccca tctagttttc ttctagaaag tcctgcttcc ccttgcaggc aggtttgtcc   21240
acaggcttgg ctctcacact acgctgcact tcaacttaca gctttgccta ttgtctgaaa   21300
tacagaactg caagtagaga tgcctacatt ccgtccttga gcgagtactg cctgactgcc   21360
aaaaatgtca gacaacccaa gctgcagaac caggctgaca gccaactcaa tgggacaaag   21420
gacagctgaa gagatgtgac ggtcagtgct ctgaagaaat gtacggcagc gctccttgtg   21480
ctcctcaagg gaacttctct gcttgtaact ccttccacaa cactgggctc tgaggaatgc   21540
acttcctaga caaggaatgc tcatttctct cacttaccag aatgtgtcct aagatgcccc   21600
tccctgtgt gcagtttaat gtggcggagg aggttacctt tctgagtaaa agatgcccca   21660
cactgattac actggaatgg aggtcccaag ttagggagaa ctaaactcaa ggactcaagg   21720
attgtgtaat aggactggat aggagaggag ggactggctc ctacatccct tccaaaaaac   21780
atcagtaagt gttgctcctc ttgctgcata ggaggaagta caactgcagc tgtgcctggc   21840
tctatattaa ctgtgtttgc ttaatagagc aagacagggc ctaaccacca tcagaggagc   21900
cagggctgcc acacagttcc gaggacataa gagagctgct cctttccctc aggattttgg   21960
ctttagttgg cctgacctgg aattcaatac gacaccatcc gctttagtcc tttaggagtc   22020
agctatagag caaggaagac agtatttgag acccagggac ataaggacac agggacaggg   22080
caaactaata tgctgtctcc tggctactat gccttctctg atcaacccag ctggaaaata   22140
gcctgctcct tcttcctggg agatgacaca acgaacaca cacacacacc ccagagagaa   22200
ttttgtaggc tgaagagaac aaaggtttgg ctcactgggg cacctgagac actgcaaaaa   22260
caatgggtcc tggaaaggat ccaacatcta aatccttcag gggcaatagc agtctcagcc   22320
tgcatcagaa taaggtccat ggcccacagt gatagccagt catctagttg acttctttgc   22380
ccattgtggt ctggcttctg actgcttaac agctgcccag taacatactt caaggctgca   22440
agcaaagatg catcctagct ctactggaaa ctgcagaggg actcctcatt tatccctcag   22500
cagggtacct tcctctagct atcaaatggc accaaggtac acaatggctc gggtcaccgt   22560
ctctccagag gatccactaa ggacagtggg cagccccatt tttctgttaa ccattgcaac   22620
tgtctgtggc tctttggcag taaaaaacgg cacttccttt tgaagcatat atttgcgtgt   22680
actaagcagt accgcgggag cctcagcgag tgcctaagcg gcggtctctc ccagctcgct   22740
ccagccaccc ttcttcacac atctaaatgt ggcggtaatt agcatccata aaccacacat   22800
tgtgcaactc aggcagggta aacagctagt gttgatgggt atcgaggtat cgtgtgtact   22860
ttttacccct acagcagctc acaagccaca ggcacagcta tcatttgcct cattctgagt   22920
gagactccat ggatgtcacc ttcaagaagt tgcacgaagc aaagtgatta gatttatcaa   22980
cataaatatc actataaaat gtgagcaata ttaatgtgaa tataatgctc aaaactcacn   23040
```

HYBRIDIZATION PROBES AND METHODS

FIELD OF THE INVENTION

The present invention relates to compositions and methods for detection, analysis, and treatment of nucleic acids. In particular, the present invention relates to compositions and methods for generating and using hybridization probes.

BACKGROUND

FISH (fluorescence in situ hybridization) is a cytogenetic technique that is used to detect and localize the presence or absence of specific DNA sequences on chromosomes. FISH uses fluorescent probes that bind to only those parts of the chromosome with which they show a high degree of sequence complementarity. Fluorescence microscopy can be used to find out where the fluorescent probe is bound to the chromosomes. FISH is often used for finding specific features in DNA for use in genetic counseling, medicine, and species identification. FISH can also be used to detect and localize specific RNA targets (mRNA, lncRNA and miRNA) in cells, circulating tumor cells, and tissue samples. In this context, it can help define the spatial-temporal patterns of gene expression within cells and tissues.

Human genomic DNA is a mixture of unique sequences and repetitive sequences that are present in multiple copies throughout the genome. In some applications, it is desirable to generate hybridization probes that anneal only to unique sequences of interest on a chromosome. Preparation of unique sequence probes is confounded by the presence of numerous classes of repetitive sequences throughout the genome of the organism (Hood et al., Molecular Biology of Eucaryotic Cells (Benjamin/Cummings Publishing Company, Menlo Park, Calif. 1975). The presence of repetitive sequences in hybridization probes reduces the specificity of the probes because portions of the probe bind to other repetitive sequences found outside the sequence of interest. Thus, to ensure binding of hybridization probes to a specific sequence of interest, probes lacking repetitive sequences are needed.

Recent contributions have addressed this question by inhibiting hybridization of the repetitive sequences with the use of unlabeled blocking nucleic acids (U.S. Pat. No. 5,447,841 and U.S. Pat. No. 6,596,479). Use of blocking nucleic acids in hybridizations is expensive, does not completely prevent hybridization of the repetitive sequences, and can distort genomic hybridization patterns (Newkirk et al., "Distortion of quantitative genomic and expression hybridization by Cot-1 DNA: mitigation of this effect," Nucleic Acids Res. vol 33 (22):e91 (2005)). Thus, methods that prevent hybridization of repeat sequences without the use of blocking DNA are desirable for optimal hybridization.

One means to achieve this is to remove unwanted repeat segments from the hybridization probes prior to hybridization. Techniques involving the removal of highly repetitive sequences have been previously described. Absorbents, like hydroxyapatite, provide a means to remove highly repetitive sequences from extracted DNA. Hyroxyapatite chromatography fractionates DNA on the basis of duplex re-association conditions, such as temperature, salt concentration, or other stringencies. This procedure is cumbersome and varies with different sequences. Repeat DNA can also be removed by hybridization to immobilized DNA (Brison et al., "General Methods for Cloning Amplified DNA by Differential Screening with Genomic Probes," Molecular and Cellular Biology, Vol. 2, pp. 578-587 (1982)). In all of these procedures, the physical removal of the repetitive sequences will depend upon the strict optimization of conditions with inherent variations based upon the base composition of the DNA sequence.

Several other methods to remove repetitive sequences from hybridization probes have been described. One method involves using a cross-linking agent to cross-link repetitive sequences either to directly prevent hybridization of repetitive sequences or to prevent amplification of repeat sequences in a PCR reaction. (U.S. Pat. No. 6,406,850). Another method uses PCR assisted affinity chromatography to remove repeats from hybridization probes (U.S. Pat. No. 6,569,621). Both of these methods rely on the use of labeled DNA to remove repeat sequences which makes these processes complex and difficult to reproduce. Further, both methods are time consuming, requiring multiple rounds of repeat removal to produce functional probes suitable for use in fluorescent in situ hybridization (FISH) or other hybridization reactions requiring high target specificity.

Thus, methods for removing repetitive sequences from probes are desired.

SUMMARY OF THE INVENTION

The present invention relates to compositions and methods for detection, analysis, and treatment of nucleic acids. In particular, the present invention relates to compositions and methods for generating and using hybridization probes.

Embodiments of the present technology provide compositions, kits, and systems for generating and using probes selectively generated or synthesized to exclude sequences of disinterest and/or include sequences of interest (e.g., substantially repeat-free nucleic acid probes). For example, in some embodiments, the present invention provides a method of generating a probe to a nucleic acid of interest, comprising: a) identifying regions of the nucleic acid target of interest substantially free of undesired sequences (e.g., free of repeats, non-conserved sequences, conserved sequences, GC rich sequences, AT rich sequences, secondary structure, or coding sequences) of the nucleic acid of interest that are at least 100 bp in length (e.g., at least 100, 200, at least 300, or at least 400) and optionally no more than 20% different in length from each other (e.g., 20% or less, 10% or less, 5% or less, 4% or less, 3% or less, 3% or less, 1% or less, or identical lengths); and b) generating (e.g., via amplification, cloning, synthesis, or a combination thereof) a plurality of probe-containing nucleic acids corresponding to the regions substantially free of undesired sequence. In some embodiments, the method further comprises one or more of the steps of c) fragmenting the probe-containing nucleic acids to generate probes; and d) further amplifying a subset of the probes to generate probes substantially free of undesired sequences (e.g., ISH probes lacking, for example, undesired repeat sequences). In some embodiments, the method further comprises the step of d) separating probes based on size. In some embodiments, the separating is conducted using chromatography or electrophoresis. In some embodiments, the method further comprises the step of isolating a subset of the probes. In some embodiments, the subset is based on size of the separated nucleic acid. In some embodiments, the probes are attached to nucleic acid adaptors. In some embodiments, the adaptors are amplification primers. In some embodiments, the amplification primers are functionalized for downstream applications (e.g., by the addition of labels, binding sites, or restriction sites). In some embodiments, the probes are separated and a subset of the probes ais isolated.

In some embodiments, the amplification is PCR. In some embodiments, regions substantially free of undesired sequence are identified using computer software and a computer processor. In some embodiments, the of probe-containing nucleic acids are fragmented by sonication (although any of a variety of other chemical, physical, or other approaches may be used). In some embodiments, the separating is by electrophoresis or chromatography. In some embodiments, the fragments are from about 100 to 500 bp in length, although other lengths may be used. In some embodiments, the probes are labeled (e.g., with a fluorescent label). In some embodiments, probes are 85%, 90%, 91%, 92%, 93%, 94%, 95%, 96%, 97%, 99%, or 100% free of undesired nucleic acid sequences.

In some embodiments, the present invention provides a method of generating a probe to a nucleic acid of interest, comprising: a) identifying regions of the nucleic acid target of interest substantially free of undesired sequences that are at least 100 bp in length; b) generating a plurality of probe-containing nucleic acids corresponding to the regions substantially free of undesired sequence; c) fragmenting the probe-containing nucleic acids to generate probes; d) attaching adaptors to the probes; and optionally e) further amplifying a subset of the probes.

Further embodiments provide a method of generating a probe to a nucleic acid of interest, comprising: a) identifying regions of the nucleic acid target of interest substantially free of undesired sequences that are at least 100 bp in length; b) generating a plurality of probe-containing nucleic acids corresponding to the regions substantially free of undesired sequence; c) fragmenting the probe-containing nucleic acids to generate probes; and optionally d) further amplifying a subset of the probes.

Additional embodiments provide a method of generating a probe to a nucleic acid of interest, comprising: a) identifying regions of the nucleic acid target of interest substantially free of undesired sequences, wherein the undesired region is, for example, repeat sequence, non-conserved sequences, conserved sequences, GC rich sequences, AT rich sequences, secondary structure, or coding sequences that are at least 100 bp in length; b) generating a plurality of probe-containing nucleic acids corresponding to the regions substantially free of undesired sequence; and c) fragmenting the probe-containing nucleic acids to generate probes; and optionally d) further amplifying a subset of the probes.

Yet other embodiments provide a method of generating a probe to a nucleic acid of interest, comprising: a) identifying regions of the nucleic acid target of interest substantially free of undesired sequences that are at least 100 bp in length; b) generating a plurality of probe-containing nucleic acids corresponding to the regions substantially free of undesired sequence; c) fragmenting the probe-containing nucleic acids to generate probes; d) separating the probes by size; e) isolating a subset of the probes; and optionally f) further amplifying a subset of the probes.

Still other embodiments provide a method of generating a probe to a nucleic acid of interest, comprising: a a) identifying regions of the nucleic acid target of interest substantially free of undesired sequences that are at least 100 bp in length; b) generating a plurality of probe-containing nucleic acids corresponding to the regions substantially free of undesired sequence; c) fragmenting the probe-containing nucleic acids to generate probes; d) separating the probes by size; e) isolating a subset of the probes, wherein the subset comprises nucleic acids of 80 to 300 bp in length (e.g., approximately 150 bp in length); and optionally f) further amplifying a subset of the probes.

Additional embodiments provide a method of generating a probe to a nucleic acid of interest, comprising: a) identifying regions of the nucleic acid target of interest substantially free of undesired sequences that are at least 100 bp in length; b) generating a plurality of probe-containing nucleic acids corresponding to the regions substantially free of undesired sequence; and c) fragmenting the probe-containing nucleic acids to generate probes; optionally d) further amplifying a subset of the probes generate a probe set; and e) performing a hybridization assay (e.g., ISH assay) with the probe set.

Further provided herein are a set of nucleic acid probes (e.g., hybridization probes (e.g., in situ hybridization (ISH) probes)) free of undesired sequences generated by the aforementioned methods and kits and systems comprising the probes. The present disclosure is not limited to a particular assay or target. In some embodiments, probes detect expression of an oncogene or chromosomal aneuploidy.

Additionally provided herein are methods of performing a hybridization assay, comprising contacting a target nucleic acid with a probe (e.g., an ISH probe) generated by the aforementioned method.

Also provided herein is the use of any a probe (e.g., a ISH probe) generated by the aforementioned method in a hybridization (e.g., ISH) assay.

Additional embodiments are described herein.

DESCRIPTION OF THE FIGURES

FIGS. 8A-8G show 80 bp portions of the HER-2 gene selected for use in designing HER-2 probes.

DEFINITIONS

Figure 1:
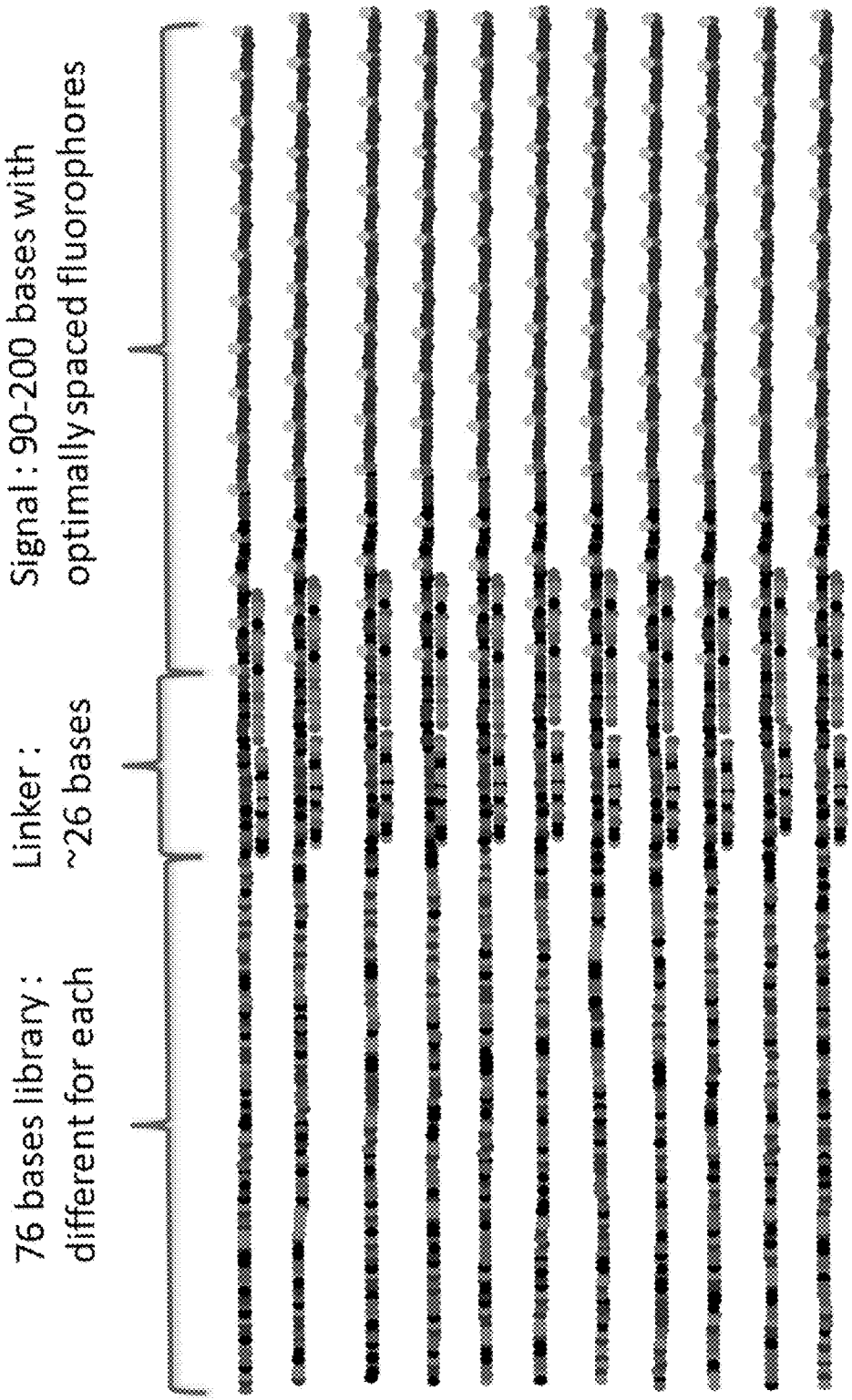
FIG. 1 shows a schematic of exemplary labeled probes of embodiments of the present invention.

As used herein, the term "substantially free of undesired nucleic acids" refers to a nucleic acid that is substantially free (e.g., 85%, 90%, 91%, 92%, 93%, 94%, 95%, 96%, 97%, 99%, or 100% free) of undesired nucleic acids. Undesired nucleic acids include, but are not limited to, repeated nucleic acids, non-conserved sequences, conserved sequences, GC rich sequences, AT rich sequences, secondary structure, or coding sequences As used, the terms "substantially repeat free nucleic acid sequence" or "nucleic acids free of repeats" refer to a region of nucleic acid that is substantially free (e.g., 85%, 90%, 91%, 92%, 93%, 94%, 95%, 96%, 97%, 99%, or 100% free) of repeated nucleic acid sequence.

As used herein, the term "sample" is used in its broadest sense. In one sense, it is meant to include cells (e.g., human, bacterial, yeast, and fungi), an organism, a specimen or culture obtained from any source, as well as biological samples. Biological samples may be obtained from animals (including humans) and refers to a biological material or compositions found therein, including, but not limited to, bone marrow, blood, serum, platelet, plasma, interstitial fluid, urine, cerebrospinal fluid, nucleic acid, DNA, tissue, and purified or filtered forms thereof. Such examples are not however to be construed as limiting the sample types applicable to the present invention.

The term "label" as used herein refers to any atom or molecule that can be used to provide a detectable (preferably quantifiable) effect, and that can be attached to a nucleic acid or protein. Labels include but are not limited to dyes; radiolabels such as $^{32}$P; binding moieties such as biotin; haptens such as digoxgenin; luminogenic, phosphorescent or fluorogenic moieties; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, and the like. A label may be a charged moiety (positive or negative charge) or alternatively, may be charge neutral. Labels can include or consist of nucleic acid or protein sequence, so long as the sequence comprising the label is detectable. In some embodiments, nucleic acids are detected directly without a label (e.g., directly reading a sequence).

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methyl cytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is to be "self-hybridized."

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (e.g., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer should be sufficiently long to prime the synthesis of extension products in the presence of the inducing agent. The exact lengths of the primers will depend on many factors, including temperature, source of primer and the use of the method. For example, in some embodiments, primers range from 10 to 100 or more nucleotides (e.g., 10-300, 15-250, 15-200, 15-150, 15-100, 15-90, 20-80, 20-70, 20-60, 20-50 nucleotides, etc.).

In some embodiments, primers comprise additional sequences that do not hybridize to the nucleic acid of interest. The term "primer" includes chemically modified primers, fluorescence-modified primers, functional primers (fusion primers), sequence specific primers, random primers, primers that have both specific and random sequences, and DNA and RNA primers The term "amplifying" or "amplification" in the context of nucleic acids refers to the production of multiple copies of a polynucleotide, or a portion of the polynucleotide, typically starting from a small amount of the polynucleotide (e.g., as few as a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR), rolling circle amplification (RCA), or a ligase chain reaction (LCR) are forms of amplification. Amplification is not limited to the strict duplication of the starting molecule. For example, the generation of multiple cDNA molecules from a limited amount of RNA in a sample using reverse transcription (RT)-PCR is a form of amplification. Furthermore, the generation of multiple RNA molecules from a single DNA molecule during the process of transcription is also a form of amplification.

As used herein, the term "solid support" is used in reference to any solid or stationary material to which reagents such as antibodies, antigens, and other test components are attached. Examples of solid supports include microscope slides, wells of microtiter plates, coverslips, beads, particles, cell culture flasks, as well as many other suitable items.

DETAILED DESCRIPTION OF EMBODIMENTS
OF THE INVENTION

The present invention relates to compositions and methods for detection, analysis, and treatment of nucleic acids. In particular, the present invention relates to compositions and methods for generating and using hybridization probes.

Embodiments of the present technology provide compositions and methods for generating probes substantially free of undesired sequences (e.g., FISH probes lacking undesired sequences, such as repeat sequences) that solve the limitations of existing methods of removing undesired sequences from probes by providing multistep or otherwise burdensome methods.

Embodiments of the present invention are illustrated for use in generating repeat free ISH probes. One of skill in art understands that the disclosed methods can also be applied to other undesired sequences and other probe applications.

The presence of repeat sequence in FISH probes leads to background signals in other loci containing similar repeats. Additionally it increases the bulk of the FISH probe unnecessarily, leading to wasted material. Finally, regardless of the repeat sequence, FISH probes are typically prepared from DNA generated directly from BAC sequences over 100 kb in length. The methods provided herein allow selection of non-repeat sequence, specific to the genomic region of interest, circumventing potential issues with availability of BACs covering the genomic region of interest and overcomes disadvantages of existing methods of generating repeat-free probes (See e.g., Rogan et al., Genome Research 11:1086-1094, 2001; Commercially available probes from Kreatech, Durham, N.C.; Sealey et al. Nuc. Acid. Res. Volume 13 Number 6 1985; Dorman et al., Nucleic Acids Research, 2013, Vol. 41, No. 7; Boyle et al., Chromosome Res. 2011 October; 19(7):901-9; and Craig et al., Hum Genet (1997) 100:472-476).

The probes described herein provide the following advantages over existing probes: decrease in interference from repeat sequence; eliminates the need for human DNA blocker; faster hybridization times; higher hybridization temperature (e.g., easier probe removal and more uniform hybridization temperatures), resulting in faster hybridization times; preparation via amplification (e.g., PCR) gives faster, less expensive, more reliable manufacture; and, once made, the template finds use in scale up and manufacturing applications.

I. Generation of Probes

Exemplary methods of generating probes substantially free of undesired sequences are described below. Embodiments of the present invention are illustrated for use in generating ISH (e.g., FISH) probes. One of skill in art understands that the disclosed methods can also be applied to other undesired sequences and other probe applications.

Embodiments of the present technology provide compositions, kits, and systems for generating and using probes selectively generated or synthesized to exclude sequences of disinterest and/or include sequences of interest (e.g., substantially repeat-free nucleic acid probes). For example, in some embodiments, the present invention provides a method of generating a probe to a nucleic acid of interest, comprising: a) identifying regions of the nucleic acid target of interest substantially free of undesired sequences (e.g., free of repeats, non-conserved sequences, conserved sequences, GC rich sequences, AT rich sequences, secondary structure, or coding sequences) of the nucleic acid of interest that are at least 100 bp in length (e.g., at least 100, 200, at least 300, or at least 400) and optionally no more than 20% different in length from each other (e.g., 20% or less, 10% or less, 5% or less, 4% or less, 3% or less, 3% or less, 1% or less, or identical lengths); and b) generating (e.g., via amplification, cloning, synthesis, or a combination thereof) a plurality of probe-containing nucleic acids corresponding to the regions substantially free of undesired sequence. In some embodiments, the method further comprises one or more of the steps of c) fragmenting the probe-containing nucleic acids to generate probes; and d) further amplifying a subset of the probes to generate probes substantially free of undesired sequences (e.g., ISH probes lacking, for example, undesired repeat sequences). In some embodiments, the method further comprises the step of d) separating probes based on size. In some embodiments, the separating is conducted using chromatography or electrophoresis. In some embodiments, the method further comprises the step of isolating a subset of the probes. In some embodiments, the subset is based on size of the separated nucleic acid. In some embodiments, the probes are attached to nucleic acid adaptors. In some embodiments, the adaptors are amplification primers. In some embodiments, the amplification primers are functionalized for downstream applications (e.g., by the addition of labels, binding sites, or restriction sites). In some embodiments, the probes are separated and a subset of the probes ais isolated. In some embodiments, the amplification is PCR. In some embodiments, regions substantially free of undesired sequence are identified using computer software and a computer processor. In some embodiments, the probe-containing nucleic acids are fragmented by sonication (although any of a variety of other chemical, physical, or other approaches may be used). In some embodiments, the separating is by electrophoresis or chromatography. In some embodiments, the fragments are from about 100 to 500 bp in length, although other lengths may be used. In some embodiments, the probes are labeled (e.g., with a fluorescent label). In some embodiments, probes are 85%, 90%, 91%, 92%, 93%, 94%, 95%, 96%, 97%, 99%, or 100% free of undesired nucleic acid sequences.

In some embodiments, the probes are approximately 50 to 1000 bp in length. For example, in some embodiments, probes are 50 to 900 bp, 50 to 800 bp, 50 to 700 bp, 50 to 600 bp, 50 to 500 bp, 50 to 450 bp, 50 to 400 bp, 50 to 350 bp, 50 to 300 bp, 50 to 250 bp, 50 to 200 bp, 50 to 150 bp, 50 to 100 bp, 80 to 900 bp, 80 to 800 bp, 80 to 700 bp, 80 to 600 bp, 80 to 500 bp, 80 to 450 bp, 80 to 400 bp, 80 to 350 bp, 80 to 300 bp, 80 to 250 bp, 80 to 200 bp, 80 to 150 bp, 80 to 100 bp, 100 to 900 bp, 100 to 800 bp, 100 to 700 bp, 100 to 600 bp, 100 to 500 bp, 100 to 450 bp, 100 to 400 bp, 100 to 350 bp, 100 to 300 bp, 100 to 250 bp, 100 to 200 bp, 100 to 150 bp, 150 to 900 bp, 150 to 800 bp, 150 to 700 bp, 150 to 600 bp, 150 to 500 bp, 150 to 450 bp, 150 to 400 bp, 150 to 350 bp, 150 to 300 bp, 150 to 250 bp, 150 to 200 bp, 150 to 150 bp, or 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 bp. In some embodiments, probes are 85%, 90%, 91%, 92%, 93%, 94%, 95%, 96%, 97%, 99%, or 100% free of undesired nucleic acid sequences.

In some embodiments, the present invention provides a method of generating a probe to a nucleic acid of interest, comprising: a) identifying regions of the nucleic acid target of interest substantially free of undesired sequences that are at least 100 bp in length; b) generating a plurality of probe-containing nucleic acids corresponding to the regions substantially free of undesired sequence; c) fragmenting the probe-containing nucleic acids to generate probes; d) attaching adaptors to the probes; and optionally e) further amplifying a subset of the probes.

Further embodiments provide a method of generating a probe to a nucleic acid of interest, comprising: a) identifying regions of the nucleic acid target of interest substantially free of undesired sequences that are at least 100 bp in length; b) generating a plurality of probe-containing nucleic acids corresponding to the regions substantially free of undesired sequence; c) fragmenting the probe-containing nucleic acids to generate probes; and optionally d) further amplifying a subset of the probes.

Additional embodiments provide a method of generating a probe to a nucleic acid of interest, comprising: a) identifying regions of the nucleic acid target of interest substantially free of undesired sequences, wherein the undesired region is, for example, repeat sequence, non-conserved sequences, conserved sequences, GC rich sequences, AT rich sequences, secondary structure, or coding sequences that are at least 100 bp in length; b) generating a plurality of probe-containing nucleic acids corresponding to the regions substantially free of undesired sequence; and c) fragmenting the probe-containing nucleic acids to generate probes; and optionally d) further amplifying a subset of the probes.

Yet other embodiments provide a method of generating a probe to a nucleic acid of interest, comprising: a) identifying regions of the nucleic acid target of interest substantially free of undesired sequences that are at least 100 bp in length; b) generating a plurality of probe-containing nucleic acids corresponding to the regions substantially free of undesired sequence; c) fragmenting the probe-containing nucleic acids to generate probes; d) separating the probes by size; e) isolating a subset of the probes; and optionally f) further amplifying a subset of the probes.

Still other embodiments provide a method of generating a probe to a nucleic acid of interest, comprising: a a) identifying regions of the nucleic acid target of interest substantially free of undesired sequences that are at least 100 bp in length; b) generating a plurality of probe-containing nucleic acids corresponding to the regions substantially free of undesired sequence; c) fragmenting the probe-containing nucleic acids to generate probes; d) separating the probes by size; e) isolating a subset of the probes, wherein the subset comprises nucleic acids of 80 to 300 bp in length (e.g., approximately 150 bp in length); and optionally f) further amplifying a subset of the probes.

Additional embodiments provide a method of generating a probe to a nucleic acid of interest, comprising: a) identifying regions of the nucleic acid target of interest substantially free of undesired sequences that are at least 100 bp in length; b) generating a plurality of probe-containing nucleic acids corresponding to the regions substantially free of undesired sequence; and c) fragmenting the probe-containing nucleic acids to generate probes; optionally d) further amplifying a subset of the probes generate a probe set; and e) performing a hybridization assay (e.g., ISH assay such as FISH) with the probe set.

Further provided herein are a set of nucleic acid probes (e.g., ISH probes) free of undesired sequences generated by the aforementioned methods and kits and systems comprising the probes.

Additionally provided herein are methods of performing a hybridization assay, comprising contacting a target nucleic acid with a probe (e.g., a ISH probe) generated by the aforementioned method.

Also provided herein is the use of any a probe (e.g., a ISH probe) generated by the aforementioned method in a hybridization (e.g., ISH) assay.

Exemplary methods of generating probes are described in detail below.

A. Probes

The present invention provides, in some embodiments, methods of generating probe libraries. In some embodiments, probes are between approximately 100 and 400 bp in length (e.g., between 100 and 300 bp in length).

In some embodiments, libraries of probes are generated that are complementary to different regions of a target sequence. In some embodiments, all of the probes in a library are of similar length (e.g., within 1%, 2%, 3%, 4%, or 5%, 10%, 20% or identical in length).

Probes can comprise any number of modified bases, modified backbones, inclusion of minor groove binders, and labels (e.g., as described in more detail below). Examples of such analogs include, without limitation, phosphorothioates, phosphoramidates, methyl phosphonates, chiral-methyl phosphonates, 2'-O-methyl ribonucleotides, and peptide-nucleic acids (PNAs).

B. Identification of Undesired Sequences

The present invention is not limited to a particular type of undesired sequences. In some embodiments, undesired sequences are, for example, repeat sequence, non-conserved sequences, conserved sequences, GC rich sequences, AT rich sequences, secondary structure, and coding sequences. In some preferred embodiments, repeat-free sequences are removed in order to optimize probe binding.

In some embodiments, substantially repeat-free or other undesired segments of genomic DNA in a region of interest are first identified. In some embodiments, contiguous repeat-free segments of genomic DNA in a region of interest are identified by bioinformatics methods. The present invention is not limited to a particular bioinformatics method. In some embodiments, commercial software packages such as, for example the RepeatMasker function of UCSC Genome Browser (available from The National Cancer Institute's Center for Biomedical Informatics and Information Technology) are utilized, although other commercial or non-commercial software packages are specifically contemplated.

In some embodiments, the Repeat-Masker function of Genome Browser is used to distinguish repeat from nonrepeat portions by presenting repeat sequence in lower case and nonrepeat in upper case, and the sequence downloaded. External software programs or manual examination of sequence information are used to remove the repeat portion of the sequence and to present the stretches of contiguous nonrepeat sequence in order of their length. The shorter stretches (usually less than 300 bp) are discarded, and a number of the longer stretches are identified such that their combined sequence length is sufficient to prepare a probe with acceptable labeling intensity for the intended use.

C. Generation of Probes

Following identification of undesired sequences, probes are designed that are substantially free of undesired sequences. Probes may be generated using any suitable method. In some embodiments, probes are amplified using the method described below.

In some embodiments, libraries of probes are synthesized. In some embodiments, synthetic probes comprise a region of complementarity to the target sequence and a label region that is not-complementary to the target sequence (See e.g., FIG. 1). In some embodiments, the labeled regions are identical across the probe library. In some embodiments, probes are generated with a labeled region that is branched or another non-linear configuration.

In some embodiments, oligonucleotides for use in amplification methods or probe generation are synthesized. Exemplary methods for oligonucleotide synthesis are described herein. To obtain the desired oligonucleotide, the building blocks are sequentially coupled to the growing oligonucleotide chain in the order required by the sequence of the product. The process has been fully automated since the late 1970s. Upon the completion of the chain assembly, the product is released from the solid phase to solution, deprotected, and collected. Products are often isolated by high-performance liquid chromatography (HPLC) to obtain the desired oligonucleotides in high purity. Typically, synthetic oligonucleotides are single-stranded DNA or RNA molecules around 15-25 bases in length.

In some embodiments, the selectivity and the rate of the formation of internucleosidic linkages is improved by using 3'-O—(N,N-diisopropyl phosphoramidite) derivatives of nucleosides (nucleoside phosphoramidites) that serve as building blocks in phosphite triester methodology. To prevent undesired side reactions, all other functional groups present in nucleosides are rendered unreactive (protected) by attaching protecting groups. Upon the completion of the oligonucleotide chain assembly, all the protecting groups are removed to yield the desired oligonucleotides.

Exemplary protecting groups and nucleoside phosphoramidite building blocks include, but are not limited to, acid-labile DMT (4,4'-dimethoxytrityl) protecting groups. Thymine and uracil, nucleic bases of thymidine and uridine, respectively, do not have exocyclic amino groups and hence do not require any protection.

Although the nucleic base of guanosine and 2'-deoxyguanosine does have an exocyclic amino group, its basicity is low to an extent that it does not react with phosphoramidites under the conditions of the coupling reaction. However, a phosphoramidite derived from the N2-unprotected 5'-O-DMT-2'-deoxyguanosine is poorly soluble in acetonitrile, the solvent commonly used in oligonucleotide synthesis. In contrast, the N2-protected versions of the same compound dissolve in acetonitrile well and hence are widely used. Nucleic bases adenine and cytosine bear the exocyclic amino groups reactive with the activated phosphoramidites under the conditions of the coupling reaction. By the use of additional steps in the synthetic cycle or alternative coupling agents and solvent systems, the oligonucleotide chain assembly are carried out using dA and dC phosphoramidites with unprotected amino groups. In some embodiments, exocyclic amino groups in nucleosides are kept permanently protected over the entire length of the oligonucleotide chain assembly.

The protection of the exocyclic amino groups is generally orthogonal to that of the 5'-hydroxy group because the latter is removed at the end of each synthetic cycle. The simplest to implement and hence the most widely accepted is the strategy where the exocyclic amino groups bear a base-labile protection. Most often, two protection schemes are used.

In some embodiments, Bz (benzoyl) protection is used for A, dA, C, and dC, while G and dG are protected with isobutyryl group. More recently, Ac (acetyl) group is often used to protect C and dC.

In the second, mild protection scheme, A and dA are protected with isobutyryl or phenoxyacetyl groups (PAC). C and dC bear acetyl protection, and G and dG are protected with 4-isopropylphenoxyacetyl (iPr-PAC) or dimethylformamidino (dmf) groups. Mild protecting groups are removed more readily than the standard protecting groups. However, the phosphoramidites bearing these groups are less stable when stored in solution.

In some embodiments, the phosphite group is protected by a base-labile 2-cyanoethyl group. Once a phosphoramidite has been coupled to the solid support-bound oligonucleotide and the phosphite moieties have been converted to the P(V) species, the presence of the phosphate protection is not mandatory for the successful conducting of further coupling reactions.

Non-nucleoside phosphoramidites are the phosphoramidite reagents designed to introduce various functionalities at the termini of synthetic oligonucleotides or between nucleotide residues in the middle of the sequence. In order to be introduced inside the sequence, a non-nucleosidic modifier has to possess at least two hydroxy groups, one of which is often protected with the DMT group while the other bears the reactive phosphoramidite moiety.

Non-nucleosidic phosphoramidites are used to introduce desired groups that are not available in natural nucleosides or that can be introduced more readily using simpler chemical designs.

Oligonucleotide synthesis is carried out by a stepwise addition of nucleotide residues to the 5'-terminus of the growing chain until the desired sequence is assembled. Each addition is referred to as a synthetic cycle and consists of four chemical reactions:

Step 1: De-Blocking (Detritylation)

The DMT group is removed with a solution of an acid, such as 2% trichloroacetic acid (TCA) or 3% dichloroacetic acid (DCA), in an inert solvent (dichloromethane or toluene). The orange-colored DMT cation formed is washed out; the step results in the solid support-bound oligonucleotide precursor bearing a free 5'-terminal hydroxyl group. Conducting detritylation for an extended time or with stronger than recommended solutions of acids leads to depurination of solid support-bound oligonucleotide and thus reduces the yield of the desired full-length product.

A solution of nucleoside phosphoramidite (or a mixture of several phosphoramidites) in acetonitrile is next activated by an acidic azole catalyst, 1H-tetrazole, 2-ethylthiotetrazole, 2-benzylthiotetrazole, 4,5-dicyanoimidazole, or a number of similar compounds. The mixing is usually very brief and occurs in fluid lines of oligonucleotide synthesizers while the components are being delivered to the reactors containing solid support. The activated phosphoramidite in 1.5-20-fold excess over the support-bound material is then brought in contact with the starting solid support (first coupling) or a support-bound oligonucleotide precursor (following couplings) whose 5'-hydroxy group reacts with the activated phosphoramidite moiety of the incoming nucleoside phosphoramidite to form a phosphite triester linkage. The coupling of 2'-deoxynucleoside phosphoramidites is very rapid and requires, on small scale, about 20 s for its completion. In contrast, sterically hindered 2'-O-protected ribonucleoside phosphoramidites utilize longer times to be coupled in high yields. The reaction is also highly sensitive to the presence of water, particularly when dilute solutions of phosphoramidites are used, and is commonly carried out in anhydrous acetonitrile. Generally, the larger the scale of the synthesis, the lower the excess and the higher the concentration of the phosphoramidites is used. In contrast, the concentration of the activator is primarily determined by its solubility in acetonitrile and is irrespective of the scale of the synthesis. Upon the completion of the coupling, any unbound reagents and by-products are removed by washing.

The capping step is performed by treating the solid support-bound material with a mixture of acetic anhydride and 1-methylimidazole or, less often, DMAP as catalysts and, in the phosphoramidite method, serves two purposes. After the completion of the coupling reaction, a small percentage of the solid support-bound 5'-OH groups (0.1 to 1%) remains unreacted and needs to be permanently blocked from further chain elongation to prevent the formation of oligonucleotides with an internal base deletion commonly referred to as (n−1) shortmers. The unreacted 5'-hydroxy groups are, to a large extent, acetylated by the capping mixture.

It has also been reported that phosphoramidites activated with 1H-tetrazole react, to a small extent, with the O6 position of guanosine. Upon oxidation with I2/water, this side product, possibly via O6-N7 migration, undergoes depurination. The apurinic sites thus formed are readily cleaved in the course of the final deprotection of the oligonucleotide under the basic conditions (see below) to give two shorter oligonucleotides thus reducing the yield of the full-length product. The O6 modifications are rapidly removed by treatment with the capping reagent as long as the capping step is performed prior to oxidation with I2/water.

The synthesis of oligonucleotide phosphorothioates (OPS) does not involve the oxidation with I2/water, and, respectively, does not suffer from the side reaction described above. On the other hand, if the capping step is performed prior to sulfurization, the solid support may contain the residual acetic anhydride and N-methylimidazole left after the capping step. The capping mixture interferes with the sulfur transfer reaction, which results in the extensive formation of the phosphate triester internucleosidic linkages in place of the desired PS triesters. Therefore, for the synthesis of OPS, it is advisable to conduct the sulfurization step prior to the capping step.

The newly formed tricoordinated phosphite triester linkage is not natural and is of limited stability under the conditions of oligonucleotide synthesis. The treatment of the support-bound material with iodine and water in the presence of a weak base (pyridine, lutidine, or collidine) oxidizes the phosphite triester into a tetracoordinated phosphate triester, a protected precursor of the naturally occurring phosphate diester internucleosidic linkage. Oxidation may be carried out under anhydrous conditions using tert-Butyl hydroperoxide or, more efficiently, (1S)-(+)-(10-camphorsulfonyl)-oxaziridine (CSO). The step of oxidation is substituted with a sulfurization step to obtain oligonucleotide phosphorothioates. In the latter case, the sulfurization step is best carried out prior to capping.

In solid-phase synthesis, an oligonucleotide being assembled is covalently bound, via its 3'-terminal hydroxy group, to a solid support material and remains attached to it over the entire course of the chain assembly. The solid support is contained in columns whose dimensions depend on the scale of synthesis and may vary between 0.05 mL and several liters. The overwhelming majority of oligonucleotides are synthesized on small scale ranging from 40 nmol to 1 µmol. More recently, high-throughput oligonucleotide synthesis where the solid support is contained in the wells of multi-well plates (most often, 96 or 384 wells per plate) became a method of choice for parallel synthesis of oligonucleotides on small scale. At the end of the chain assembly, the oligonucleotide is released from the solid support and is eluted from the column or the well.

In contrast to organic solid-phase synthesis and peptide synthesis, the synthesis of oligonucleotides proceeds best on non-swellable or low-swellable solid supports. The two most often used solid-phase materials are controlled pore glass (CPG) and macroporous polystyrene (MPPS).

CPG is commonly defined by its pore size. In oligonucleotide chemistry, pore sizes of 500, 1000, 1500, 2000, and 3000 Å are used to allow the preparation of about 50, 80, 100, 150, and 200-mer oligonucleotides, respectively. To make native CPG suitable for further processing, the surface of the material is treated with (3-aminopropyl)triethoxysilane to give aminopropyl CPG. The aminopropyl arm may be further extended to result in long chain aminoalkyl (LCAA) CPG. The amino group is then used as an anchoring point for linkers suitable for oligonucleotide synthesis (see below).

MPPS suitable for oligonucleotide synthesis is a low-swellable, highly cross-linked polystyrene obtained by polymerization of divinylbenzene (min 60%), styrene, and 4-chloromethylstyrene in the presence of a porogeneous agent. The macroporous chloromethyl MPPS obtained is converted to aminomethyl MPPS.

To make the solid support material suitable for oligonucleotide synthesis, non-nucleosidic linkers or nucleoside succinates are covalently attached to the reactive amino groups in aminopropyl CPG, LCAA CPG, or aminomethyl MPPS. The remaining unreacted amino groups are capped with acetic anhydride. Typically, three conceptually different groups of solid supports are used.

In a more recent, more convenient, and more widely used method, the synthesis starts with the universal support where a non-nucleosidic linker is attached to the solid support material. A phosphoramidite respective to the 3'-terminal nucleoside residue is coupled to the universal solid support in the first synthetic cycle of oligonucleotide chain assembly using the standard protocols. The chain assembly is then continued until the completion, after which the solid support-bound oligonucleotide is deprotected. The characteristic feature of the universal solid supports is that the release of the oligonucleotides occurs by the hydrolytic cleavage of a P—O bond that attaches the 3'-O of the 3'-terminal nucleotide residue to the universal linker as shown in Scheme 6. The critical advantage of this approach is that the same solid support is used irrespectively of the sequence of the oligonucleotide to be synthesized. For the complete removal of the linker and the 3'-terminal phosphate from the assembled oligonucleotide, the solid support 1 and several similar solid supports require gaseous ammonia, aqueous ammonium hydroxide, aqueous methylamine, or their mixture and are commercially available. The solid support utilizes a solution of ammonia in anhydrous methanol and is also commercially available.

In general, the 3'-hydroxy group of the 3'-terminal nucleoside residue is attached to the solid support via, most often, 3'-O-succinyl arm as in compound 3. The oligonucleotide chain assembly starts with the coupling of a phosphoramidite building block respective to the nucleotide residue second from the 3'-terminus. The 3'-terminal hydroxy group in oligonucleotides synthesized on nucleosidic solid supports is deprotected under the conditions somewhat milder than those applicable for universal solid supports. However, the fact that a nucleosidic solid support has to be selected in a sequence-specific manner reduces the throughput of the entire synthetic process and increases the likelihood of human error.

Oligonucleotide phosphorothioates (OPS) are modified oligonucleotides where one of the oxygen atoms in the phosphate moiety is replaced by sulfur. Only the phosphorothioates having sulfur at a non-bridging position are widely used and are available commercially. The replacement of the non-bridging oxygen with sulfur creates a new center of chirality at phosphorus. In a simple case of a dinucleotide, this results in the formation of a diastereomeric pair of Sp- and Rp-dinucleoside monophosphorothioates. In a n-mer oligonucleotide where all (n−1) internucleosidic linkages are phosphorothioate linkages, the number of diastereomers m is calculated as m=2(n−1). Being non-natural analogs of nucleic acids, OPS are substantially more stable towards hydrolysis by nucleases, the class of enzymes that destroy nucleic acids by breaking the bridging P—O bond of the phosphodiester moiety. This property determines the use of OPS as antisense oligonucleotides in in vitro and in vivo applications where the extensive exposure to nucleases is inevitable. Similarly, to improve the stability of siRNA, at least one phosphorothioate linkage is often introduced at the 3'-terminus of both sense and antisense strands. In chirally pure OPS, all-Sp diastereomers are more stable to enzymatic degradation than their all-Rp analogs. However, the preparation of chirally pure OPS remains a synthetic challenge. In laboratory practice, mixtures of diastereomers of OPS are commonly used.

Synthesis of OPS is very similar to that of natural oligonucleotides. The difference is that the oxidation step is replaced by sulfur transfer reaction (sulfurization) and that the capping step is performed after the sulfurization. Of many reported reagents capable of the efficient sulfur transfer, only three are commercially available:

3-(Dimethylaminomethylidene)amino)-3H-1,2,4-dithiazole-3-thione, DDTT (3) provides rapid kinetics of sulfurization and high stability in solution. 3H-1,2-benzodithiol-3-one 1,1-dioxide (4) also known as Beaucage reagent displays a better solubility in acetonitrile and short reaction times. However, the reagent is of limited stability in solution and is less efficient in sulfurizing RNA linkages.

N,N,N'N'-Tetraethylthiuram disulfide (TETD) is soluble in acetonitrile and is commercially available. However, the sulfurization reaction of an internucleosidic DNA linkage with TETD requires 15 min.

In the past, oligonucleotide synthesis was carried out manually in solution or on solid phase. The solid phase synthesis was implemented using, as containers for the solid phase, miniature glass columns similar in their shape to low-pressure chromatography columns or syringes equipped with porous filters. Currently, solid-phase oligonucleotide synthesis is carried out automatically using computer-controlled instruments (oligonucleotide synthesizers) and is technically implemented in column, multi-well plate, and array formats. The column format is best suited for research and large scale applications where a high-throughput is not required. Multi-well plate format is designed specifically for high-throughput synthesis on small scale to satisfy the growing demand of industry and academia for synthetic oligonucleotides. A number of oligonucleotide synthesizers for small scale synthesis and medium to large scale synthesis are available commercially.

Amplification methods are described below, although other methods may be used. Next, amplification (e.g., PCR) primers are designed to amplify stretches of sequence from the longest of the repeat-free segments identified using bioinformatics methods. In some embodiments, such segments are amplified using genomic or genome derived BAC DNA as an amplification template. In some embodiments, (e.g., in the case of longer stretches) multiple overlapping primer sets are used.

Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA).

In general, amplification methods utilize a DNA polymerase, a primer, and dNTPs. Exemplary DNA polymerases include, but are not limited to, phi29 DNA Polymerase, Taq DNA polymerase, DNA polymerase I, T7 DNA Polymerase, T7 DNA Polymerase, T4 DNA Polymerase, Pfu DNA Polymerase, and Bsm DNA Polymerase.

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399,491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPs to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

In some embodiments, amplification is isothermal amplification. In some embodiments, amplification methods are solid-phase amplification, polony amplification, colony amplification, emulsion PCR, bead RCA, surface RCA, surface SDA, etc., as will be recognized by one of skill in the art. In some embodiments, amplification methods that results in amplification of free DNA molecules in solution or tethered to a suitable matrix by only one end of the DNA molecule are used. In some embodiments, methods that rely on bridge PCR, where both PCR primers are attached to a surface (see, e.g., WO 2000/018957, U.S. Pat. Nos. 7,972,820; 7,790,418 and Adessi et al., Nucleic Acids Research (2000): 28(20): E87; each of which are herein incorporated by reference) are used. In some cases the methods of the invention can create a "polymerase colony technology", or "polony", referring to a multiplex amplification that maintains spatial clustering of identical amplicons (see Harvard Molecular Technology Group and Lipper Center for Computational Genetics website). These include, for example, in situ polonies (Mitra and Church, Nucleic Acid Research 27, e34, Dec. 15, 1999), in situ rolling circle amplification (RCA) (Lizardi et al., Nature Genetics 19, 225, July 1998), bridge PCR (U.S. Pat. No. 5,641,658), picotiter PCR (Leamon et al., Electrophoresis 24, 3769, November 2003), and emulsion PCR (Dressman et al., PNAS 100, 8817, Jul. 22, 2003).

Examples of nucleic acid polymerases suitable for use in embodiments of the present invention include, but are not limited to, DNA polymerase (Klenow fragment, T4 DNA polymerase), thermostable DNA polymerases (Perler F. B. et al., Adv. Protein Chem. 1996, 48:377-435) identified and cloned in a variety of thermostable bacteria (such as Taq, VENT, Pfu, Tfl DNA polymerases) as well as their genetically modified derivatives (TaqGold, VENTexo, Pfu exo). Preferably the nucleic acid polymerase used for colony primer extension is stable under temperature at which the primer and template hybridization results enough specific to avoid incomplete or spurious amplifications of the template.

The amplification solution contains preferably, deoxyribonucleoside triphosphates, for example dATP, dTTP, dCTP, dGTP, naturally or non-naturally occurring, for example modified with a fluorescent or radioactive group. A large variety of synthetically modified nucleic acids have been developed for chemical and biological methods in order to increase the detectability and/or the functional diversity of nucleic acids. These functionalized/modified molecules (e.g., nucleotide analogs) can be fully compatible with natural polymerizing enzymes, maintaining the base pairing and replication properties of the natural counterparts, as recently reviewed (Thum O et al., Angew. Chem. Int. Ed. 2001, 40 (21): 3990-3993).

Other components of the amplification solution are added consequently to the choice of the nucleic acid polymerase, and they are essentially corresponding to compounds known in the art as being effective to support the activity of each polymerase. The concentration of compounds like dimethyl sulfoxide (DMSO), Bovine Serum Albumin (BSA), polyethylene glycol (PEG), Betaine, Triton X-100, or $MgCl_2$ is well known in the prior art as being important to have an optimal amplification, and therefore the operator can easily adjust such concentrations for the methods of the present invention on the basis of the examples presented hereafter.

D. Fragmentation

In some embodiments, before or after amplification, the DNA is then fragmented (e.g., by sonication or other suitable method such as DNAse I) to lengths ranging from approximately 50 to 5000 bp (e.g., 50 to 4000, 50 to 3000, 50 to 2500, 50 to 2000, 50 to 1500, 50 to 1000, 100 to 5000, 100 to 4000, 1000 to 3000, 100 to 2500, 100 to 2000, 100 to 1500, 100 to 1000, or 100-500 bp), and the resultant repeat-free DNA library attached (e.g., via ligation, chemical, extension reaction, etc.) to adapters. In some preferred embodiments, probes are approximately 150 bp (e.g., 50 to 900 bp, 50 to 800 bp, 50 to 700 bp, 50 to 600 bp, 50 to 500 bp, 50 to 450 bp, 50 to 400 bp, 50 to 350 bp, 50 to 300 bp, 50 to 250 bp, 50 to 200 bp, 50 to 150 bp, 50 to 100 bp, 80 to 900 bp, 80 to 800 bp, 80 to 700 bp, 80 to 600 bp, 80 to 500 bp, 80 to 450 bp, 80 to 400 bp, 80 to 350 bp, 80 to 300 bp, 80 to 250 bp, 80 to 200 bp, 80 to 150 bp, 80 to 100 bp, 100 to 900 bp, 100 to 800 bp, 100 to 700 bp, 100 to 600 bp, 100 to 500 bp, 100 to 450 bp, 100 to 400 bp, 100 to 350 bp, 100 to 300 bp, 100 to 250 bp, 100 to 200 bp, 100 to 150 bp, 150 to 900 bp, 150 to 800 bp, 150 to 700 bp, 150 to 600 bp, 150 to 500 bp, 150 to 450 bp, 150 to 400 bp, 150 to 350 bp, 150 to 300 bp, 150 to 250 bp, 150 to 200 bp, 150 to 150 bp, or 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150 bp, etc.). In some embodiments, the adapted library is then fractionated (e.g., by electrophoresis, chromatography, or other separation method) to give a pool containing all the selected sequence at a variety of fragment sizes. Fractions (e.g., gel slices) corresponding to the desired fragment sizes are isolated.

E. Amplification

In some embodiments, fractions of the desired size are used as templates with amplification (e.g., PCR or another method described herein) primers corresponding to the adapters under preparatory amplification conditions.

All the chosen repeat-free sequence are represented in the amplified library. The probes (e.g., isolated after fragmentation or optional further amplification) are then labeled (e.g., with a fluorescent label, biotin, quantum dot label, or labels for colorimetric or silver stain detection) for use (e.g., as a FISH reagent).

In some embodiments, libraries of probes are cloned into expression vectors (e.g., one or more probes per vector). In some embodiments, such expression vectors find use in the future generation of libraries (e.g., via amplification or expression).

II. Uses of Probes

The probes described herein find use in a variety of diagnostic, research, clinical, and screening applications. The described nucleic acid hybridization probes have broad utility for use in all forms of nucleic acid detection that is achieved by use of nucleic acid hybridization probes. The nucleic acid hybridization probes find use in detecting nucleic acid sequence targets in solution or bound to immobilized supports. Examples of applications where the composition and methods can be used to detect nucleic acid sequence targets in solution include PCR, real-time PCR, quantitative PCR, PNA clamp-mediated PCR and digital PCR. Examples of applications where the compositions and methods can be used to detect nucleic acid sequence targets immobilized to solid supports include northern blots, southern blots, dot blots, slot blots, microarrays, particle-based assays, In situ hybridization assays (ISH) such as, for example, chromagen in situ hybridization (CISH), RNA in situ hybridization (RISH), rapid FISH, Silver In Situ Hybridization (SISH), and FISH assays. Such applications are amenable to numerous fields, including medical diagnostics, molecular medicine, forensic science, specimen and organism cataloging, and microbial pathogen epidemiology.

The present invention is not limited to a particular target. The compositions and methods described herein find use in the detection of a variety of target nucleic acids (e.g., human or mammalian genomic nucleic acids), bacterial, viral, etc.

Probes may also be employed as isolated nucleic acids immobilized on a solid surface (e.g., nitrocellulose), as in aCGH. In some embodiments, the probes may be members of an array of nucleic acids as described, for instance, in WO 96/17958, which is hereby incorporated by reference it its entirety and specifically for its description of array CGH. Techniques capable of producing high density arrays are well-known (see, e.g., Fodor et al. Science 767-773 (1991) and U.S. Pat. No. 5,143,854), both of which are hereby incorporated by reference for this description.

A detailed description of the utility of the nucleic acid hybridization probes is presented below for FISH applications, although the probes find use in other applications.

FISH and other in situ hybridization methods may be performed on a variety of sample types. Example, include, but are not limited to formalin-fixed paraffin embedded (FFPE) tissue), fresh tissue, frozen tissue, cells (e.g., eukaryotic or prokaryotic cells); prepared using any suitable fixative. In some embodiments, touch prep or brushing (See e.g., Smoczynski et al., Gastrointest Endosc. 2012 January; 75(1):65-73) is utilized.

Touch prep specimens are generated by smearing or pressing onto a slide, applying pressure to the tissue, and fixing in ethanol under cool temperatures. In a specific embodiment the tissue is extracted surgically and smeared onto a glass slide by applying relatively weak pressure to tumor tissue and relatively strong pressure to normal tissue, followed by fixing in about 100% ethanol for approximately 10 minutes at about 4° C. In another specific embodiment, the samples to be analyzed by methods of the present invention are originally frozen in liquid nitrogen and stored at about −80° C.

For a typical ISH application, the following represents a typical procedure. Cells of a specimen are harvested, washed and pelleted. The cells of the pellet are usually washed in phosphate-buffered saline (PBS). The cells are suspended in PBS and re-collected by centrifugation. The cells can be fixed, for example, in acid alcohol solutions, acid acetone solutions, or aldehydes such as formaldehyde, paraformaldehyde, and glutaraldehyde. For example, a fixative containing methanol and glacial acetic acid in a 3:1 ratio, respectively, can be used as a fixative. A neutral buffered formalin solution also can be used, and includes approximately 1% to 10% of 37-40% formaldehyde in an aqueous solution of sodium phosphate. Slides containing the cells can be prepared by removing a majority of the fixative, leaving the concentrated cells suspended in only a portion of the solution.

The cell suspension is applied to slides such that the cells do not overlap on the slide. Cell density can be measured by a light or phase contrast microscope. The density of cells in these wells is then assessed with a phase contrast microscope. If the well containing the greatest volume of cell suspension does not have enough cells, the cell suspension is concentrated and placed in another well.

Prior to in situ hybridization, chromosomal probes and chromosomal DNA contained within the cell each are denatured. Denaturation process is performed in several ways. For example, denaturation can be effected with buffered solutions having elevated pH, with elevated temperatures (for example, temperatures from about 70° C. to about 95° C.), or with organic solvents such as formamide, ethylene carbonate, and tetraalkylammonium halides, or combinations thereof. For example, chromosomal DNA can be denatured by a combination of temperatures above 70° C. (for example, about 73° C.) and a denaturation buffer containing 70% formamide and 2×SSC (0.3M sodium chloride and 0.03 M sodium citrate). Denaturation conditions typically are established such that cell morphology is preserved. Chromosomal probes can be denatured by heat. For example, probes can be heated to about 73° C. for about five minutes.

After removal of denaturing chemicals or conditions, probes are annealed to the chromosomal DNA under hybridizing conditions. "Hybridizing conditions" are conditions that facilitate annealing between a probe and nucleic acid sequence target. Hybridization conditions vary, depending on the concentrations, base compositions, complexities, and lengths of the probes, as well as salt concentrations, temperatures, and length of incubation. The greater the concentration of probe, the greater the probability of forming a hybrid. For example, in situ hybridizations are typically performed in hybridization buffer containing 1-2×SSC, 50% formamide and blocking DNA to suppress non-specific hybridization. In general, hybridization conditions, as described above, include temperatures of about 25° C. to about 55° C., and incubation lengths of about 0.5 hours to about 96 hours. More particularly, hybridization can be performed at about 37° C. to about 40° C. for about 2 to about 16 hours.

Non-specific binding of chromosomal probes to DNA outside of the target region can be removed by a series of washes. Temperature and concentration of salt in each wash depend on the desired stringency. For example, for high stringency conditions, washes can be carried out at about 65° C. to about 80° C., using 0.2×SSC to about 2×SSC, and about 0.1% to about 1% of a non-ionic detergent such as Nonidet P-40 (NP40) or other suitable surfactant. Stringency can be lowered by decreasing the temperature of the washes or by increasing the concentration of salt in the washes.

Slides containing the samples are typically incubated in 2×SSC at 37° C. for 10-30 min. The slides are then incubated in 0.2 mg/ml pepsin at 37° C. for 20 min. Slides are subsequently washed twice in PBS at room temperature for 2 min. Cells are fixed in 2.5% Neutral Buffered Formalin at room temperature for 5 min. Slides are subsequently washed twice in PBS at room temperature for 2 min. The slides are subjected to dehydration by successive contact in solutions of 70%, 85%, and 100% ethanol at room temperature for 1 min. The slides are used immediately thereafter or stored at room temperature in the dark.

Hybridization can be performed with the HYBRITE method or a conventional method. In the HYBRITE method, a HYBRITE system from Abbott Molecular (Downers Grove, Ill.) is used.

Conditions for specifically hybridizing the probes to their nucleic acid targets generally include the combinations of conditions that are employable in a given hybridization procedure to produce specific hybrids, the conditions of which may easily be determined by one of skill in the art. Such conditions typically involve controlled temperature, liquid phase, and contact between a chromosomal probe and a target. Hybridization conditions vary depending upon many factors including probe concentration, target length, target and probe G-C content, solvent composition, temperature, and duration of incubation. At least one denaturation step may precede contact of the probes with the targets. Alternatively, both the probe and nucleic acid target may be subjected to denaturing conditions together while in contact with one another, or with subsequent contact of the probe with the biological sample. Hybridization may be achieved with subsequent incubation of the probe/sample in, for example, a liquid phase of about a 50:50 volume ratio mixture of 2-4×SSC and formamide, at a temperature in the range of about 25 to about 55° C. for a time that is illustratively in the range of about 0.5 to about 96 hours, or more preferably at a temperature of about 32 to about 40° C. for a time in the range of about 2 to about 16 hours. In order to increase specificity, use of a blocking agent such as unlabeled blocking nucleic acid as described in U.S. Pat. No. 5,756,696 (the contents of which are herein incorporated by reference in their entirety, and specifically for the description of the use of blocking nucleic acid), may be used in conjunction with the methods of the present invention. Other conditions may be readily employed for specifically hybridizing the probes to their nucleic acid targets present in the sample, as would be readily apparent to one of skill in the art.

Upon completion of a suitable incubation period, non-specific binding of chromosomal probes to sample DNA may be removed by a series of washes. Temperature and salt concentrations are suitably chosen for a desired stringency. The level of stringency required depends on the complexity of a specific probe sequence in relation to the genomic sequence, and may be determined by systematically hybridizing probes to samples of known genetic composition. In general, high stringency washes may be carried out at a temperature in the range of about 65 to about 80° C. with about 0.2× to about 2×SSC and about 0.1% to about 1% of a non-ionic detergent such as Nonidet P-40 (NP40). If lower stringency washes are required, the washes may be carried out at a lower temperature with an increased concentration of salt.

Chromosomal probes can be directly labeled with a detectable label. Examples of detectable labels include fluorophores, e.g., organic molecules that fluoresce after absorbing light, and radioactive isotopes, e.g., $^{32}P$, and $^{3}H$. Fluorophores can be directly labeled following covalent attachment to a nucleotide by incorporating the labeled nucleotide into the probe with standard techniques such as nick translation, random priming, and PCR labeling. Alternatively, deoxycytidine nucleotides within the probe can be transaminated with a linker. The fluoropore can then be covalently attached to the transaminated deoxycytidine nucleotides. See, e.g., U.S. Pat. No. 5,491,224 to Bittner, et al., which is incorporated herein by reference. Useful probe labeling techniques are described in Molecular Cytogenetics: Protocols and Applications, Y.-S. Fan, Ed., Chap. 2, "Labeling Fluorescence In Situ Hybridization Probes for Genomic Targets", L. Morrison et. al., p. 21-40, Humana Press, © 2002 (hereafter cited as "Morrison-2002"), incorporated herein by reference.

Attachment of fluorophores to nucleic acid probes is well known in the art and may be accomplished by any available means. Fluorophores can be covalently attached to a particular nucleotide, for example, and the labeled nucleotide incorporated into the probe using standard techniques such as nick translation, random priming, PCR labeling, and the like. Alternatively, the fluorophore can be covalently attached via a linker to the deoxycytidine nucleotides of the probe that have been transaminated. Methods for labeling probes are described in U.S. Pat. No. 5,491,224 and Molecular Cytogenetics: Protocols and Applications (2002), Y.-S. Fan, Ed., Chapter 2, "Labeling Fluorescence In Situ Hybridization Probes for Genomic Targets," L. Morrison et al., p. 21-40, Humana Press, both of which are herein incorporated by reference for their descriptions of labeling probes.

Exemplary fluorophores that can be used for labeling probes include TEXAS RED (Molecular Probes, Inc., Eugene, Oreg.), CASCADE blue aectylazide (Molecular Probes, Inc., Eugene, Oreg.), SPECTRUMORANGE-(Abbott Molecular, Des Plaines, Ill.) and SPECTRUMGOLD (Abbott Molecular).

Additional examples of fluorophores that can be used in the methods described herein are: 7-amino-4-methylcoumarin-3-acetic acid (AMCA); 5-(and -6)-carboxy-X-rhodamine, lissamine rhodamine B, 5-(and -6)-carboxyfluorescein; fluorescein-5-isothiocyanate (FITC); 7-diethylaminocoumarin-3-carboxylic acid, tetramethylrhodamine-5-(and -6)-isothiocyanate; 5-(and -6)-carboxytetramethylrhodamine; 7-hydroxy-coumarin-3-carboxylic acid; 6-[fluorescein 5-(and -6)-carboxamido]hexanoic acid; N-(4,4-difluoro-5,7-dimethyl-4-bora-3a, 4a diaza-3-indacenepropionic acid; eosin-5-isothiocyanate; erythrosine-5-isothiocyanate; 5-(and -6)-carboxyrhodamine 6G; and Cascades blue aectylazide (Molecular Probes, Inc., Eugene, Oreg.).

Probes can be viewed with a fluorescence microscope and an appropriate filter for each fluorophore, or by using dual or triple band-pass filter sets to observe multiple fluorophores. See, e.g., U.S. Pat. No. 5,776,688 to Bittner, et al., which is incorporated herein by reference. Any suitable microscopic imaging method can be used to visualize the hybridized probes, including automated digital imaging systems, such as those available from MetaSystems or Applied Imaging. Alternatively, techniques such as flow cytometry can be used to examine the hybridization pattern of the chromosomal probes.

Probes can also be labeled indirectly, e.g., with biotin or digoxygenin by means well known in the art. However, secondary detection molecules or further processing are then used to visualize the labeled probes. For example, a probe labeled with biotin can be detected by avidin conjugated to a detectable marker, e.g., a fluorophore. Additionally, avidin can be conjugated to an enzymatic marker such as alkaline phosphatase or horseradish peroxidase. Such enzymatic markers can be detected in standard colorimetric reactions using a substrate for the enzyme. Substrates for alkaline phosphatase include 5-bromo-4-chloro-3-indolylphosphate and nitro blue tetrazolium. Diaminobenzoate can be used as a substrate for horseradish peroxidase. Fluorescence detection of a hybridized biotin or other indirect labeled probe can be achieved by use of the commercially available tyramide amplification system.

One of skill in the art will recognize that other agents or dyes can be used in lieu of fluorophores as label-containing moieties. Suitable labels that can be attached to probes include, but are not limited to, radioisotopes, fluorophores, chromophores, mass labels, electron dense particles, magnetic particles, spin labels, molecules that emit luminescence, electrochemically active molecules, enzymes, cofactors, and enzyme substrates. Luminescent agents include, for example, radioluminescent, chemiluminescent, bioluminescent, and phosphorescent label containing moieties. Alternatively, detection moieties that are visualized by indirect means can be used. For example, probes can be labeled with biotin or digoxygenin using routine methods known in the art, and then further processed for detection. Visualization of a biotin-containing probe can be achieved via subsequent binding of avidin conjugated to a detectable marker. The detectable marker may be a fluorophore, in which case visualization and discrimination of probes may be achieved as described above for ISH.

In some embodiments, probes are designed to have labels placed at a common interval throughout the nucleic acid (e.g., one label group every 3, 4, 5, 6, 7, 8, 9, 10, 11, or 12).

In some embodiments, a probe library comprises probes with different detectable labels (e.g., different colors of fluorescent signal).

Probes hybridized to target regions may alternatively be visualized by enzymatic reactions of label moieties with suitable substrates for the production of insoluble color products. A biotin-containing probe within a set may be detected via subsequent incubation with avidin conjugated to alkaline phosphatase (AP) or horseradish peroxidase (HRP) and a suitable substrate. 5-bromo-4-chloro-3-indolylphosphate and nitro blue tetrazolium (NBT) serve as substrates for alkaline phosphatase, while diaminobenzidine serves as a substrate for HRP.

In embodiments where fluorophore-labeled probes or probe compositions are used, the detection method can involve fluorescence microscopy, flow cytometry, or other means for determining probe hybridization. Any suitable microscopic imaging method may be used in conjunction with the methods of the present invention for observing multiple fluorophores. In the case where fluorescence microscopy is employed, hybridized samples may be viewed under light suitable for excitation of each fluorophore and with the use of an appropriate filter or filters. Automated digital imaging systems such as the MetaSystems, BioView or Applied Imaging systems may alternatively be used.

In array CGH, the probes are not labeled, but rather are immobilized at distinct locations on a substrate, as described in WO 96/17958. In this context, the probes are often referred to as the "target nucleic acids." The sample nucleic acids are typically labeled to allow detection of hybridization complexes. The sample nucleic acids used in the hybridization may be detectably labeled prior to the hybridization reaction. Alternatively, a detectable label may be selected which binds to the hybridization product. In dual- or multi-color aCGH, the target nucleic acid array is hybridized to two or more collections of differently labeled nucleic acids, either simultaneously or serially. For example, sample nucleic acids and reference nucleic acids are each labeled with a separate and distinguishable label. Differences in intensity of each signal at each target nucleic acid spot can be detected as an indication of a copy number difference. Although any suitable detectable label can be employed for aCGH, fluorescent labels are typically the most convenient.

Exemplary methods of visualizing signals are described in WO 93/18186, which is hereby incorporated by reference for this description. To facilitate the display of results and to improve the sensitivity of detecting small differences in fluorescence intensity, a digital image analysis system can be used. An exemplary system is QUIPS (an acronym for quantitative image processing system), which is an automated image analysis system based on a standard fluorescence microscope equipped with an automated stage, focus control and filterwheel (Ludl Electronic Products, Ltd., Hawthorne, N.Y.). The filterwheel is mounted in the fluorescence excitation path of the microscope for selection of the excitation wavelength. Special filters (Chroma Technology, Brattleboro, Vt.) in the dichroic block allow excitation of the multiple dyes without image registration shift. The microscope has two camera ports, one of which has an intensified CCD camera (Quantex Corp., Sunnyvale, Calif.) for sensitive high-speed video image display which is used for finding interesting areas on a slide as well as for focusing. The other camera port has a cooled CCD camera (model 200 by Photometrics Ltd., Tucson, Ariz.) which is used for the actual image acquisition at high resolution and sensitivity. The cooled CCD camera is interfaced to a SUN 4/330 workstation (SUN Microsystems, Inc., Mountain View, Calif.) through a VME bus. The entire acquisition of multicolor images is controlled using an image processing software package SCIL-Image (Delft Centre for Image Processing, Delft, Netherlands).

In some embodiments, the present disclosure provides kits and systems for the amplification and/or analysis of nucleic acids. In some embodiments, kits include reagents necessary, sufficient or useful for analysis and detection of copy number or gene expression changes (e.g., primers, probes, anchors, solid supports, reagents, controls, instructions, etc.). For example, in some embodiments, kits comprise primers and anchors for amplification and sequencing of regions of interest and control regions. In some embodiments, kits include analysis software (e.g., to analyze sequencing data).

In some embodiments, kits comprise one or more containers that comprise reagents, primers, probes, anchors, solid supports, buffers, and the like. In some embodiments, each component of the kit is packaged in a separate container. In some embodiments, the containers are packed and/or shipped in the same kit or box for use together. In some embodiments, one or more components of the kit are shipped and/or packaged separately.

The assays and kits of the can be adapted or optimized for point of care assay systems, including Abbott's Point of Care (I-STAT) electrochemical immunoassay system Immunosensors and methods of manufacturing and operating them in single-use test devices are described, for example in U.S. Pat. No. 5,063,081 and published U.S. Patent Application Nos. 20030170881, 20040018577, 20050054078, and 20060160164 (incorporated by reference herein for their teachings regarding same).

In some embodiments, systems include automated sample and reagent handling devices (e.g., robotics).

EXPERIMENTAL

Example 1

Generation of Probes

Figure 2:
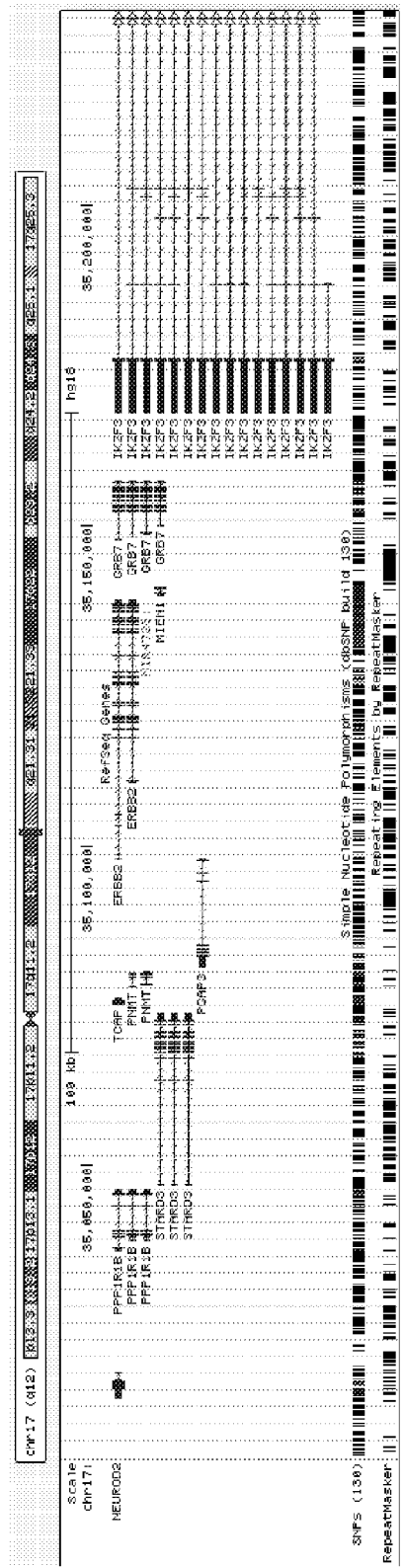
FIG. 2 shows a map of the HER2 locus.

UCSC Genome browser was used to identify sequence in the region of the HER2 locus with coordinates hg18_dna range chr17:35004678-35230380. This sequence was downloaded, coded such that regions identified by RepeatMasker were masked as lower case. The 225703 base sequence was treated with a software program that removed all sequence with more than 3 consecutive lower case letters, returning the stretches of repeat-free sequence along with their positions in the original sequence (FIG. 2).

These sequences ranged in size from very small to 5615 bases. Only the longest fragments are selected for generating sequence library. A minimum length cutoff of 1200 bp yielded 35 sequences containing 76904 bp of sequence. PCR amplification of each individual sequence is expected to give variable yields of subdomains of sequence depending on the length of the amplicon, therefore sequences were divided into multiple overlapping subsequence, 1200 bp each. All subfragments were designed to include at least 100 bp overlap with neighboring subfragments to accommodate variations in primer positions. This process generated 95 candidate sequences.

For each sequence a primer pair was designed with the web based program "BatchPrimer3" seeking generic primers to generate amplicons with Min 800, Opt 1200, Max 1200; primer length min22, opt 25, max 30; Tm min 65, opt 70, max 75. Primer sequences were downloaded as an xls file and copied into the spreadsheet for adjusting format to make it suitable for placing the order.

Primers were ordered from IDT as Mixed Forward and Reverse primers 12 nmole each dried in deep-well plate. To each well, 240 uL water (5 Prime 2900132) was added to give 50 uM each. Dilutions were prepared as needed for PCR.

PCR of genomic DNA yielded clean 1200mer product for only about half of the wells, therefore a preparation of BAC DNA containing the desired locus was used to generate a much higher success rate. BAC clones in E. coli covering the locus were obtained from Genome Systems, Inc. St. Louis, cultures grown and DNA isolated by "mini-prep."

PCR Master Mix: A PCR kit containing Phire Hot Start II DNA Polymerase (Thermo F-122L) was used. It contained 400 uL 5× reaction buffer+40 uL 25 mM dNTP (Roche Diagnostics, Indianapolis, Ind.)+40 uL Phire polymerase+60 uL DMSO+1260 uL water+0.5 ug BAC DNA template.

Figure 3:
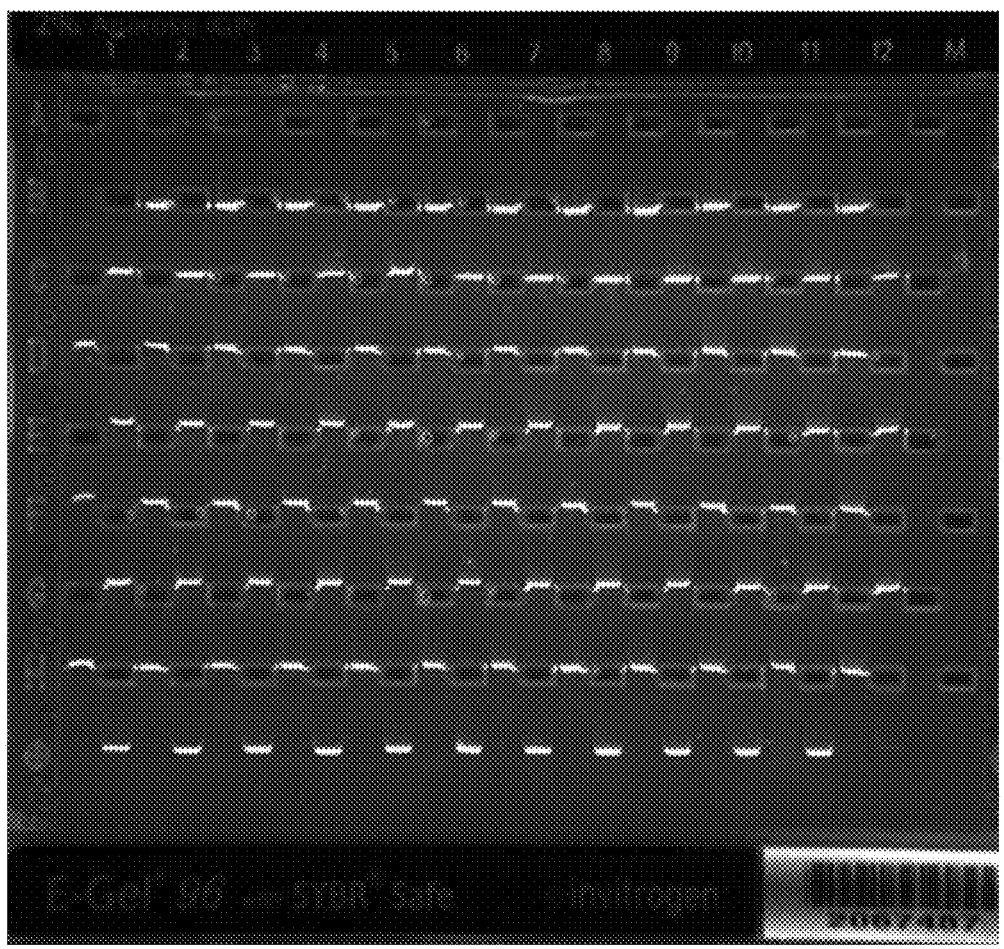
FIG. 3 shows amplification of repeat-free probes from the HER locus.

PCR: To wells of a 96 well plate was added 2 uL each primer pair 5 uM+18 uL Master Mix; capped wells, placed on thermocycler with program 98 deg 30 sec, 30× (98 deg 8 sec, 72 deg 30 sec, 72 deg 2 min), 72 deg 10 min, 4 deg. At completion 5 uL of each reaction was sampled into 20 uL water with trace 6×DNA Loading dye (Thermo R0611), 20 uL was transferred to wells of an eGel 96 agarose gel (Life Technologies), and electrophoresed was 8 min. 94 of 96 wells show clean bands at expected MW (FIG. 3).

Extend PCR to maximize yield. To each well containing the remaining 5 uL from electrophoresis sample, 10 uL of the same 5 uM primers+10 uL water+25 uL DreamTaq Green 2×pcrMM was added, and the tube was capped and placed on a thermocycler with program 10× (95 deg 30 sec, 55 deg 30 sec, 72 deg 2 min) 72 deg 6 min.

At completion, to each well 6 uL of (30 uL 1M MgCl2+ 192 uL 25 mM dNTP+378 uL water+100 uL DreamTaq Green 2×pcrMM) was added and the tube was capped and placed on thermocycler with program 6× (95 deg 30 sec, 55 deg 30 sec, 72 deg 2 min) 72 deg 10 min.

The contents of columns were combined to give 6 amplicon mixtures representing different loci of the genomic range, and the DNA isolated by precipitation with isopropanol and resuspended in water, yielding 100 uL solutions containing 52-75 ug DNA.

Figure 4:
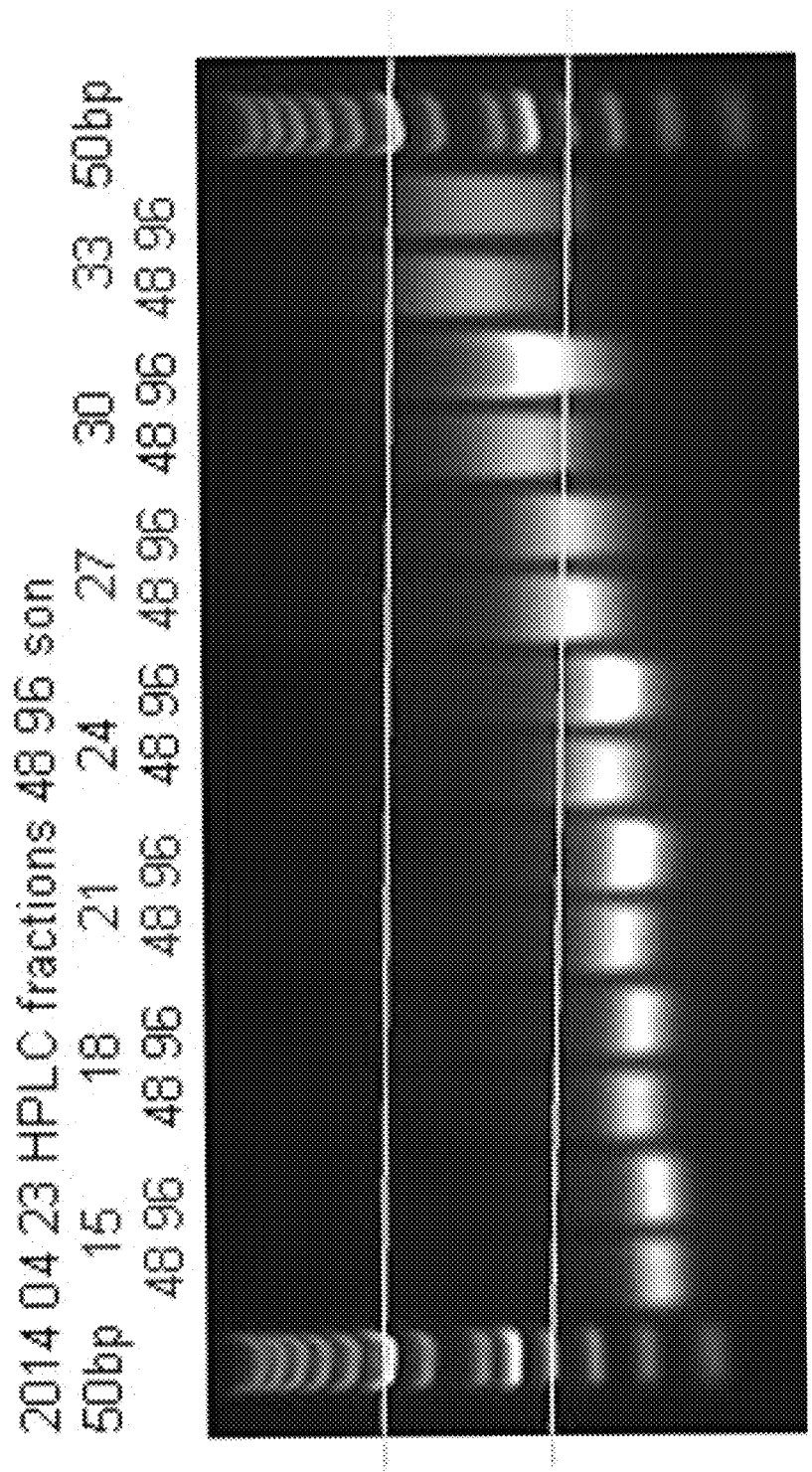
FIG. 4 shows fragmented probes from the HER2 locus.

Fragmentation by sonication: Approx 180 ug DNA 1200-mers from PCR wells 1-48 and 49-96 were combined in tubes with water to give 400 uL, with sodium acetate at 300 mM. The tubs were placed in beaker of ice water in a sonicator cabinet, sonicated (sonicator Branson 450) output control 3, 30% duty cycle 16 min. The sonication products were precipitated with isopropanol and resuspended in 200 uL 600 mM NaCl in 20 mM Tris pH 8.2. The samples were fractionated by HPLC with MonoQ column (GE Life Sciences), BufferA=20 mM Tris pH 8.2; Buffer B=A+2.0M NaCl, 0.4 mL/min % B=40-50 over 32 min, collecting fractions. DNA elutes in a broad peak centered at about 15 min. Fractions were combined to give 7 pools for each. Electrophoresis on a 3% Agarose gel visualized with Ethidium Bromide shows fractions (labeled H15, H18, H21, H24, H27, H30, H33) ranging from about 80 bp to about 400 bp (FIG. 4).

Amination of fragmented DNA: The pooled fractions were concentrated by isopropanol precipitation, resuspended in 20 uL water and denatured by heating 1 min in boiling water. To the 20 uL denatured DNA was added 180 uL of a mixture of 1000 uL water, 600 uL trifluoroacetic acid (Sigma, St Louis Mo.) 348 uL ethylenediamine and 190 mg sodium metabisulfite, and the mixture incubated 20 min at 65 deg. The mixtures were then desalted by sephadex G25 and the desalted product concentrated by isopropanol precipitation and resuspension in water.

The aminated products were labeled with carboxytetramethylrhodamine using its NHS ester (Life Technologies C1171) by means well known in the art. Labeled product was isolated from residual unbound dye by ultrafiltration using 10 kDa filters (Nanosep 10 Omega, Pall Corporation, Ann Arbor, Mich.), followed by filtration through 0.22u filters (Millipore UFC30GV00, Billerica, Mass.).

Preparation of Probes Via Adaptor Mediated PCR

Fragments of the desired size were also modified by ligating adaptors, and using the product as a template for PCR using primers corresponding to the adaptor sequence. This provides an efficient means of producing larger quantities of product of the desired size, as well as providing a means of coupling additional functional groups to the product. The process consists of modifying the fragments to give 5' phosphorylated, blunted ends, followed by ligating adaptors of the desired sequence. The adaptors can be designed to contain restriction sites such that the dsDNA PCR product can be cleaved with appropriate restriction enzymes either to remove unwanted adaptor sequence or to reveal sticky ends suitable for ligating additional groups.

End repair of the fragments was by using the Thermo Fast DNA End Repair Kit K0771 according to directions, starting with 4 ug each fraction H18, H24, H30. Blunted products were isolated using spin columns (Invitrogen K310001) Treatment of 4 ug sonicated, fractionated DNA yielded approx 3.5 ug blunted product H18b, H24b, H30b, with respective concentrations 74, 66, 70 ng/uL.

An adaptor mix was prepared by combining each oligonucleotide G6a, G6b, Gc6a, Gc6b, BsPD, BsTB, BsPDc, BsTBc with 20 mM Tris pH 8.0 and 250 mM NaCl, the mixture heated 1 min in boiling water and cooled to room temperature. T4 DNA Ligase (Invitrogen A13726, a kit containing the ligase at 5 Units/uL, and reaction buffer) was used to ligate the adaptors to each blunted DNA fraction: to 10 uL blunted DNA fraction was added 5 uL adaptor mix, 2 uL 10× Ligase buffer, 2 uL 50% PEG4000 and 1 uL, and the mixture left overnight at room temp. Adapted products were isolated using spin columns (Invitrogen K310001) eluting in 50 uL elution buffer, and labeled H18T, H24T, H30T with respective concentrations 37, 39, 30 ng/uL.

PCR of adapted HER2 fractions was performed at 20 uL scale each using 1 uL of the adapted template H18T, H25T, H30T, and a commercial PCR Master Mix (DreamTaq Green Thermo K1081). Each reaction contained a single primer G6a or BsPD at 5 or 10 uM. Cycling conditions were 24× (95 deg 30 sec, 52 deg 30 sec, 72 deg 30 sec). Products were denatured by adding 1 uL 1M sodium hydroxide to 4 uL product, and analyzed on 3% Agarose/EtBr gel. For all primers and primer concentrations tested PCR products show bands corresponding to the template sizes (FIG. 5).

Figure 5:
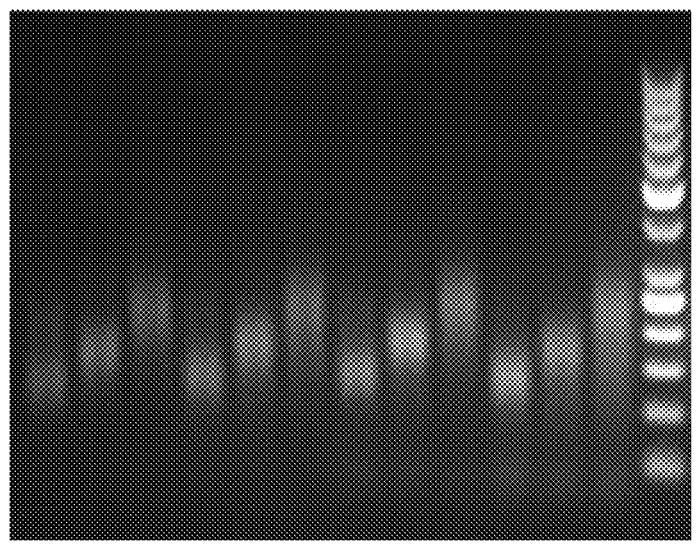
FIG. 5 shows amplification of adapted HER2 probes.
Figure 6:
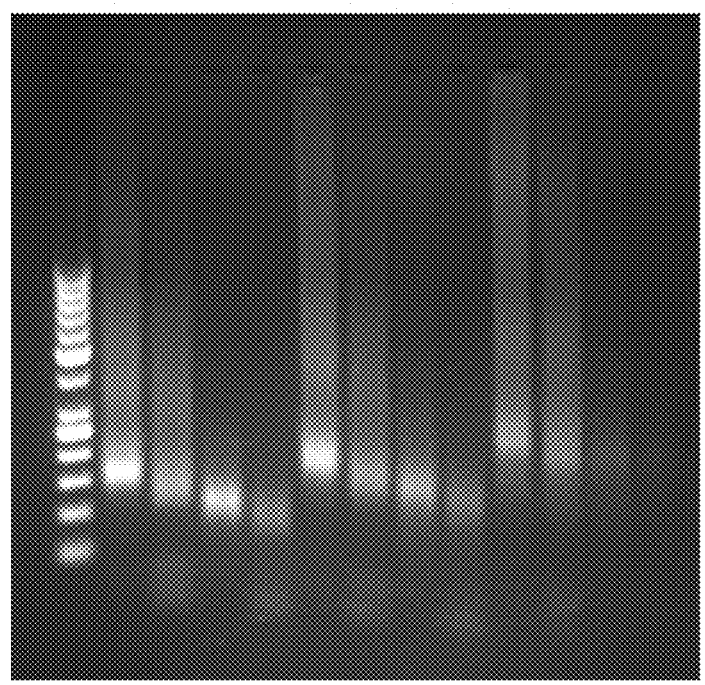
FIG. 6 shows HER2 repeat-free probes.

Products from the PCR shown in FIG. 5 were used as template for amplification using 10 uM BsPD24 primer; 10 uL of BsPD 10-18, BsPD 10-24 and BsPD 5-30 were added to give 800 uL in final 1× Master Mix. These were split to 8×100 uL portions and amplified with cycling conditions 12× (95 deg 30 sec, 60 deg 30 sec, 72 deg 2 min). An additional volume of 2.1 uL of a mixture of 41.5 uL 25 mM dNTP (Roche Diagnostics, Indianapolis, Ind.) and 13 uL 1.0M magnesium chloride (Sigma, St Louis Mo.) were added to each well and the mixtures subjected to an additional 8× (95 deg 30 sec, 60 deg 30 sec, 72 deg 4 min). The combined products were precipitated with isopropanol, resuspended in 200 uL water each and further precipitated with polyethylene glycol to separate PCR product from primers. Final PCR products were dissolved in 200 uL water, labeled H18B, H24B, H30B, concentrations measured at 1126, 1270, 1357 ng/uL.

Restriction digestion of PCR products to decrease adaptor portion: Restriction enzyme BspDI (New England Biolabs Ipswich Mass.) was used. To 260 uL water, 40 uL 10×

CutSmart buffer BspDI (New England Biolabs Ipswich Mass.), 100 uL of the above PCR products H18B, H24B, H30B, and 10 uL 10 U/uL BspDI was added, and the mixtures were incubated for 16 h at 37 deg. Reactions were labeled H18R, H24R, H30R.

After a 16 h incubation, samples of each were taken for electrophoresis, comparing digested with undigested products. To wells of a PCR strip were added 8 uL 2× loading dye (Thermo Fisher Scientific), 0.6 uL (H18B, H24B, H30B), 2.4 uL (H18R, H24R, H30R)+water to 10 uL; Each mixture was split to 2×5 uL each, to all added 4 uL water. To one of each added 1 uL 1M NaOH and heated 95 deg 30 sec to denature. Five μL was loaded each to well of 3% Agarose/EtBr gel and electrophoresed. In the gel image "−" and "+" correspond to absence and presence of NaOH. All digestions show the smaller size and presence of end fragments expected for successful cleavage by BspDI (doublet probably from annealing fragment with residual primer). Denaturation by NaOH shows further decrease in size for both undigested and digested products. Higher MW smears from extended annealing of fragments are eliminated by denaturation.

The products H18B, H24B, H30B, H18R, H24R, H30R were precipitated with isopropanol, resuspended in 20 uL water and subjected to amination and labeling with carboxytetramethylrhodamine by the procedure described above.

FISH Hybridization Conditions

The targeting probes were hybridized to human chromosomal DNA in lymphocytes bound to glass microscope slides. In a typical experiment the reagent mixture consists of 7 μL of LSI/WCP hybridization buffer (Abbott Molecular (Des Plaines, Ill.)) and 3 μL water containing 2000 ng sonicated human placental DNA, 500 ng COT-1 DNA (LIFE TECHNOLOGIES (Grand Island, N.Y.)), 50 ng of probe CEP17-SG buffer (Abbott Molecular (Des Plaines, Ill.)) and 100 ng of test probe.

The microscope slide was dehydrated by successive immersion in 70%, 85% and 100% ethanol, then air dried. The test solution (10 μL) was placed on the slide and covered with a 22×22 mm slip, causing the solution to spread over the covered area. Rubber cement was applied to seal the edges and the slide placed in an instrument that controls the temperature. The temperature was raised to 70° C. for 5 min. to denature the DNA of both the sample and the reagent, then lowered to 45° C. 1 h to allow time for the reagent to hybridize to its target. After completion of the hybridization time, the rubber cement and slips were removed, and the slide washed 2 min. in a solution of 0.4×SSC and 0.3% NP40 at 73° C., then 1 min in 2×SSC, 0.1% NP40 at room temperature, then air dried.

The slide was prepared for viewing by placing 10 uL of a solution of DAPI on the target area and covering with a slip. The slide was viewed with a fluorescence microscope equipped with filters suitable for the fluorophore of interest.

Fluorescence Microscopy of Resultant Hybridization Patterns

Figure 7:
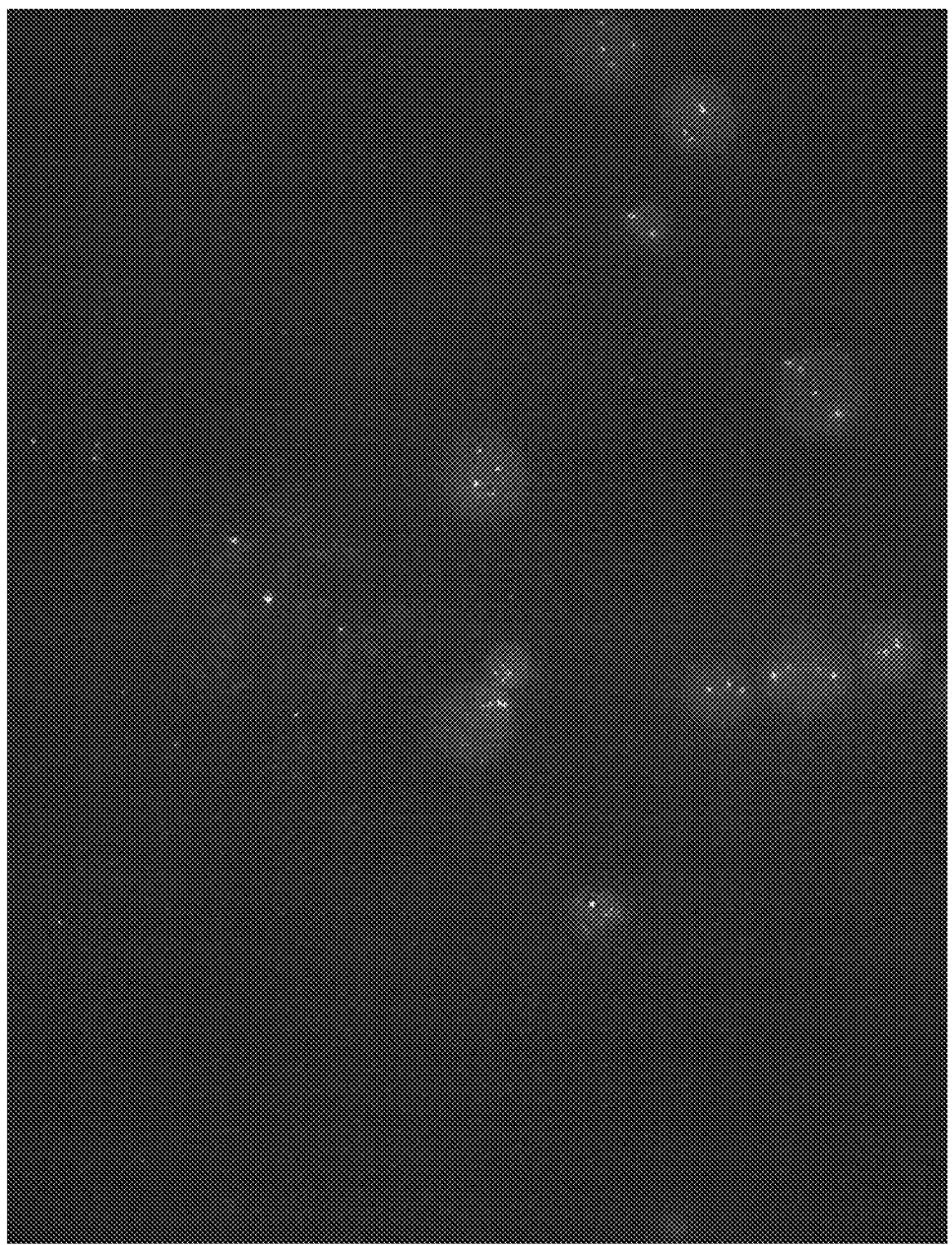
FIG. 7 shows FISH hybridization of the HER2 locus using probes of embodiments of the present disclosure.

Ten μL of DAPI-II (Abbott Molecular (Des Plaines, Ill.)) was placed on the slide at the position of the target, covered with a 22×22 mm slip and viewed under fluorescence microscope equipped with filters that allow simultaneous visualization of DAPI, fluorescein (green) and TAMRA (orange) signals. The photograph (FIG. 7) shows the pattern of orange and green signals consistent with those expected for the HER2 locus (orange) stained by the test probe and the centromeric position stained by CEP17-SG (green). On Metaphase chromosomes the orange and green signals are at adjacent positions on the same chromosome, while interphase nuclei show two strong signals for each, at arbitrary distances. Similar results were seen for probes prepared via Adaptor Mediated PCR of the same HPLC fractions. Removal of the adaptor ends by restriction digestion prior to labeling yielded probe with indistinguishable performance characteristics.

Primer Sequences Used for 1200 Mer Fragments:

| Well-Position | Name | Sequence | SEQ ID NO |
|---|---|---|---|
| A1 | HER2_P_F_01 | AAAGGGGCCAGTTATGCAG | 1 |
| A1 | HER2_P_R_01 | GGTCCGTGGAATTGGATTATT | 2 |
| B1 | HER2_P_F_02 | CTGGCGAAGGGGATCTATTT | 3 |
| B1 | HER2_P_R_02 | CATCTGTGTGCGGAATGACT | 4 |
| C1 | HER2_P_F_03 | TTGTCTGGAAGACGCAGAAC | 5 |
| C1 | HER2_P_R_03 | GTGCCAGTCTGTGCCACTC | 6 |
| D1 | HER2_P_F_04 | GGAGTGAGCTGGTTGGTCAC | 7 |
| D1 | HER2_P_R_04 | ATCTGTTCTCGCCAGAGTCG | 8 |
| E1 | HER2_P_F_05 | GGTTTTGCTTTGGCTCTTTG | 9 |
| E1 | HER2_P_R_05 | GACGTGAGAAGAAGGCCAAG | 10 |
| F1 | HER2_P_F_06 | GACCTGACCTAGCAGCCTTG | 11 |
| F1 | HER2_P_R_06 | TCTCTTGGCAACCTTTGCTT | 12 |
| G1 | HER2_P_F_07 | TCACCCAGGGAAACTTTGTC | 13 |
| G1 | HER2_P_R_07 | CCCAGAGATGCTCCAAGAAC | 14 |
| H1 | HER2_P_F_08 | AAAAGAGAAGCAGGCACAGC | 15 |
| H1 | HER2_P_R_08 | ACTTATCCCGAGGCCTGATT | 16 |
| A2 | HER2_P_F_09 | CTGCTCATCACACCATCTCG | 17 |
| A2 | HER2_P_R_09 | CTCCCTGACAAGCAGGAAAG | 18 |
| B2 | HER2_P_F_10 | GGGGTATGTGCCTTGCTCTA | 19 |
| B2 | HER2_P_R_10 | TGACATGTTTAGGGGTGTGG | 20 |
| C2 | HER2_P_F_11 | GGCCAACTCCTTTCTTCCAT | 21 |
| C2 | HER2_P_R_11 | TTGTATTTCGGTGGACTCAGG | 22 |
| D2 | HER2_P_F_12 | TTTCTCTCCCTGCCTTCTCC | 23 |
| D2 | HER2_P_R_12 | GACACCTGGGTTTGATCCAC | 24 |
| E2 | HER2_P_F_13 | GGTTCCCATGGAGACATAGC | 25 |
| E2 | HER2_P_R_13 | GACCTCGGTCTCTCAGCATC | 26 |
| F2 | HER2_P_F_14 | CCGCTCCACCAAAATACATA | 27 |
| F2 | HER2_P_R_14 | GCATTTGACCAAAGGGAAAC | 28 |
| G2 | HER2_P_F_15 | GAGTCCTGCCCCATGCTC | 29 |
| G2 | HER2_P_R_15 | AATACCGGCTCAGGACAGG | 30 |
| H2 | HER2_P_F_16 | CCCCCTCACATCTGACAATC | 31 |
| H2 | HER2_P_R_16 | TGCTGAACAGTTCTCCAGCTAA | 32 |
| A3 | HER2_P_F_17 | ACACGCTGAGCCAGATTGAC | 33 |

| Well-Position | Name | Sequence | SEQ ID NO |
|---|---|---|---|
| A3 | HER2_P_R_17 | GGCACAAACGAGTACAGCAG | 34 |
| B3 | HER2_P_F_18 | CCCTCCCCATGTGAATTTT | 35 |
| B3 | HER2_P_R_18 | TGGGCTCCTCTCTTTCTCTG | 36 |
| C3 | HER2_P_F_19 | CTTGGCCCCAGGATTTAGA | 37 |
| C3 | HER2_P_R_19 | GGAGACAGGTGTGAGCCTCT | 38 |
| D3 | HER2_P_F_20 | TCCCACTCCTATGAGCAACA | 39 |
| D3 | HER2_P_R_20 | TGGAGTCCAGCAGAGAGGAT | 40 |
| E3 | HER2_P_F_21 | GAAGCATTCAGACCCTCTGC | 41 |
| E3 | HER2_P_R_21 | GCGTGTGTCTCTGCCTCTG | 42 |
| F3 | HER2_P_F_22 | CGAGACGCAGAGACACTCAG | 43 |
| F3 | HER2_P_R_22 | CTGCATCTCAGCTCAGCAAC | 44 |
| G3 | HER2_P_F_23 | GCAAGAGAGTTCCTGGCAGT | 45 |
| G3 | HER2_P_R_23 | GCCCTTCCTCTCTCCAGTTT | 46 |
| H3 | HER2_P_F_24 | GCAAGAGAGTTCCTGGCAGT | 47 |
| H3 | HER2_P_R_24 | GCCCTTCCTCTCTCCAGTTT | 48 |
| A4 | HER2_P_F_25 | AGCACTGTTTGTTCCCTGCT | 49 |
| A4 | HER2_P_R_25 | CTCGGGACTCCTGTGTTTTG | 50 |
| B4 | HER2_P_F_26 | AAAGCTGGAGACTGGGGAGT | 51 |
| B4 | HER2_P_R_26 | GTGCAGATCTGTGCAAATGG | 52 |
| C4 | HER2_P_F_27 | AATTTAACAGGCAGGCAAGG | 53 |
| C4 | HER2_P_R_27 | GTAAGGCAGGAGAGCAGGTG | 54 |
| D4 | HER2_P_F_28 | AAGACCTGGCTCTTGACTGC | 55 |
| D4 | HER2_P_R_28 | CCAAAAGATGGAAAGGAGCA | 56 |
| E4 | HER2_P_F_29 | GGCTCAAGATGAAGCTCTGC | 57 |
| E4 | HER2_P_R_29 | GGCAGAGAATACCCCCTCA | 58 |
| F4 | HER2_P_F_30 | AGCATAGCACCCTGCTCACT | 59 |
| F4 | HER2_P_R_30 | TCTGAGGCCTGGTTCTCATT | 60 |
| G4 | HER2_P_F_31 | CCCTGGAAAGCTTAACCTCA | 61 |
| G4 | HER2_P_R_31 | GCTTCCCCTGAAAGAGGAGT | 62 |
| H4 | HER2_P_F_32 | GGAGGATTCCAAGTCACCAC | 63 |
| H4 | HER2_P_R_32 | GCCAAGAGTCATTGCTGGAG | 64 |
| A5 | HER2_P_F_33 | GTAATGGGGCGTCCTGATAG | 65 |
| A5 | HER2_P_R_33 | TGTCAGAGCGGTACGAAGAA | 66 |
| B5 | HER2_P_F_34 | AGGCTGGAAAGAGGAAGGAG | 67 |
| B5 | HER2_P_R_34 | CCTGCTCCAAGTTCTTACGG | 68 |
| C5 | HER2_P_F_35 | AGAGGAGAGGTGGCATCAGA | 69 |
| C5 | HER2_P_R_35 | AAGGATGGGAGCCGAGTCT | 70 |
| D5 | HER2_P_F_36 | AAGACCCCTGTGCAAGGTTA | 71 |
| D5 | HER2_P_R_36 | CAAGATACCCTGGAGGAGCA | 72 |
| E5 | HER2_P_F_37 | CTTAGCCCCTTGCAGCTCTA | 73 |
| E5 | HER2_P_R_37 | GGGATCTGGGCTGGTCTC | 74 |
| F5 | HER2_P_F_38 | CTGTTCTCCGGTGCTCTGTC | 75 |
| F5 | HER2_P_R_38 | GGGCATGTTGCTCTCTGTTT | 76 |
| G5 | HER2_P_F_39 | AGAGAGAGAACAGGCCACGA | 77 |
| G5 | HER2_P_R_39 | TCTTGTTCCACAGCACCATC | 78 |
| H5 | HER2_P_F_40 | AGAGAACAGGCCACGAACAT | 79 |
| H5 | HER2_P_R_40 | CCCATCTGTGCCTTAAGAGG | 80 |
| A6 | HER2_P_F_41 | GCCGTTGTAGGAGGATTCAA | 81 |
| A6 | HER2_P_R_41 | CAGAGCAATCTGGTCCTCCA | 82 |
| B6 | HER2_P_F_42 | CGTGTTTGCACCTTTGTCTG | 83 |
| B6 | HER2_P_R_42 | ATACAAAGGTCCCCCAGGAG | 84 |
| C6 | HER2_P_F_43 | AGGTGTTGGGGTAGAACTGG | 85 |
| C6 | HER2_P_R_43 | CCCTGCTGGTGGTAGGTCT | 86 |
| D6 | HER2_P_F_44 | GAGGTGTCGGAGGAGAACTG | 87 |
| D6 | HER2_P_R_44 | TATTGCGGCACTAACAGAGG | 88 |
| E6 | HER2_P_F_45 | AGCACAGAGAGGCTGAGAGG | 89 |
| E6 | HER2_P_R_45 | CCTTCCCCTCTGGATGAGTC | 90 |
| F6 | HER2_P_F_46 | CAGTCCTGGCTTCTGTGTCC | 91 |
| F6 | HER2_P_R_46 | TCCCTTAGAACTGCCACACA | 92 |
| G6 | HER2_P_F_47 | CTGTGTCTCGCTCCACACC | 93 |
| G6 | HER2_P_R_47 | CCCCTCCCATCTCTCTTCTC | 94 |
| H6 | HER2_P_F_48 | CAGACCAGAACGAGGGAGAG | 95 |
| H6 | HER2_P_R_48 | GTGGGCATGTGAGATGAGTG | 96 |
| A7 | HER2_P_F_49 | GAAACCAGACCCAGCCATAA | 97 |
| A7 | HER2_P_R_49 | CCAGCCTTGGAGTCTGTTCT | 98 |
| B7 | HER2_P_F_50 | GCCCTGAAAGGGAGTATGGT | 99 |
| B7 | HER2_P_R_50 | GATGATCCTGGGGTCAGAGA | 100 |
| C7 | HER2_P_F_51 | TTGAGGCACACAGCTCTGAC | 101 |
| C7 | HER2_P_R_51 | TCTGTGCCTCCACTGTCATC | 102 |
| D7 | HER2_P_F_52 | ATCCAGGACCCAGAAGAGC | 103 |
| D7 | HER2_P_R_52 | AGCGTCCCTAAAGCCTTGTT | 104 |
| E7 | HER2_P_F_53 | CCATACTCCTCCCAGTGCTC | 105 |
| E7 | HER2_P_R_53 | GGCCAGTTTTCCTGGTACAT | 106 |
| F7 | HER2_P_F_54 | GGAGGAGTAGAGGGCAGGAC | 107 |
| F7 | HER2_P_R_54 | CTCTTCTCACCTCCCCCTTC | 108 |

| Well-Position | Name | Sequence | SEQ ID NO |
|---|---|---|---|
| G7 | HER2_P_F_55 | TCGTGACAACCAAAGGAACA | 109 |
| G7 | HER2_P_R_55 | CCTCCCAAATCTGAGGAAAG | 110 |
| H7 | HER2_P_F_56 | CCCCATTGTTGTTGTTTTCC | 111 |
| H7 | HER2_P_R_56 | GATTCCAGTTGTGGGCATCT | 112 |
| A8 | HER2_P_F_57 | CCAGGTGATTCATCTCACCA | 113 |
| A8 | HER2_P_R_57 | GGCAGGTAGGTGAGTTCCAG | 114 |
| B8 | HER2_P_F_58 | GTCTTGCCCTGAGGAGGTG | 115 |
| B8 | HER2_P_R_58 | TGATCATGCTGGCAAGAGAG | 116 |
| C8 | HER2_P_F_59 | AGCATCTGGACCTAGCATGG | 117 |
| C8 | HER2_P_R_59 | GCACAAAGCAGAGGCACATA | 118 |
| D8 | HER2_P_F_60 | CCTGCTGCCTCTTCTCTCAG | 119 |
| D8 | HER2_P_R_60 | CATGACCAGCTCTCAAAGCA | 120 |
| E8 | HER2_P_F_61 | GGCTTTGAAGCCCAGGAT | 121 |
| E8 | HER2_P_R_61 | GACCGCAGGGGACTTTTAG | 122 |
| F8 | HER2_P_F_62 | GCCCACCTTTCTCCCATAGT | 123 |
| F8 | HER2_P_R_62 | ACCCTAGCACAGCCACAGTC | 124 |
| G8 | HER2_P_F_63 | GCTGTGGTTTGTGATGGTTG | 125 |
| G8 | HER2_P_R_63 | GGGATCCCATCGTAAGGTTT | 126 |
| H8 | HER2_P_F_64 | AGGACCTGCTGAACTGGTGT | 127 |
| H8 | HER2_P_R_64 | CCTCAAGAGTGGCTTTGGAC | 128 |
| A9 | HER2_P_F_65 | CCAAAGGTTCTGGCTGAAGA | 129 |
| A9 | HER2_P_R_65 | GGCAACGTAGCCATCAGTCT | 130 |
| B9 | HER2_P_F_66 | CAGCTCATCTACCAGGGTCA | 131 |
| B9 | HER2_P_R_66 | CTTGATGCCAGCAGAAGTCA | 132 |
| C9 | HER2_P_F_67 | CTTCCCCTAATGGGTCACCT | 133 |
| C9 | HER2_P_R_67 | CTGGATGTCTGGCTCCTCAT | 134 |
| D9 | HER2_P_F_68 | CTCGTTGGAAGAGGAACAGC | 135 |
| D9 | HER2_P_R_68 | TAGAAGATTCCGTGGCCTTG | 136 |
| E9 | HER2_P_F_69 | CCCTTTGACGACCAGATCAT | 137 |
| E9 | HER2_P_R_69 | GCAATCGTGTAGGGTTGGAG | 138 |
| F9 | HER2_P_F_70 | TTCCTAAGGCCACTCACCAG | 139 |
| F9 | HER2_P_R_70 | GCCTGTGGGAAAAACCTAT | 140 |
| G9 | HER2_P_F_71 | CCAGAGCTTTCTCCAGGTCA | 141 |
| G9 | HER2_P_R_71 | GAGACCCAGCCTTTCCCTAC | 142 |
| H9 | HER2_P_F_72 | CCGCCTCTGACTTCTCTGTC | 143 |
| H9 | HER2_P_R_72 | TGCATTCATTCTCTGTCCTCA | 144 |
| A10 | HER2_P_F_73 | CTCTCCTCCGACTTGGCTTT | 145 |
| A10 | HER2_P_R_73 | ATCAGTTTGTCCCCTCAACG | 146 |
| B10 | HER2_P_F_74 | ACTGCAGAGACACTCCAGCA | 147 |
| B10 | HER2_P_R_74 | CCCTGTGTGGATGAAGTTCC | 148 |
| C10 | HER2_P_F_75 | CTGGCCCTCTCTGATCTCTG | 149 |
| C10 | HER2_P_R_75 | TCACTTATAGGGGCTGCACA | 150 |
| D10 | HER2_P_F_76 | CTAACCCCTTCCAAGCACTG | 151 |
| D10 | HER2_P_R_76 | ATCCACCCATTTGTCTGAGG | 152 |
| E10 | HER2_P_F_77 | TCATTCTGTCCTTCCCCAAG | 153 |
| E10 | HER2_P_R_77 | GTTTTTCCGGAAGACGAAGC | 154 |
| F10 | HER2_P_F_78 | CCTCTGCCTGAGGAGGTAAA | 155 |
| F10 | HER2_P_R_78 | GCACAGGACTTAAGGGTGGA | 156 |
| G10 | HER2_P_F_79 | CAAGTCCTGCTCACTCATGC | 157 |
| G10 | HER2_P_R_79 | CCAGCACCTCAGGAAGGTAG | 158 |
| H10 | HER2_P_F_80 | ATCGAAGGCAGAAACACAGC | 159 |
| H10 | HER2_P_R_80 | CTGGTGAGGAGGACAGGTTG | 160 |
| A11 | HER2_P_F_81 | CCTCTCGACCTCAAGCTCTC | 161 |
| A11 | HER2_P_R_81 | CTTCTTGTGCAGGGAAAAGG | 162 |
| B11 | HER2_P_F_82 | CTGGACAGGTGGTGAAATGC | 163 |
| B11 | HER2_P_R_82 | GGGCTCTGGGAAGGAGTTAG | 164 |
| C11 | HER2_P_F_83 | GGGCTGGGACCTCAGATACT | 165 |
| C11 | HER2_P_R_83 | TTCGAGAACGCTTGTGGAG | 166 |
| D11 | HER2_P_F_84 | GCCCCACACATCTACTGGAG | 167 |
| D11 | HER2_P_R_84 | GCTTCACAGCTCCCTCCTC | 168 |
| E11 | HER2_P_F_85 | GTTGGGGTAGGGGAGGATAC | 169 |
| E11 | HER2_P_R_85 | CAGCTGCACTTCTGAGAAACA | 170 |
| F11 | HER2_P_F_86 | ACAGGCACACATGGAGACAG | 171 |
| F11 | HER2_P_R_86 | TTTCAGCCCTGGAGAGAAGA | 172 |
| G11 | HER2_P_F_87 | GGCCAGTGTTTCTGGTCTTC | 173 |
| G11 | HER2_P_R_87 | CCTGGTTCCACTGGTCCTTA | 174 |
| H11 | HER2_P_F_88 | GCCTAGCCCCACATTTGTTA | 175 |
| H11 | HER2_P_R_88 | ACACGTGTGGTCTGTGGATG | 176 |
| A12 | HER2_P_F_89 | CGGGATGAAACCCTTCTACA | 177 |
| A12 | HER2_P_R_89 | TTTTAATGCACAAGGGCAGA | 178 |
| B12 | HER2_P_F_90 | CTTACAGGGTTCCAGCAAGG | 179 |
| B12 | HER2_P_R_90 | AGGGGTGGTGTGCATTATGT | 180 |
| C12 | HER2_P_F_91 | CCAGCATTTTGTGACCTCCT | 181 |
| C12 | HER2_P_R_91 | GCTGTGTTCACAGGGGTAGC | 182 |
| D12 | HER2_P_F_92 | TTTCACTGGAGATGGGAAGG | 183 |

-continued

| Well-Position | Name | Sequence | SEQ ID NO |
|---|---|---|---|
| D12 | HER2_P_R_92 | TGTATCCCATAGCCCTCACC | 184 |
| E12 | HER2_P_F_93 | ATACCGATCATGGCTTCGAT | 185 |
| E12 | HER2_P_R_93 | AGTGTCCCCACTCTTTGCAG | 186 |
| F12 | HER2_P_F_94 | CGCTTCTCACCTGGAACAAG | 187 |
| F12 | HER2_P_R_94 | GGGCAGTGACAAATTTTGGA | 188 |
| G12 | HER2_P_F_95 | GTTAAGTTGCCTGCTGCTCA | 189 |
| G12 | HER2_P_R_95 | TGGAGACACCTCAAGAACAGG | 190 |

Sequences Used in Adaptor Modification and Adaptor Mediated PCR

| | | SEQ ID NO |
|---|---|---|
| BsPD | CTCTACCATCGATCACAGTG | 191 |
| BsTB | CTCTACCTTCGAAGAACGAC | 192 |
| BsPD24 | CCAGCTCTACCATCGATCACAGTG | 193 |
| BsTB24 | CCAGCTCTACCTTCGAAGAACGAC | 194 |
| BsPDc6 | CACAGTG | 195 |
| BsTBc6 | GAACGAC | 196 |
| BsPDc | CACTGTGATCGATGGTAGAG | 197 |
| BsTBc | GTCGTTCTTCGAAGGTAGAG | 198 |
| Gc6a | CACTTCTCTC | 199 |
| Gc6b | CACTCACATT | 200 |
| G6a | GGAGATGAGTGGATGGGAGAGAAGTG | 201 |
| G6b | GTGGTAGGAGGGATGAATGTGAGTG | 202 |

Example 2

Designs were carried out using model targets p53, HER2 and p16 based on available BAC probes for comparison. Genomic sequence corresponding to the targets, with repeat sequence flagged for removal, was identified with UCSC Genome Browser.

For PCR probes, computer applications were used to isolate the repeat-free portions of the sequence, and to identify fragments to target for preparation as "kilomers". The web based application "BatchPrimer3" was used to generate primer sequences to amplify as much of each kilomer sequence as possible, and the identified primer sequences were synthesized by IDT in a 96-well format. For Oligo and Oligo-PCR hybrid probes, the repeat-free portions of sequence were further processed to identify fragments of specified size and GC content. Excel spreadsheets were used for such processes as appending common adaptor sequences, sorting and formatting the sequence lists for placing synthesis orders.

Bulk DNA, which ends up in the final probe, was generated either by oligo synthesis, Oligo-PCR hybrid, or by 1- or 2-step PCR. The 1-step PCR method is as follows: After PCR using BAC or genomic DNA template the products are combined and fragmented by sonication to give a product that can be chemically labeled by the same process used for BAC based FISH probes. FISH probes made this way are structurally identical to the AM BAC probes—the only difference is that the PCR probes exclude the repeat sequence and vector sequence present in BAC DNA. The 2-step method is as follows: The sonicated product is ligated to adaptors to make a single template mixture containing all the chosen targeting sequence. This template can then be used in a single PCR reaction using a single set of primers to generate bulk DNA for amination and labeling. In this case sonication is no longer needed since the amplified product is already the desired size. The template is prepared once, stored indefinitely and samples taken for each new preparation. The adaptor sequences are present at the 5' and 3' ends of the product. While they can be removed by restriction digestion, testing shows that their presence does not damage the performance in FISH assays.

Amine groups for attachment of fluorophore labels were introduced either by inclusion of aminoallyl dUTP in the PCR reaction, or by chemical amination. The chemical amination was performed by the bisulfite/TFA/ethylenediamine process used with AM probes, but with the exception that a small amount of tetramethylethylenediamine was added after desalting the reaction mixture, but prior to ethanol precipitation. This displaces residual unlinked ethylenediamine that would otherwise compete for fluorophore in the labeling reaction.

Labeling the aminated DNA with fluorophore was done by a modification of an established process more suited to the numerous small scale reactions. In this modification the aminated DNA is combined with a reaction buffer of tetramethylethylenediamine and sodium chloride in 25% DMSO, the active fluorophore added and the mixture is incubated 2 h at 60° C. The product is isolated by ethanol precipitation and subjected to 75° C. 72 h formamide treatment standard.
HER2 PCR Probes:

For HER2 PCR probes, three variants were generated, all using 76 kb of repeat-free sequence. For the simplest "1-step PCR" probe, the PCR generated DNA was treated the same as BAC DNA in conventional probes: fragmentation by sonication, followed by chemical amination and labeling. For the "2-step PCR" probe, the sonication fragments were ligated to adaptors to make a template. This template was amplified with a single primer to generate bulk DNA ready for amination and labeling. In the third format, "2-step PCR with aminoallyl dUTP", this same template was amplified with a primer pair in the presence of aminoallyl dUTP to generate the aminated product, ready for labeling with any desired fluorophore.
Generation of Repeat-Free Sequence in HER2 Locus:

Sequence for the HER2 PCR format was identified using the locus defined by the P1 clones pVYS 174 C, E, H, I. These clones include 226 kb at hg18_dna range chr17: 35004678-35230380. These coordinates were entered into UCSD Genome Browser, and the corresponding sequence presented using the Repeat Masker function to give the portions known to be repeat sequence in lower case. The upper case "unique" sequence portions were copied using an application to select out the upper case unique subsequences, retaining the position information of each. This yielded 35 sequences longer than 1200 bp (1234 to 5615 bp), totaling 76904 bp. These were processed with another application to break all the sequences into a total of 95 sequences, 1200 bp each, with at least 300 bp overlap. The 1200 bp sequences were entered into the web based application "BatchPrimer3", with settings adjusted to give primers with Tm at least
65 deg, to include as much as possible (at least 800 bp) of each sequence in the amplicon.

The identified primer sequences were synthesized and placed as primer pairs in 96-well plate format. The primers were dissolved in water and prepared to give 5 uM each primer, while still in the 96-well plate format. PCR was in a 96-well plate in the same format as the primer pairs, using a master mix containing Phire polymerase, template consisting of a mixture of the P1 clones pVYS 174 C, E, H, I, and primers at 0.5 uM. (Note, Genomic DNA can be used as template, but locus specific clones such as BACs and PAC's are preferred). The products were analyzed by 96-well eGel, and show strong clean bands for 94 of the 95 wells. When Taq polymerase was used only 87 of the 95 reactions showed product.

Fragmentation of HER-2 Repeat-Free Sequence:

The contents of the PCR wells were combined and the DNA 1200mers were isolated by ethanol precipitation and PEG precipitation. The 1200mer mixture was sonicated by the same means used for fragmenting BAC DNA for other AM probes, and the sonicated product fractionated by HPLC with an ion exchange column to give narrow size fractions ranging from about 120 to about 400 bp. In some embodiments, the fractionation step is eliminated HER-2 Probe from 1-Step PCR Process:

To prepare Probe 5/13-76A the fraction centered at 150 bp was aminated by a standard procedure and labeled with Spectrum Orange.

HER-2 Probe from 2-Step PCR Process:

To prepare a HER-2 probe from the 2-step process, a portion of the same 150 bp HPLC fraction was treated with a blunting agent and ligated to adaptors. The adapted product was used as a template in a second PCR reaction, this time using only a single primer, with sequence corresponding to the adaptor. The use of a single primer to amplify the adapted template suppresses amplification of the shortest fragments via a stem-loop structure, and gives a product enriched in the longer fragments. The PCR product was aminated and labeled with Spectrum Orange, then subjected to 75° C. 72 h formamide treatment.

HER-2 PCR Probe Via Aminoallyl dUTP Amination:

To prepare a HER-2 PCR probe via aminoallyl dUTP amination, the HPLC fractions of sonicated 1200mer were recombined (to simulate unfractionated fragments), treated with blunting agent and ligated to adaptors containing common 5' end containing a BspQI restriction site. The adapted product was used as template in a second PCR reaction, this time using two primers corresponding to the adaptor sequences, and with aminoallyl dUTP replacing half of the dTTP. The PCR product was treated with the restriction enzyme BspQI to digest off the common ends, and the DNA product labeled with Spectrum Orange, then subjected to 75° C. 72 h formamide treatment.

HER-2 Oligo Probe:

Design of the HER-2 oligo probe started with the same repeat-free sequence as the HER2 PCR probes. An application was used to select non-overlapping 80-base portions of this sequence, all with approximately 50% GC content (G+C min=39, max=41). A total of 401 such sequences were found. These were entered into the web application QuickFold with parameters Na+=0.05M, Mg++=0.001M, maximum of 1 Folding and the results copied as text and deltaG. The Find feature of Excel was used to flag sequences containing certain restriction sites for removal (to allow these sequences to be used in adaptors without interference with target sequence). The remaining sequences were sorted by deltaG, and the 288 (three 96-well plates) with lowest tendency to fold were selected for further processing and sorted by genomic location. The 80mer sequences were joined in pairs via a common 20 base connecting sequence and a different common 20 base was also added to the 3' end of the pair, bringing the total to 200 bases to be synthesized. All 288 of the 80mers (Figure were represented in 144 separate "Forward" 200mers. The complements of the target 80mers and common 20mers were also calculated, and assembled the same way to give 144 separate "Reverse" 200mers. The assembly of these was designed such that upon mixing the sequences should duplex in a staggered fashion, giving long chains of annealed product.

Nucleic acids were chemically aminated by the procedure above, and labeled with Spectrum Orange. The labeled products were purified by gel electrophoresis to remove truncated synthesis products, and the full-length products combined to give the final probe.

Design of additional HER2 Oligo Probes started with the same sequence as for HER2 PCR probes, masking repeat sequences. Additional masking was introduced to flag for removal other undesirable subsequences: 5 or more consecutive "G" or "C" bases, and sequences corresponding to the BspQI restriction site "GCTCTTC" and "GAAGAGC". The remaining sequence was processed to identify 60 base stretches with 55-65% GC. Very few acceptable sequences were found in the downstream 40 kb of the sequence, so only those in the range 1-180 kb were carried to the next stage. To the 3' end of each sequence was added the bases "GGTTGAAGAG" polymerase using a complementary primer. The web based application "Zipfold" was used to determine the energy of folding. Of the 1027 60-mers assessed, the 960 with the lowest tendency to fold were retained. These were separated into 5 groups (192 members each=two 96-well plates) according to energy of folding, with each group sorted by position in the overall genomic sequence. The oligonucleotides were dissolved in water, and combined into groups according to folding tendency. Samples of each group were annealed with a primer containing sequence corresponding to the common 3' end and Phire polymerase to elongate each to a blunt ended duplex mixture. These were purified by ion exchange HPLC to remove products of truncated oligomers.

p53 PCR Probes:

Same as with the HER-2 probes, the p53 PCR probes were designed based on the sequence of the BAC for the corresponding BAC p53 probe. Kilomers were generated by PCR, combined and fragmented by sonication. For the 1-step PCR probe the sonication fragments were simply aminated and labeled. For the 2-step PCR variants the sonication fragments were blunted and ligated to adaptors to make the template. To generate bulk DNA for amination and labeling the template was amplified using primers corresponding to the adaptor sequences. Bulk DNA containing the amines for labeling was prepared from the same template but including aminoallyl dUTP in the reaction mixture. For an additional variant, the adaptor sequences were removed by digesting the PCR product with a restriction enzyme specific to a recognition site included in the adaptors.

Generation of Repeat-Free Sequence in p53 Locus:

Sequence for the p53 PCR format was identified using the locus defined by the BAC clone pVYS 173i. This clone consists of of 172 kb at hg18_dna range chr17:7435119-7606823. These coordinates were entered into UCSD Genome Browser, and the corresponding sequence presented using the Repeat Masker function to give the portions known to be repeat sequence in lower case. Table 1 below shows primer sequences.

TABLE 1

|   | Direction | Name | Sequence | SEQ ID NO. |
|---|---|---|---|---|
| 1 | 01 FORWARD | p53 AF01 | TCCCCTCACGCTTCTCCTTCAGTTC | 203 |
| 2 | 01 REVERSE | p53 AR01 | AGGGTCAGGGATTGGGGAGCTAGTG | 204 |
| 3 | 02 FORWARD | p53 AF02 | TGATGAGGGGAAGGCTGTCTACCTGA | 205 |
| 4 | 02 REVERSE | p53 AR02 | GCTGACTCTCAGCCCCTCCTCCAG | 206 |
| 5 | 03 FORWARD | p53 AF03 | GTGAGGGGCGAGAAACAAGACAAGC | 207 |
| 6 | 03 REVERSE | p53 AR03 | TGCAGAAGGGAAGAAGGTTGTTACGC | 208 |
| 7 | 04 FORWARD | p53 AF04 | GCCCAGCCTTAACCCCAGAACTCAG | 209 |
| 8 | 04 REVERSE | p53 AR04 | GCATCGGAACTCTGCTCATGGAAAG | 210 |
| 9 | 05 FORWARD | p53 AF05 | ATGGCTCTGCTGACCCAACAAACAG | 211 |
| 10 | 05 REVERSE | p53 AR05 | AAAACAGGATGGCCTGGCTCAGTTC | 212 |
| 11 | 06 FORWARD | p53 AF06 | TCCCCATTTCTTGGAGTGGGATTGA | 213 |
| 12 | 06 REVERSE | p53 AR06 | TTATAAGCCACTCGGAAGCCCCTCA | 214 |
| 13 | 07 FORWARD | p53 AF07 | GGAGCCCTTAAGCAACTAGCCTCTCC | 215 |
| 14 | 07 REVERSE | p53 AR07 | GGGCTGGCCATAGCGAAAAACACTA | 216 |
| 15 | 08 FORWARD | p53 AF08 | AAAGTGTGAAAAGCGCCTGCCCATC | 217 |
| 16 | 08 REVERSE | p53 AR08 | CCTGGGGTTCAAAAACAGCCTGACT | 218 |
| 17 | 09 FORWARD | p53 AF09 | GGGCATCACTTTCTTTTCCCCCATC | 219 |
| 18 | 09 REVERSE | p53 AR09 | TTGAAGATCTGGCAGGCAGTGATCC | 220 |
| 19 | 10 FORWARD | p53 AF10 | CGGTCCTGCTCTGGTCAATAAAGGA | 221 |
| 20 | 10 REVERSE | p53 AR10 | GACCCTAGCCGGGCTGTCCCTAC | 222 |
| 21 | 11 FORWARD | p53 AF11 | GGGCCTTCACCTTGATAGGCACTCG | 223 |
| 22 | 11 REVERSE | p53 AR11 | AGCTAGCAAAGGGGGAGATTGCACA | 224 |
| 23 | 12 FORWARD | p53 AF12 | CAGTCACTTCGTCGCGGCTAAAACA | 225 |
| 24 | 12 REVERSE | p53 AR12 | GGAGCTGAGCTGTAGTCTCCGAGCA | 226 |
| 25 | 13 FORWARD | p53 AF13 | CAGAAAGGGTCACCCCCTTATGTCG | 227 |
| 26 | 13 REVERSE | p53 AR13 | GAACCAAGCATTTCATGGCTCACAA | 228 |
| 27 | 14 FORWARD | p53 AF14 | TTGTGGACTGTCCCTGACCTGGGTA | 229 |
| 28 | 14 REVERSE | p53 AR14 | CTCCTGCCATAGGACCCAAGCTACG | 230 |
| 29 | 15 FORWARD | p53 AF15 | ATGAGCACCTGCCTCTCTCTGCTCA | 231 |
| 30 | 15 REVERSE | p53 AR15 | CATGCATCTTCTCGGTGAGCCAGTC | 232 |
| 31 | 16 FORWARD | p53 AF16 | TGTTAAGCCGTGGATTCAAGGACCA | 233 |
| 32 | 16 REVERSE | p53 AR16 | GTTTTCCCTGTTGGTGGGAAGGTCA | 234 |
| 33 | 17 FORWARD | p53 AF17 | CCATCACCCAGGCAGTCATCTTCAT | 235 |
| 34 | 17 REVERSE | p53 AR17 | TGAGGAGAGCCTCTGGGATCTGGAG | 236 |
| 35 | 18 FORWARD | p53 AF18 | TGACCTTCCCACCAACAGGGAAAAC | 237 |
| 36 | 18 REVERSE | p53 AR18 | TTGCTTGGCAGTTGTGGCAAGTAGC | 238 |
| 37 | 19 FORWARD | p53 AF19 | AACCTCCAGATCCCAGAGGCTCTCC | 239 |
| 38 | 19 REVERSE | p53 AR19 | GGCTCTTGGTAGTCCTGTGGCTGGT | 240 |

TABLE 1-continued

| | | Direction | Name | Sequence | SEQ ID NO. |
|---|---|---|---|---|---|
| 39 | 20 | FORWARD | p53 AF20 | CAGTCGGGAGAAGGGAGGGAGAGAA | 241 |
| 40 | 20 | REVERSE | p53 AR20 | CACCACGTGCTGGGCAGAGACTT | 242 |
| 41 | 21 | FORWARD | p53 AF21 | AGGCCAGCAGAAGAGCCCGATTAAA | 243 |
| 42 | 21 | REVERSE | p53 AR21 | GCGCTGTTGGAATTGTAAAGCTTGC | 244 |
| 43 | 22 | FORWARD | p53 AF22 | CCAGGTAGTCCAAGGTGCCCTTTCC | 245 |
| 44 | 22 | REVERSE | p53 AR22 | CGGTGACTTCCCCACTGGCACTAAT | 246 |
| 45 | 23 | FORWARD | p53 AF23 | GCGGAGAAAGGCAGGGGTGTAAATC | 247 |
| 46 | 23 | REVERSE | p53 AR23 | ACACTCTGACTGTCCCTGGCCCCTA | 248 |
| 47 | 24 | FORWARD | p53 AF24 | TGGAGGTGATCTTGAGAAGGGGTGA | 249 |
| 48 | 24 | REVERSE | p53 AR24 | TCAGATGGGGAGAACCCTGAGGTTG | 250 |
| 49 | 25 | FORWARD | p53 AF25 | GCCAGCTCTCAGCCATCACAGTCTT | 251 |
| 50 | 25 | REVERSE | p53 AR25 | CCTCTAACCCTCATGGACGCAGACC | 252 |
| 51 | 26 | FORWARD | p53 AF26 | GACTGAGTCTGGACGGCAGAGTGGA | 253 |
| 52 | 26 | REVERSE | p53 AR26 | GCCCCTCTTCTGGAGCCTTGGTG | 254 |
| 53 | 27 | FORWARD | p53 AF27 | ACGGCTGTTTTCCTCTTGGGGAGTC | 255 |
| 54 | 27 | REVERSE | p53 AR27 | GCAAAGGCTCCGGTTTAAGCTCTGG | 256 |
| 55 | 28 | FORWARD | p53 AF28 | CTTCTCGTCCTCGTCCAGCAGCTT | 257 |
| 56 | 28 | REVERSE | p53 AR28 | CCCAAGCACCTGCTGGAATGACTC | 258 |
| 57 | 29 | FORWARD | p53 AF29 | TGGCAAGTTTTAGCTTCAGTCGTCCA | 259 |
| 58 | 29 | REVERSE | p53 AR29 | GACCTGCGCTGGAGCTGCTCTTATC | 260 |
| 59 | 30 | FORWARD | p53 AF30 | AAAGAAGGCACAGGAGCCAGACAGC | 261 |
| 60 | 30 | REVERSE | p53 AR30 | TCTTAATCTCCTGCCTTCCCCAGTGA | 262 |
| 61 | 31 | FORWARD | p53 AF31 | GGGGTGCAGGTTGGAGGTTTTATGA | 263 |
| 62 | 31 | REVERSE | p53 AR31 | GCTCAGGTACCAGACAGCTGGGTTC | 264 |
| 63 | 32 | FORWARD | p53 AF32 | CACTGAACCCGAACCCCTGATTTTC | 265 |
| 64 | 32 | REVERSE | p53 AR32 | ATTGATGAGCAGCTTCGGCAGATTG | 266 |
| 65 | 33 | FORWARD | p53 AF33 | AGCTCGGTTGGGCTCCTCTCTCTTC | 267 |
| 66 | 33 | REVERSE | p53 AR33 | GATTGTCCTCTGAGGGCTGGGATTG | 268 |
| 67 | 34 | FORWARD | p53 AF34 | CCAAGCGAAGCTGCTCTACCTCCTG | 269 |
| 68 | 34 | REVERSE | p53 AR34 | TCTTCCTTTAGACTCCCGAGGCTTGC | 270 |
| 69 | 35 | FORWARD | p53 AF35 | ATGGAAGGCAAATCGCCTGAAACTG | 271 |
| 70 | 35 | REVERSE | p53 AR35 | CGGAGGTAGGCCCTTCTCTCTCGAC | 272 |
| 71 | 36 | FORWARD | p53 AF36 | AACCCCAGGCCCTGCTCCATAGTAG | 273 |
| 72 | 36 | REVERSE | p53 AR36 | ATGCATGGCTTTGGCCTCCTTAGTG | 274 |
| 73 | 37 | FORWARD | p53 AF37 | TGAAGTACAGGCAGAAACCACCCAAGA | 275 |
| 74 | 37 | REVERSE | p53 AR37 | TCAGGCCATTATTGTCCCTGGCTTG | 276 |
| 75 | 38 | FORWARD | p53 AF38 | CTGGGCAAAGGGGGAGGTGAAATAA | 277 |
| 76 | 38 | REVERSE | p53 AR38 | GGCCCGCACTCAGACTGCTGCT | 278 |

TABLE 1-continued

|  |  | Direction | Name | Sequence | SEQ ID NO. |
|---|---|---|---|---|---|
| 77 | 39 | FORWARD | p53 AF39 | CCCAACACCACATCAGGACATGTAA | 279 |
| 78 | 39 | REVERSE | p53 AR39 | GCCGAATTCGAAAAACTCTCGGATCA | 280 |
| 79 | 40 | FORWARD | p53 AF40 | CCCCCTCCATATACCCTTGCTTCTTCA | 281 |
| 80 | 40 | REVERSE | p53 AR40 | CCGGAATCCCAGCTCCACTTACCAG | 282 |
| 81 | 41 | FORWARD | p53 AF41 | CTTCTGGAAGCCTGTGGGGAGACCT | 283 |
| 82 | 41 | REVERSE | p53 AR41 | ATGCAAATGCCCCCAAGAGGTAACA | 284 |
| 83 | 42 | FORWARD | p53 AF42 | CACATAAGGAGGTGAGTTCCGACGTG | 285 |
| 84 | 42 | REVERSE | p53 AR42 | AACTGCGATGAAAAGGGGTGCTGTC | 286 |
| 85 | 43 | FORWARD | p53 AF43 | GCGGGCCCAACCTCTCCATATTTAC | 287 |
| 86 | 43 | REVERSE | p53 AR43 | AGGCCCCGAGAGGGAGTGTGAG | 288 |
| 87 | 44 | FORWARD | p53 AF44 | CTTTTGGGTGTGTGGAGGGCTTCAG | 289 |
| 88 | 44 | REVERSE | p53 AR44 | ATCCCAGGGGCTGGAGTTTGAGTTC | 290 |
| 89 | 45 | FORWARD | p53 AF45 | GGTTCTTCACGGCGGAAGTTGTCTG | 291 |
| 90 | 45 | REVERSE | p53 AR45 | TCCTGGTCCTAGGGCACAGTGAAGC | 292 |
| 91 | 46 | FORWARD | p53 AF46 | TCTGAGATGGAAGGATTGGGAGTCCA | 293 |
| 92 | 46 | REVERSE | p53 AR46 | TGAGGGACTGCACACAGAGGGAAGA | 294 |
| 93 | 47 | FORWARD | p53 AF47 | GGCTCTGTGATCAGTCCCAGTGCAG | 295 |
| 94 | 47 | REVERSE | p53 AR47 | GCATCCAGCCTTCTAACTGCAGAGC | 296 |
| 95 | 48 | FORWARD | p53 AF48 | TGGGAAGAAACTGCGGAATGAAACA | 297 |
| 96 | 48 | REVERSE | p53 AR48 | AGGAGTGGAGCTTTGGGGAACCTTG | 298 |
| 97 | 49 | FORWARD | p53 AF49 | AGTGAGCTGCTCCGGCAAAAGAAA | 299 |
| 98 | 49 | REVERSE | p53 AR49 | GCAAAAGCTTTCTTCCTTCCACCCTTC | 300 |
| 99 | 50 | FORWARD | p53 AF50 | GGGAGACAGGTCTGAAGCCTGGAGAA | 301 |
| 100 | 50 | REVERSE | p53 AR50 | TTGGGTGCTGAACTCTGACCAGGAA | 302 |
| 101 | 51 | FORWARD | p53 AF51 | AAAAATGCGGACTCTGAACTGATGC | 303 |
| 102 | 51 | REVERSE | p53 AR51 | TGCTGCCACAAGAAATTCACTACTTTTT | 304 |
| 103 | 52 | FORWARD | p53 AF52 | GTGCGCGAGGTGAGGGAGGTGT | 305 |
| 104 | 52 | REVERSE | p53 AR52 | GCTGTGGGAAGAGTTGGGAGACAG | 306 |
| 105 | 53 | FORWARD | p53 AF53 | CGGGCACAGCAGGAAGCAGGTC | 307 |
| 106 | 53 | REVERSE | p53 AR53 | GAAGTGGGATCCGCATGTAGGCAAG | 308 |
| 107 | 54 | FORWARD | p53 AF54 | CCAGCCTCCCTCACACTTCTCTGCT | 309 |
| 108 | 54 | REVERSE | p53 AR54 | CCTGGAACCTATGGGGAGGAGGGTA | 310 |
| 109 | 55 | FORWARD | p53 AF55 | ACTGGTCTGGACCACCCTCCACACA | 311 |
| 110 | 55 | REVERSE | p53 AR55 | GAAGACCCAGAGAGGGGCTGAGACA | 312 |
| 111 | 56 | FORWARD | p53 AF56 | TGCCCCAAACCTCCTTCTCACTTGT | 313 |
| 112 | 56 | REVERSE | p53 AR56 | CTGCCACGCCCAGCAAGAGCAG | 314 |
| 113 | 57 | FORWARD | p53 AF57 | ACCCTCCCTCCCTCTTCAGTTTTGG | 315 |
| 114 | 57 | REVERSE | p53 AR57 | GCCAACCAAAAGGTGGGCTGTTC | 316 |

TABLE 1-continued

| | | Direction | Name | Sequence | SEQ ID NO. |
|---|---|---|---|---|---|
| 115 | 58 | FORWARD | p53 AF58 | CCCCTTCTGCCCCCACTATGAGAA | 317 |
| 116 | 58 | REVERSE | p53 AR58 | TGAAAGGAAGTTCTTCCCGCCCTTC | 318 |
| 117 | 59 | FORWARD | p53 AF59 | AACCACTCCCCTCAGTCTGCCAAAA | 319 |
| 118 | 59 | REVERSE | p53 AR59 | CCGCCACCATGGCAATATCAACTTC | 320 |
| 119 | 60 | FORWARD | p53 AF60 | TGGACTTGAATTGGGACAAAGGCTTG | 321 |
| 120 | 60 | REVERSE | p53 AR60 | TTCCCTCTTGTCTCTCCACCTGTGC | 322 |
| 121 | 61 | FORWARD | p53 AF61 | GAAGGGATGTGGCTGATCAGAAGGA | 323 |
| 122 | 61 | REVERSE | p53 AR61 | TCCTGTGCCTGTAGTCGTTTTGCTG | 324 |
| 123 | 62 | FORWARD | p53 AF62 | AGTGGGAATTTCTGATGCGGAATGG | 325 |
| 124 | 62 | REVERSE | p53 AR62 | GGGAAAGGGAGCCAGAGGCTAAGGT | 326 |
| 125 | 63 | FORWARD | p53 AF63 | GTGGCTGCCTCCTCCCTCATCAAT | 327 |
| 126 | 63 | REVERSE | p53 AR63 | TGCTCAATCCGATTAAACGCTGCTG | 328 |
| 127 | 64 | FORWARD | p53 AF64 | CCAGCTCACCCCAAATCTGCTGTTC | 329 |
| 128 | 64 | REVERSE | p53 AR64 | TGGCAGTCCCTGGTACTCCTGAAGA | 330 |
| 129 | 65 | FORWARD | p53 AF65 | TGCAACCCTGGCTGTTTCTCTAGCC | 331 |
| 130 | 65 | REVERSE | p53 AR65 | GGGAAGACGGGAACTGGAGTTTTGG | 332 |
| 131 | 66 | FORWARD | p53 AF66 | ATTTTTAGCCCAGTGCCCCGAAGAC | 333 |
| 132 | 66 | REVERSE | p53 AR66 | GTGCTCTCAGGGAGATCCCAGCAAT | 334 |
| 133 | 67 | FORWARD | p53 AF67 | CAAGGAGGAGCCTGGTGGGTACTTG | 335 |
| 134 | 67 | REVERSE | p53 AR67 | GGAGCTGGGAGAGGCAGAAATCCTT | 336 |
| 1 | 01 | FORWARD | p53 BF01 | GCCATGGAAACGTCACAGTTCATCC | 337 |
| 2 | 01 | REVERSE | p53 BR01 | CTGCGTGGGGGAAGGACACATTGTA | 338 |
| 3 | 02 | FORWARD | p53 BF02 | TCCACCTCCAAGCCCAGATTCAGAT | 339 |
| 4 | 02 | REVERSE | p53 BR02 | ACTTTGCCCAAAGACCCCTGTGTG | 340 |
| 5 | 03 | FORWARD | p53 BF03 | ATTCCAACCAGCCTCTTCCGCTGAC | 341 |
| 6 | 03 | REVERSE | p53 BR03 | AGACGGTGAAGGTGGGGACCAATTT | 342 |
| 7 | 04 | FORWARD | p53 BF04 | TTCTCCTCCACCATGTTAGGCTTGG | 343 |
| 8 | 04 | REVERSE | p53 BR04 | CAGGGCGCAATCTTCCTACTCCAAA | 344 |
| 9 | 05 | FORWARD | p53 BF05 | CAACAGGGCCCAATTCTGAGAGAGG | 345 |
| 10 | 05 | REVERSE | p53 BR05 | GGGACTTTTCTTCTAGCCTGCCTCCA | 346 |
| 11 | 06 | FORWARD | p53 BF06 | GGCAGAAAATGCTAACCTGCCCAGA | 347 |
| 12 | 06 | REVERSE | p53 BR06 | CCCATTTTGCCTTACTTCCCTCATCA | 348 |
| 13 | 07 | FORWARD | p53 BF07 | GGCCTCTGATTTTGCTTCCCACCTT | 349 |
| 14 | 07 | REVERSE | p53 BR07 | CCTGCTTGAGTCCCAGGTCCAAAGA | 350 |
| 15 | 08 | FORWARD | p53 BF08 | CAGGGGTGGAACCCTAGCCAAGACT | 351 |
| 16 | 08 | REVERSE | p53 BR08 | GTTCCCTGGGCTGGAAACCTTCCTA | 352 |
| 17 | 09 | FORWARD | p53 BF09 | ACAGAGGCAAGGACAGGGACTGAGC | 353 |
| 18 | 09 | REVERSE | p53 BR09 | TGGCCATCTGCTCCATCAGAAAGTG | 354 |

TABLE 1-continued

| | | Direction | Name | Sequence | SEQ ID NO. |
|---|---|---|---|---|---|
| 19 | 10 | FORWARD | p53 BF10 | AAGGGGCTCCTGCTTGCACCTTC | 355 |
| 20 | 10 | REVERSE | p53 BR10 | GGAACAAAGGCTGGAGACTGGGTCA | 356 |
| 21 | 11 | FORWARD | p53 BF11 | TGAGCTCCTCAACCCGACTCTCCTC | 357 |
| 22 | 11 | REVERSE | p53 BR11 | CATCTGCATTTTCACCCCACCCTTC | 358 |
| 23 | 12 | FORWARD | p53 BF12 | TCAGGCAAAGTCATAGAACCATTTTCA | 359 |
| 24 | 12 | REVERSE | p53 BR12 | TTAACCTGTGGCTTCTCCTCCACCT | 360 |
| 25 | 13 | FORWARD | p53 BF13 | GGTTTCTTCTTTGGCTGGGAGAGG | 361 |
| 26 | 13 | REVERSE | p53 BR13 | TGGCCTCATCTTGGGCCTGTGTTAT | 362 |
| 27 | 14 | FORWARD | p53 BF14 | ACCCTGTCAGCTGTGGAGCTTTTGG | 363 |
| 28 | 14 | REVERSE | p53 BR14 | AGATCCCAGCACAGGAGCTCAGCAT | 364 |
| 29 | 15 | FORWARD | p53 BF15 | CAGAGCGGCATCATCTCCTGCATAG | 365 |
| 30 | 15 | REVERSE | p53 BR15 | TCCTTCTGGGGCAGAAAACTCAACA | 366 |
| 31 | 16 | FORWARD | p53 BF16 | CTGCACCCTAGCCTGCCTCTCCTG | 367 |
| 32 | 16 | REVERSE | p53 BR16 | AGGAGAGTGCTCCTGCTCCCCTCAG | 368 |
| 33 | 17 | FORWARD | p53 BF17 | GCATATGAGTGAGGTGGGGGACCAG | 369 |
| 34 | 17 | REVERSE | p53 BR17 | TCGTCCCTTCCCTTTGATTGTGAGG | 370 |
| 35 | 18 | FORWARD | p53 BF18 | TGAGCAGGAGCTGGGTCAGACTGTT | 371 |
| 36 | 18 | REVERSE | p53 BR18 | CCAAGTGCTGTTGTTACCTGGGGGTTA | 372 |
| 1 | 01 | FORWARD | p53 CF01 | AGGGATGGGCCCTGAGACCTGTT | 373 |
| 2 | 01 | REVERSE | p53 CR01 | GCCCAGTGATTGTGCAGTTGGATCT | 374 |
| 3 | 02 | FORWARD | p53 CF02 | TGTCTGTCTCTGACATGTCCCTACTCAGC | 375 |
| 4 | 02 | REVERSE | p53 CR02 | GTTCCCTTTCCTCAGACCAGCTCCA | 376 |
| 5 | 03 | FORWARD | p53 CF03 | GGATGGCACTCAGGTGGGTGGTAG | 377 |
| 6 | 03 | REVERSE | p53 CR03 | CCCAGAGGTTTCCTTCCCCTCAAAA | 378 |
| 7 | 04 | FORWARD | p53 CF04 | GCCAGTAGGTGGAGGCATAGCGAAG | 379 |
| 8 | 04 | REVERSE | p53 CR04 | GAGGGAGGTAGTGCAAAGGTGGCATT | 380 |
| 9 | 05 | FORWARD | p53 CF05 | CTGGTCTTGGGACTCCCTCTTCAGC | 381 |
| 10 | 05 | REVERSE | p53 CR05 | GGTGGAGCTTTAATGGGAAGCGTCA | 382 |
| 11 | 06 | FORWARD | p53 CF06 | CAGCAAAAACCCCGACAGACAGACA | 383 |
| 12 | 06 | REVERSE | p53 CR06 | GGTAGGGGCTATGGGCTTGGATACG | 384 |
| 13 | 07 | FORWARD | p53 CF07 | TGAGACCAGTTTCCTGCCTCTGTGG | 385 |
| 14 | 07 | REVERSE | p53 CR07 | GGCTTTAGCCCCAGGGCTCCTTAGT | 386 |
| 15 | 08 | FORWARD | p53 CF08 | GGTCTGGATGCCCATCTTCGACAAC | 387 |
| 16 | 08 | REVERSE | p53 CR08 | GAACAGGGTCCCAAGGACAACGAAC | 388 |
| 17 | 09 | FORWARD | p53 CF09 | TTCTTTGCTCCTAGAGGCCCCATCA | 389 |
| 18 | 09 | REVERSE | p53 CR09 | GATGAGGGGATGGTCTGTCCCTGTC | 390 |
| 19 | 10 | FORWARD | p53 CF10 | TCCAGGGAGGCAGACTTGAGACAGG | 391 |
| 20 | 10 | REVERSE | p53 CR10 | CAAAAATACCTTTGGGGTGGGTGAGG | 392 |

TABLE 1-continued

| | | Direction | Name | Sequence | SEQ ID NO. |
|---|---|---|---|---|---|
| 21 | 11 | FORWARD | p53 CF11 | GTGCGGGTGGTGAGCTAGGGAAG | 393 |
| 22 | 11 | REVERSE | p53 CR11 | ACTCTCAGGGGATATGCAGGCAGGA | 394 |

The upper case "unique" sequence portions were copied as above to select out the upper case "unique" subsequences, retaining the position information of each. This yielded only 17 sequences longer than 1200 bp totaling 35930 bp. To these were added 13 fragments with lengths 800-1200 and 10 fragments 650-800 bp to give a final total of 55661 bp. The application "SeqChop3" was used on the first set to generate 1200-mers with 400 base overlap, yielding 65 sequences. The second set (800-1200) for 800mers with 200 base overlap gives 26 sequences. To complete a 96 well plate an additional 5 sequences in the 650-800 base region are accepted. The sequences so generated were adjusted to give primers with Tm at least 65 deg, to include as much as possible of each sequence in the amplicon. The primers were dissolved in water to give 5 uM each primer, while still in the 96-well plate format. PCR was in a 96-well plate in the same format as the primer pairs, using a master mix containing Phire polymerase, template consisting of the BAC clone pVYS 173i and primers at 0.5 uM. At the conclusion of the PCR, additional primer, Taq polymerase and dNTP was added and the plate subjected to an additional 8 cycles to increase the product yield. The products were analyzed by 96-well eGel, and show strong clean bands for 91 of the 96 wells. The contents of the PCR wells were combined, and the DNA isolated by ethanol precipitation and PEG precipitation. The mixture was sonicated by the same means used for fragmenting BAC DNA for other probes.

p53 Probe from 1-Step PCR Process:
To prepare p53 probes from the 1-step PCR process, the sonicated product was aminated and labeled with Spectrum Orange, then subjected to 75° C. 72 h formamide treatment.

p53 Probe from 2-Step PCR Process:
To prepare p53 probes from the 2-step PCR process, a portion of the sonicated product was fractionated using disposable silica based spin columns (PureLink PCR Purification Kit) but adjusting the binding buffer to isolate a fraction ranging from 100-300 bp. A portion of this fraction was treated with a blunting agent and ligated to adaptors. This adapted product was used as template in a second PCR reaction, this time using only a single primer, with sequence corresponding to the adaptor. The PCR product was aminated, labeled with Spectrum Orange, and subjected to 75° C. 72 h formamide treatment.

p53 PCR Probe Via Aminoallyl dUTP Amination:
This probe was prepared as described above except the PCR step included aminoallyl dUTP added to the PCR mixture. The PCR product was labeled with Spectrum Orange and subjected to 75° C. 72 h formamide treatment.

A portion of the sonicated blunted repeat-free p53 DNA was ligated to adaptors containing a BspQI restriction site. The product was used as template with a pair of primers corresponding to adaptors in a PCR reaction containing aminoallyl dUTP and the product exposed to BspQI restriction enzyme to remove the adaptor ends. The digestion product, containing only the sequence specific to p53, was labeled with Spectrum Orange and then subjected to the 7° C. 72 h formamide treatment.

Oligo-PCR Probe for p53
Sequences for p53 Oligo Probe were identified as above; however in this case, in addition to masking repeat sequence, all subsequences of 5 or more consecutive "G" and "C" were masked. Parameters were set to identify subsequences of length 140, with GC content of 45-60%. The 289 sequences identified were subjected to NCBI BLAST to find matches to other loci in the human genome. 281 unique sequences remained after this. To 280 of these was appended a common Forward and Reverse sequence, each 25 bases, and containing restriction sites, to give 280 sequences each 190 bases. These sequences were sent to IDT for synthesis as "Ultramers" in 96-well plate format. The products were combined and used as template in PCR with primer sequences corresponding to the adaptors. The adaptor ends were removed by digestion with the restriction enzyme, and the product aminated, labeled with Spectrum Orange, and subjected to 75° C. 72 h formamide treatment.

Table 2 shows the 190 bp sequences.

TABLE 2

| Sequence Name | Sequence | SEQ ID NO.: |
|---|---|---|
| p53F193 | TAT ACG CAG TGC TAC CAT CGA TCA CTT GCA GTG GGA ATT TCT GAT GCG AAA TGG TTG ACA TCA TAT CTG GAA TTT TAA TTA GAA TGA AAA ATG GCC CTT CCT AAG GGG CTA TAT GGG CCA CCG TGG ACA TGG GGC TTG GGA GAG TTT TGA GAC CTG GGA GAA ATG GAC TTC GAA AGA CGC TCC ACG ATA T | 395 |
| p53F194 | TAT ACG CAG TGC TAC CAT CGA TCA CAA GGA AAA GGG ACA CAG AAT GAA TGG GAA TGA CAA CTG GGC AGC CAG AGA GCT ACT TGA AAG GTA GCA GGG AAA GTG GAG TTC TGA AGG GAG TTC TGA GGG GAC CAG GCC CCA GGT ACC CCA ATT CCC ACA GGG AAT CGA GAC TTC GAA AGA CGC TCC ACG ATA T | 396 |
| p53F195 | TAT ACG CAG TGC TAC CAT CGA TCA CAG AAG GAT GAG TCA GGC TGT AGA GTA ATC TAC TCT GGT TCT CAC GGG ACC AGC CCA GGG CAC AGC CGG CAG GGA GGC TGC TGG CAT AGA GGC CCT GTC TCC CCT GGC CTC TGT CTC TGA TGA ATG ATC CGG ACA GCA GGC GAC TTC GAA AGA CGC TCC ACG ATA T | 397 |

TABLE 2-continued

| Sequence Name | Sequence | SEQ ID NO.: |
|---|---|---|
| p53F196 | TAT ACG CAG TGC TAC CAT CGA TCA CCT CTC CGT GGA GAT GGC TCT GAG AAA TCA AAT ATT GAC AAT GAG GGA ACA GAA CTT ATT AAA TCT GGG ACA GGG ATG TGT GTG GGG AGC TGT GGG AAT GGC CGG ATG CCT GGG TTC GGA GGG TAA TGA AGG TTC TGG GAG GAC TTC GAA AGA CGC TCC ACG ATA T | 398 |
| p53F197 | TAT ACG CAG TGC TAC CAT CGA TCA CGT TTA AGA AAA GAA ATG GGG TCT GTG CAA AGT TCC TTT CCC CGA GGG ACC CAT GAA CCT TGC CCC TGA GGC TCC CCA CCC CAC GCC TCC AGC AAA TTT TCA CTC CTT GGA CTT TCC CTA GGG GTT CTG GCC AAC CAC GAC TTC GAA AGA CGC TCC ACG ATA T | 399 |
| p53F198 | TAT ACG CAG TGC TAC CAT CGA TCA CTC ACC TCT GTC TGC CAC CCA TGG CCT ATC TGG CTA GAG GAA CAC CTC CAC GTT CCA TCT TAG CTG TGC TAG CTG TGC AGC TGG TTT TGG GGT GGG CGG TAC TCC TCT CCT TCC ATT CCT GCT GTC AGC AAC AGG AGT CTG GAC TTC GAA AGA CGC TCC ACG ATA T | 400 |
| p53F199 | TAT ACG CAG TGC TAC CAT CGA TCA CGA GGG AAA GGG TTG ACA CTT CTG GGA ATA AAG ATA CGG TAG GTG GGA GGG TGA GGT CAG CGC TGG GAT AGG GTG TGG TTA ATC CAC TTG CTC TTC AGG AGT ACC AGG GAC TGC CAC TCC TGG TAG TGC CAG GCT GGC ATA GAC TTC GAA AGA CGC TCC ACG ATA T | 401 |
| p53F200 | TAT ACG CAG TGC TAC CAT CGA TCA CAA CTG AGG TGC CAG CTT CTC TTC TCC TCA TCC AGC AAA GAA AAT GTC ATA AAT TTC GCT CCT CAT GGA AAT GTA ATC AGT GGG CTC GCT GCT GGC TTT GTC TTA ATT AGG CAC TAT TGA TGG AAA CAG GGA GGG CGC CTT GAC TTC GAA AGA CGC TCC ACG ATA T | 402 |
| p53F201 | TAT ACG CAG TGC TAC CAT CGA TCA CGG AAG AGC CAT TCT GAG GGG AAA TTT GCC TGC TGG TAA CCA GTT TAA GGA TAC CAG CTG CTG GTA TAA ATA CTG CTG GAT AAA TAC TGC TGG ATT TAT ACT GCA GGA TAA ATA CTG CTG GCC CCT GCG GTA TTT CCT AGT GAC TTC GAA AGA CGC TCC ACG ATA T | 403 |
| p53F202 | TAT ACG CAG TGC TAC CAT CGA TCA CCT AGA GTG AGC CCC GAC TTA GCA GAG CAG TTC CTC CTG GGG CCT GCG GTG TGG GAT CGC GTG GTG AAC CCC ACG GTG CAT GCG CCT CAG GCT CTA GTT TGA GGC AGG AAA GCG CAG CTT GAT GCT TCT CTG GAG ACT GAT GAC TTC GAA AGA CGC TCC ACG ATA T | 404 |
| p53F203 | TAT ACG CAG TGC TAC CAT CGA TCA CGC TGT AGT TGG TTT TAT TGA TTT GCT GGC CTA ACA GAA CGT TTT TCC TTG GAG CAA AGT ACA AAT CCT TCA AGT TTG AAA TTC ATA ACC TGA GAT CAA TGC CTG TGG CAG CCT CGT GTG GGG ATG AGG AAG GAG AGC CAC AGG GAC TTC GAA AGA CGC TCC ACG ATA T | 405 |
| p53F204 | TAT ACG CAG TGC TAC CAT CGA TCA CGC CGT TAG GCT GCA GCC TAA TGA AAA GAG AGT GCC CAG CGC CTC AGA CTT TGC GCC TGG GAT TCT GAG CAC CTG TCC GAG ATC CCC GCT TCC TGC CAT CCT ACC TTT CTG AGA GAG GCA CCA CTG TGA CCT TCC TCG TGC GAC TTC GAA AGA CGC TCC ACG ATA T | 406 |
| p53F205 | TAT ACG CAG TGC TAC CAT CGA TCA CCC AAT CTG TTC TCA GGG CAT TTT GAG TCA AAT AAA TGA TCC TGA CTG ATC TTA ACC ATT AGC ACA GAG TTC CTC AGC CAA CTC TGC TAA GAG ACC TCA GTA CAC ACA AAA CAG TGT TCC TGC CCC TCA GGA CTT CAA AGC GAC TTC GAA AGA CGC TCC ACG ATA T | 407 |
| p53F206 | TAT ACG CAG TGC TAC CAT CGA TCA CAT GTG CAC CCC TTC CTT GAT CCT CTC TCA CTC ACT CAT GGT CCT GGA GGG TAG AGT GGA TGA GGG TTT GGG CAA CCA CAC TTC AGC TTG ATA GAT CTT TTC CTG ATT ATC TTA TGT TCT CAT ACC CCG GGG CAG AGA TAG GAC TTC GAA AGA CGC TCC ACG ATA T | 408 |
| p53F207 | TAT ACG CAG TGC TAC CAT CGA TCA CTG GCC ATC ATC TTT AAC TCC CAT TTG TTC CTA GTG CCT TGA GGG ACT GAC TTT GAT TTT TAG CCC AGT GCC CCG AAG ACA GTA GGA TAT CCT AGG GAA AAA CAG CAA GGC CTC CCA GGC CCC TGT GGA GTA CAG AGC CCT GAC TTC GAA AGA CGC TCC ACG ATA T | 409 |
| p53F208 | TAT ACG CAG TGC TAC CAT CGA TCA CCT GGT TCA GGG GTG GTA TCT GCT TGT AGA CTC TCC ACT CCT GTA TAC CTG TAG GTT TTG CCT GCA CGA TGT CCA GCA AAG CTG AGA AGA AGC AGC GAT TGA GTG CCG AGG AAG CTC CCA GGC AAG CTG GGT CAG GGC GGG GAC TTC GAA AGA CGC TCC ACG ATA T | 410 |
| p53F209 | TAT ACG CAG TGC TAC CAT CGA TCA CTC CCC AAG GAG GAG CCT GGT GGG TAC TTG CTG GGG CAG AGG ATG CTT AGC AAT GGA GGG TGG GGA AAG TCA GAG GGG CTT GGA GGC ATT TTA GGG CTG GGA GCA GGC GCT GTT GCT TCT GGG CAG GAA ACG GGC TAA GTG ACT TCG AAA GAC GCT CCA CGA TAT | 411 |
| p53F210 | TAT ACG CAG TGC TAC CAT CGA TCA CAG CCA TGG AGG TTC AGC AGC CCT GCC ACT GAG TCC TTT TTT GTA TGT CTC TCC TCC TGG CCA GCC TCA TCC TTG TTC TTT CTG TCT TAA AAT TCC CAA CAA TAT ACC AGG AGT TCA CCA ACC AGT CCT TTC TCT AGC CTC GAC TTC GAA AGA CGC TCC ACG ATA T | 412 |

TABLE 2-continued

| Sequence Name | Sequence | SEQ ID NO.: |
|---|---|---|
| p53F211 | TAT ACG CAG TGC TAC CAT CGA TCA CTC CTC CTT ATT TCA AGT GTT CCT GGT TGC TCC TAC CCC ACT GAA GAG GGT TTG ATC TCT TCC TTT TTC CCA TTT TCA CCC TGG GTG GCA AAA CAA ATA ATG TTT TTC TCC CAT TAA GCC CAT CAC CAT GGA GAC TCA GCC GAC TTC GAA AGA CGC TCC ACG ATA T | 413 |
| p53F212 | TAT ACG CAG TGC TAC CAT CGA TCA CGT TTT GCC ACC CTT TGA ATC CAA AGC CCG GCT GAT GCT TTC TAC CAT CTG TTG AGG GCT GTT CTA TCT CCG CCC TCA TTT TGG CAG GGA CTT GGT AGA CTG CGG AGG TTC AGG TTC AGG ATG ACA GGA AAG AAG TCT AGA GAC TTC GAA AGA CGC TCC ACG ATA T | 414 |
| p53F213 | TAT ACG CAG TGC TAC CAT CGA TCA CCT AGG GAG GAA AGA GTT TAA CGA GGC AGC CTC TTG TGG CTT GAC CCT GAG GGA TTC CTT TCC TGT GGG TGA GCC GGA GCC AGT AAG GTT GGA AGG TTT TTG GTA GTT GTT GCT ATT GCT GGG ATC TCC CTG AGA GCA CTG GAC TTC GAA AGA CGC TCC ACG ATA T | 415 |
| p53F214 | TAT ACG CAG TGC TAC CAT CGA TCA CAG ACA GGA CTA TGA GCT AAG TGT AGA CCT CCT TCT TTA CCT GGA GCT CCT TTA CAC TGA TAG TAG CTT GTG AAA TAG AAT CCC CTT CTA AAA TTA AAG GTT GAG AGG TTA AGC GTG GGC ATG GGA GAA AAG TCC CTG GGC GAC TTC GAA AGA CGC TCC ACG ATA T | 416 |
| p53F215 | TAT ACG CAG TGC TAC CAT CGA TCA CAT AAG AAC TTG CAT TAG GTT CCA GGA TCT TAG AAA TGT GCA GAA TGT ATC CTT CTG AGT TCT GAA GTG CTC AGG TGA AAG CAG TTA AAA TGG GAT GCT CGC TGC TA GGA GGA GTA GGG GAA GAT GGG AGG GAA GAC AGT GAC TTC GAA AGA CGC TCC ACG ATA T | 417 |
| p53F216 | TAT ACG CAG TGC TAC CAT CGA TCA CTC CCC TGG CCT AGT TCT TGC CTG GAA CCT GAA TGC CAG CAG TTT TCC CAA GGG AGT TGG ATC ATC TCA CCT ACT CAC CTA CTA CTA AGC TCC GGA ATC GCC TGT TCC ATC TTT TCA CGC CTT CCT GCC TCG GCC TCT GTG GAC TTC GAA AGA CGC TCC ACG ATA T | 418 |
| p53F217 | TAT ACG CAG TGC TAC CAT CGA TCA CCT CAT TCC CCT CTT AGT TTT CCT TTC TGG AAG CCA GAG GGA GTT TCC TGT TCC TCA TGG TCT TTT GGT TAT ATC TCA TTT GTT CCT TCC TCC TTT CAG CCC CTG GGG AAT GGG AAA GCC ACC AGT TTT ACT CCA ATC TCC GAC TTC GAA AGA CGC TCC ACG ATA T | 419 |
| p53F218 | TAT ACG CAG TGC TAC CAT CGA TCA CGT GTG ACT AGT AGA TCA GGA GGC AGA GAA ACA GAG CCG CTG GGT TTT ATG GGA GTC AGA GTG GGT GTG GCA GAA CTG AAT GCT CAG CAG GCC AGT GGT TTG GAG AAG GGC TGA TTC CTA TGA GCC CCA ACT TCT CCA TGT GAC TTC GAA AGA CGC TCC ACG ATA T | 420 |
| p53F219 | TAT ACG CAG TGC TAC CAT CGA TCA CGA CTG TGT TTA ACT TTC CAA GAA ATG CCT TCC TTT TTG TAT GTT TAT TCT TCC TAG AGC CAC GGT TGG AGG GAC CTC AAG CAC AGA GTG AAG AAT CAG TGG AGC CCG AGG CAG ATG TGG TAG GCT TGG GTC TTC CCT GTG GAC TTC GAA AGA CGC TCC ACG ATA T | 421 |
| p53F220 | TAT ACG CAG TGC TAC CAT CGA TCA CCT GGT GAA TCA AAG GAT CAG TTG TGG ATG GCA CAT GAG GAA TTC TCT CTT GTC TGC CAC TTC TTC TAC TTG CTC TCT GCT GTT AGC CTA CTC ACC ACA AAT CCA GTT CAC TGA GTA AAA GAC AAA GTC ATC TGT GCC TTC GAC TTC GAA AGA CGC TCC ACG ATA T | 422 |
| p53F221 | TAT ACG CAG TGC TAC CAT CGA TCA CCC AGG ACA GAG GAG GGC TTT AAG TAA GGC GCA GGT CTC TCT TGT CTC CCC ACC TTG GGT CAA ACT GTG ATG AGC TTA TTC ATC ATG CGG GTG AAC ACC TGA ACA AGT TGA ATG AGC TGG GAA GAT ATT GTC CTA ATT GGA GAC TTC GAA AGA CGC TCC ACG ATA T | 423 |
| p53F222 | TAT ACG CAG TGC TAC CAT CGA TCA CTC TTT TGG ACT CCA TCG TGA AGA AAT TGC TCC TAT ACC CTC TCC CTT TTC CAG CTT GTG GTC TCC CTG CTC CTA ATT GCT TGA TCT AGG CTA ATA TCC TAC ACA TTC CCT TAA TTC ACC TTT ACC TTT GAG ATC GAG GGC GAC TTC GAA AGA CGC TCC ACG ATA T | 424 |
| p53F223 | TAT ACG CAG TGC TAC CAT CGA TCA CCT GTT TCT TCC AAA GCT GGA AAG CTA TCT TTC AGT TTC TCC TAA CCA TTC TGA ACC TGT CTG GCT TCT CTC ATC TCC CAT GTC CTC ACT TGT GAT TGT GGA TGG GAG GAA TGA CTC ATC CTG GCA GTT GTA GTT ACT TTG GAC TTC GAA AGA CGC TCC ACG ATA T | 425 |
| p53F224 | TAT ACG CAG TGC TAC CAT CGA TCA CCC CTC TGC TCT CCT TCT GTA GAA GCC CCT CTT CCT TTC CCG AGC TGC GCT GAC AGG ACT GGC GGA TGC AGT GTG GAC ACA GGA GCA TGA TGC CAT TCT GGA ACA CTT GCC CCA GGA CCC TAC AGA ATC ATC CTC ACC ATT GAC TTC GAA AGA CGC TCC ACG ATA T | 426 |
| p53F225 | TAT ACG CAG TGC TAC CAT CGA TCA CTT CAT TGA CCC TTG TTT GGC TGA AGC TAGA GCT GGG CAT GCC TGT ACA GGT GCG TAC CCT ACA TTC CCA GAT CAA AGG TGG TCC TAC AGA GAG CCG AGG GCT CTC AGT TCC TTC ATC ATC CTT AAG TCT TGT CAT CTC GAC TTC GAA AGA CGC TCC ACG ATA T | 427 |

TABLE 2-continued

| Sequence Name | Sequence | SEQ ID NO.: |
|---|---|---|
| p53F226 | TAT ACG CAG TGC TAC CAT CGA TCA CCA TAC TCT CTG CAT TTC CTC CCC ACA TCT CTG GAT ATG AAA TCA TAT CCG TGA AAA GAA CAG GAA GCA CTT CAT GGC ACT TCC ATT TAG AGA AGG ATC AGG ATA CCC TGA GGG ACG TGA GAA AGA ACT CAG CCG GGC TTT GAC TTC GAA AGA CGC TCC ACG ATA T | 428 |
| p53F227 | TAT ACG CAG TGC TAC CAT CGA TCA CGT GAC TGG GTG TCA TGG CTG GGC CTG GAG ACT GAA CTC TGA TCT GCT GTC TTC CAT GCA GAC CCA GAA CCA GCT TGT CTA CTT CAT TCG CCA AGC ACC AGT TCC CAT CAC CTG GGA GAA CTT CGA GGC AAC TGT GCA GTT GAC TTC GAA AGA CGC TCC ACG ATA T | 429 |
| p53F228 | TAT ACG CAG TGC TAC CAT CGA TCA CGG GAC GGT GCG GGG CCC CTA TAT CCC GGC CCT GCT TCG GCT GCT CGG TGG AGT CTT TGC CCC TCA GAT CTT TGC AAA CAC AGG CTG GCC TGA GAG CAT TAG AAA TCA TTT GCT TCT TCA TCT GCA CAA GTT CTT GGC CTG GAC TTC GAA AGA CGC TCC ACG ATA T | 430 |
| p53F229 | TAT ACG CAG TGC TAC CAT CGA TCA CAA AGG GAA ATA TAG GTG CTG TGG GGA CAC TGG GAG GAC TCA CAT GTC TCG TGG TAG AGA GTG TTG AAG GCG CGA TAC AGA TCT TTG ACC TTA TTT TAT GGC AAT TTC TTG TTA TAA CTC CAT GAG GTT TCC CTC TTG CCT GAC TTC GAA AGA CGC TCC ACG ATA T | 431 |
| p53F230 | TAT ACG CAG TGC TAC CAT CGA TCA CTG GTC ATT TCT TGA TAT CAA AAA AGC ATG AGT CAC CAT TTC TTC TAC CTG CTC TCC TGA AAT GCA TAT GCT TCC TGG TCC CCT ACC GAT CAT CAA CCG TGA TTC CTA CGG GGC CAG CAA GAA CTC ATC CCC TCT GTC CAC GAC TTC GAA AGA CGC TCC ACG ATA T | 432 |
| p53F231 | TAT ACG CAG TGC TAC CAT CGA TCA CTC CAC AAA CTT TCC TTT CCT TAG ACA CTC GGT ACA AAC TGG AGG GGC ACA CGG TCC TCT ACA TCC CTG CAG AGG CCA TGA ACA TGA AGC CTG AGA TGG TGA TAA AGG ACA AAG AGC TGG TGC AAC GGC TAG AGA GTG AGT GAC TTC GAA AGA CGC TCC ACG ATA T | 433 |
| p53F232 | TAT ACG CAG TGC TAC CAT CGA TCA CGC TGG CAC TGC TAG CAT CAC CTG GCG ATC ACA GGG GAG AGG GAA AGG GGA GGC TCG GAT GCT GAC AAT GGA GTT GGG TTA GGA GGT CTC TGT CGG GGT TGC GGG GAG TGA AGG ATG CTG TTG GGA AGC AGT GTG AAG AAA GAC TTC GAA AGA CGC TCC ACG ATA T | 434 |
| p53F233 | TAT ACG CAG TGC TAC CAT CGA TCA CGA AGG AGA TTT TGT ACT CTC CCC TGC AGC CTC CAT GAT CCA CTG GAC CCG GCA GAT AAA GGA GAT GCT CAG TGC CCA GGA GAC TGT GGA GAC AGG AGA AAA TTT AGG TCC TCT GGA GGA GAT TGA GTT CTG GCG CAA CCG GAC TTC GAA AGA CGC TCC ACG ATA T | 435 |
| p53F234 | TAT ACG CAG TGC TAC CAT CGA TCA CTG CAT GGA CCT GTC TGG CAT CAG TAA GCA GCT GGT GAA GAA AGG AGT GAA GCA CGT TGA ATC CAT CCT GCA CCT TGC CAA GTC GTC CTA CTT GGC GCC CTT TAT GAA ACT GGC ACA GCA GAT CCA GGT TTG TGA GCG AAT GAC TTC GAA AGA CGC TCC ACG ATA T | 436 |
| p53F235 | TAT ACG CAG TGC TAC CAT CGA TCA CAA AGG ATT CAG GCT CAG CAA GAA GTG GGC AAT GGT TGG GAT GAT ACA GGG AGC TAA GTA AGG AGA GGG AGC CAA GGC AAT CTT CGA TAG CAC AGA CTG ACC CAC CCA GGG TTC GGC CTT GTA CTT GCA GGA GAG TAT AAA GAC TTC GAA AGA CGC TCC ACG ATA T | 437 |
| p53F236 | TAT ACG CAG TGC TAC CAT CGA TCA CGT AGA ATA GAG GGT CCC TAA GGA GAG AGA CAT CAA GTT AAC CAA TAA ATA TAC ATC AAG TAC CTT CTG TGA GCA CAA CCC CTG CCA CCC AGC TGG GAA AAT AAG ATT ACC CAA AAC AGG ATT ACT AGA CAG CGT GGG AGC GAC TTC GAA AGA CGC TCC ACG ATA T | 438 |
| p53F237 | TAT ACG CAG TGC TAC CAT CGA TCA CAT GAT GTG ACA GGC TGA TTA TGT TAG TGC TAG GTC ACA CAG GAG GTA AGA GTG GCC TGT AGA ATA CAG ATA GAA GAC CTG TCT TCC TAG GTG AAA ATT TCA GCT GGG CAT TAA GGG AAT TGA GCC AGA ACT AAC TGG AGG GAC TTC GAA AGA CGC TCC ACG ATA T | 439 |
| p53F238 | TAT ACG CAG TGC TAC CAT CGA TCA CGC CTA AAG CCC TGG CTG AGA ACA GGG CAG TGA AAG GGA ACT GGG TGA CAA CTA TGG GGA CGA ATG AGA GTG ATA TGC GGC CAG TTG ATC CGA CAG CAA CAG AGT ATC ACC TTA GTG CGG AGT CCT GAA TTC AAC TGG AGA GAC TTC GAA AGA CGC TCC ACG ATA T | 440 |
| p53F239 | TAT ACG CAG TGC TAC CAT CGA TCA CCA GAC ACA AAA TCT AGA AAA ATC TAG ACT CGA GGG AAT TCT TAG TCT GGT AGG GGA GCT AGG GCA CAC ACA TGA GAA AAG AAA AGT TGA CAT GTG CTA ACT CTG GTC CGA AGG CTC ACA GAG ACC TGA AAT GAT CGC TAC GAC TTC GAA AGA CGC TCC ACG ATA T | 441 |
| p53F240 | TAT ACG CAG TGC TAC CAT CGA TCA CTC AGT GCT TTC TAG TGC ATA AAT CTA TTT CTC ATC TCT CTT TAC TGC CAG GAT GGC TCT CGT CAA GCA CAG TCA AAC CTG ACC TTT TTG TCA ATC CTG AAG GAA CCT TAC CAG GAG TTG GCT TTC ATG AAG CCC AAG GAC GAC TTC GAA AGA CGC TCC ACG ATA T | 442 |

TABLE 2-continued

| Sequence Name | Sequence | SEQ ID NO.: |
|---|---|---|
| p53F241 | TAT ACG CAG TGC TAC CAT CGA TCA CTC TCT AGC AAG CTC CCT AAG CTG ATC AGT CTC ATC CGC ATC ATC TGG GTC AAC TCT CCC CAC TAC AAC ACT CGG GAG AGA CTG ACC TCG CTC TTC CGA AAG GTG TGC ATA TGC TGA GGG TGG GAT GGA GGG GTT TAT GAG GAC TTC GAA AGA CGC TCC ACG ATA T | 443 |
| p53F242 | TAT ACG CAG TGC TAC CAT CGA TCA CAA TGC ATT CGG CAG AGG ATC TGT GGT TGA AAA GGT AGT GAA GAT TGC CCT TCT GCT CAG AGA CTG AGC TCA GAA GGC TTC TAC CGG CAT GAT CTG CTT TAG GGT TGC TCA GCA TTG GAG CCT GGG CTG GAC TTT CTG TTT GAC TTC GAA AGA CGC TCC ACG ATA T | 444 |
| p53F243 | TAT ACG CAG TGC TAC CAT CGA TCA CCA GGG TGG CTG CAG AGC TGG GCT GAG GCA GAG TAA GGG GCC ACC TAG GAC AAG GAG TGG GCA TGG AAC CCA GAG GTG TCG GCC TGG CCA GGG GTG GAG AAC CAG GGG TGG GAT GAG TTT CAG GAG TCA AAT TAA GGA GTA GAC TTC GAA AGA CGC TCC ACG ATA T | 445 |
| p53F244 | TAT ACG CAG TGC TAC CAT CGA TCA CAT GCA GAG AAG GAG TTG GGT GTC AAG GAG GTG GGG ACA GAG GCT GTG GGG ACT CCT TCT GCA GAT GAG CAA TGA GAT CAT CCG CTT ATG CTG CCA CGC CAT CTC CCT GGA CCG GAT CTT TGA GGG ATA TGT CTC TTC CAG GAC TTC GAA AGA CGC TCC ACG ATA T | 446 |
| p53F245 | TAT ACG CAG TGC TAC CAT CGA TCA CAA GGA GGA CCT GCA GGC TGC ATC TCT CTG TTG TCA CGC TTG AAA GAT CTA CGT ACA GGC TGT GCA GAT GCA CAT CCA GTA TGA TAC GCC TCC CCT AAC ATC CCA TGT CTC AAC TCC CTT GTC AGC CCT GTA AGA GGG GAC TTC GAA AGA CGC TCC ACG ATA T | 447 |
| p53F246 | TAT ACG CAG TGC TAC CAT CGA TCA CTA ATC TCT CCT CCC TGA TCC CAG GAA CCC TAC CTG GTC TTT TCC TCC TAT CTT GAC CCC ATC GTC TAA AAT TCT ATT ATG TAT GAA TCT GCT CCT AGA ACT TAG ATG CTC TGT CTC CTG TCT GGT TCT TCT CAC CTT GAG GAC TTC GAA AGA CGC TCC ACG ATA T | 448 |
| p53F247 | TAT ACG CAG TGC TAC CAT CGA TCA CCT TGT CCT TTG GGA TTC AGG AGG GTT GTT TCT CGG GGT CTG ATT TTT CTA GGG CTT TCC CTG AAT GCA GGG CTC CTG GTC TAG GTT TGC ATA GCC AGA CTG CTC TTG CCT TCC AAT TCA GTC GGC CTT TCT CCT GAC ACA GAC TTC GAA AGA CGC TCC ACG ATA T | 449 |
| p53F248 | TAT ACG CAG TGC TAC CAT CGA TCA CGT TCT CCA GTC GGG GCT GGG TCC TAG ATC AGA CCA GCA TCT TTG CTC AGG TTG ATG CCT TTG TGC AGC GCT GCA AGG ACC TTA TTG AGG TGG GAA GAC TGA AGA ACC AAA AGC TAA CAG CAG ACC CTC CAG AAT CCC TCC GAC TTC GAA AGA CGC TCC ACG ATA T | 450 |
| p53F249 | TAT ACG CAG TGC TAC CAT CGA TCA CTT TTA GAC ATT TGA AGC TAA ACC AAA TAG CTT AGG ACT TTG GAG TTT GGA AGG AAA GCA GGA ACC CTC ATG CTG TCT TCT TTT TTA GGT ATG TGA CTG TCA GTA TCA CTT CGC CCG CTG GGA AGA TGG CAA GCA GGG TCC GAC TTC GAA AGA CGC TCC ACG ATA T | 451 |
| p53F250 | TAT ACG CAG TGC TAC CAT CGA TCA CTA TCC TGG ATG TCA AGA ACA CCT GTT GGC ATG AAG ACT ACA ATA AGT GAG GGA ACC ACA GGC TGA TGC CAG GCG TGG GCA GGG AAG GCA GAT CAG GCA GCC AAG AGT GGG AGG AGT GGC GAG AGT ATG CAA AGG AAA TGG GAC TTC GAA AGA CGC TCC ACG ATA T | 452 |
| p53F251 | TAT ACG CAG TGC TAC CAT CGA TCA CAC TCC CGC AGC GGG GTG CAG CTT TCC TCT GGG ATG AGT GAC CGG AGG GAA CCC GCC TTC CCG GGC ACG TCG CCA GCC TCT TCC TCT TCT CCC CTA GGC TGT CAA GCG GAC TTA TGA CAA GAA GGC GGT GGA TCT CTA CAT GAC TTC GAA AGA CGC TCC ACG ATA T | 453 |
| p53F252 | TAT ACG CAG TGC TAC CAT CGA TCA CCT GTT CAA TAG CGA GCT GGC CCT GGT GAA CCG TGA ACG GAA CAA GAA ATG GCC AGA CCT GGA GCC CTA CGT GGC CCA GTA TTC CGG AAA GGC GCG CTG GGT GCA CAT CCT CCG GCG TCG CAT CGA CAG AGT CAT GAC CGT GAC TTC GAA AGA CGC TCC ACG ATA T | 454 |
| p53F253 | TAT ACG CAG TGC TAC CAT CGA TCA CAT GGC TCC TGA GAG TTC CCA AGA GTC TTC AGG ACC AGC ACC TAT GTC GGT GAG GGG AGT GGC AGG TCC AGT TCA GTG AGG TCA GTC GTG GGT TAA GAT CTG CAG AGG TGG TGT GTG AGG CTG GTA GAA CAT GCG CCA GAC TTC GAA AGA CGC TCC ACG ATA T | 455 |
| p53F254 | TAT ACG CAG TGC TAC CAT CGA TCA CTC ATT TTA GGA ATT TCA TAT CAG GCT GCA GAG GAG GAA TAG GGC CGG TAT CTG GGG TGT TGG GTC AGT AGA AGA TAC AGC CTC ATG ATC CAG AGA CCT GGA CAG GTG ACA CCC TTA CAG AGC TGT CTC TCT GAA AGA GAC TTC GAA AGA CGC TCC ACG ATA T | 456 |
| p53F255 | TAT ACG CAG TGC TAC CAT CGA TCA CTG AAC ACA CAC ACC CTT GGA ATA AGG TTG AAA GCT GTT GAG GTA GTG ACC TGC ATC ATG CAG CTG GTG CTG GTA GAG TTA GGC AGC CTG CAG ATA GCT GGA GGC TGG TTT GGG CCT GGT GGA CTA CGC CCA GGC GAC TTC GAA AGA CGC TCC ACG ATA T | 457 |

TABLE 2-continued

| Sequence Name | Sequence | SEQ ID NO.: |
|---|---|---|
| p53F256 | TAT ACG CAG TGC TAC CAT CGA TCA CGA CTC CTT TTC TCA TTG CGC CTT GGT CTC TTC CTA TCA CCT TCC TTT TTG ACT CTA CCT TCC TTC TAA GTT ATC AAA ACT CAA TCC ATC TCC ATA GCA AGC TTA TGC ATA TTG TTG GGG TAT GTG CGC ATG CGC GCC ATG GAC TTC GAA AGA CGC TCC ACG ATA T | 458 |
| p53F257 | TAT ACG CAG TGC TAC CAT CGA TCA CGT AGG TCT CAG GGA GAT GGT GGC CCC TGG AGG AAG GTG GCA GGC CGA CTC CAC CCA CCT GTT CTT CTT CCC CTC AGT GCC TTG CTG GTG CTC ATT TCC TGC CCC GTA TTG GGA CTG GAA AGG AGA GTG TGC ACA CCT ATC GAC TTC GAA AGA CGC TCC ACG ATA T | 459 |
| p53F258 | TAT ACG CAG TGC TAC CAT CGA TCA CGC AGA TGG TCC AGG CCA TTG ATG AGC TGG TTC GAA AAA CCT TCC AAG AGT GGA CAT CAA GTC TGG ACA AGG ATT GCA TTC GGC GGT TGG ATA CCC CAT TGC TGC GAA TCA GCC AGG AGA AGG CGG GCA TGC TGG ATG TCA GAC TTC GAA AGA CGC TCC ACG ATA T | 460 |
| p53F259 | TAT ACG CAG TGC TAC CAT CGA TCA CCC ACT CCA CTA TCT GAC TAA ACC AGT GAT GTC GCT GTT CTG CCA CTA GAT GGC CAT AAT GGC TCA GCT AAG TCA CCC AAA CCC TGT CCC TTT CCT GAC TGT TGG TGG GGC TGT CAG ACC ATG CCT TCT TCT ACA GCT TCA GAC TTC GAA AGA CGC TCC ACG ATA T | 461 |
| p53F260 | TAT ACG CAG TGC TAC CAT CGA TCA CTG CTT GTG GGG CCA AAT GTA GGA GGG GCT TTG CCA GAG AAG TGC TGT GTG GAG ACG GAG TCC CAG GGA CAG ATG AGA CTG TGA GTG TTT GTC CTG GGC AGC AAA AGG TGG CCC AAC CAG GGG AAG AGG GCA CAT TCT GGC GAC TTC GAA AGA CGC TCC ACG ATA T | 462 |
| p53F261 | TAT ACG CAG TGC TAC CAT CGA TCA CGA GAA AGG AAG CAA AAG AAC CAG GAT GGA GAA GCA GAG CGG AGT GTC AGG TGA GAG GGG TGA GGC AGA GGC ATC AGT GAG GAG GAC AGG GAT GTT GGG AGC TGC AGG GAT GAG GAA GCC GTT GAG GAG CAG AGT GTG CAC GAC TTC GAA AGA CGC TCC ACG ATA T | 463 |
| p53F262 | TAT ACG CAG TGC TAC CAT CGA TCA CTG GCT AGG TCG AGA GGT TTG AGA AAA GGC TTC GAG TAG TGA GAG TTG TTG GAG ATT GGC TTT GCT GAG CTT CCT GGT TTT GTG AGT TAT GGC CAA GCA CAG CCA CGT AAA CAT TGC CTC ATA AAT CAA CGA TAA GAT TCT GAC TTC GAA AGA CGC TCC ACG ATA T | 464 |
| p53F263 | TAT ACG CAG TGC TAC CAT CGA TCA CAC AGT TTC TGT AAG GTT CTT GAC TAT TCC GTG CTG GTG GAT TTC AAC TGT GAT TCC CGC ACT TTG TTC CCT TCC CTC TGC AGC ACT GTG TTT ACT GAA ATT TGA ACA CAG TGT CCC TCT AGT TAG GAT AAA CCA GGA GAC GAC TTC GAA AGA CGC TCC ACG ATA T | 465 |
| p53F264 | TAT ACG CAG TGC TAC CAT CGA TCA CTG CTC TTT GTG TTC AAG CTC CAG TTA AGA TCT TGA AAT AAG CAC GTC CAA ATG TTC TGA TGT TCC TCG GAA TTA CCT GGC TCT CTT AGT CCT GGA GCC TTC CAG TCC CTA ATA GCA CTG ATT TAA TCC CAC AAG GGG GAC TTC GAA AGA CGC TCC ACG ATA T | 466 |
| p53F265 | TAT ACG CAG TGC TAC CAT CGA TCA CTG GCT TTT ATC ACG TTT TAC GGA CAG AAC AGC TTC ACA GAT TGC ACT TAA CAC AAA CAT ATT CCA GAT GTC ATC CAC ACC CTG GCT GAA GGA GCT GTA TTA TCA CCC TGT GTG GAG CAG AGT AGA ATT CCT GAG AG GAG GAC TTC GAA AGA CGC TCC ACG ATA T | 467 |
| p53F266 | TAT ACG CAG TGC TAC CAT CGA TCA CTC TGC TTC ATT TCT CAT CTC GAC ATT TCC CTG TGC TTC CCA GCC TCT CCA CCT GTT CGA TTG TTG CTC TAG TTT ATC CCC TCG TGC GGT CCC CTC ACT GCC TGG CTG CTC TCT CTC AAA GGT CCC TTC TGA TTC TCT TTG GAC TTC GAA AGA CGC TCC ACG ATA T | 468 |
| p53F267 | TAT ACG CAG TGC TAC CAT CGA TCA CGG AAA TTG ACT ACT GGG AGC GGC TGC TGT TTG AGA CGC CCC ATT ACG TGG TGA ACG TAG CTG AGC GAG CCG AGG ACC TGC GCA TTC TGC GTG AAA ATC TGC TAC TCG TTG CTA GAG ACT ACA ATA GGT AGG GCT TCA GTC GAC TTC GAA AGA CGC TCC ACG ATA T | 469 |
| p53F268 | TAT ACG CAG TGC TAC CAT CGA TCA CTC TGT CCT CTA CAT CTT TTC CAT CTC AAA AAA AAA AAA TTG TCT CCC ACT CTT ACG GCC CTA TCA TTA TTC CTA CCC CTT GTA GTT TTA TTT TCT AGC TGC AGG GTG GAG AGT AAA GCC AAC CAG GTC CCC TCC CAC CCC GAC TTC GAA AGA CGC TCC ACG ATA T | 470 |
| p53F269 | TAT ACG CAG TGC TAC CAT CGA TCA CTG GTC TAG AAA TGT TCA CAT TTC TCC ACT GTT CCT GAA GTT GGA GGA AAG ATC TTC AGG GCT TGT CCC CTC TGG ATA CCA GGC CTC TCT TAT GCA CAG GAT TAT TGC CAT GCT GTC CCC AGA TGA GCA GGC CCT ATT CAA GAC TTC GAA AGA CGC TCC ACG ATA T | 471 |
| p53F270 | TAT ACG CAG TGC TAC CAT CGA TCA CAT GAC GGG GCC TGA CTC TAG GTG CAG ATG ATT GTG AAT GAG TTC AAG GCA TCC ACT CTG ACC ATT GGC TGG CGA GCC CAA GAG ATG TCA GAG AAG CTG CTG GTA CGC ATT AGT GGC AAA CGG GTA TAC AGG GAC CTG GAA GAC TTC GAA AGA CGC TCC ACG ATA T | 472 |

TABLE 2-continued

| Sequence Name | Sequence | SEQ ID NO.: |
|---|---|---|
| p53F271 | TAT ACG CAG TGC TAC CAT CGA TCA CTT GAA GAG GAC CAA AGA GAG CAT CGG GCA GCT GTA CAG CAG AAA TTG ATG AAC CTG CAC CAG GAT GTG GTG ACC ATC ATG ACC AAC TCC TAT GAG GTC TTC AAG AAT GAT GGT CCT GAG GTA GGG TTC CTG TGG CCA GGA GAC TTC GAA AGA CGC TCC ACG ATA T | 473 |
| p53F272 | TAT ACG CAG TGC TAC CAT CGA TCA CAG TTC CAT CAG GCC ATT CTC TTG CTC CCC GAC CCT TTT TTC TTT TTT ACC AGT GTG TAC TTC TCA AAC ATC GTG CTC TAG TCT TGG ACT CAG CCA ACC TTC AGT CCT CAC ACC TCT TCC TCC AGG ACT CAG CGT CCT GCG GAC TTC GAA AGA CGC TCC ACG ATA T | 474 |
| p53F273 | TAT ACG CAG TGC TAC CAT CGA TCA CTT CCA TTA AAC CAA CTT GTT TCC TTC CCT GTT GGC TGG TTC TCA CTT CCC AGG ATG TGC CCT GTC TTC CCT GAA AAG TTC TCT TTT TCC TCC CTC CAT CCC ATC AGA TTC AGC AGC AGT GGA TGC TGT ACA TGA TTC GGC GAC TTC GAA AGA CGC TCC ACG ATA T | 475 |
| p53F274 | TAT ACG CAG TGC TAC CAT CGA TCA CGG ACC GCA TGA TGG AGG ATG CCC TGC GCC TGA ATG TGA AGT GGT CAC TGC TAG AAC TAT CCA AGG CTA TCA ACG GGG ATG GAA AGA CCA GCC AAA CCA CTC TCC AAG TCC TTG TCA TTT TGA AGA ATG ATC TGC AAG GAC TTC GAA AGA CGC TCC ACG ATA T | 476 |
| p53F275 | TAT ACG CAG TGC TAC CAT CGA TCA CTC TCA AAA CCA TTG CAT CTT ATT TGT CAG TTT CCC TTA ATT CCT AAA CTT GGT CCT TGG CCT TGA CTT TAT CCT ATG GCC TTC AGA CCT GCT GCT GAA GTG TGT GAC CTT CCC AGT CCT AAG GCT TTT CTC TCC ATC TCC GAC TTC GAA AGA CGC TCC ACG ATA T | 477 |
| p53F276 | TAT ACG CAG TGC TAC CAT CGA TCA CCT GGG TTC CTC ACA GGT GGA ATT CTC ACC CAC TCT GCA GAC TTT GGC AGG TGT GGT CAA TGA CAT TGG CAA CCA CCT CTT TTC CAC CAT CTC TGT CTT CTG CCA CCT CCC TGA CAT TCT CAC CAA GCG CAA GTT ACA TCG GAC TTC GAA AGA CGC TCC ACG ATA T | 478 |
| p53F277 | TAT ACG CAG TGC TAC CAT CGA TCA CTT GAG ATT AGG TGA CTG ATG CTC ATG GGT TTT GGG ATT TGG GAT GGG AGA TGA GGA AAG ACA AGC TTG GGA CTG GGA CTG GGA CTG GCC TGT AAG AGG CCT AGA TAC AAC AGA CAA GAA CAT CAC ATC CTA TGA AGG AGA GAC TTC GAA AGA CGC TCC ACG ATA T | 479 |
| p53F278 | TAT ACG CAG TGC TAC CAT CGA TCA CAC TAA GAG TCA CAT TTT CAC TTT CTG CCT ACT CCT TTA CCT TCT AAT GTG CAT GTT GAA GCT GTA TTT CTC TGG GAA GCT GGT TTT AGA GTG GAA GGT CTG GAG CAG TGG GCA GGG CTC AGG CAG AAG TTG GGT TGG GGT GAC TTC GAA AGA CGC TCC ACG ATA T | 480 |
| p53F279 | TAT ACG CAG TGC TAC CAT CGA TCA CGA AGT CAG TGA GAA GCA TCT TTC TTG GTC CTT TGA AGA AGA TGA GGA CAT CAA GAA GAT CCA CGA CCA AAT CAG CAG CGG CAT GAC TAA CAA CGC AAG CCT GCT GCA GAA CTA CCT CAA GAC CTG GGA CAT GTA CCG GAC TTC GAA AGA CGC TCC ACG ATA T | 481 |
| p53F280 | TAT ACG CAG TGC TAC CAT CGA TCA CGA GAT CTG GGA GAT CAA CAA GGA CTC CTT CAT TCA TCG CTA CCA GCG CCT CAA CCC TCC TGT CTC TTC TTT TGT TGC CGA CAT TGC CCG GTG AGT GGT GAG GGT GGA TTG AAA GTC TGT CTG TAG GAG GCA CAG CAC TGC GAC TTC GAA AGA CGC TCC ACG ATA T | 482 |
| SigFolig1 | TGC GTA AGT GCA TCA GTC CAT CAT GCA TCC GTC GCT ACA TGA GTG ACT AGA TGA ATC CGT CAG TCA ATG CCT GGA TGA GTA GAT CGC TGA CTG CAT ACG TGT TCA GTC AGT CAG TCA GGC ATC TAT ATA CGC AGT GCT ACC ATC GAT CAC | 483 |
| SigRolig1 | TAG ATG CCT GAC TGA CTG ACT GAA CAC GTA TGC AGT CAG CGA TCT ACT CAT CCA GGC ATT GAC TGA CGG ATT CAT CTA GTC ACT CAT GTA GCG ACG GAT GCA TGA TGG ACT GAT GCA CTT ACG CAA TAT CGT GGA GCG TCT TTC GAA GTC | 484 |
| SigFolig2 | TGC GTA AGT GCA TCA GTC CAT CAT GAC CTA GCT ACA TGA CTC AGT CCA TAC CTG CGT CAG TCA ATG GAT GGC TAA CTG GAT CCG TCG ATC AGT AGA TGA GTA ACT GAG TCG CTG CGT CAG TGA CTG TTC AGT CAG TCA GTC AGG CAT CTA TAT ACG CAG TGC TAC CAT CGA TCA C | 485 |
| SigRolig2 | TAG ATG CCT GAC TGA CTG ACT GAA CAG TCA CTG ACG CAG CGA CTC AGT TAC TCA TCT ACT GAT CGA CGG ATC CAG TTA GCC ATC CAT TGA CTG ACG CAG GTA TGG ACT GAG TCA TGT AGC TAG GTC ATG ATG GAC TGA TGC ACT TAC GCA ATA TCG TGG AGC GTC TTT CGA AGT C | 486 |
| SigFolig3 | TGC GTA AGT GCA TCA GTC CAT CAT GGC ATC AAT GCA TGC CTG AGT AGA TCC GTA ACT GAG TCG CTG TTC AGT CAG TCA GTC AGG CAT CTA TAT ACG CAG TGC TAC CAT CGA TCA C | 487 |
| SigRolig3 | TAG ATG CCT GAC TGA CTG ACT GAA CAG CGA CTC AGT TAC GGA TCT ACT CAG GCA TGC ATT GAT GCC ATG ATG GAC TGA TGC ACT TAC GCA ATA TCG TGG AGC GTC TTT CGA AGT C | 488 |

TABLE 2-continued

| Sequence Name | Sequence | SEQ ID NO.: |
|---|---|---|
| SigFolig4 | TGC GTA AGT GCA TCA GTC CAT CAT GAA CTA GAT ACA TAA ATC AAT CAG TGC GTC AAT GAG TAA ATA GGT AAG TAG ATG ACT AGC TCC ATC GAT GCA TCA CTG CGT AGC TAG CTA CAT GAC TGC ATG TTC AGT CAG TCA GTC AGG CAT CTA TAT ACG CAG TGC TAC CAT CGA TCA C | 489 |
| SigRolig4 | TAG ATG CCT GAC TGA CTG ACT GAA CAT GCA GTC ATG TAG CTA GCT ACG CAG TGA TGC ATC GAT GGA GCT AGT CAT CTA CTT ACC TAT TTA CTC ATT GAC GCA CTG ATT GAT TTA TGT ATC TAG TTC ATG ATG GAC TGA TGC ACT TAC GCA ATA TCG TGG AGC GTC TTT CGA AGT C | 490 |
| p53F001 | TAT ACG CAG TGC TAC CAT CGA TCA CAA TTC CCA GAA GTA AGA CCA TCT TTG GGA CAA GAG ACA ATG AAG AGA AGT CAG ATG TGG AGG AAC AGA AAA CAA GAG CCA GGG GCC AGG GCA GGT CAG TCC TAG AGA AAC AAA TGG ACC AAA CTG GGG ACA AAG AAG GCA GAC TTC GAA AGA CGC TCC ACG ATA T | 491 |
| p53F002 | TAT ACG CAG TGC TAC CAT CGA TCA CCG GAG AGC TCC CCA TTC TCC GAG GGG CCC TTA GGA AGC TTG CTG ACA GAG TCA CCC TGA GGG GAA AGT GGG AAA GAA AAC AGA AAA GCA AGA AGC GGT GAG TAG AAA TTC AGG TGG GAG ACA TTC CCT ACC ATC CAA GCC GAC TTC GAA AGA CGC TCC ACG ATA T | 492 |
| p53F003 | TAT ACG CAG TGC TAC CAT CGA TCA CTG GTG ATC CAG AGG TTG GTT CCC TGA TCT CAT GAT CCA GTC TCT CTT ACT TGG GAT CCA GAA GTG AAC CAC ACT TTC TTC TCT ATC CTA TTC AAA GTT TAC ACT GGT CTA AAC TCC ATC AGA CAC AGC TGC CTC TGC GAC TTC GAA AGA CGC TCC ACG ATA T | 493 |
| p53F004 | TAT ACG CAG TGC TAC CAT CGA TCA CTG CCC CAG AGT AAC AAC AAA AAA GGG ATG GGG TAA AGC ACA TCT TGC CTG CCT ACC TTC TGT CCT GAA AGA GAG TCT TCT GAG GGT TTA GTG CGT TCC AGG GGT GGC CTC TGG CGG CTC TGA GAC TCT GCT CGT GAG ATA GAC TTC GAA AGA CGC TCC ACG ATA T | 494 |
| p53F005 | TAT ACG CAG TGC TAC CAT CGA TCA CAG TCA GCC ACA GTC ACT GGG GAA GGC AGG AGA TTA AGA CTT TCA GAT GGA ATT CTG GTA GCC AGC CTA AGA CAC CCA CTG AAC CCG AAC CCC TGA TTT TCA CAG GGG TGA GCA TCC ATC TCT CAG CTC TGA GGA AGG AGA CTT CGA AAG ACG CTC CAC GAT AT | 495 |
| p53F006 | TAT ACG CAG TGC TAC CAT CGA TCA CTC TGG TGT CCA GAG TTG GCT GAC CTG GCT GGC GGT CTC CAC TGA TAG AGC CAT CAG TCC GAT TAC CAC GGT TAC GGC GGC GGC GGC TGC GAT TAC GAC GTT GAG GTC TTG ATT CAT CTT CTG TAG GGT AGG AAA AAA CCA GAC TTC GAA AGA CGC TCC ACG ATA T | 496 |
| p53F007 | TAT ACG CAG TGC TAC CAT CGA TCA CAG TCA CAC ATC CAA CCT CCC ACC CTC GAT TCC TAC CCA TCT CTA ACT TTC CAG ACC CCA GGC ACA CCC TCA CCC AGG CCA TTC TCT GTC ATG TTG GGC CCA TCT GAT TCC AGG CCT CCA TCC ATG ACG TCC TGT CT TCA GAC TTC GAA AGA CGC TCC ACG ATA T | 497 |
| p53F008 | TAT ACG CAG TGC TAC CAT CGA TCA CCT CTG GTT CAG ACG TGT CCA ATA GGC TGT AGG GAT TAC TGT CTG GAT CCT TCA GCA CTG GTC AGA GGA AGA AGA GGA GGA GTT GGC AGT CAG GTG CCC ATC ATC TTT CCT TTT GGC CCA TAT TCA TGA ACC CAG CTG TCT GAC TTC GAA AGA CGC TCC ACG ATA T | 498 |
| p53F009 | TAT ACG CAG TGC TAC CAT CGA TCA CAT CCC TGT CGC CAG GCC CAG CTC GGT TGG GCT CCT CTC TCT TCT CTG ACT CAG TCT CTG AAG CTG TAG ACA CAT CTG AGC TGG GGC CTG AAG AAC ACA ATG GGA TTT ATT CAC GGC CAT TCA TCC CAC CTC AGG ATC CAT GAC TTC GAA AGA CGC TCC ACG ATA T | 499 |
| p53F010 | TAT ACG CAG TGC TAC CAT CGA TCA CAA ACT GGA AGA ATT CTC CTT CTC ACT CAC AAG CCT CCC AGC CAA TCA ATC ACT TTT TCA TCA TCT CCA TTC CAG ATT TCC CCA AAC TTC CAT CCA GAC CTC TGC CTC TAC CCA CAA GCC CTG CCA CTC CTT GCC TCC TGT GAC TTC GAA AGA CGC TCC ACG ATA T | 500 |
| p53F011 | TAT ACG CAG TGC TAC CAT CGA TCA CAT AGG TTC GAG TCG CAT GGA GGG AGG AGG AGG AGC TCT CAT CAG TGC TAT ATC CAG CCT TGT CGC TGC CAC CGC TGC CCC GCC CAC TCC CAG GAG GGC GAA AGC CCA GCC CAA TCT GCC GAA GCT GCT CAT CAA TTT GTA GAC TTC GAA AGA CGC TCC ACG ATA T | 501 |
| p53F012 | TAT ACG CAG TGC TAC CAT CGA TCA CCC TCT CCA AGC GAA GCT GCT CTA CCT CCT GGT TGG GTA AAA GAT GGA AGA AGG GGA AGG AGA AAT AAG ATC AGT GCC TTG CTT CAT GCT TCT GCA CCC TGA CTG TCC CTC TAT ATC TAA CCT CTC AGG AAT GCA GGG AGA GAC TTC GAA AGA CGC TCC ACG ATA T | 502 |
| p53F013 | TAT ACG CAG TGC TAC CAT CGA TCA CAC AGC AGT CTT AGT TCC CTT TTC ACA CCC AGC ATT TTT CTC TCC CGG CCT GGG TAC CTG CAG GTA GGA GAG GTG ATA CTC CAG CAA AGC CTG GGC ATT GCT GAT GTT CTC TCG GGT GCC AAC AAA AAT GAA GGG AAC CAT GAC TTC GAA AGA CGC TCC ACG ATA T | 503 |
| p53F014 | TAT ACG CAG TGC TAC CAT CGA TCA CCC CTA GAG AAC AGA GAG CAG AAA CGA TGG ATC AGA AAG GAA AAT GAA ATG AAG GA TTA ACG CCG CCC AGT CTC CTA GGG | 504 |

TABLE 2-continued

| Sequence Name | Sequence | SEQ ID NO.: |
|---|---|---|
| | GAG CCT GCC CAG TGG GAT CAT TCT GGG CTC TAA ATC TAC TAG TGT TAA ACA ACT TTC CGT GAC TTC GAA AGA CGC TCC ACG ATA T | |
| p53F015 | TAT ACG CAG TGC TAC CAT CGA TCA CCT CCA CCC TCT CAA AGA ACA ATC CCA GCC CTC AGA GGA CAA TCC CAT TTA CTT CTG GAA ACC AAT CTC TAT GCC CAC TTG CCC CGT ACC CAT ACC TCC TCC CTG GGG TTC TTC TTG TCA TTA TCA CCT TCC ACT CGA ACC GAC TTC GAA AGA CGC TCC ACG ATA T | 505 |
| p53F016 | TAT ACG CAG TGC TAC CAT CGA TCA CTC ACT CCC ATT ACA GAC TGT TTC TCT GTC CTT GTG AAA CTG GGA GTC CAC AGG GAG GTG CCA ATC CTG GAT AAA AGC TCA GAA TCA CTG TAG AGA ATC TTG ATT CTG ACC TCT AAC TGT ATA TAC ACA CCA CCA ACT CAC GAC TTC GAA AGA CGC TCC ACG ATA T | 506 |
| p53F017 | TAT ACG CAG TGC TAC CAT CGA TCA CTT TTC GGG CCT GCT GGA TGT TGG CAC CGT GAG TCC CAA TTG CCA GTC CCA TCA GGT CCT CTC GCA CTG TGA ACT CCT CTT GGA AGG CTG CTG CCA ACT GCT TGC TTG TCT GAA AGG AAA AGT CAC TGT AGG AAT CAT GGT GAC TTC GAA AGA CGC TCC ACG ATA T | 507 |
| p53F018 | TAT ACG CAG TGC TAC CAT CGA TCA CGT GAG GGG TTA AGA AAA ACA GAA AAC ATG CCT CTA GAA CAC CAG GCT TTC ACT TCA TTT CTC AAT CAG TCC TTA GAG GAA CCC CTG GGT TCA GGG GCA GGA GAA CAG GAA AGG TTT TAG AGG AGT GAA TCC CAT GTT GTA GAC TTC GAA AGA CGC TCC ACG ATA T | 508 |
| p53F019 | TAT ACG CAG TGC TAC CAT CGA TCA CCA GGG GCT TCT GTG GTT GAC TGG GAG GAA ACC AGT GGG AAA GTC ATT AAA ACT GGC TTG GAA TAA ACA CTA AGG GAG AGC CAG GGA CTA GAA ATC AGG ATG CCT AAG TCC CGG GAA AAG GGT AAA GAA ATG AAG CTA GGA GAC TTC GAA AGA CGC TCC ACG ATA T | 509 |
| p53F020 | TAT ACG CAG TGC TAC CAT CGA TCA CTT CAG GCA GAA TAA ACT CAC CAG AAT GAA GAG CTC ACT GTT TGT GAT GTT GAG AAA GAT GCA GTT GGC TCC CAG GGC TTT CTT GAA CTC TTT ATG GAC GTT TTC ATT GGA GCA GCT GCA GAG GAA AAA AGT ACT CAG CGG GAC TTC GAA AGA CGC TCC ACG ATA T | 510 |
| p53F021 | TAT ACG CAG TGC TAC CAT CGA TCA CGA AGA GGG ACC ACA GTT AAA GAA CAA GGA TGG GAA AAT AAA GAA ACT AAG TGT CTT CTT AGC AAG AAG GGC TCT AGT AGA GGG CCA GGG GAA CAA CAG AGA AAA CTG CAA AGT GGG AGT GAT GCC TGG GAG AAA TAA AGC GAC TTC GAA AGA CGC TCC ACG ATA T | 511 |
| p53F022 | TAT ACG CAG TGC TAC CAT CGA TCA CGA CAT AGA ACT GGC ACA TGG TAA AAA AGG AGA AGT TGT GGA TGA CCT GAG CAA CTT TCT ATG AAT AAC ATA TTT GTT TCA GTA GTT CTC CAA AGG CAT TCC CAG TCA CTC ACA TCT CCC TTC ATC ATC CGC ACC CGG GCC GAC TTC GAA AGA CGC TCC ACG ATA T | 512 |
| p53F023 | TAT ACG CAG TGC TAC CAT CGA TCA CGT TAC CAT AAA TGG AAG GCA AAT CGC CTG AAA CTG GGG ATG TTC CTG AGA GTT TGG CTG ATC ACA ACA GTG ATA AAA GGG AAA CTG TTG CAT TTT ACA TTT CCA TAG GCT ACA TGG CTG GAT ATG GCT TAG TTG GGG AGG GAC TTC GAA AGA CGC TCC ACG ATA T | 513 |
| p53F024 | TAT ACG CAG TGC TAC CAT CGA TCA CAG GAA CAT GAA CCA ACC AGA GAA AAG CCT AGA ATC CTG GGG AAA AGT GAC ATT TAG AAA GGT GTA CTC CAC AGC CCT TAC CTC CAC TTC ATC CCC TTC TGT GAT CTC CTT ATT ATA GTC AGC TGG AGG TGG TAG CCG GAC GAC TTC GAA AGA CGC TCC ACG ATA T | 514 |
| p53F025 | TAT ACG CAG TGC TAC CAT CGA TCA CAA TAT GAA AAA GCT ACT CTG ACT GAT ATG GTT GCC CAT TTC TTT ACA AAA GGG TTA TTG CCT CAG CTG GGC GAG TTC CAC CTA TCT GGA TAA TTA GAG GCT AAA CCC CAG GCC CTG CTC CAT AGT AGT GTC TTC CAT CTC GAC TTC GAA AGA CGC TCC ACG ATA T | 515 |
| p53F026 | TAT ACG CAG TGC TAC CAT CGA TCA CCT TGA GTT TTA GAT AGG GAC ACA AGT GGT GTA ATG AGA CAG CCT GAA AGG CTG CAC TGG GGA AAG AAT ATG GGC AGT CAA ACA GAG AAA GGA AAT GAT ATT GTC ATG GAG AGG TGT ATG TAC CAC CTG CAT CAG AAC AGC GAC TTC GAA AGA CGC TCC ACG ATA T | 516 |
| p53F027 | TAT ACG CAG TGC TAC CAT CGA TCA CTG GAA ACC AAT GAT CTA CTC AGG CTC CCA CAG GGG CCT CCC TAT CTG TCT GCC TCC TGT TGT GCT AAG CAG CCT GCC AGA GTT CAA TTA AAA TAC CAA CAA CAT TCA GCA GGC TAG AAT ACC ATG AGA CAG TGT TGA GAC TTC GAA AGA CGC TCC ACG ATA T | 517 |
| p53F028 | TAT ACG CAG TGC TAC CAT CGA TCA CGC TGT CCT GGA ACA CCT AGA GGA CAT GAG GAT CTG TCG AGA GAG AAG GGC CTA CCT CCG CAA TAC AGC AAG AGA TCT GAG CAG ACT CGC TGC CCT GAT GCA TGG GTC CTA AGA CAA TAA TCG GAA CAC TAG ACA AGT TCA GAC TTC GAA AGA CGC TCC ACG ATA T | 518 |
| p53F029 | TAT ACG CAG TGC TAC CAT CGA TCA CAA AGG ATA ATA AAA TTT ATG GAA GAC TCC AAT CTT GAT ATT TGA CAG AGC AGA GGG ATG ACT GAA CAG CTG ATC ACC CTC CTG TGG TCT GTG TCC TCA CTA AGG AGG CCA AAG CCA TGC ATT CAC CCC TAT GCT CCC GAC TTC GAA AGA CGC TCC ACG ATA T | 519 |

TABLE 2-continued

| Sequence Name | Sequence | SEQ ID NO.: |
|---|---|---|
| p53F030 | TAT ACG CAG TGC TAC CAT CGA TCA CAG AAC CTG AGT TAT GAG CAT GTT CAT TCA GGT TTA ATG CCA ACT CCT ACT GTT CTC CAT TCA AGT CTT CTG AGG CAC TTT TAC TTC TAC TTG CCT GGG TCT CTC TTC CCT TTT GGG TTC TTC CCT TAG CTC CTG CTC AAG GAC TTC GAA AGA CGC TCC ACG ATA T | 520 |
| p53F031 | TAT ACG CAG TGC TAC CAT CGA TCA CTA CTG CTT TGG AGA GAT TTC TAC TCC TAG ATA TAT TCA AAT CGG CTA TGC CTA TGG TGT AAT CCA ATT CTC CTC CAC CAT GTT AGG CTT GGC CCC AGG GTG AGC AGC AAT ATT ACC CTA GTT TTC CCA GCT ACC ATG GAC TTC GAA AGA CGC TCC ACG ATA T | 521 |
| p53F032 | TAT ACG CAG TGC TAC CAT CGA TCA CCC TTC AAT TAG TCT CCA AAA CTA GCT CTG TCC CCA ACT TCA TAT TCC AAT CCT GTC TCT GCT CCT AAA TTC CAC CCA TTC ATC CCA TAC TAG TTT TTT TCT CCA AGG GTA TCT GTG GTG GAA GTG AGC CCC AAG TTC TGC GAC TTC GAA AGA CGC TCC ACG ATA T | 522 |
| p53F033 | TAT ACG CAG TGC TAC CAT CGA TCA CCA GTC TAC GCT CAT TGT GAA AAT AAG CAG GTG AAG GCA AGA GCA GGT GGG TGG AAT GTA TTA GGG AGC CAC CTA GAT CCA GAG GAT AAC TTG ATT CAG TGG CCA TAG CAT CAC CTG GCT TTG GCT TCT GGA GCC TGG CAC GAC TTC GAA AGA CGC TCC ACG ATA T | 523 |
| p53F034 | TAT ACG CAG TGC TAC CAT CGA TCA CTT CTA GGA GAA GAG CAG GAA CAG TCT GAG TAA AAA CCA AGT ACT GAA GCT GAG GAT GCC ATG TTG ATT AAG AAA GGA ATG GGG ATT AGG ATA TCC AGA TGA GGT TTG GAG TAG GAA GAT TGC GCC CTG GAC GGT GAA TAC GAC TTC GAA AGA CGC TCC ACG ATA T | 524 |
| p53F035 | TAT ACG CAG TGC TAC CAT CGA TCA CAA CTG ACA ACA GGG CCC AAT TCT GAG AGA GGA GAA AGG GAC CTT CCC AAA TGT ACA ATT CCA GAA GCA GTG TAA ATA CTC CCT GAC CCA TCC CAA GTT TGC TGA GTC ATG AAT ATT AAA TCA GCA GCA AGG TCA AAA CGG GAC TTC GAA AGA CGC TCC ACG ATA T | 525 |
| p53F036 | TAT ACG CAG TGC TAC CAT CGA TCA CGT ATC TGT AGG GTA CTG AGA GTG GAA GAT TAG CCT GAA TTT AGG GAT TTG TGG TTT TTA ACT CAG GAA CAG GGC AGA AAA TGC TAA CCT GCC CAG ATC CAC ATT ACC ACA TTA CCT GGC TTT CAG CTC AAC CCC AAA CTC GAC TTC GAA AGA CGC TCC ACG ATA T | 526 |
| p53F037 | TAT ACG CAG TGC TAC CAT CGA TCA CAC TCT CTG AAT CAC AGT ATC CTG GTC CCC ATC TAT TCA AGT CTA TCA CTG CCA CAG CAC ACA GGA GAA AGG GAA AAG ATT CAG AGA GAC TTT CTG CTG GAC ACT TAT ATG TGG GAC AGA AAA CGT GTC CCT TCC CAG CCA GAC TTC GAA AGA CGC TCC ACG ATA T | 527 |
| p53F038 | TAT ACG CAG TGC TAC CAT CGA TCA CAT CCA CTC TTA ACA GTC GAT GCC ATG GGA AGG TAT CTC TTC CCC AGC TCC CCA GGG TGA AAT CAA AGA ATG AGA CAG AAA TCA GGA GAG TCT CTA GGA CAA TTC CAG GCA TCA AAT CCA AGA GGT TCA GAA TAC CAA CAG GAC TTC GAA AGA CGC TCC ACG ATA T | 528 |
| p53F039 | TAT ACG CAG TGC TAC CAT CGA TCA CTG ACT ATG AAG CTT ACA TGC CTC AAG ACG AAG AAA CTA TAT GAA TGA CCT GAA GGT ATC TGA GGT CTA AGT GAG ACC TCA AAT CCA TTC CTG AGT AGA ATG GTA GAG CAG TGG GTC TTG AGA TCA AGG TGT GGT GGG GAG GAC TTC GAA AGA CGC TCC ACG ATA T | 529 |
| p53F040 | TAT ACG CAG TGC TAC CAT CGA TCA CGA GAC TTG CGA AAG ATG CCA CCT TAT GGC TGG CTG GGA AGC AAC TTG ACT GAT CCA ACC CAG GGT TCC TGA GGT CAA AGA TGC CAA ACG TCG TAA ATG GAT CTG ACC ATT TCT CCT TGG CTT GGG AAC CGG AAT ATA AGA GAC TTC GAA AGA CGC TCC ACG ATA T | 530 |
| p53F041 | TAT ACG CAG TGC TAC CAT CGA TCA CGA AAG TGG GGT GAG TGT TCC AGA GCC AGT AGG CAG AGG CCT CTC TGA GGA AGA TGA AAG GAT CTT TTA CGG GAC AGA GGG CCT TCC CAA AGG GAC CGT GTG GAA GAA AGA CAA TTC TCC ATG TGC TTG GAT CGT GGG GAA GAC TTC GAA AGA CGC TCC ACG ATA T | 531 |
| p53F042 | TAT ACG CAG TGC TAC CAT CGA TCA CAT GTG ATT AAG GTC TAA GGT ATG TCT TCC ACC AGA CAA CGG ACA CAG TCA ATT AGA AGC TGG GTA AAG GGT CTC TCC TGG CGG AGC GGG GAG CGC CAA GCC AGG GAC AAT AAT GGC CTG AAG TTC ATT CTC CCG GAG ATT GAC TTC GAA AGA CGC TCC ACG ATA T | 532 |
| p53F043 | TAT ACG CAG TGC TAC CAT CGA TCA CTA GAA GCA GGT GCA GGT GCC TTA GAG GGG TCA AAA ATA GGA GGA CAG GGT TAC TCT AGC GGT CTC CCA GGG AAG GCT GCG GGT TGG AGC AAG GGT CCA GGA TTC TAA GGG CCA GGA CTC AGC TCC AGA AGC TCG ATC GAC TTC GAA AGA CGC TCC ACG ATA T | 533 |
| p53F044 | TAT ACG CAG TGC TAC CAT CGA TCA CAC AGC GCT CAG GCC ACA CCC ACT CCG CCG CCG CTG GCC CCA CCG GGC TTG GAC AAG TTA GGG ATG GGC ATG CGC CTG AAC GAC TGC TTG GTC ACT TTC CCC ACC TTT GTC TTT CTT GGT GCG CAC GCT CCA AAA AGA AAA GAC TTC GAA AGA CGC TCC ACG ATA T | 534 |

TABLE 2-continued

| Sequence Name | Sequence | SEQ ID NO.: |
|---|---|---|
| p53F045 | TAT ACG CAG TGC TAC CAT CGA TCA CAA AAA GAA GAG GAG TCG CCG CAA GGA AAA AGG TGC TTG GTG CGC ACG CGC TGA GCT TTA CCC TCT TCG CGT ATG CAT CGC CGA TAT TTT AAG AAT CTG TAA CTC TCT ACT GTA GTA GAT TTA ACA GTC ATG GCT CTT ACC GAC TTC GAA AGA CGC TCC ACG ATA T | 535 |
| p53F046 | TAT ACG CAG TGC TAC CAT CGA TCA CGA CCC AAC ACC ACA TCA GGA CAT GTA ATT CTT ATT TAT TTT TCA CCC TCA ACA GGA AGA AAA GGT CTC TCC CTC AAT TCT GCT CTT CCA ATA CTT GAG GAT AGG CAC CCC TAA CCC TCC TTC CTC CAG GGA GGC CTC AGC GAC TTC GAA AGA CGC TCC ACG ATA T | 536 |
| p53F047 | TAT ACG CAG TGC TAC CAT CGA TCA CTC AGT GTC TGT GGA CGT AGT CTC TGA AGA GTG CTT CAG CTG ATG GGG AAG GAG AAA CTC AAG ACA GAG ATC CTC CTA GGG ATG GCG TCA CTT TCC TGC CAA CTT TCT CGT TGC CTC TCC TTG AAA GCA GAA GAA GTG CCA GAC TTC GAA AGA CGC TCC ACG ATA T | 537 |
| p53F048 | TAT ACG CAG TGC TAC CAT CGA TCA CCC CTC AGC TTC CGT CAG ATC TTG GGC TCC TAG GGC CTT GTA CAA GTC CAT GGC CCT CTG GTT CCA GTC CAG GAC GGC CAG GCG GAA TTG GGA GCA GCC CTT ATC CAA GGC CAC CTG TGG GAG AAG ACA ACA CTA ACT TTT GAC TTC GAA AGA CGC TCC ACG ATA T | 538 |
| p53F049 | TAT ACG CAG TGC TAC CAT CGA TCA CCT CCA TAT ACC CTT GCT TCT TCA GGT CCT CAC TTG TCG CCC CAC CCA TCT CCT CAC CTC AGC CAC CTT TTT GAT TAT TTT GGA ACC AAT CCC TTG ACC TGT TGT GGA GAG AAA GAG GCA AAA AAT AGC TAT TGT TTG AGC GAC TTC GAA AGA CGC TCC ACG ATA T | 539 |
| p53F050 | TAT ACG CAG TGC TAC CAT CGA TCA CGA AGG GGA TCA GAA AAT GAC ACC GGC TGG GCT CTG GGG ACA GGG GAT AAC AGT GGG GTC TGT GGG GTG CTT TGC TCC CAC CCC AGC CTC AGC TTC TGC CCA GTA CCC CGA TAT TCC GGC ATC ACA TAG ATA TCC TCC AGA GAC TTC GAA AGA CGC TCC ACG ATA T | 540 |
| p53F051 | TAT ACG CAG TGC TAC CAT CGA TCA CAA ATG GTG CGT CCC TTC CAT GTA CTG TAG ATG AAA TAG TAT ATC CCA TAG CCC ACC ACG CAG GGC CCT GAG AGA GAG AAA AGG GGA GTA AGG CTT CTG GAA GCC TGT GGG GAG ACC TCT GAG GCC GGC TGG AGA GGT GGA GAC TTC GAA AGA CGC TCC ACG ATA T | 541 |
| p53F052 | TAT ACG CAG TGC TAC CAT CGA TCA CTT CTA AGG GCC AGG TGC TCT TAC CCA GTA GCT TCC CGG GCG CTG GAA GAA TCT CTG CTA CCA AAC AGT GAT AGA AAG GAT TGT CTC CAA AGC CAT CTG CTC TCA GGG CTG CCG AGA TTG GAG TTG TGA CAA AGA GAT AGA GAC TTC GAA AGA CGC TCC ACG ATA T | 542 |
| p53F053 | TAT ACG CAG TGC TAC CAT CGA TCA CTG CAG TCT TCA CCC GAA TCA GCC TCA GGA TAT CTC CAC AGT CTC CCT CCT TGG CCT CTC GGA TCC GCA CGG AAG CCA TCC GGA TCC CCG CTG TCT GGG ACC AAA GTC CCA GGG CCT CGC AAA CGG CAA CTA GAC CCC TTA GAC TTC GAA AGA CGC TCC ACG ATA T | 543 |
| p53F054 | TAT ACG CAG TGC TAC CAT CGA TCA CGC AGT GCT TTT TAA ATT GAC ATA TGC AGT GAT AAC CTG CTT TAG CCT CAG GCT CAC TCA CCC GCC CAG ACC CTG GGT AAG CCT TAA GAC CCT CAG CTC TGA AAG CTG TTT CCT GCA GCT CTT GAG TAG CAT GAA GTG TTA GAC TTC GAA AGA CGC TCC ACG ATA T | 544 |
| p53F055 | TAT ACG CAG TGC TAC CAT CGA TCA CTT TAG GAT TCC ATT ATC TCA TTT CTA GTC CTG ATA CAG GAT GCT ACT TGG GAC GCA GGG GAG GAC TGT TTC TAG ACC TCA GGC CTG TGA ATG CAG GCT CCC CGA GTG GAC AGA AAT CTT GGA GGA CCT AGA TCA GGC CCT GAC TTC GAA AGA CGC TCC ACG ATA T | 545 |
| p53F056 | TAT ACG CAG TGC TAC CAT CGA TCA CGA GGA GGA GAG GGG AGA TGG AAT ATC CTC TCC CAG TTC AGA AAC TTT CTC GGC AGT GGA GGA TGA TAG TGG AGG GGA CTC TGT CCT TCA CCC CAT TGA TCC CCA GAG GGG TGA TAG CTG AGT CTT GTG ACT GGG CCC CTG GAC TTC GAA AGA CGC TCC ACG ATA T | 546 |
| p53F057 | TAT ACG CAG TGC TAC CAT CGA TCA CGC CCT GAG ACC TGT TCT CCC CAC CCA GGT GCA GGA GCG GGA CAG GGC ACT CAG CTC ATG CAG TCT TCC CTT CTC TCC TCT GGC CCT GTA GCA GGG CCT CTC CCT CTG TCT GTC TCT GAC ATG TCC CTA CTC AGC TTT GTT GAC TTC GAA AGA CGC TCC ACG ATA T | 547 |
| p53F058 | TAT ACG CAG TGC TAC CAT CGA TCA CGT TTT CTC TTT CTG ATA GAG TGC CCA CGA CCC TCC GGC TGT CCA ACC TCA GCA ATG GCC CAG GAC AGA GCC TAT CGC TGT CAT GAC CTT TGA CCT CAC CAA GAT CAC AAA GTA TGG GGT TGG CCT AGC CCT TGA CCC AGT GAC TTC GAA AGA CGC TCC ACG ATA T | 548 |
| p53F059 | TAT ACG CAG TGC TAC CAT CGA TCA CAA ACC CAC ACT GGT TCT CAA AGG ACA CAT GAC ATA CAC AAT CTT TCC TTC TGT GTC CTT CCA GAA CCT CCT CCT CCT TTG AGG TTC GAA CCT GGG ACC CAG AGG GAG TGA TTT TTT ATG GGG ATA CCA ACC CTA AGG ATG GAC TTC GAA AGA CGC TCC ACG ATA T | 549 |

TABLE 2-continued

| Sequence Name | Sequence | SEQ ID NO.: |
|---|---|---|
| p53F060 | TAT ACG CAG TGC TAC CAT CGA TCA CCT GGT TTA TGC TGG GAC TTC GAG ACG GCA GGC CTG AGA TCC AAC TGC ACA ATC ACT GGG CCC AGC TTA CGG TGG GTG CTG GAC CAC GGC TGG ATG ATG GGA GAT GGC ACC AGG TAA GCT AGC TCT GGT CCT CAG GGG AGG GAC TTC GAA AGA CGC TCC ACG ATA T | 550 |
| p53F061 | TAT ACG CAG TGC TAC CAT CGA TCA CGC TGC TCT TCC CCG CTT CCA ACC TTC GGT TGC GGT AAC TAC ACC CCA GGG GTG GAA CCT AGC CAA GAC TGG TAA AGC ACT GCT GGG TGG CTG GCC GTG GGA ATC TAA GTC CAC ACT TTT AGG GAG AAG GGA AGG GTT GAC TTC GAA AGA CGC TCC ACG ATA T | 551 |
| p53F062 | TAT ACG CAG TGC TAC CAT CGA TCA CGC CAA ATG CTC AGA GGG GAG TCA ACT GAG GGC AGG GAG GTC GGG ACT GCG GCT CCG ATG CCC TGA TTT CTA CAT CCC CGT ATC TTA TCT CTG TCA CAC TCC AGC TGG TTC CTG CCC TGG ATG GCT GCC TGC GCC GGG ATT GAC TTC GAA AGA CGC TCC ACG ATA T | 552 |
| p53F063 | TAT ACG CAG TGC TAC CAT CGA TCA CTC TAC CAC TGG CCC CTT TCC TCC TTG AGA CCC CAG CTT TGA GGC CTC AGG ATA ATC ATT TCT CCA CAG ATC ATC CCA GCC TCA TGC AGA GCC CTG GGC CTT CTC TTT GGA CCT GGG ACT CAA GCA GGC AGC AGG CTC GAC TTC GAA AGA CGC TCC ACG ATA T | 553 |
| p53F064 | TAT ACG CAG TGC TAC CAT CGA TCA CAC AGT GGG GCA TTG CCT GTA TTC AGT GGA GCC TGG AGC AAT GAG GGA AGA GGG GAG TCC AAC ATG TCA ATA TTA GGA AGG TTT CCA GCC AGG AGA CAA TAA CAA GAC TGG CTC CAC AGA ATT GTT TTT CAT TAA TAA TTT GAC TTC GAA AGA CGC TCC ACG ATA T | 554 |
| p53F065 | TAT ACG CAG TGC TAC CAT CGA TCA CGG CTT ATG GAT GGC ACT CAG GTG GGT GGT AGG GGC GAG GGA CAT ATC TTG AAG CTC CCC ACA GCA AGC AAA CAG TTT TGA CTT AGA CTG CAT ATT TAC TTG GGG CAG GTG TGG TTT CAA AAA GGG TCA AGC CAA AAA AAA GAC TTC GAA AGA CGC TCC ACG ATA T | 555 |
| p53F066 | TAT ACG CAG TGC TAC CAT CGA TCA CTG GGG CAG GAT TTA AGT GGT GAG AAT GGC CAG TAG GTG GAG GCA TAG CGA AGA GGC AGA ATT AAG GCA GCT AGG GGT GAG GCC ACA GGC AGT AGG CCC GGC TCA TTC TTC CCT CTC TCT CTA CCG TCC CTT TCC CAC ACA GAC TTC GAA AGA CGC TCC ACG ATA T | 556 |
| p53F067 | TAT ACG CAG TGC TAC CAT CGA TCA CTC TGC AGA AGG TGG TGT TGT CTT CTG GGT CGG GGC CAG GGC TGG ATC TGC CCC TGG TCT TGG GAC TCC CTC TTC AGC TGA AGC TGA GTA TGT CCA GGG TGG TCT TGA GCC AAG GGT CGA AGA TGA AGG CCC TTG CCC TGC GAC TTC GAA AGA CGC TCC ACG ATA T | 557 |
| p53F068 | TAT ACG CAG TGC TAC CAT CGA TCA CCA GTG GAA GGT AGT GCT TTT GCA AAC TCA GGT TGG AGG AGT GGA AAA GTG GGG AGA AGA TTC TGG ATC CGA GCC ACC TTA ATG CTC TAA TGC CAC CTT TGC ACT ACC TCC CTC TAG GAG AAG ACT CTT CCA CCT CTT TTT GAC TTC GAA AGA CGC TCC ACG ATA T | 558 |
| p53F069 | TAT ACG CAG TGC TAC CAT CGA TCA CGG AAA TGA GGA CTT CTT AGG CTG AGA TCC CAG CAA AAA CCC CGA CAG ACA GAC ATA CTC TGG ATA CAG TCA CTT CTG GAA G CCA GGA CCC ACC TGG TTC CGC AGA GCT ACT CCT TGA GAC CAG TTT CCT GCC TCT GAC TTC GAA AGA CGC TCC ACG ATA T | 559 |
| p53F070 | TAT ACG CAG TGC TAC CAT CGA TCA CCG TGA GAG GGT CAC AGA GAG ATG TGG GTA GGG GTT CTG GAA AAA GGG GTG GAG GCA GGG AGA AAG AAA AAG GGA GGA GAG CAG AGG GAG AAA GTC GCG TCT CTC TCT CTC TCT CCT AGT CTT GGT CCA CTT GCT GCC TTC GAC TTC GAA AGA CGC TCC ACG ATA T | 560 |
| p53F071 | TAT ACG CAG TGC TAC CAT CGA TCA CCA GAC AAA TTT GTC TCT ACT CCA TTA AGC AAG AAC TGG CTT GTG CTG GTC CCA GCT GGG AAA AAC AGA CAG ATT TGG AAT ATT CTC TCC CCT CAA AGA ATA CGG TGA CCC AGC TCT CAA CCA CAG ACC TCT AGA GAA TGC GAC TTC GAA AGA CGC TCC ACG ATA T | 561 |
| p53F072 | TAT ACG CAG TGC TAC CAT CGA TCA CTG CCC AGC ATC CCT CCC TGG GGA ACC CTC GTA TCC AAG CCC ATA GCC CCT ACC CCT CAG CTC CCA GTC TTC TGC CCT CTT AGG AAC CCT TGT GTC CTA GCC CAA AGC TCC CAG CCT ACT AAG GAG CCC TGG GGC TAA AGT GAC TTC GAA AGA CGC TCC ACG ATA T | 562 |
| p53F073 | TAT ACG CAG TGC TAC CAT CGA TCA CTT AAA AAG AAC CAT TAG GTT AAA GCA TCC TCC ATC TCC AGA CCC CAT GAG AAT CCC AGT GTC CAA GAC TCC TAA TTT CTT ACA AGA ATC TTT TCA CCA GTA ACC CAG GCA GCA GGT GAG TCA CTC ACT GGA GCT GC TGT GAC TTC GAA AGA CGC TCC ACG ATA T | 563 |
| p53F074 | TAT ACG CAG TGC TAC CAT CGA TCA CCC CTT CTG CAG AGA TCA GCC GGG ACC TAA ATG ACT CCA GGG TAA GGA GGC CCT GGG GAG TCT GTA GGG TAG AAG ACA CAA ATC CCA AGC CCC ACC TTC TAC CTC TCC TAA TCT TGA CCC TAT AGA CCC TCT CAG GAT CTA GAC TTC GAA AGA CGC TCC ACG ATA T | 564 |

TABLE 2-continued

| Sequence Name | Sequence | SEQ ID NO.: |
|---|---|---|
| p53F075 | TAT ACG CAG TGC TAC CAT CGA TCA CTT GTT CCG AGT GCC AAT ATC CTG ACC TTT TGT CCC TGG AAT CTC CTC GGA GCT GGC TTT TCT CTC CTC CCT CCA CCC CAC CTT CTC CAG GAC ACT GTG CCA CCA ACC TCT CTT TCC CCA GCC TGC CCT AGA TTC CAG GAT GAC TTC GAA AGA CGC TCC ACG ATA T | 565 |
| p53F076 | TAT ACG CAG TGC TAC CAT CGA TCA CAT GTT GTT CTT ATT AAT CTC ACA CAG TTC CTG ACA TAT TAG TTC TCA CAT AGT TCC TGA CAT ACT AGT CTG AGC TGC TGG GGT ATC AAA GAT CTG GGA GGG CGT GTG ACA TGG ATG AAC CAT GGA GAG GCT GAG ATG GAG GAC TTC GAA AGA CGC TCC ACG ATA T | 566 |
| p53F077 | TAT ACG CAG TGC TAC CAT CGA TCA CTG TGA AGG CTT TCA TGC CCT GGT TTC TTT CTG GAG ATG CTG TGG GAA AGT GTG GCC AGG AAA AGG CTG GAG GTT TGT AAC AGC TCT TCT CCT GGA AAT TTT TCA GAT CTC CCC TCT CTC AGC GTG TTT CCC TCA GAA GAC TTC GAA AGA CGC TCC ACG ATA T | 567 |
| p53F078 | TAT ACG CAG TGC TAC CAT CGA TCA CTA CAG TGC AGA GAA GAC ATT TCT TTC TTT CCA AGT GAA CAT GGG GTA CAA GGG TAG AGA CTG AGC CGG GAA TCC GGA GGC CAC CCC TGG CTG TGT TTG CTA AGC TTT ACG ATT TGA GGA TAG GAC CAG GTT TCA TCT TTA GAC TTC GAA AGA CGC TCC ACG ATA T | 568 |
| p53F079 | TAT ACG CAG TGC TAC CAT CGA TCA CAA ACA GAG GCT GTA TCA CTT CCG TGC TGC TTG CCT GAG GAA GGA AAG AGC AAG TTG CCT CTG AGG TCC CTT GCA GAA GGA GCC TTT CCA TGT TCA TGC CAA TTT AAC CAG GCA CTA TCT TTG GTA GCT CTA TGG GTT TCT GAC TTC GAA AGA CGC TCC ACG ATA T | 569 |
| p53F080 | TAT ACG CAG TGC TAC CAT CGA TCA CAC CAC ATC CAC TAG ATG AGA TAG GAG GTC AAA AAT ATC CAG CCA TTC TCT AGG GTC TAC AAG GAC CCT TTA TGG TTT GGC CCC TGC CTA GGT CTT CAA TCT CTT GCT GTA TTC ATC TTG TCT TTG CTC ATT AAA GCC CAG GAC TTC GAA AGA CGC TCC ACG ATA T | 570 |
| p53F081 | TAT ACG CAG TGC TAC CAT CGA TCA CTT AAT CTT TCT TCA AAT CTT GCC GGT TTT CCT TGG AGA GGT TTT TCT TCT CCT TTC AAC TGT CAC CTT AAA TCC TTA GCC CAG TTT CTC AAC ACC TCA CAT CCA AAC TGC CGT CCA CAT CCT CAA ACC CAC TCC CTC CAG GAC TTC GAA AGA CGC TCC ACG ATA T | 571 |
| p53F082 | TAT ACG CAG TGC TAC CAT CGA TCA CAG AGA ACC GAA GTA GAC CTG GCT GCA GGG CTG GGA TCT CAG GGC AGT GCT GGG GAC TGG GAA TGT GGT GTT GAG AGG GCT TCA GGG AGA CGT GAT GGG AAG ATG GGG AAG CCT CTG CAC GTG GAC AGA GCC AGG TGG TGT GAC TTC GAA AGA CGC TCC ACG ATA T | 572 |
| p53F083 | TAT ACG CAG TGC TAC CAT CGA TCA CTG GCC TTT ATC CAT CTC TGC GGG GCC TGT CCT AGC TTC CCT CCT GGC TCG GCC AGC CTC CCG GCT GGT CTC TTC GCT CTC TTT CTT GAT CTC TAG CTC TTT ATT CCT CTG ACA TTC TGC CCC ATC TGC TCC CGG ACT CTT GAC TTC GAA AGA CGC TCC ACG ATA T | 573 |
| p53F084 | TAT ACG CAG TGC TAC CAT CGA TCA CGC TGC TGA TAG TAT GAG TTT TAC CGA GGC TGC AGG TTT TGC TCC CAT GTC GGT GAC GGA GGG AGT GGT CGC TGT GGT GAT TTG TGT GCA TCA GCC AGC CAG GTG TCT GTG ACA GTC GGA TGA CTT GGA AGC CTC CCC GAC TTC GAA AGA CGC TCC ACG ATA T | 574 |
| p53F085 | TAT ACG CAG TGC TAC CAT CGA TCA CTC TGG TGA CCG GCA CAG GTG CAG GTG AGG GGT GGA ATT CTT CCA AGA GGG ATG GTC AAG CTG GAC GTT GAC ACA GGG GAC AGA GGA CAC TGT GTG ACA CGA TTT ACA ATC TTT CCA CAC TGG GCA CCG TCC CCA TCA GAC TTC GAA AGA CGC TCC ACG ATA T | 575 |
| p53F086 | TAT ACG CAG TGC TAC CAT CGA TCA CTC CAC CCA TTC GGG GCC TAC ACG AAG TGG GTC CCA TGC AAT CCA TTC CCT CAG GGA ACT CAA ACT CCA GCC CCT GGG ATG AGA AGA ATC CAG CAA TGC TTG GGA GAG CCA GAG GAC TTC ATG GAA GAA GTG TCC TCT GAG GAC TTC GAA AGA CGC TCC ACG ATA T | 576 |
| p53F087 | TAT ACG CAG TGC TAC CAT CGA TCA CAG CCA TGG AGA GAT CCC ACC AAG GGA AGG CTG TGG GAG ATT CTG CCT TTC CTC CCT GCC TCT GCC CAG GGT GCT GGG TGT GAA CTG AGG GTG GGG TGA CTG TTG AAG GTT CTA ACA AGC CGT CTC TGA GAG ATT TGT AGC GAC TTC GAA AGA CGC TCC ACG ATA T | 577 |
| p53F088 | TAT ACG CAG TGC TAC CAT CGA TCA CAG GCT AGT GTT AGG TCT TTC ATT TCA GGA ACT GTG TTC AAA GTT TGG CTT CTG AAG GGC ACC AGG AGA GAG ATG TTG CTA TTC AAA TCT GAG GGT CCA GTC TCT GCG GGG TGG TAT GAG GGT TTG CTT GTG AAT GGT GGC GAC TTC GAA AGA CGC TCC ACG ATA T | 578 |
| p53F089 | TAT ACG CAG TGC TAC CAT CGA TCA CGT ACC CGC TTT AAA AGG CAC CAT GCT AGC ACA GCT TTA AGC ATG AGT ACG AAT GCA GAG GTA ACA GAT GTG TGC CTT GTC AGG ACT ATG CAT GGT TGA GAA GTT GGA AAT GTA ATT GGA GGC AAA ATA ACA GAC CTC CAC GAC TTC GAA AGA CGC TCC ACG ATA T | 579 |
| p53F090 | TAT ACG CAG TGC TAC CAT CGA TCA CCT GGG AGT CAT GGC TAG AAG CCA GAC ACA ACT GCC TGT TTC CAG TTT GTC TCA TTT TGC CTC CAG AGG AAG GCT CTA AGA CAT | 580 |

TABLE 2-continued

| Sequence Name | Sequence | SEQ ID NO.: |
|---|---|---|
| | CCC TGT GGC TCT GTG ATC AGT CCC AGT GCA GAA CTT CAG AGT GGG TAG AGG GGT GTG GAC TTC GAA AGA CGC TCC ACG ATA T | |
| p53F091 | TAT ACG CAG TGC TAC CAT CGA TCA CGG GGA TAG TTG AGG TTA TGG TGG AAC CTT TGG GCC CTG ACC CTG TTT CCT CCT CCC TAG CCT TTA TCC TCC TCT TCT ACC TCG TTT TTT ATG GGT TCC TCA CCG CCA TGT TCA CCC TCA CCA TGT GGG TGA TGC TGC GAC TTC GAA AGA CGC TCC ACG ATA T | 581 |
| p53F092 | TAT ACG CAG TGC TAC CAT CGA TCA CAA ACC TCC AGA AGG AAC TCA TAG TTC CTT CCA GGA GTT TGA TTT TGA TGA CCC AAT CCC CAC GTG CTT GGA AGT TCT TGA AAT CTG TCC ACC TTC CCA TTT ACT GCA GTT GGG AGC TGT GTG ATT TGG GCA TGT GGC AGA GAC TTC GAA AGA CGC TCC ACG ATA T | 582 |
| p53F093 | TAT ACG CAG TGC TAC CAT CGA TCA CAA CTT CTG CCT TTG TTG GCT GTA GGC TTG ATG ATT CGC CCC AAG ACT GAG AAC CTT GAT GTC ATT GTC AAT GTC AGT GAC ACT GAA AGC TGG GAC CAG CAT GTT CAG AAG CTC AAC AAG TTC TTG GAG CGT GAG TGT GGG GAC TTC GAA AGA CGC TCC ACG ATA T | 583 |
| p53F094 | TAT ACG CAG TGC TAC CAT CGA TCA CCT GGT TAT GTG TCA GTT CAA GAC TTC GGG CAG GGG ACT GGG GAC CTT GGA AGT GGA ACA TCT GGC CCC TGA GTC TCT CCC TCC CAC CTC TTT AGC TTA CAA CGA CTC TAT CCA AGC CCA AAA GAA TGA TGT CTG CCG CCC GAC TTC GAA AGA CGC TCC ACG ATA T | 584 |
| p53F095 | TAT ACG CAG TGC TAC CAT CGA TCA CGG ACG CTA TTA CGA ACA GCC AGA TAA TGG AGT CCT CAA CTA CCC CAA ACG TGC CTG CCA ATT CAA CCG GAC CCA GCT GGG CAA CTG CTC CGG CAT TGG GGA CTC CAC CCA CTA TGG TTA CAG CAC TGG GCA GCC CTG TGT GAC TTC GAA AGA CGC TCC ACG ATA T | 585 |
| p53F096 | TAT ACG CAG TGC TAC CAT CGA TCA CTT CAT CAA GAT GAA CCG GGT ATC TAT GAC CTT GGT CCC CAG GGT GAA TGG AGG AAG GAT CTG GGG ACA CCA CCT GCA GAC AAT TGC ATC CTT TCA CTG GGG CTA ATG GGC ATG AGA AAG ACT TGG ATG TTT GTG TAG CTG ACT TCG AAA GAC GCT CCA CGA TAT | 586 |
| p53F097 | TAT ACG CAG TGC TAC CAT CGA TCA CTC CCC GGC TTA GCT TGG TCT GGA TGC CCA TCT TCG ACA ACT TCT TCC TCT GAC TCT CTT CAC CTT CCA CCC TCA CTC CAG GTC ATC AAC TTC TAT GCA GGA GCA AAC CAG AGC ATG AAT GTT ACC TGT GCT GGG AAG GTG GAC TTC GAA AGA CGC TCC ACG ATA T | 587 |
| p53F098 | TAT ACG CAG TGC TAC CAT CGA TCA CCG CAC TCC TCT TGC TTC TCT CTG GGA TGC AGA GGC CTG CTC TCC TAG GGG CCA GAC ACA CGC CCT CCT CCA CCA ACG CCC TGG CCT CTG GCT TCT CTC CCT AAC GCT TCC ACC TTC TCC TTC ATT CCC AGA TTG TCC GTA GAC TTC GAA AGA CGC TCC ACG ATA T | 588 |
| p53F099 | TAT ACG CAG TGC TAC CAT CGA TCA CCC GGT CTG TCC TTT CTA GAA ACT GGC TGC TCC CTC CAC ATC CCC TTC CTT GCT TCC TAT TCA ACC CTT AAT CAT GTA TCT CTT CTT TCT TGG CTC TGC TCC AGA AAC TGA TTC CTG AGG ATG GGT AAG AAC TTG GGG TAG ACT TCG AAA GAC GCT CCA CGA TAT | 589 |
| p53F100 | TAT ACG CAG TGC TAC CAT CGA TCA CAC AGC GAG ATG AAG ATG CTG AGA ATC TCG GCA ACT TCG TCA TGT TCC CCG CCA ACG GCA ACA TCG ACC TCA TGT ACT TCC CCT ACT ATG GCA AAA AGT TCC ACG TAA GTC CCA GGG GAG GCC CAG GCT GAT GGC GGG TGC GAC TTC GAA AGA CGC TCC ACG ATA T | 590 |
| p53F101 | TAT ACG CAG TGC TAC CAT CGA TCA CAA CGT GGA GGT GAA TGT AGA ATG TCG CAT CAA CGC CGC CAA CAT CGC CAC AGA CGA TGA GCG AGA CAA GTT CGC CGG CCG CGT GGC CTT CAA ACT CCG CAT CAA CAA AAC CTG TAG GCC CCT TCC TCC CAC CCA TCT CTC GAC TTC GAA AGA CGC TCC ACG ATA T | 591 |
| p53F102 | TAT ACG CAG TGC TAC CAT CGA TCA CCC TGT GGA TGC TCC TGG AAT GTC CCT GAC CCT GCC TGA TCC CTC CCT CAC CCA CCC CAA AGG TAT TTT TGA TAA CAG AGC TAT GAC TTG TCT GAG CCT CAC ATC CTT TTC CTT GAC TTC TCA ACC CAG CCT GAA GTC CAT GAC TTC GAA AGA CGC TCC ACG ATA T | 592 |
| p53F103 | TAT ACG CAG TGC TAC CAT CGA TCA CGC GGT TCC GTC ACT CGC CTT TCC CAC CAA CTT CTC CCA ACC TCA GAT CAG TCA GAC AGG GAG CTG GGC TAA GAT GGC CAC GGA GGA GTT AGG AGC CTT TCT AGT TCT GGT TTA GCT GTG AGA GCT ATC CAC TCT CCT GCC GAC TTC GAA AGA CGC TCC ACG ATA T | 593 |
| p53F104 | TAT ACG CAG TGC TAC CAT CGA TCA CAA CGT GCA CAC GCG TCT CAT TTG ACC CCT TTG CTT CCA GAG ATG AAT GTG GCA CTC CTC CTT CCA TTC CTA AGC TCT GGC CA CCG TCC CTT GAT CTC TCA TAC TTT CTC CCT GTC TAC ACA GTC GCC ATC TTG GTG ACT GAC TTC GAA AGA CGC TCC ACG ATA T | 594 |
| p53F105 | TAT ACG CAG TGC TAC CAT CGA TCA CTG AAT TTA TCT GGC TCC TGG GCA GGT CTT CTC CTC CTC TCC ATC CCT ATT CCC TCC TCT GAA ATG CAC CCC TTT GTA ATT GAG GAC AAG GTG GTT CTG TGG CCT TTT CCC TCT TTG CTG GCA CGT TCT GCT TCT CAC CCT GAC TTC GAA AGA CGC TCC ACG ATA T | 595 |

TABLE 2-continued

| Sequence Name | Sequence | SEQ ID NO.: |
|---|---|---|
| p53F106 | TAT ACG CAG TGC TAC CAT CGA TCA CAA CCC ATA ATG CCC ACA GAA TGT CAA ATG AGG GGC CTC CTG CCT CCT GCT CTG AAT ATT CTG TAG CTG TAG AGG CAT TTT AAC CCT TTG TCC TCC AGC ATC CCT TCA CTT CCT CAT CCT CTC TAA CCT CCT TTT TCT TTT GAC TTC GAA AGA CGC TCC ACG ATA T | 596 |
| p53F107 | TAT ACG CAG TGC TAC CAT CGA TCA CGG AAG CTC ATC AAG GTG ACC TGT CTA CAG AGG CAA GGA CAG GGA CTG AGC TTC AGG AGC TCT AGT TTG CCT GCT GGG TAG GGA CAG ATG TTT AAG TTA AAA GTC TCT GAA AGA GGC GGG TCT GGA TCT CCT GGG GAG AGT GAC TTC GAA AGA CGC TCC ACG ATA T | 597 |
| p53F108 | TAT ACG CAG TGC TAC CAT CGA TCA CTT TGG CAT TCC CTA GTA AGA AAG AGA AAA AAA AAA GGT GGT CTT GAG GTC AGG AAG GCT GGT GGC TTC ATA GCT GTC TGG GAT CCT TGG GGC AAG GCA AGG GGC TCC TGC TTG CAC CTT CAG CCT GGT TGA TGA GCT GAC GAC TTC GAA AGA CGC TCC ACG ATA T | 598 |
| p53F109 | TAT ACG CAG TGC TAC CAT CGA TCA CCT CCC TGG GAG CCA GCA GCC CTG AGG AGC ATG GGC AGG CAG TAC TGA GCT CCT CAA CCC GAC TCT CCT CCC TAT CCC AAG AAG CCC TTT GAA AGG TTT TCC TGG CAG AGT TTA AAG CTT CAA TTC ATT CAG CTA CCT GGC GAC TTC GAA AGA CGC TCC ACG ATA T | 599 |
| p53F110 | TAT ACG CAG TGC TAC CAT CGA TCA CGA CCC TGG CTA GCA GGC CTC CCA CTG GCC TCT CTC CAT CCA GTA GCA CCC ACC CCT GTT CCC CTT GGG AAC CCA GGT ATC CTG CCA CTT TCT GAT GGA GCA GAT GGC CAC CCT GGA GGC TCA GCC TTG CTA AAT CAG ACA GAC TTC GAA AGA CGC TCC ACG ATA T | 600 |
| p53F111 | TAT ACG CAG TGC TAC CAT CGA TCA CCA GCC CAC ACT CAT TGC AGA CTC AGG TGG CTG CTT CCC AGC ACC TCC TCA CTC ACC CCT GCA CCT GCT GAC CCC AGT AGC CTG CAC TGG CGT TCA CCC CTC AGA CAC ACA GGT GGC AGC AAA GTT TTA TTG TAA AAT AAG GAC TTC GAA AGA CGC TCC ACG ATA T | 601 |
| p53F112 | TAT ACG CAG TGC TAC CAT CGA TCA CAA TTG ACC CTG AGC ATA AAA CAA GTC TTG GTG GAT CCA GAT CAT CAT ATA CAA GAG ATG AAA TCC TCC AGG GTG TGG GAT GGG GTG AGA TTT CCT TTT AGG TAC TAA GGT TCA CCA GAA GGT TGT CAG ACA GGG TTT GGC GAC TTC GAA AGA CGC TCC ACG ATA T | 602 |
| p53F113 | TAT ACG CAG TGC TAC CAT CGA TCA CGA AGT GGG CCC CTA CCT AGA ATG TGG CTG ATT GTA AAC TAA CCC TTA ACT GCA AGA ACA TTT CTT ACA TCT CCC AAA CAT CCC TCA CAG TAA AAA CCT TAA AAT CTA AGC TGG TAT GTC CTA CTC CCC ATC CTC CTC CCC GAC TTC GAA AGA CGC TCC ACG ATA T | 603 |
| p53F114 | TAT ACG CAG TGC TAC CAT CGA TCA CCA ACA AAA CAC CAG TGC AGG CCA ACT TGT TCA GTG GAG CCC CGG GAC AAA GCA AAT GGA AGT CCT GGG TGC TTC TGA CGC ACA CCT ATT GCA AGC AAG GGT TCA AAG ACC CAA AAC CCA AAA TGG CAG GGG AGG GAG AGA GAC TTC GAA AGA CGC TCC ACG ATA T | 604 |
| p53F115 | TAT ACG CAG TGC TAC CAT CGA TCA CTG GGA GGC TGT CAG TGG GGA ACA AGA AGT GGA GAA TGT CAG TCT GAG TCA GGC CCT TCT GTC TTG AAC ATG AGT TTT TTA TGG CGG GAG GTA GAC TGA CCC TTT TTG GAC TTC AGG TGG CTG TAG GAG ACA GAA GCA GGG GAC TTC GAA AGA CGC TCC ACG ATA T | 605 |
| p53F116 | TAT ACG CAG TGC TAC CAT CGA TCA CGG AGA GAT GAC ATC ACA TGA GTG AGA GGG TCT GTG CCC CTT TTC CCT GAC CAA TGC TTT GAA GGG CCT AAG GCT GGG ACA ACG GGA ATT CAA ATC AAG ATG GTG GCC ACA CCC CAT GCA AAT ATG TTT ACT GAG CAC CTC GAC TTC GAA AGA CGC TCC ACG ATA T | 606 |
| p53F117 | TAT ACG CAG TGC TAC CAT CGA TCA CGG TGC ATG GCA GGG CTG AGT ATA TGA CCT GAA ACT CTG GCT GTA TTC AGT ATT ACA CAA TTA TTA GGC CCC TCC TTG AGA CCC TCC AGC TCT GGG CTG GGA GTT GCG GAG AAT GGC AAA GAA GTA TCC ACA CTC GTC CCT GAC TTC GAA AGA CGC TCC ACG ATA T | 607 |
| p53F118 | TAT ACG CAG TGC TAC CAT CGA TCA CGG TTT GGA TGT TCT GTG GAT ACA CTG AGG CAA GAA TGT GGT TAT AGG ATT CAA CCG GAG GAA GAC TAA AAA AAT GTC TGT GCA GGG CTG GGA CCC AAT GAG ATG GGG TCA GCT GCC TTT GAC CAT GAA GGC AGG ATG AGA GAC TTC GAA AGA CGC TCC ACG ATA T | 608 |
| p53F119 | TAT ACG CAG TGC TAC CAT CGA TCA CCA GTC AAG AAG AAA ACG GCA TTT GAG TGT TA GAC TGG AAA CTT TCC ACT TGA TAA GAG GTC CCA AGA CTT AGT ACC TGA AGG GTG AAA TAT TCT CCA TCC AGT GGT TTC TTC TTT GGC TGG GGA GAG GAG CTG GTG TTG GAC TTC GAA AGA CGC TCC ACG ATA T | 609 |
| p53F120 | TAT ACG CAG TGC TAC CAT CGA TCA CCA GCT CGT GGT GAG GCT CCC CTT TCT TGC GGA GAT TCT CTT CCT CTG TGC GCC GGT CTC TCC CAG GAC AGG CAC AAA CAC GCA CCT CAA AGC TGT TCC GTC CCA GTA GAT TAC CAC TAC TCA GGA TAG GAA AAG AGA AGC GAC TTC GAA AGA CGC TCC ACG ATA T | 610 |
| p53F121 | TAT ACG CAG TGC TAC CAT CGA TCA CAG AGG CAG TAA GGA AAT CAG GTC CTA CCT GTC CCA TTT AAA AAA CCA GGC TCC ATC TAC TCC CAA CCA CCC TTG TCC TTT CTG | 611 |

TABLE 2-continued

| Sequence Name | Sequence | SEQ ID NO.: |
|---|---|---|
| | GAG CCT AAG CTC CAG CTC CAG GTA GGT GGA GGA GAA GCC ACA GGT TAA GAG GTC CCA GAC TTC GAA AGA CGC TCC ACG ATA T | |
| p53F122 | TAT ACG CAG TGC TAC CAT CGA TCA CAG CCA GAG AAA AGA AAA CTG AGT GGG AGC AGT AAG GAG ATT CCC CGC CGG GGA TGT GAT GAG GAT GGG ATG GGT AGT AGT ATG GAA GAA ATC GGT AAG AGG TGG GCC CAG GGC TCA GAG GCA AGC AGA GGC TGG GGC ACA GAC TTC GAA AGA CGC TCC ACG ATA T | 612 |
| p53F123 | TAT ACG CAG TGC TAC CAT CGA TCA CCA GGC CAG TGT GCA GGG TGG CAA GTG GCT CCT GAC CTG GAG TCT TCC AGT GTG ATG ATG GTG AGG ATG GGC CTC CGG TTC ATG CCG CCC ATG CAG GAA CTG TTA CAC ATG TAG TTG TAG TGG ATG TGT GTA CAG TCA GAG GAC TTC GAA AGA CGC TCC ACG ATA T | 613 |
| p53F124 | TAT ACG CAG TGC TAC CAT CGA TCA CCT ACT GCT CAC CTG GAG GGC CAC TGA CAA CCA CCC TTA ACC CCT CCT CCC AGA GAC CCC AGT TGC AAA CCA GAC CTC AGG CGG CTC ATA GGG CAC CAC CAC ACT ATG TCG AAA AGT GTT TCT GTC ATC AAA ATA CTC CAC GAC TTC GAA AGA CGC TCC ACG ATA T | 614 |
| p53F125 | TAT ACG CAG TGC TAC CAT CGA TCA CCG CAA ATT TCC TTC CAC TCG GAT AAG ATG CTG AGG AGG GGC CAG ACC TAA GAG CAA TCA GTG AGG AAT CAG AGG CCT GGG GAC CCT GGG CAA CCA GCC CTG TCG TCT CTC CAG CCC CAG CTG CTC ACC ATC GCT ATC TGA GAC TTC GAA AGA CGC TCC ACG ATA T | 615 |
| p53F126 | TAT ACG CAG TGC TAC CAT CGA TCA CTG TGG AAT CAA CCC ACA GCT GCA CAG GGC AGG TCT TGG CCA GTT GGC AAA ACA TCT TGT TGA GGG CAG GGG AGT ACT GTA GGA AGA GGA AGG AGA CAG AGT TGA AAG TCA GGG CAC AAG TGA ACA GAT AAA GCA ACT GGA GAC TTC GAA AGA CGC TCC ACG ATA T | 616 |
| p53F127 | TAT ACG CAG TGC TAC CAT CGA TCA CAT ACG GCC AGG CAT TGA AGT CTC ATG GAA GCC AGC CCC TCA GGG CAA CTG ACC GTG CAA GTC ACA GAC TTG GCT GTC CCA GAA TGC AAG AAG CCC AGA CGG AAA CCG TAG CTG CCC TGG TAG GTT TTC TGG GAA GGG ACA GAC TTC GAA AGA CGC TCC ACG ATA T | 617 |
| p53F128 | TAT ACG CAG TGC TAC CAT CGA TCA CAC CCT TCC CCA CCT GAT ACA CGG CTC CAT TTC TTT GAT TCC TTT CAC TGC AAA GCT TCT GGA AGA ACA ACT GTC TCA CCG CTC ACC TGC CCA TTC TCT TCG GAC ACT CCT CAG CCC TGC ATT ACA AAC CCC TCA CGA ATG GAC TTC GAA AGA CGC TCC ACG ATA T | 618 |
| p53F129 | TAT ACG CAG TGC TAC CAT CGA TCA CGA ATA ACA CAC AAG CCT GTT ATA TGA GAG GTT AAG AGA GCG AGA AAG AGC AAG GGG CAG CCC CTG TGT GGA CCA GCA TCT TGC ACG AAG TTA TGC AAC TAT CAT CGC ACC TTC TCC AGA CAG CTT TCA AGG CTT TGC GAC TTC GAA AGA CGC TCC ACG ATA T | 619 |
| p53F130 | TAT ACG CAG TGC TAC CAT CGA TCA CGC CCA AAG TCT CAA TCC CAC TTG GAG GGA CAC AGG TCT ACA GAC AGG TCT CCC TGT CTT TAT CTC TCA AAT CTT CAG TAG CAA CTA AAA TCT CCG TGT TTT TCA GAG CAG GAC CTT CCC AGG GGT ACC AGC ATC AGT GGG GAC TTC GAA AGA CGC TCC ACG ATA T | 620 |
| p53F131 | TAT ACG CAG TGC TAC CAT CGA TCA CCA GGA TAC AAA TGT GCC AGG CTG AAC TAG GCC TTC CAA ATG GCC AGG GAG CCA AGA GAA ATG CAG GTG CCC TTG GCT GGG TGG GAA GGC AAT GAG ATC AAC TGA GAC CCC AAA CAG GGG CAG GCC TGA CCA GAA TCT TAA GAC TTC GAA AGA CGC TCC ACG ATA T | 621 |
| p53F132 | TAT ACG CAG TGC TAC CAT CGA TCA CAG ATG ACG TAA GTA CGG CAC AAA GTG GCC GGT ACG CGG CAG GTG CAT GGG AAG AAA CTG CGG AAT GAA ACA ACC GCG AGC TAA GAG ATG GGG CAG CGG GAG AAA TGA ATT CGA GTT CCG CCT CCT ACC AGG AAG AAC CGG GAC TTC GAA AGA CGC TCC ACG ATA T | 622 |
| p53F133 | TAT ACG CAG TGC TAC CAT CGA TCA CTC GGG CCG GAG GGC TGC ACG GAG GAC CAC ACG GAC GCC TGC GGG CCC GCC CCT TCC GCT TCA CGA CGT TCA GCC TGC GTC TGG AAC TGG AAT GGC CTA GCC CAA AGC TAG ATA ACA GGT AGA TTG TTT TTC CGA CAA ATT GAC TTC GAA AGA CGC TCC ACG ATA T | 623 |
| p53F134 | TAT ACG CAG TGC TAC CAT CGA TCA CTT CAA AAT TTG ATT CTC AGA CGT ACC CAT TCT TTT TTT TTT TCC TCC GGG AAG ATG AGA TAT ACT CAT TCT TGA AAA TAC CTC CGG GCT TGC CTT CTG CAC ACT TCT TTC CCT CCC TGT CTC ACG CCA TGG TAG CGT CCG GAC TTC GAA AGA CGC TCC ACG ATA T | 624 |
| p53F135 | TAT ACG CAG TGC TAC CAT CGA TCA CCT AGG TTG CAG GCG ACC CGC GGG GTG GGG CAC ACC ATT CAA AGA AGG GGA GGG ATT GAG GTT GCA TCA AAA CAA ATA CCC CCT GCC TTT GCA AAG GCC ATA ACT AAG TAA TCC AGA AAA AGA AAT GCA GGC GGA GAA TAG GAC TTC GAA AGA CGC TCC ACG ATA T | 625 |
| p53F136 | TAT ACG CAG TGC TAC CAT CGA TCA CAG CCT CCC TCT GCC AAG TAA GAG GAA CCG GCC TAA AGG ACA TTT TCT CTC TCT CTC CCC TCT CAT CGG GTG AAT AGT GAG CTG CTC CGG CAA AAA GAA ACC GGA AAT GCT GCT GCA AGA GGC AGA AAT GTA AAT GTG GAC TTC GAA AGA CGC TCC ACG ATA T | 626 |

TABLE 2-continued

| Sequence Name | Sequence | SEQ ID NO.: |
|---|---|---|
| p53F137 | TAT ACG CAG TGC TAC CAT CGA TCA CTC GGA ATG GAG CCC CAG TTT TCA CTA GGA TGC CAT GGG CTC TAA AAT ATA CAG CTA TGA GTT CTC AAT GTT TCG AGA TCC AAA AGT CTC AGA CCT CAA TGC TTT GTG CAT CTT TTA TTT CAG GGA TTC CCT ACG CCC AGC GAC TTC GAA AGA CGC TCC ACG ATA T | 627 |
| p53F138 | TAT ACG CAG TGC TAC CAT CGA TCA CCC GGG TGG ATG TGC AAA GAA GTA CGC TTT AGG CCG GCT CAA GGT TCC CCA AAG CTC CAC TCC TCT GCC TAG GCG TTC AAC TTT GAG TTC GGA TGG TCC TAA CAT CCC CAT CAT CTA CAC CCA GGT CTC CCA ACA ATG CAA GAC TTC GAA AGA CGC TCC ACG ATA T | 628 |
| p53F139 | TAT ACG CAG TGC TAC CAT CGA TCA CAG CCC CAG CGA TTT TCC CGA GCT GAA AAT ACA CGG AGC CGA GAG CCC GTG ACT CAG AGA GGA CTC ATC AAG TTC AGT CAG GAG CTT ACC CAA TCC AGG GAA GCG TGT CAC CGT CGT GGA AAG CAC GCT CCC AGC CCG AAC GAC TTC GAA AGA CGC TCC ACG ATA T | 629 |
| p53F140 | TAT ACG CAG TGC TAC CAT CGA TCA CCA AAG TGT CCC CGG AGC CCA GCA GCT ACC TGC TCC CTG GAC GGT GGC TCT AGA CTT TTG AGA GGG TCA AAA CTT TTA GCG CCA GTC TTG AGC ACA TGG GAG GGG AAA ACC CCA ATC CCA TCA ACC CCT GCG AGG CTC CTG GAC TTC GAA AGA CGC TCC ACG ATA T | 630 |
| p53F141 | TAT ACG CAG TGC TAC CAT CGA TCA CCA CAA AGC TGG ACA GTC GCC ATG ACA AGT AAG GGC AAG TAA TCC GCC TGC CGG AGG AAG CAA AGG AAA TGG AGT TGG GGA GGA GGG TGC AGA GTC AGG ATT CTC GCC GAC CTG GTG CCG TAG ATA CTA ACA TTT TGG GGT GAC TTC GAA AGA CGC TCC ACG ATA T | 631 |
| p53F142 | TAT ACG CAG TGC TAC CAT CGA TCA CGT AGG CGC TTC TCG CCA AGA TAG AAG CGT TCA GAC TAC AAC TCC CAG CAG CCA CGA GGA GCC CTA GGG CTT GAT GGG AAC GGG AAA CCT TCT AAC CTT TCA CGT CCC GGC TCC GCG GGT TCC GTG GGT CGC CCG CGA AAT GAC TTC GAA AGA CGC TCC ACG ATA T | 632 |
| p53F143 | TAT ACG CAG TGC TAC CAT CGA TCA CGC CCA ATC GGA AGG TGG ACC GAA ATC CCG CGA CAG CAA GAG GCC CGT AGC GAC CCG CGG TGC TAA GGA ACA CAG TGC TTT CAA AAG AAT TGG CGT CCG CTG TTC GCC TCT CCT CCC GGG AGT CTT CTG CCT ACT CCC AGA GAC TTC GAA AGA CGC TCC ACG ATA T | 633 |
| p53F144 | TAT ACG CAG TGC TAC CAT CGA TCA CGA GGA GGG AAG CAC AGG TGG GTT TCT TTA GCT CTG CGT CGG ATC CCT GAG AAC TTC GAA GCC ATC CTG GCT GAG GCT AAT CTC CGC TGT GCT TCC TCT GCA GTA TGA AGA CTT TGG AGA CTC AAC CGT TAG CTC CGG ACT GAC TTC GAA AGA CGC TCC ACG ATA T | 634 |
| p53F145 | TAT ACG CAG TGC TAC CAT CGA TCA CAC CCA GTT TCT CTC TCC ACT CCC CTG GAA ACA GAG TTT GGT TCC CCT AGT GAG TTG AGT CCT CGA ATC GAG GAG CAA GAA CTT TCT GAA AAT ACA AGC CTT CCT GCA GAA GAA GCA AAC GGG AGC TTT CTG AAG AAG GAA GAC TTC GAA AGA CGC TCC ACG ATA T | 635 |
| p53F146 | TAT ACG CAG TGC TAC CAT CGA TCA CCG AAC GGG CCA GAG TTG GGG TCT GGA AAA GCC ATG GAA GAT ACC TCT GGG GAA CCC GCT GCA GAG GAC GAG GGA GAC ACG TAA GTG GTG ATG GCA GTG GAG TGT GGA GTC TGG GGA GAT GAA GTG TGA GGT CGA TCT GTC GAC TTC GAA AGA CGC TCC ACG ATA T | 636 |
| p53F147 | TAT ACG CAG TGC TAC CAT CGA TCA CAT CTT CCT TTC AGC GCT TGG AAC TAC AGC TTC TCC CAG CTG CCT CGA TTT CTC AGT GGT TCC TGG TCA GAG TTC AGC ACC CAA CCT GAG AAC TTC TTG AAA GGC TGT AAG TGG TAA GGA TAA CAA CGG GGC AGG GAG CTG GAC TTC GAA AGA CGC TCC ACG ATA T | 637 |
| p53F148 | TAT ACG CAG TGC TAC CAT CGA TCA CGC TTA CCT ACC CCA GAG GCA GGC TCA GCC CTA GCC CTA CAC TTG AAA AGC ATA GGT CTG GCC AGC TTT CTA ACT CTC CCC TGT TTC TAG GGC TCC TGA CGG TTC CTG CAT CTT GAC CAA TAG TGC TGA TAA CAT CTT GCG GAC TTC GAA AGA CGC TCC ACG ATA T | 638 |
| p53F149 | TAT ACG CAG TGC TAC CAT CGA TCA CAG CAG GTG AAA TAT GCA GAA ATG GTA AGG ACT GGG GCT AAC TGC CTC TTC ATC AAT GCT GCA CAT TTA AGT CCT TCG TGG AGA TGG AAA AAG TGT AGT CCA AGT GTT TCC TGT TCA CAA ACG GGA CTG TTT TTC AAG ACG GAC TTC GAA AGA CGC TCC ACG ATA T | 639 |
| p53F150 | TAT ACG CAG TGC TAC CAT CGA TCA CTT CCA TAT ACT TGT GTG TAC TGA GTC TTC TTC CCA ATA TAG TTT CTC GGG TTT TCT CCT TTC TTT TCC ACC TTT TCA CAG AAC TTT CTG CAA GTC TCA TTT CCA GCT CCC CAG CGT CTT TCC TGA GTA CTT GCC CTG CCC GAC TTC GAA AGA CGC TCC ACG ATA T | 640 |
| p53F151 | TAT ACG CAG TGC TAC CAT CGA TCA CGT GGG TCT TGC AGG AAG CCT TTA CTC CTC GTC TTG CCC TCT CCA GGA GAC ACT TTG CAT CCT CTG TAC CCT TTA TCT CTC AGG GTG GGG ACG GGG AAT GTC CTC ATT CCC AAA TGC TGT AGC CAC ACA ATT GCT CTT TCG GAC TTC GAA AGA CGC TCC ACG ATA T | 641 |

TABLE 2-continued

| Sequence Name | Sequence | SEQ ID NO.: |
|---|---|---|
| p53F152 | TAT ACG CAG TGC TAC CAT CGA TCA CCC TTT TGC TCA TTA AAA CCG TAT TTG TTG ACT CTG CTT ATT CTG CAC CAC GTG TTG GGG AAG CAG TGG TGA GAG CGA GGC AGA TGT GAT TCC CTC CTT CTC TGA TAG GTA TGA CGG AAG GGG AGT GAG GAG CAC CAG GGG GAC TTC GAA AGA CGC TCC ACG ATA T | 642 |
| p53F153 | TAT ACG CAG TGC TAC CAT CGA TCA CAA AGT ATG AAT CTA TAT GGC TTT TGG TGG CTA AAT TTG ACA TTA AAG TCT GAG CTC ACC CTT GAA CAT TGA GAC AGA GTC TGT GCT CCA TAT ATA CAC CCC ATC TGC CAC AAC ACT GCT AGA GGC ACG CGC CTC AGA CTC GAC TTC GAA AGA CGC TCC ACG ATA T | 643 |
| p53F154 | TAT ACG CAG TGC TAC CAT CGA TCA CGT CTC TGT ATA GGT CCC TGT CCT TCG AAT GGT GGA AGG TGA TAC CAT CTA TGA TTA CTG CTG GTA TTC TCT GAT GTC CTC AGC CCA GCC AGA CAC CTC CTA GTA AGT AAT GTT TGC CTC CCT GCT CGC CGC CCC ACC ACC GAC TTC GAA AGA CGC TCC ACG ATA T | 644 |
| p53F155 | TAT ACG CAG TGC TAC CAT CGA TCA CAT TCC TCC CCT TCC TTT GAC AGC ACC GGG GTT TCA GTG TCC ATG TCT CTC TCA GCG TGG CCA GCA GCA GCC GGG AGA ACC CGA TTC ATA TCT GGG ACG CAT TCA CTG GAG AGC TCC GGG CTT CCT TTC GCG CCT ACA ACC GAC TTC GAA AGA CGC TCC ACG ATA T | 645 |
| p53F156 | TAT ACG CAG TGC TAC CAT CGA TCA CCA TAC CCT GTC AGC TGT GGA GCT TTT GGT CTC TGA AAT CTT TCT AGA AAA TTG TTG ATA AAG CTG ATT CCG TTT TCC TGT AGG CCT TCA ACT TGC ATC TCT CCA GGA AGA ACT GGA TTT GAG AGG GAT GAA GTG GGC GAC TTC GAA AGA CGC TCC ACG ATA T | 646 |
| p53F157 | TAT ACG CAG TGC TAC CAT CGA TCA CAC TTT GTT CCT TCC CTC TCT AGC AAA AAA GCA GGG CCA GAG CGG CAT CAT CTC CTG CAT AGC CTT CAG CCC AGC CCA GCC CCT CTA TGC CTG TGG CTC CTA CGG CCG CTC CCT GGG TCT GTA GCC TGG GA TGA TGG CTC GAC TTC GAA AGA CGC TCC ACG ATA T | 647 |
| p53F158 | TAT ACG CAG TGC TAC CAT CGA TCA CTT TCA TCC CGA TGG CAA CCG CTT CTT CTC AGG AGC CCG CAA GGT AGG GGT CAC ACC CTG AGA GCC CAA AGC AGC TGG GCA GCG GGG CAG GAG CAG GGA TGT AGT CTG CAG TGT AGG GGA ATG GGT GGG GAT GGG GAA AAA GAC TTC GAA AGA CGC TCC ACG ATA T | 648 |
| p53F159 | TAT ACG CAG TGC TAC CAT CGA TCA CTG ACT CCA GGT CCT GTT CCT TGT CTC CAG GAT GCT GAG CTC CTG TGC TGG GAT CTC CGG CAG TCT GGT TAC CCA CTG TGG TCC CTG GGT CGA GAG GTG ACC ACC AAT CAG ACG CAT CTA CTT CGA TCT GGA C CCG TGA GTG GAC TTC GAA AGA CGC TCC ACG ATA T | 649 |
| p53F160 | TAT ACG CAG TGC TAC CAT CGA TCA CAG TTC CTA GTG AGT GGC AGC ACG AGC GGG GCT GTC TCT GTG TGG GAC ACG GAC GGG CCT GCC AAT GAT GGG AAG CCG GAG CCC GTG TTG AGT TTT CTG CCC CAG AAG GAC TGC ACC AAT GGC GTG AGG TCC TCA GTT CAA GAC TTC GAA AGA CGC TCC ACG ATA T | 650 |
| p53F161 | TAT ACG CAG TGC TAC CAT CGA TCA CTC AGG GTG AGC GGG GCT GAG CAG GAG CTG GGT CAG ACT GTT GGG TGT GAC CGT GTG AGA CTG TGC AGA CAG TGA CAG GGC GCC TGT CGC CCA CAC TCC ACA CTG TTT GCC ATT CTC CAG CAG CAT GGG GAC CAT TAC TCA GAC TTC GAA AGA CGC TCC ACG ATA T | 651 |
| p53F162 | TAT ACG CAG TGC TAC CAT CGA TCA CCT CTG AGG GGA GCA GGA GCA CTC TCC TCC GCT CCC CGG GGC TCC CCA GGA GGC AGA CAA CCC AGT TGC CAG AGT CAA GGA CAC ACA TAA AAG AGT AAA GGT GTT GAA AAA TAC AGT CGT CAC CTT TGA TAT TGC TGT TCC GAC TTC GAA AGA CGC TCC ACG ATA T | 652 |
| p53F163 | TAT ACG CAG TGC TAC CAT CGA TCA CGA CTT TGA AGA AAT ACT GCC AGC AGG GGA TGT GAT TTT GGA CCT CAC AAT CAA AGG GAA GGG ACG AAA GGC CTG GGG AGG CTT GAG AGG GAG AGG AAT GTC ACC CCT GCC CAG AGG TGC TGA AAG CCA GGG CTC TTA CAC GAC TTC GAA AGA CGC TCC ACG ATA T | 653 |
| p53F164 | TAT ACG CAG TGC TAC CAT CGA TCA CCT TCA GGT TAT TTA TTC TCT CCA AAC CTG CCG GGA GCA GCG GTG TTG TTT GGA TGG AGG AGG AGG CTG CGG GAG C GAA AGG GGT GGG TTC CTC GGG GTG GAG AGG GCG AGA GCC TTT CTG GAT TCG AGA GAG GAA GAC TTC GAA AGA CGC TCC ACG ATA T | 654 |
| p53F165 | TAT ACG CAG TGC TAC CAT CGA TCA CCT TCT GTG GGC AGG GAG GAG GCG GGA GGG AAG GTG CTG GTG CTC TGA TGT GTG ATG GGT TAC TAG ACA GGT GAT CTT GGG AGC CAG ACT CCG GGT CCC ACG CAG AGC TGG ATG CGG GTG GTG CTA TGG ATG TCA GGA GTT GAC TTC GAA AGA CGC TCC ACG ATA T | 655 |
| p53F166 | TAT ACG CAG TGC TAC CAT CGA TCA CCT CTG GGG ACA ACT TCC CAG GCT CTT GAC TCT CTT CAC AGT CTG TCT CCC AAC TCT TCC CAG CCA GAG GGT CAG TGA ACT GTT GGC TGA ACG ATT CCC AGC CAG AAC ATA TTC CTG CCT TCT GCT TGC CGG GAC TTC GAA AGA CGC TCC ACG ATA T | 656 |

TABLE 2-continued

| Sequence Name | Sequence | SEQ ID NO.: |
|---|---|---|
| p53F167 | TAT ACG CAG TGC TAC CAT CGA TCA CAA TCT TTG CTG CAA ACT CTT CCA TCA GAC CCT CTG TTC CAT GGC ATG CCA GCT TTG CTC TGA AAA GAG GCC AGG GGT CAG ATG AAA CTT CAA GCC ACG CTG GGT AGG ACA GAA CCT TCG GGA GGT CAC CTG GGT CCC TTG GAC TTC GAA AGA CGC TCC ACG ATA T | 657 |
| p53F168 | TAT ACG CAG TGC TAC CAT CGA TCA CGC GGT AAG GTG TTT GAA TGT ATT ATG TGC TCA TTA AAG GAG AGC TAG GAT TAT TGT TCC TCT CTT TAC TTC CCA GCC TCC CTC ACA CTT CTC TGC TCT GCC ATC CCT CCC TCT CTT TCC TGG ATC TCT TGG GTA TAA GAC TTC GAA AGA CGC TCC ACG ATA T | 658 |
| p53F169 | TAT ACG CAG TGC TAC CAT CGA TCA CCT CTT TCG GAT GTG GGG TGG GAG TGG GAC ACT TGG GAG TCT GGG AAG ATA TCA AGT AGC AGT CCC CTG GGA CCC AGT CCT GAG ACC CTG TCT CAG CAG CTA TTG ATG TCC AAG GGG CTG CAG GGG TTG GCA AGT TGT GAC TTC GAA AGA CGC TCC ACG ATA T | 659 |
| p53F170 | TAT ACG CAG TGC TAC CAT CGA TCA CGC TGT GCT GGG ACA GTG GAT GCC TGG GTG CAC TGG CCA AGG AGA TGG TGA AGT GTG TTG GTT GTG GTT AGA AAA GTC AAC TCC TTT CCT TTC CAA AGC AAT AGA GCA CTT GCC CCA GAA GTC TAA GAC CCA GTG TGG GAT GAC TTC GAA AGA CGC TCC ACG ATA T | 660 |
| p53F171 | TAT ACG CAG TGC TAC CAT CGA TCA CCT GAG TGG GAG AAT GAC TCA GGC AGC AGG TTC CTA GAC CCT GGT TCC CAT CAG CCC CAA TGA TGG TCG TGG CCA AAC CAG GCA TTT GCC TTC TGT GCT ATT AGC TGG CTA ACT TAG GAC ACT GGT CTG GAC CAC CCT CCA GAC TTC GAA AGA CGC TCC ACG ATA T | 661 |
| p53F172 | TAT ACG CAG TGC TAC CAT CGA TCA CTT GCC CCG GAA ATC CCT GAA ATT CAG TGG TGG CCT GAA GGA GGG GAG GCT CTG CCC GCA TGG TTG GCT GCC ATG GAA TAG TGA AAT CAC CTG GGA GGG GTG GGC TGT GTG GTT CCA GAG AGG CCA GCT CCT TGG TAA CTG GAC TTC GAA AGA CGC TCC ACG ATA T | 662 |
| p53F173 | TAT ACG CAG TGC TAC CAT CGA TCA CTG GTG ATG GAG CGG GAG ATG GCG GTG TGC ATG TGG TGA GGG CGG GCT GAA GAG TGG AGT GCA TTT GGG CAC ACC AAG GGG CAG GAG ACC CCT GAG CCT GGC TTC CTG CTG CTT CCA ATG TGA ATG CAC AGA GTC CTT GGT GAC TTC GAA AGA CGC TCC ACG ATA T | 663 |
| p53F174 | TAT ACG CAG TGC TAC CAT CGA TCA CTG CCC CAA ACC TCC TTC TCA CTT GTG ATC GCC CAG ACC TGG ATC TCC GCT TCA CCA TCA AGT TCC AGG AGT ATA GCC TAA ATC TCT GGG GCC ACA GTT CCG CTT CGC ACC ACG ATT ACT ACA TCA TTG GTA CTG CTG GGC GAC TTC GAA AGA CGC TCC ACG ATA T | 664 |
| p53F175 | TAT ACG CAG TGC TAC CAT CGA TCA CTG GGG CCA GAA TCA GGG CTA GAT TCT GGA GTG CCA ACC TCT TCC TCT GGC TTT TCT CTC CCA GCC ACA TCG GAT GGG ACC CGG GAG GGC CTG GAG AGC CTG CAG GGA GGT GTG TGC CTA ACC AGA GGC ATG AAG GTG CTT GAC TTC GAA AGA CGC TCC ACG ATA T | 665 |
| p53F176 | TAT ACG CAG TGC TAC CAT CGA TCA CCG GTG ATA CAG GAA AGA GGA GAA GAG AGG ATG GGA GGG TGG GAG GGG AAT GGA AAC CAA ATG AGG AAA AGA CTC AAT TAG AAC TAA TTA GCC AGT CAC TCG CTT CAA TCA GTG CTG TCA GAG AAG TGG GGA GGA CTC CGT GAC TTC GAA AGA CGC TCC ACG ATA T | 666 |
| p53F177 | TAT ACG CAG TGC TAC CAT CGA TCA CTC ACC CAC CCA GAG CTA GGG GCG GGA ACA GCC CAC CTT TTG GTT GGC ACC GCC TTC TTT CTG CCT CTC ACT GGT TTT CTC TTC TCT ATC TCT TAT TCT TTC CCT CTC TTC CGT CTC TAG GTC TGT TCT TCT TCC CTA GCA GAC TTC GAA AGA CGC TCC ACG ATA T | 667 |
| p53F178 | TAT ACG CAG TGC TAC CAT CGA TCA CCC TTA TGG GGA AGG CTC TGA CAC TCC ACC CCA GCT CAG GCC ATG GGC AGC AGG GCT CCA TTC TCT GGC CTG GCC CAG GCC TCT ACA TAC TTA CTC CAG CCA TTT GGG GTG GTT GGG TCA TGA CAG CTA CCA TGA GAA GAA GAC TTC GAA AGA CGC TCC ACG ATA T | 668 |
| p53F179 | TAT ACG CAG TGC TAC CAT CGA TCA CTG TCC CGT TTT GTC CAG TGG CCA ATA GCA AGA TAT GAA CCG GTC GGG ACA TGT ATG GAC TTG GTC TGA TGC TGA ATG GCA CTT GGG ACC GAA GTG ACT TGC TCC AGA CAA GAG GTG ACC AGG CCC GGA CAG AAA TGG GAC TTC GAA AGA CGC TCC ACG ATA T | 669 |
| p53F180 | TAT ACG CAG TGC TAC CAT CGA TCA CAT CAG GAG GTG GGA GGT GGA TGG TTC TTA TTC TGT GGA GAA GAA GGG CGG GAA GAA CTT CCT TTC AGG AGG AAG CTG GAA CTT ACT GAC TGT AAG AGG TTA GAG GTG GAC CGA GAA GGA CTT TTC CCA GTC TTC AGT GGC GAC TTC GAA AGA CGC TCC ACG ATA T | 670 |
| p53F181 | TAT ACG CAG TGC TAC CAT CGA TCA CTC CCA AGA TCT CCC TTC CCT TGT GCT CTG TGC TGA TTT TAG GAC AGC TAA GAT GAC TGC CAT GTG CTG TGG CAG GCC TAA TTT GTC TTG TTC TTT CCT TTC CAT ATC CCA GTA TAA TCT CTG TTA ATC AAC AGG ACT ACC GAC TTC GAA AGA CGC TCC ACG ATA T | 671 |

TABLE 2-continued

| Sequence Name | Sequence | SEQ ID NO.: |
|---|---|---|
| p53F182 | TAT ACG CAG TGC TAC CAT CGA TCA CCA AGA ACC CAT GTG CTC TCC CGA GTA ACC CAG ATG GCT GTC TTG TTC ATT CCA TCC TAC ATT TCT GAC TCC TTT CAG ACT CAA CAC AGT TCC CTT CTT AGT GAC CAA AAT GGT GGC CTA CTG GCT GGT CTA GCT GAC AGT GAC TTC GAA AGA CGC TCC ACG ATA T | 672 |
| p53F183 | TAT ACG CAG TGC TAC CAT CGA TCA CGT ACT TAG CAA AGG CCA CTG TTT CCA TAG TGA CCA GCT GAT ACC TCT TCC TGC CCT CTA GTG TGC AAT TGG GTG TTG CCT CAG TTT CCT CCC AGC TCA GTT TTA TTA GAT CAA AGC TGT TGT TGG GCA CCA GGT TGG CCA GAC TTC GAA AGA CGC TCC ACG ATA T | 673 |
| p53F184 | TAT ACG CAG TGC TAC CAT CGA TCA CCT CAA TCA CCA GCC AAG ATG GTT GCT TTG TCC ACC AGA GGT CAA GTT CAC CTC TCT GGT GCT GTA GTT CCC AGC TCC TTC CTG ATT TTT CTA ATC GCT CCT TCT GGG GAA CAG GAA GTT GAT ATT GCC ATG GTG GCG GGG GAC TTC GAA AGA CGC TCC ACG ATA T | 674 |
| p53F185 | TAT ACG CAG TGC TAC CAT CGA TCA CGT GGG TAG GGA TAG GGC TAG TTT GGA GTG GTG AGG TTG GCA GTG CTT GGG GAG GCG AAA ATG GGC TGG GCG AGA AGG CAG AGG AAG GTG TCA CCT CTA GGG GAG GGA GAG AGT AAT GCA GGC AGG AGT GGG GTC GCC AAT GAC TTC GAA AGA CGC TCC ACG ATA T | 675 |
| p53F186 | TAT ACG CAG TGC TAC CAT CGA TCA CCA TCC ATG GGG ACA GTC TGA GTG TCT TGC TAA GCC AAA GCA CCA GAG ACA GGG TAA GAC GCA ATT AGG ATC AAA GTG GTA AAA ACA TGT TCA CAT GTT AAA GTC TAT TCC CTA CCA TCC CTA CCC AAG GCA CTT GAG AAG GAC TTC GAA AGA CGC TCC ACG ATA T | 676 |
| p53F187 | TAT ACG CAG TGC TAC CAT CGA TCA CAA AAA GCC CAG GTG CCC AGT CCC CTA GAC TTA GCC CCA TTC TCC AAC CAC AAA AGC AGC CGT CAG GAG CAT CAC TGG AGC GAG TCA GCA GGG TCA CAA CCT CTG CCC TCC CCT GCC CCT CCC CTG ACT TTA GGT CCC CTC GAC TTC GAA AGA CGC TCC ACG ATA T | 677 |
| p53F188 | TAT ACG CAG TGC TAC CAT CGA TCA CAG CAA GAT GCC TGG GTC TTG AGA GGT GCG GGC ACC GCA GGA GGG GAG TTG AAA GCT GGG AGG CCA GGT ACT GGG CTG TCT GGA ATT TAC TCT GCC TTC TGA GCC CAC TGG AGC TGC CCG AAG TGG GGA GGC TCG TAT GAC TTC GAA AGA CGC TCC ACG ATA T | 678 |
| p53F189 | TAT ACG CAG TGC TAC CAT CGA TCA CTC CAC CTA CAT CTA GAG GCA CAG GTG GAG AGA CAA GAG GGA AGA GAC GTG GGG ATA AAT AGT CTC CGT GAC AGA CAA GCA CCT CGC CAA AGC AGC CAA GAC ATC ATA ACA TGC TGA GAG ACA GGA AGA CAC CTG GGG ACA GAC TTC GAA AGA CGC TCC ACG ATA T | 679 |
| p53F190 | TAT ACG CAG TGC TAC CAT CGA TCA CTC AGA GCG CTG GCA TCC AGA GAC TCC CCG CAG CCC CGC TCG AAT AGC ACA AGA CCA ACA GCC TTT CAC ATG TGT AGT GAC TTG GGT GTC TGG AGC TAT TTG AAA ATG CTG GTG ACT TCC ACG CAG AAT AAC ACA GGC CGT GAC TTC GAA AGA CGC TCC ACG ATA T | 680 |
| p53F191 | TAT ACG CAG TGC TAC CAT CGA TCA CTC ACC ACC ACA TGC ATG TTT CGG ATG TGT CCT GTT CTT CCC TAG CCT CGG CCT GGA GGG GAG TAA GTC ACT TAG GGT CTT GGA TCC ACA TTA AGG AAG TTG ATC TCA CTC AGT CTC CCA TCC CCT TGC CTT TTG TTT CTT GAC TTC GAA AGA CGC TCC ACG ATA T | 681 |
| p53F192 | TAT ACG CAG TGC TAC CAT CGA TCA CCT GTG GCA CAG CTG CTG GCA GAG TCC AGA GCA GGA AGG CAG AGC GGA AGT AAA GGA ACC GAG AGG GCT GGG ACC ACA GAA GCT AGA GCT GTC GCC CTG CCA TCC CCA AAC CGC ATA GGA TTG AGG CTG TCT TGG GGC TGA GAC TTC GAA AGA CGC TCC ACG ATA T | 682 |

Table 3 shows the summary of the probe designs and the downstream/cleanup methods.

TABLE 3

| Probe loci | Method | Kb coverage | PCR Steps (1 or 2) | Fractioned? (Yes/No) | Fraction Size(bp) | Amination or Allylamine | Linker Removed? (Yes/No) |
|---|---|---|---|---|---|---|---|
| HER2 | HER2 1-step PCR | 76 | 1 | Y | 100-300 | Amination | NA |
| HER2 | HER2 2-step PCR | 76 | 2 | Y | 120-180 | Amination | N |
| HER2 | HER2 2-step PCR-Aminoallyl dUTP | 76 | 2 | Y | 100-300 | Allyl | Y |
| p53 | p53 1-step PCR | 60 | 1 | N | 50-400 | Amination | NA |
| p53 | p53 2-step PCR | 60 | 2 | Y | 70-300 | Amination | N |
| p53 | p532 2-step PCRAminoallyl dUTP | 60 | 2 | Y | 70-300 | Allyl (2%) | N |

TABLE 3-continued

| Probe loci | Method | Kb coverage | PCR Steps (1 or 2) | Fractioned? (Yes/No) | Fraction Size(bp) | Amination or Allylamine | Linker Removed? (Yes/No) |
|---|---|---|---|---|---|---|---|
| p53 | p532 2-step PCRAminoallyl dUTP | 60 | 2 | Y | 70-300 | Allyl (3%) | Y |
| HER2 | HER2 oligo | 21 | NA | NA | NA | Amination | NA |
| HER2 | HER2 Oligo + PCR hybrid | 76 | 1 | NA | NA | Amination | N |
| p53 | p53 Oligo + PCR hybrid | 60 | 1 | NA | NA | Amination | Y |

Testing Results

Probes were first tested on male lymphocyte slides, and probe intensity, specificity, background and cross-hybridization were evaluated, with corresponding BAC probe as the control.

All probes tested passed the cross-hybridization test on lymphocyte slides. Once a probe design passed on lymphocyte slides, it was then tested on FFPE slides. All probes were tested on breast cancer tissue FFPE slides. Some probes were tested on both breast and gastric slides. Universal pretreatment method was used for all FFPE slides. HER2 and p53 BAC probes from AM inventory were used as controls for all experiments. BAC control probes passed overnight hybridization on both lymphocyte slides and FFPE tissue slides, but failed 1 hour hybridization on both slide types.

Results indicate that RF PCR probe designs surpassed the performance of synthesized oligo designed either by direct synthesis or oligo-PCR hybrid. Directly synthesized HER2 oligo probe and oligo-PCR hybrid p53 probe failed 1 hr FFPE, while oligo-PCR hybrid HER2 probe failed all quality evaluation. Based on these data, oligo probe designs were excluded from further evaluation, while RF PCR method was used for the selection of optimal probe designs.

All RF PCR designs passed quality evaluation for 1 hour and overnight hybridization on both lymphocytes and FFPE slides, except some sub-optimal specificity data points observed on lymphocyte slides.

2-step PCR design has several downstream or cleanup options, such as DNA fragment fractionation after sonication, 2nd PCR with aminoallyl-dUTP, and adaptor removal after 2nd PCR. Table 1 lists all the downstream or cleanup steps for each probe designs For both HER2 2-step probes, the different fractionation size, 2nd PCR with aminoallyld-UTP or not, and adaptor removal or not after 2nd PCR did not have a positive impact on the final probe quality.

Same as the three p53 2-step PCR probes, 2nd PCR with aminoallyl-dUTP vs. amination, and adaptor removal or not after 2nd PCR did not impact final probe quality.

The final procedure for Repeat-Free PCR FISH Probe design and preparation is the following.
1: Identify desired coordinates of locus on Genome Browser.
2: Download sequence with repeats masked to N.
3: Enter sequence in Sequence Processing program.
4: Process to identify kilomers of unique sequence, and format for BatchPrimer3
5: Use BatchPrimer3 (web) to identify F and R primers for each kilomer.
6: Order mixed primers in 96-well plate format.
7: PCR in plate using Phusion polymerase, assess by eGel-96.
8: Combine PCR products, fragment by sonication.
9: Blunt sonicated DNA.
10: Ligate Adaptors to make template.
11: PCR with: Adaptor-primers to make bulk DNA for amination, labeling. OR Adaptor-primers and AAdUTP to make aminated DNA for labeling.
13: Aminate (if needed)
14: Label, formamide treat.

Example 3

Figure 9:
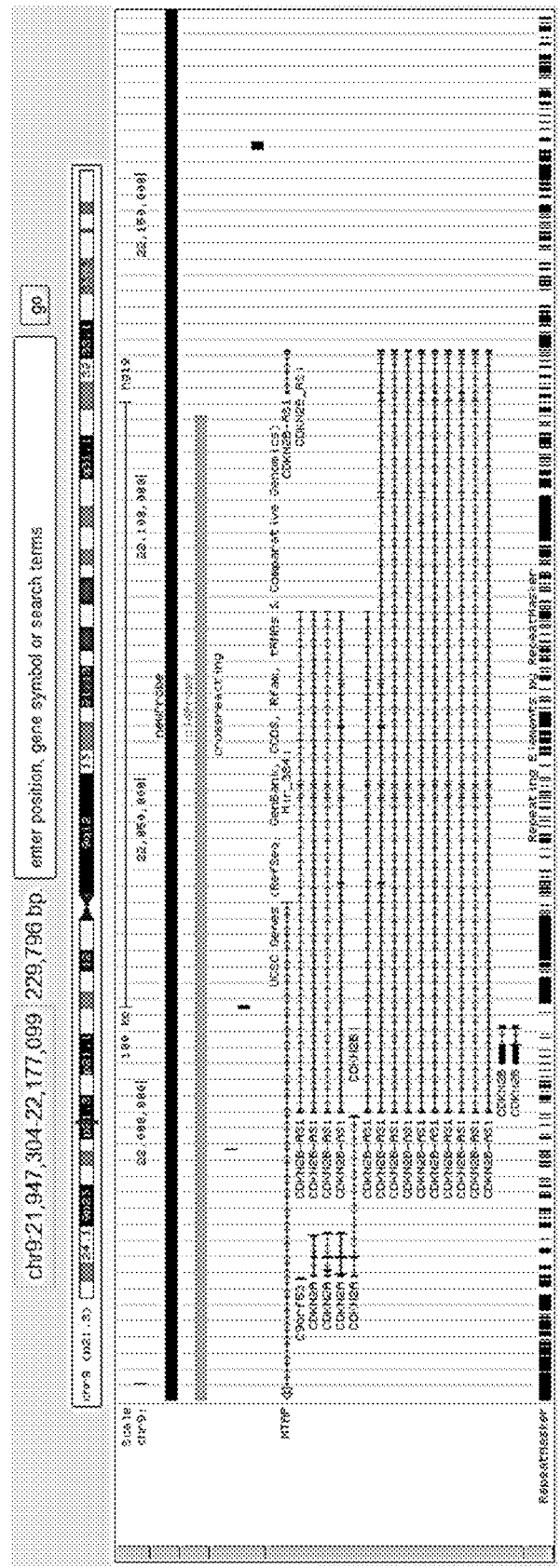
FIG. 9 shows a map of an exemplary repeat-free p16 probe.

This example describes the development of repeat-free probes targeting p16. A map of the p16 probe is shown in FIG. 9. Primer sequences are shown in Table 4.

TABLE 4

| Name | Sequence | SEQ ID NO.: |
|---|---|---|
| 17603_1_F | AATGAGACACGTGAGATCTGGAAGG | 683 |
| 17603_1_R | CAATTTGTTTTGTTTTAGGGCAGGA | 684 |
| 20736_1_F | ATTTACGGTAGTGGGGGAAGGCATA | 685 |
| 20736_1_R | AATGCAAGCTACGGGAGAAAGAAAC | 686 |
| 22171_0_F | TTAATTGTGCTTGAAGAGGGGGTGT | 687 |
| 22171_0_R | TTATACTTCCCAAAGCATACCACCA | 688 |
| 22171_545_F | CGTGTTAATTCCCGTGTACTGTTTCA | 689 |
| 22171_545_R | CGAGTGGCGGAGCTGCTG | 690 |
| 22171_1090_F | CCTCTAGCCTCTTGAGTCTTCATTGC | 691 |
| 22171_1090_R | TGAAGTTCAACATTCCCAGAAGCTAA | 692 |
| 25362_1_F | TCCCAGGTTTATGATTTGAGAGTTCA | 693 |
| 25362_1_R | GGAACTTAGGAAATAATGAGCCACA | 694 |
| 26887_0_F | TTCCAACATACACCACAGATTTCCA | 695 |
| 26887_0_R | GCCATACTTTCCCTATGACACCAAA | 696 |
| 26887_494_F | GACCGTAACTATTCGGTGCGTTG | 697 |
| 26887_494_R | TGTGAGAAGTGTGAAGGAGACAGGA | 698 |
| 31895_1_F | TTATTCCTGAAAACCAGCCTGTGAA | 699 |
| 31895_1_R | TTGATGGTTGTTACCAATACATGCTC | 700 |
| 34379_1_F | ACAGATTGTGGTTTAGCCCCGAAGT | 701 |
| 34379_1_R | TGTTCTCAGCTGATCAAATAGCTACAAA | 702 |
| 36757_0_F | TGAAGTTATTCATTTAGGTCATCAA | 703 |
| 36757_0_R | ATTCTGTTATCATTGCCTTTTTGAA | 704 |

TABLE 4-continued

| Name | Sequence | SEQ ID NO.: |
|---|---|---|
| 36757_584_F | GGTTTTCACTACTGGGAGTGGAGGT | 705 |
| 36757_584_R | TCCTGGTATGTTCCAAGGTGTTAGG | 706 |
| 44110_1_F | TCAGTTTTAGTTCGGCCTAGAATGTT | 707 |
| 44110_1_R | TTGCCTCTGAAAATCTGTAGTAACAA | 708 |
| 45454_1_F | CAGTTACCGGTCACAGTGGCTAAAC | 709 |
| 45454_1_R | TCAAGCACACTTTCTTTCTCCTTGG | 710 |
| 47238_0_F | CCAAGATCTCGGAACGGCTCT | 711 |
| 47238_0_R | GTCCTCGACTCACCCCTCCTTT | 712 |
| 47238_654_F | ACAAGCACCGAGTCCTTTGTGTCTA | 713 |
| 47238_654_R | ACGGTGTTGGGTAAATTCTGAGTGA | 714 |
| 53456_1_F | AAGAGAGAAACCCGAAGAACAATGG | 715 |
| 53456_1_R | CGTTTCTCAATTTCAGCTATCCAAATG | 716 |
| 54621_1_F | CTCAACTGTTGTTGCCCCTTTAAGT | 717 |
| 54621_1_R | CATTCATTTG GCTTCATTTTTATCTT | 718 |
| 55625_1_F | CCAGATCTTCTTGGAATAAATGTCAGG | 719 |
| 55625_1_R | CACAATGATCTCCCTTGTAAGCTCCT | 720 |
| 56854_1_F | CCTTTCCCCAATAACATATGCTCTGA | 721 |
| 56854_1_R | CGGAAATCCCCTTATGACTTGCTAC | 722 |
| 57838_0_F | AACCGTTACAATTGCTCTCACTCCA | 723 |
| 57838_0_R | GGTGTTTCTTTAAATGGCTCCACCT | 724 |
| 57838_736_F | GGGTGGGAAATTGGGTAAGAAAATA | 725 |
| 57838_736_R | AAAATGATGAACTGTTAAGGAAAAATCA | 726 |
| 60520_0_F | TGCTCCTTTAAAAATCCCTCATTTG | 727 |
| 60520_0_R | GAGTGTCGTTAAGTTTACGGCCAAC | 728 |
| 60520_779_F | GGATTTTGCTGGGTAAAAGCCTGT | 729 |
| 60520_779_R | GAAACTTGTGAAGCCCAAGTACTGC | 730 |
| 60520_1558_F | AAGCCTGCCCAAAGATGCTAGGAC | 731 |
| 60520_1558_R | TAATTCTACAGGGATTTGGGGGATG | 732 |
| 60520_2337_F | GGGCTTGTCATTAAACAGGCTGAAC | 733 |
| 60520_2337_R | TCATATTTGAAAACCAGGTTGAGCAG | 734 |
| 81987_1_F | AATAGGAGAGCCTGATCATGTGTGG | 735 |
| 81987_1_R | TCTGCCAGTAGTTTTAAAGGGCTGA | 736 |
| 87808_0_F | TTTAGAGAAAATAAGTGCTGCTGAGG | 737 |
| 87808_0_R | GCACTACTGGTTGTTTAGGCTTTTTC | 738 |
| 87808_643_F | TGCCTGATAGAAGTCAGACTCTGTGG | 739 |
| 87808_643_R | GAGCCACCTTTCAATCCCATTCTAC | 740 |
| 89872_1_F | TAGCAATTCTCATTTGGATTCCTGT | 741 |
| 89872_1_R | CCTCTCTCCTCTAGGTGGCAAACTC | 742 |
| 91063_1_F | CTATTTTGCCAGCGCAGATTTGATA | 743 |
| 91063_1_R | CAACAACAATGCTATCCACACAGATG | 744 |
| 93683_1_F | TGGTTTTGTACCACTCCCTCTCTCA | 745 |
| 93683_1_R | AGCCCCTAGACAGCTGGTAGAAGAA | 746 |
| 96599_1_F | ATATTCAAGCATGAGGAATGGCAAA | 747 |
| 96599_1_R | TTTCCAAAAGAAAAATACTTCTCCTCA | 748 |
| 103078_0_F | AAGTCCCAGCTGAAAGGTAACCAAA | 749 |
| 103078_0_R | AACTGCCTTTGGAAGAAAATTCAGG | 750 |
| 103078_648_F | GGTTTTCATGAACCTCACATGGACT | 751 |
| 103078_648_R | CTCGAAATTCCAAGGGCACTGAAAA | 752 |
| 105020_0_F | GAAAAGCTAGAGTCACATTTTAGTGACC | 753 |
| 105020_0_R | AAACCAAACAGAATTTCCACAGACC | 754 |
| 105020_376_F | TCAGTCCAGAGCAAGTGAATACTGC | 755 |
| 105020_376_R | TTTTTCCTTCGATGGCTGTAACAAT | 756 |
| 114540_1_F | ATGTAGGCTTGTGCCTGACATTAAA | 757 |
| 114540_1_R | TTAGGGGAAATTTTAGAGCCAACGA | 758 |
| 116353_1_F | TGCTGATGAGTGACCAGTTTAGATGA | 759 |
| 116353_1_R | GCCCACCTTTTAGGTTTGTCGTTAG | 760 |
| 117676_1_F | CCCACACCTTTGATGTATTTCTCTTTG | 761 |
| 117676_1_R | GATTTCAGCTCTTCATCACCCACAT | 762 |
| 121286_1_F | TCTTTTCCAGTGACGTAGTGTGTGG | 763 |
| 121286_1_R | TCTCTCAGTGAATCATTTTCCTAGGAGTT | 764 |
| 125649_1_F | TGCTATTATGGCACAATTGATGTTGA | 765 |
| 125649_1_R | CATGATCTTATTTCAACCAACTCTCAAA | 766 |
| 132233_1_F | GAGGGAACAACTTGTGGAAAAGTGA | 767 |
| 132233_1_R | GAAGCATAGGCTAATTCTCATGCAA | 768 |
| 136934_1_F | TAGGGCTATTTCACAAAAGGGCTGT | 769 |
| 136934_1_R | GTGTGGCTAGGTCCTTGGGATAAAC | 770 |
| 141163_1_F | AAGGTCAGTAGGTTCACAGGCCCTA | 771 |
| 141163_1_R | TTCACTTGAAGATAATGAACATCTTACC | 772 |
| 149647_1_F | CTGGATTTGCAGTGTTGTGTCCTAT | 773 |
| 149647_1_R | CAACATTCTGTTCTGAGTGCTGGTG | 774 |
| 156352_1_F | GAGTAGACAGCCAACCCCCTGTATT | 775 |
| 156352_1_R | AGCATGTAGGAGAGGTACGGTGGTA | 776 |
| 159972_1_F | AGCCGTTAGTCAACTCTGAGTCAG | 777 |
| 159972_1_R | TGACCAAGCAATGTGCATAGACAAG | 778 |
| 161650_1_F | CCCAAAACTGAAAGATGAAAACATA | 779 |
| 161650_1_R | TGCAGAAAGGATCCTATTGTTGGTG | 780 |

TABLE 4-continued

| Name | Sequence | SEQ ID NO.: |
|---|---|---|
| 168102_1_F | CTCAGAAGCGAGGGAGACTTAAACC | 781 |
| 168102_1_R | CCCTGGCTCATCTCCATACCTACTC | 782 |
| 169536_1_F | CCATTCTTCCTGAATAACTTGGCTA | 783 |
| 169536_1_R | TCAAAGGTTTGAACTTGCCTCTCAC | 784 |
| 176637_1_F | AACAAAGCAAATTGCAGGCAATAAA | 785 |
| 176637_1_R | AGCCTGTGGTCATAAAACACCTCAC | 786 |
| 181078_0_F | GAAGCATAAAGCAATGGACCAGGTT | 787 |
| 181078_0_R | TTTTCCTCACCTTATGTCAACAAGGA | 788 |
| 181078_648_F | CTTGGGGTTTCAGGAGAGAAATTGT | 789 |
| 181078_648_R | TGACACAGACAAACAGGTGACTCAA | 790 |
| 181078_1296_F | AATTTGTTCTTTCAATTTGGCATGG | 791 |
| 181078_1296_R | TCAATTTTCTGCATGAATTTCCACT | 792 |
| 185793_1_F | CATAATGGGCCACATGATTTTTACC | 793 |
| 185793_1_R | GTAAAGTCAAAAACCTTCCCCATCC | 794 |
| 187891_0_F | CAACTGCTGAACATAGACCCAAGG | 795 |
| 187891_0_R | AAATTCATAACATTTTTCCTTTGAA | 796 |
| 187891_480_F | TTGTTGGAAAGCACATTAGGTGTGT | 797 |
| 187891_480_R | TCCTGTGAAGAAAGCTATGCAGTTG | 798 |
| 187891_960_F | AAAATCTTGGTCTTTCCCACAGAGG | 799 |
| 187891_960_R | AGACTCTTATTGGTGGTTTGTGGAA | 800 |
| 194665_1_F | GCCAGCATTGAGCTGATAAAGACCT | 801 |
| 194665_1_R | CAAAAGTGAAAGAAAATGAATGAAACA | 802 |
| 197665_1_F | CCGGATTTATTTATTGTTCCTGGTTG | 803 |
| 197665_1_R | TGCCAGGCTCTATATGTGTTTTGTG | 804 |
| 199017_1_F | TGAAAAGAGTGGTGCTAGATACTTGGA | 805 |
| 199017_1_R | TCACCTACAACTGATTGGCAGTGTC | 806 |
| 208772_1_F | GGCCTAAGAATTAGTGAAAATCCCAAC | 807 |
| 208772_1_R | TCATCCTTCACAGATCAACCTCCTC | 808 |
| 210208_1_F | CTGAACTCAGAAGGTGAACCACACC | 809 |
| 210208_1_R | CCTGTAAAAGTCCTCAGGTCAACTCA | 810 |
| 211384_1_F | TGAGAATTTGTGATTTCCTGGTGTTG | 811 |
| 211384_1_R | GAAATCCTATAGATAGAAAAGCATTCA | 812 |
| 212493_1_F | ATATCTCTCTTTGGTTCCCTTTTT | 813 |
| 212493_1_R | TCCTTAAGAAATCAGTATTCCAATGCAAA | 814 |
| 214609_1_F | CATCCAAAGGAGAGTTTGGATTTG | 815 |
| 214609_1_R | CATGCCTAGAAAATCGTGGCTGATA | 816 |
| 216869_0_F | AAAAAGGGTGTGGCTTTATTTATTT | 817 |
| 216869_0_R | CCAACAAATCTGTAGATTGCTGACA | 818 |
| 216869_500_F | AAAGAAAGCCAAGTTAGGTTCAGACA | 819 |
| 216869_500_R | TGAGAGGTTGCTGAGGAATTCTTGT | 820 |
| 222534_0_F | GCCTAGTGGAAAAACATTTCCAAGC | 821 |
| 222534_0_R | ACAGCTGGACATGCATGCTCTTAAT | 822 |
| 222534_366_F | TTGCAACTTTCCAGACATTTATTTTC | 823 |
| 222534_366_R | AGGGTTTCCAAAGTTTTGGTGAATG | 824 |
| 225452_1_F | TAAAATTTGTTTGGAGGTGGGGTCT | 825 |
| 225452_1_R | ACCCACAGAAACTTCCATTTCACTG | 826 |
| 228586_1_F | CACAAGAAAAGGTTTCATGAGATAGG | 827 |
| 228586_1_R | TG CCATCTAAAATATTGCTCCTACCA | 828 |

PCR of 1200mers with Phusion: To 2 μL each p16RF 5 uM, 18 μL Phusion MM was added and placed on thermocycler with program 98 deg 30 sec, 25× (98° C. 8 sec, 68° C. 30 sec, 72 deg 1 min), 72° C. 10 min, 4° C. Extend PCR: To each well, 2 μL of the same 5 μM primer and 2 μL (80 uL 2×pcrMM+60 μL dNTP+204, 1M MgCl$_2$) was added and thermocyling was performed: 10× (98° C. 8 sec, 68° C. 30 sec, 72° C. 2 min). Loaded 3 μL to wells of eGel, electrophoresed 8 min. Most wells (68/73) showed strong clean bands at expected (same) MW. However some show closely spaced doublets. Wells of p16RF Phusion PCR were combined to total 1200 μL, split to 3×400 μL in tubes and 404, 3M NaAc and 1 mL EtOH was added and tubes were placed at −20° C. Tubes were spun at 15000 rpm at 4 deg for 12 min, pellets were washed in 4004, 70% EtOH, dried in speedvac, combined, and resuspended in 200 μL water, placed in 65 deg oven 5 min, and spun at 4000 rpm 5 min to sediment polymerase. The supernate was transferred to a new tube, 300 μL PEG rgt was added. After 15 min, the tube was spun at 14000 rpm for 5 min, the pellet was resuspended in 400 μL water. Electrophoresis showed bands consistent with 1200mer mix.

Sonicate p16-1200mer: (reserved 20 μL for use as template) To 380 uL p16-1200mer, 40 uL 3M NaAc was added, the tube was sonicated intensity 3, 30% duty cycle 2×10 min, and 1 mL EtOH was added. The tube was spun at 15000 rpm 4° C. for 10 min, the pellet washed in 400 μL, 70% EtOH, dried, and resuspended in 100 μL water. The tubes was then spun at 15000 rpm 4 deg 5 min to sediment residue from sonicator probe. Electrophoresis showed a size range of approximately 50-400 bp.

Fractionation: To 10 μL of the sonicated 1200mer, 40 μL water and 10 μL buffer was added, the tube was mixed and pipetted to spin column 1, spun 14000 rpm 1 min; to effluent added 10 μL buffer, mixed, pipetted to spin column 2, spun 14000 rpm 1 min; to effluent added 10 μL buffer, mixed, pipetted to spin column 3, spun 14000 rpm 1 min. Columns were washed with 2×200 μL wash buffer and eluted with 50 μL elution buffer. Electrophoresis showed size of approximately 100-300 bp.

Blunt p16son and p16s2 using Fast DNA End Repair Kit: To 3 μL of the above in 40 μL water, 5 μL of 10× buffer and 2.5 uL enzyme mix was added and the tube was vortexed and placed in 20° C. bath for 20 min. An Inverse PCR purification kit (Life Technologies) was used according to directions to isolate products in 50 µL buffer.

Ligate Adaptors to p16sonB, p16s2B: One µL each of 1000 µM PadBsPD1, CadBsPD1, PadEcoR1, CadEcoR1, 5 µL 10× Ligase Buffer, 5 µL 50% PEG4000, 5 µL 7/28 (p16sonB, p16s2B) was added to each tube, the tube was vortexed and 1 µL Ligase was added. An Inverse PCR purification kit was used to isolate products.

PCR of adapted p16: To wells of strip added (8,8,2,8,2) µL water and (1 µL each 20 µM, 2, 8 µL 20 uM PadBsPD1; 2, 84, 20 uM PadEcoR1). To wells added 10 µL of 50 µL DreamTaq Green 2×pcrMM+2 µL of the above probe. Thermocycling was performed with program 25× (95° C. 30 sec, 55° C. 30 sec, 72° C. 30 sec). Analysis showed product bands from p16sonA template slightly broader than those from p16p2A. For both, single primer at 2 µM gave yield similar to 8 µM; no difference between PadBsPD1 and PadEcoR1 primers. PadEcoR1 gave best overall performance.

Prep PCR of adapted p16 with PadEcoR1 single primer 5 µM. To wells of strip added 100 µL (400 µL water+4 µL 1000 µM PadEcoR1+2 µL (p16sonA, p16s2A)+200 µL DreamTaq 2×pcrMM), capped, placed on thermocycler with program 25× (95° C. 30 sec, 55° C. 30 sec, 72° C. 30 sec). Next, an additional 3.0 (30 µL, 25 mM dNTP+10 µL, 1M MgCl$_2$+8 µL 1000 µM PadEcoR1) was added to each well and thermocycling was performed with program 10× (94° C. 30 sec, 55° C. 30 sec, 72° C. 2 min). Product was precipitated and resuspended as above.

Aminate p16 preps: Transferred 50 µL of above p16son to tube and used speedvac to reduce volume to 20 µL. Placed this and remaining 20 µL 7/29 p16sp, p16sp2p in boiling water bath 1 min, then to each added 180 µL (500 µL water+300 µL TFA+174 µL ethylenediamine+95 mg Na$_2$S$_2$O$_3$ and placed in 65° C. water bath for 15 minutes. Next, solutions were desalted into water and 450 µL of each nanodrop was collected. TMED/NaCl was added, the tubes were placed in 65° C. bath 5 min, 50 µL, 3M NaAc and 1 mL isopropanol were added. The resulting solutions were precipitated and resuspended in water.

Label aminated p16 products with TAMRA, CR6G: One µL 1M NaOH was added to above; after 1 min 25 µL (75 µL TMED/NaCl+75 µL DMSO), were added, the tubes were vortexed, and 2 µL (100 mM TAMRA, 100 mM CR6G) was added. Resulting solutions were precipitated and resuspended in water+15 µL 20×SSC and 105 µL formamide to give 150 µL at 2×SSC. Resulting solutions were purified as above.

All publications and patents mentioned in the present application and/or listed below are herein incorporated by reference. Various modification, recombination, and variation of the described features and embodiments will be apparent to those skilled in the art without departing from the scope and spirit of the invention. Although specific embodiments have been described, it should be understood that the invention as claimed should not be unduly limited to such specific embodiments. Indeed, various modifications of the described modes and embodiments that are obvious to those skilled in the relevant fields are intended to be within the scope of the following claims.

We claim:

1. A method of generating a probe to a nucleic acid target, comprising:
   a) amplifying a plurality of regions of said nucleic acid target that are at least 85% free of undesired sequences wherein said undesired sequences are at least 100 bp in length to generate amplification products in a first amplification, wherein said amplifying comprises a primer pair complementary to said plurality of regions;
   b) combining said amplification products to generate a mixture;
   c) isolating said amplification products in said mixture;
   d) fragmenting said mixture of said isolated amplification products to generate a mixture of fragmented amplification products;
   e) size fractionating said fragmented amplification products;
   f) ligating said size fractionated amplification products to nucleic acid adaptors wherein said adaptors are each ligated to two or more amplification products, and wherein said adaptors comprise amplification primer sequences;
   g) amplifying said amplification products comprising said adaptors to generate amplification products in a second amplification wherein said amplifying comprises a primer pair complementary to said adaptor primer sequences; and
   h) labeling said amplification products generated in step g) to generate one or more said probes.

2. The method of claim 1, wherein said undesired sequences are selected from the group consisting of repeat sequences, non-conserved sequences, conserved sequences, GC rich sequences, AT rich sequences, secondary structure, and coding sequences.

3. The method of claim 2, wherein said undesired sequences are repeat sequences.

4. The method of claim 1, wherein one or more of said amplification adaptors that comprise amplification primers comprise a label, a binding site, or a restriction site.

5. The method of claim 1, wherein said regions of said nucleic acid target or said probes are from 100 to 600 bp in length.

6. The method of claim 1, wherein said regions of said nucleic acid target or said probes are 150 bp in length.

7. The method of claim 1, wherein said isolating is precipitating said amplification products.

8. The method of claim 1, wherein said fragmenting is sonication.

9. The method of claim 1, wherein said size fractionating is electrophoresis, chromatography or spin column size fractionating.

10. The method of claim 1, wherein said size fractionated amplification products of step e) are 5' phosphorylated and/or blunt ended before step f).

11. The method of claim 1, wherein said amplification products generated in step g) are aminated.

12. The method of claim 1, wherein said labeling is fluorophore labeling.

13. The method of claim 1, further comprising i) denaturing said labeled amplification products generated in step g).

14. The method of claim 13, wherein said denaturing is formamide denaturing.

* * * * *